US010053453B2

(12) United States Patent
Bürli et al.

(10) Patent No.: US 10,053,453 B2
(45) Date of Patent: Aug. 21, 2018

(54) COMPOUNDS AND THEIR USE AS BACE INHIBITORS

(71) Applicant: AstraZeneca AB, Södertälje (SE)

(72) Inventors: Roland Bürli, Hertfordshire (GB);
Mark E. Duggan, Tequesta, FL (US);
Jörg Holenz, Bolton, MA (US); Patrik Johansson, Göteborg (SE); Karin Kolmodin, Hagersten (SE); Philip Vellacott Thorne, Leicestershire (GB);
Michael John McKenzie,
Loughborough (GB)

(73) Assignee: AstraZeneca AB, Södertilje (SE)

( * ) Notice: Subject to any disclaimer, the term of this patent is extended or adjusted under 35 U.S.C. 154(b) by 0 days.

(21) Appl. No.: 15/516,848

(22) PCT Filed: Oct. 7, 2015

(86) PCT No.: PCT/IB2015/002101
§ 371 (c)(1),
(2) Date: Apr. 4, 2017

(87) PCT Pub. No.: WO2016/055858
PCT Pub. Date: Apr. 14, 2016

(65) Prior Publication Data
US 2017/0313686 A1    Nov. 2, 2017

Related U.S. Application Data

(60) Provisional application No. 62/060,752, filed on Oct. 7, 2014.

(51) Int. Cl.
*C07D 413/04*    (2006.01)
*C07D 263/52*    (2006.01)
*C07D 265/12*    (2006.01)

(52) U.S. Cl.
CPC ......... *C07D 413/04* (2013.01); *C07D 263/52* (2013.01); *C07D 265/12* (2013.01); *C07B 2200/05* (2013.01)

(58) Field of Classification Search
CPC .. C07D 263/52; C07D 263/62; C07D 265/12; C07D 413/04; C07D 413/10; A61K 31/506
USPC ......... 544/71, 122, 124, 137, 238, 242, 331, 544/336; 546/271.7; 548/216
See application file for complete search history.

(56) References Cited

U.S. PATENT DOCUMENTS

| 2012/0165347 A1 | 6/2012 | Csjernyik et al. |
| 2013/0210837 A1 | 8/2013 | Csjernyik et al. |
| 2013/0345246 A1 | 12/2013 | Karlstrom et al. |
| 2013/0345247 A1 | 12/2013 | Karlstrom et al. |
| 2013/0345248 A1 | 12/2013 | Karlstrom et al. |
| 2013/0345272 A1 | 12/2013 | Karlstrom et al. |
| 2014/0031379 A1 | 1/2014 | Bohlin et al. |
| 2014/0288091 A1 | 9/2014 | Minidis et al. |
| 2015/0133471 A1 | 5/2015 | Csjernyik et al. |
| 2016/0184303 A1 | 6/2016 | Csjernyik et al. |

FOREIGN PATENT DOCUMENTS

| WO | WO-2009/064418 A1 | 5/2009 |
| WO | WO-2010/105179 A2 | 9/2010 |
| WO | WO-2011/123674 A1 | 10/2011 |
| WO | WO-2012/163790 A1 | 12/2012 |
| WO | WO-2013/044092 A1 | 3/2013 |
| WO | WO-2013/134085 A1 | 9/2013 |
| WO | WO-2013/181202 A2 | 12/2013 |

OTHER PUBLICATIONS

Layzer, Degenerative Diseases of the Nervous System, Cecil Textbook of Medicine, 20th Edition, vol. 2, pp. 2050-2057, 1996.*
Damasio, Alzheimer's Disease and related dementias, Cecil Textbook of Medicine, 20th Edition, vol. 2, pp. 1992-6, 1996.*
Zlokovic, New Therapeutic Targets in the Neurovascular Pathway in Alzheimer's Disease, Neurotherapeutics, vol. 5, No. 3, pp. 409-414 (2008).*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Oh et al., Maximizing the Potential of Plasma Amyloid-Beta as a Diagnostic Biomarker for Alzheimer's Disease, Neuromol Med (2008) 10:195-207.*
Huang, et al., "Structure- and Property-Based Design of Aminooxazoline Xanthenes as Selective, Orally Efficacious, and CNS Penetrable BACE Inhibitors for the Treatment of Alzheimer's Disease," The Journal of Medicinal Chemistry, 55, pp. 9156-9169 (2012).

* cited by examiner

*Primary Examiner* — Deepak R Rao
(74) *Attorney, Agent, or Firm* — White & Case LLP

(57) ABSTRACT

The present application relates to compounds of formula (I), (Ia), or (Ib) and their pharmaceutical compositions/preparations. This application further relates to methods of treating or preventing Aβ-related pathologies such as Down's syndrome, β-amyloid angiopathy such as but not limited to cerebral amyloid angiopathy or hereditary cerebral hemorrhage, disorders associated with cognitive impairment such as but not limited to MCI ("mild cognitive impairment"), Alzheimer's disease, memory loss, attention deficit symptoms associated with Alzheimer's disease, neurodegeneration associated with diseases such as Alzheimer's disease or dementia, including dementia of mixed vascular and degenerative origin, pre-senile dementia, senile dementia and dementia associated with Parkinson's disease.

25 Claims, No Drawings

COMPOUNDS AND THEIR USE AS BACE INHIBITORS

CROSS-REFERENCE TO RELATED APPLICATIONS

This application is a national stage application under 35 U.S.C. § 371 of International Application No. PCT/IB2015/002101, filed Oct. 7, 2015, which claims the benefit of and priority to U.S. Provisional Patent application No. 62/060,752, filed Oct. 7, 2014, the entire contents of which are herein incorporated by reference in their entireties. International Application No. PCT/IB2015/002101 was published under PCT Article 21(2) in English.

BACKGROUND

The prime neuropathological event distinguishing Alzheimer's disease (AD) is deposition of the 40-42 residue amyloid β peptide (Aβ) in brain parenchyma and cerebral vessels. A large body of genetic, biochemical and in vivo data supports a pivotal role for Aβ in the pathological cascade that eventually leads to AD. Patients usually present early symptoms (commonly memory loss) in their sixth or seventh decades of life. The disease progresses with increasing dementia and elevated deposition of Aβ. In parallel, a hyperphosphorylated form of the microtubule-associated protein tau accumulates within neurons, leading to a plethora of deleterious effects on neuronal function. The prevailing working hypothesis regarding the temporal relationship between Aβ and tau pathologies states that Aβ deposition precedes tau aggregation in humans and animal models of the disease. Within this context, it is worth noting that the exact molecular nature of Aβ mediating this pathological function is presently an issue under intense study. Most likely, there is a continuum of toxic species ranging from lower order Aβ oligomers to supramolecular assemblies such as Aβ fibrils.

The Aβ peptide is an integral fragment of the Type I protein APP (Aβ amyloid precursor protein), a protein ubiquitously expressed in human tissues. Since soluble Aβ can be found in both plasma and cerebrospinal fluid (CSF), and in the medium from cultured cells, APP has to undergo proteolysis. There are three main cleavages of APP that are relevant to the pathobiology of AD, the so-called α-, β-, and γ-cleavages. The α-cleavage, which occurs roughly in the middle of the Aβ domain in APP, is executed by the metalloproteases ADAMI10 or ADAMI17 (the latter also known as TACE). The β-cleavage, occurring at the N terminus of Aβ, is generated by the transmembrane aspartyl protease Beta site APP Cleaving Enzyme 1 (BACE1). The γ-cleavage, generating the Aβ C termini and subsequent release of the peptide, is carried out by a multi-subunit aspartyl protease named γ-secretase. ADAM10/17 cleavage followed by γ-secretase cleavage results in the release of the soluble p3 peptide, an N-terminally truncated Aβ fragment that fails to form amyloid deposits in humans. This proteolytic route is commonly referred to as the nonamyloidogenic pathway. Consecutive cleavages by BACE1 and γ-secretase generate the intact Aβ peptides; hence this processing scheme has been termed the amyloidogenic pathway. With this knowledge at hand, it is possible to envision two possible avenues of lowering Aβ production: stimulating non-amyloidogenic processing, or inhibiting or modulating amyloidogenic processing. This application focuses on the latter strategy, inhibition or modulation of amyloidogenic processing.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHW A-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630). β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease or Asp2 or Beta site APP Cleaving Enzyme (BACE), as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324). BACE is a membrane-bound type 1 protein that is synthesized as a partially active proenzyme and is abundantly expressed in brain tissue. It is thought to represent the major β-secretase activity, and is considered to be the rate-limiting step in the production of amyloid-β-peptide (Aβ).

Drugs that reduce or block BACE activity should therefore reduce Aβ levels and levels of fragments of Aβ in the brain, or elsewhere where Aβ or fragments thereof deposit, and thus slow the formation of amyloid plaques and the progression of AD or other maladies involving deposition of Aβ or fragments thereof. BACE is therefore an important candidate for the development of drugs as a treatment and/or prophylaxis of Aβ-related pathologies such as Down's syndrome; β-amyloid angiopathy, such as but not limited to cerebral amyloid angiopathy or hereditary cerebral hemorrhage; disorders associated with cognitive impairment such as but not limited to MCI ("mild cognitive impairment"); Alzheimer's Disease; memory loss; attention deficit symptoms associated with Alzheimer's disease; neurodegeneration associated with diseases, such as Alzheimer's disease or dementia, including dementia of mixed vascular and degenerative origin, pre-senile dementia, senile dementia, and dementia associated with Parkinson's disease; progressive supranuclear palsy or cortical basal degeneration. It would therefore be useful to inhibit the deposition of Aβ and portions thereof by inhibiting BACE through inhibitors such as the compounds provided herein.

The therapeutic potential of inhibiting the deposition of Aβ has motivated many groups to isolate and characterize secretase enzymes and to identify their potential inhibitors.

SUMMARY OF APPLICATION

The present application provides a compound of formula (I),

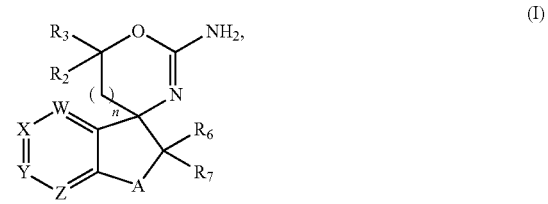

or a prodrug thereof, or a pharmaceutically acceptable salt of the compound of formula (I) or its prodrug, wherein:

A represents O, CH$_2$, CH$_2$CH$_2$, S, or SO$_2$;

X, Y, Z, and W each independently represent N or CR$_1$;

n is 0 or 1;

R$_1$, independently for each occurrence, is selected from hydrogen, halogen, CN, and optionally substituted alkyl, alkenyl, alkynyl, alkoxy, aryl, heteroaryl, or oxime;

R$_2$ and R$_3$ are independently selected from protium, deuterium, tritium, and optionally substituted alkyl (e.g., lower alkyl), provided that when n is 1, R$_2$ and R$_3$ are independently selected from protium, deuterium, and tritium; and R$_6$ and R$_7$ are independently selected from hydrogen, halogen, and optionally substituted alkyl, alkoxyalkyl, cycloalkyl, or heterocycloalkyl, provided that R$_6$ and R$_7$ are not simultaneously hydrogen and further provided that when A is CH$_2$CH$_2$ and n is 0, R$_6$ and R$_7$ are not simultaneously lower alkyl, such as methyl; or R$_6$ and R$_7$ together with the carbon to which they are attached, form an optionally substituted carbocyclic or heterocyclic ring, such as an optionally substituted 3-14 membered carbocyclic or heterocyclic ring.

In certain embodiments, R$_2$ and R$_3$ both represent deuterium or tritium.

In certain embodiments, A represents CH$_2$.

In certain embodiments, X represents CR$_1$, and Y, Z, and W each represent CH.

In certain embodiments, n is 0. In other embodiments, n is 1.

In certain embodiments, the compound of formula I can be represented by formula (Ia),

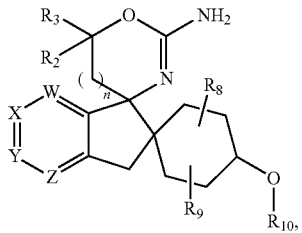

(Ia)

such as a compound of formula (Ia'),

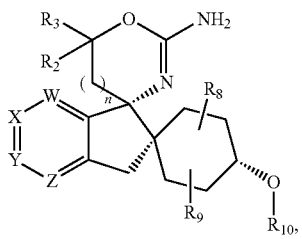

(Ia')

or a prodrug thereof, or a pharmaceutically acceptable salt of the compound of formula (Ia) or (Ia') or its prodrug, wherein:

X, Y, Z, and W each independently represent N or CR$_1$;

n is 0 or 1;

R$_1$, independently for each occurrence, is selected from hydrogen, halogen, CN, and optionally substituted alkyl, alkenyl, alkynyl, alkoxy, aryl, heteroaryl, or oxime;

R$_2$ and R$_3$ are independently selected from protium, deuterium, tritium, and optionally substituted alkyl (e.g., lower alkyl);

R$_8$ and R$_9$, independently for each occurrence, represent hydrogen or optionally substituted alkyl (e.g., lower alkyl, such as methyl or ethyl), or R$_8$ and R$_9$ when bound to the same carbon, taken together with the carbon to which they are attached, form a carbocyclic ring, such as a C$_{3-6}$ carbocyclic ring; and R$_{10}$ represents hydrogen or an optionally substituted alkyl (e.g., optionally substituted lower alkyl).

In certain embodiments, n is 1, and R$_2$ and R$_3$ are independently selected from protium, deuterium, and tritium.

In certain embodiments, both R$_2$ and R$_3$ are deuterium or tritium.

In certain embodiments, n is 0. In other embodiments, n is 1.

In certain embodiments, the compound of formula I can be represented by formula (Ib),

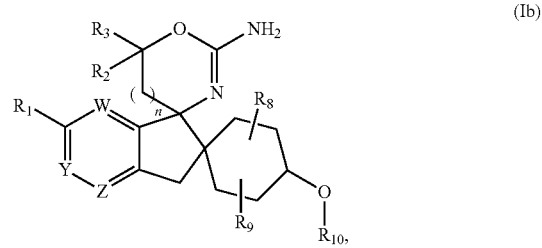

(Ib)

such as a compound of formula (Ib'),

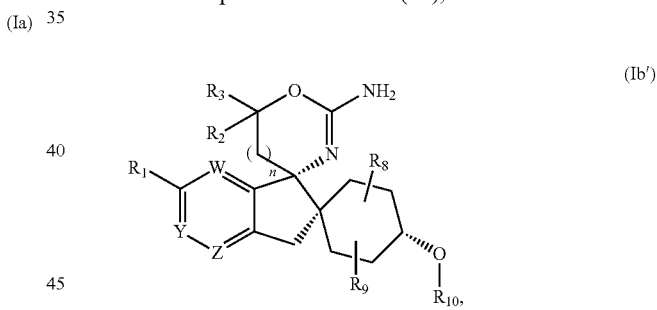

(Ib')

or a prodrug thereof, or a pharmaceutically acceptable salt of the compound of formula (Ib) or (Ib') or its prodrug, wherein:

Y, Z, and W each independently represent N or CR$_1$;

n is 0 or 1;

R$_1$, independently for each occurrence, is selected from hydrogen, halogen, CN, and optionally substituted alkyl, alkenyl, alkynyl, alkoxy, aryl, heteroaryl, or oxime;

R$_2$ and R$_3$ are independently selected from protium, deuterium, tritium, and optionally substituted alkyl (e.g., lower alkyl);

R$_8$ and R$_9$, independently for each occurrence, represent hydrogen or optionally substituted alkyl (e.g., lower alkyl, such as methyl or ethyl), or R$_8$ and R$_9$ when bound to the same carbon, taken together with the carbon to which they are attached, form a carbocyclic ring, such as a C$_{3-6}$ carbocyclic ring (e.g., cyclopropyl ring); and R$_{10}$ represents hydrogen or an optionally substituted alkyl (e.g., optionally substituted lower alkyl, such as methyl or d$_3$-methyl).

In certain embodiments, n is 1, and $R_2$ and $R_3$ are independently selected from protium, deuterium, and tritium.

In certain embodiments, both $R_2$ and $R_3$ are deuterium or tritium.

In certain embodiments, Y, Z, and W each represent CH.

In certain embodiments, n is 0. In other embodiments, n is 1.

In certain embodiments, the application relates to a method of inhibiting activity of BACE with a compound according to formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug.

In certain embodiments, the application relates to the use of a compound according to formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib') or its prodrug, in the manufacture of a medicament for treatment or prevention of Aβ-related pathologies.

In certain embodiments, the application relates to a method of treating or preventing an Aβ-related pathology in a patient in need thereof, comprising administering to said patient a therapeutically effective amount of a compound of formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug.

In certain embodiments, the application relates to a method of treating or preventing an Aβ-related pathology in a patient in need thereof, comprising administering to said patient a therapeutically effective amount of the compound of formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug, and at least one cognitive enhancing agent, memory enhancing agent, or choline esterase inhibitor.

In certain embodiments, said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration.

In certain embodiments, the application relates to the use of a compound according to formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib') or its prodrug, in the manufacture of a medicament for treatment or prevention of Alzheimer's Disease.

In certain embodiments, the application relates to a method of treating or preventing Alzheimer's Disease in a patient in need thereof, comprising administering to said patient a therapeutically effective amount of the compound of formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug.

In certain embodiments, the application relates to a method of treating or preventing an Alzheimer's Disease in a patient in need thereof, comprising administering to said patient a therapeutically effective amount of a compound according to structure formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib') or its prodrug, and at least one cognitive enhancing agent, memory enhancing agent, or choline esterase inhibitor.

DETAILED DESCRIPTION OF THE APPLICATION

The present application provides a compound of formula (I),

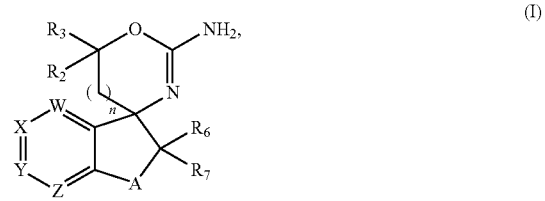

or a prodrug thereof, or a pharmaceutically acceptable salt of the compound of formula (I) or its prodrug, wherein:

A represents O, $CH_2$, $CH_2CH_2$, S, or $SO_2$;

X, Y, Z, and W each independently represent N or $CR_1$;

n is 0 or 1;

$R_1$, independently for each occurrence, is selected from hydrogen, halogen, CN, and optionally substituted alkyl, alkenyl, alkynyl, alkoxy, aryl, heteroaryl, or oxime;

$R_2$ and $R_3$ are independently selected from protium, deuterium, tritium, and optionally substituted alkyl (e.g., lower alkyl), provided that when n is 1, $R_2$ and $R_3$ are independently selected from protium, deuterium, and tritium; and $R_6$ and $R_7$ are independently selected from hydrogen, halogen, and optionally substituted alkyl, alkoxyalkyl, cycloalkyl, or heterocycloalkyl, provided that $R_6$ and $R_7$ are not simultaneously hydrogen, and further provided that when A is $CH_2CH_2$ and n is 0, $R_6$ and $R_7$ are not simultaneously lower alkyl, such as methyl; or $R_6$ and $R_7$ together with the carbon to which they are attached, form an optionally substituted carbocyclic or heterocyclic ring, such as a 3-14 membered carbocyclic or heterocyclic ring.

In certain embodiments, $R_2$ and $R_3$ both represent deuterium or tritium.

In certain embodiments, A represents $CH_2$.

In certain embodiments, X represents $CR_1$, and Y, Z, and W each represent CH.

In certain embodiments, n is 0. In other embodiments, n is 1.

In certain embodiments, $R_6$ and $R_7$ are independently selected from hydrogen and optionally substituted alkyl, alkoxyalkyl, cycloalkyl or heterocycloalkyl, provided that $R_6$ and $R_7$ are not simultaneously hydrogen, and further provided that when A is $CH_2CH_2$ and n is 0, $R_6$ and $R_7$ are not simultaneously lower alkyl, such as methyl. In certain embodiments, A is $CH_2$ and $R_6$ and $R_7$ are independently selected from hydrogen and optionally substituted alkyl, alkoxyalkyl, cycloalkyl or heterocycloalkyl, provided that $R_6$ and $R_7$ are not simultaneously hydrogen. In certain such embodiments, $R_6$ and $R_7$ are not simultaneously lower alkyl, such as methyl.

In certain embodiments, n is 1 and A is $CH_2$.

In certain embodiments, $R_1$, independently for each occurrence, is selected from optionally substituted aryl and heteroaryl, such as optionally substituted phenyl, pyridine, pyrazine, pyridazine, or pyrimidine. In certain such embodiments, the aryl or heteroaryl is optionally substituted with one or more $R_{11}$, wherein $R_{11}$, independently for each occurrence, represents CN, halogen, optionally substituted alkyl (e.g., optionally substituted lower alkyl, such as methyl or 1,1,1-trifluoromethyl), cycloalkyl (e.g., optionally substituted $C_{1-6}$ cycloalkyl, such as cyclopropyl), heterocycloalkyl, alkynyl (e.g., optionally substituted $C_{1-6}$ alkynyl, such as 3-methylbut-1-yn-1-yl), alkenyl, or alkoxy, (e.g., methoxy). For example, in certain embodiments, $R_1$ represents

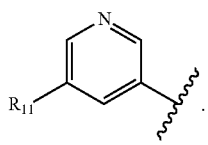

In certain embodiments, $R_1$ is an oxime, wherein the oxime is optionally substituted with optionally substituted alkyl or cycloalkyl. In certain embodiments, $R_1$ is selected from one of the following:

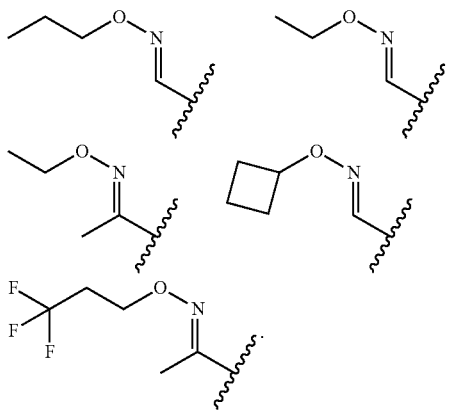

In certain embodiments, $R_1$, independently for each occurrence, is selected from hydrogen and optionally substituted alkyl (e.g., optionally substituted lower alkyl, such as $C_{1-6}$ haloalkyl or $C_{1-6}$ deuterated alkyl), alkenyl, alkynyl, or alkoxy.

In certain embodiments, $R_2$ and $R_3$ are not both protium. In certain embodiments, $R_2$ and $R_3$ both represent deuterium or tritium. For example, in certain embodiments, $R_2$ and $R_3$ both represent deuterium. In other embodiments, $R_2$ and $R_3$ both represent tritium.

In certain embodiments, n is 1, and $R_2$ and $R_3$ both represent deuterium or tritium. For example, in certain embodiments, when n is 1, $R_2$ and $R_3$ both represent deuterium. In other embodiments, when n is 1, $R_2$ and $R_3$ both represent tritium.

In certain embodiments, $R_6$ is hydrogen and $R_7$ is selected from an optionally substituted alkyl (e.g., lower alkyl, such as methyl), alkoxyalkyl (e.g., 2-methoxyethyl or 3-methoxypropyl), cycloalkyl, and heterocycloalkyl. In certain such embodiments, $R_7$ is an optionally substituted tetrahydropyran or morpholine.

In certain embodiments, $R_6$ and $R_7$, together with the carbon to which they are attached, form an optionally substituted carbocyclic ring, such as an optionally substituted a 3-14 membered carbocyclic ring. For example, $R_6$ and $R_7$, together with the carbon to which they are attached, form a cyclohexyl ring. In certain such embodiments, the cyclohexyl ring is optionally substituted with one or more $R_{12}$, wherein $R_{12}$ is selected from OH and optionally substituted alkyl (e.g., lower alkyl, such as methyl, ethyl, $d_3$-methyl or trifluoromethyl) or alkoxy group (e.g., $C_{1-6}$alkoxy, such as methoxy or $d_3$-methoxy). In certain embodiments, two occurrences of $R_{12}$ bound to the same carbon, taken together with the carbon to which they are attached, form a carbocyclic ring, such as a $C_{3-6}$ membered carbocyclic ring (e.g., a cyclopropyl ring).

In certain embodiments, $R_6$ and $R_7$, together with the carbon to which they are attached, form a ring with the structure

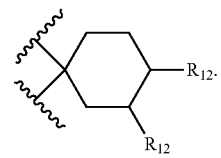

In certain such embodiments, $R_6$ and $R_7$, together with the carbon to which they are attached, form a ring with the structure

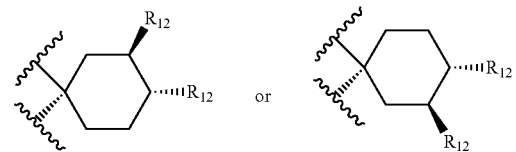

In certain embodiments, $R_6$ and $R_7$, together with the carbon to which they are attached, form a ring with the structure

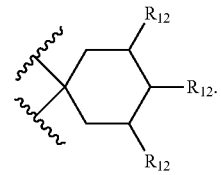

In certain such embodiments, $R_6$ and $R_7$, together with the carbon to which they are attached, form a ring with the structure

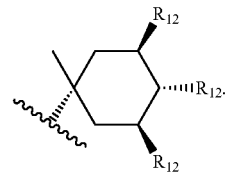

In certain embodiments, $R_6$ and $R_7$, together with the carbon to which they are attached, form a ring with the structure

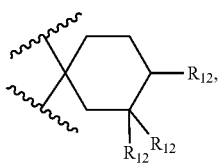

such as

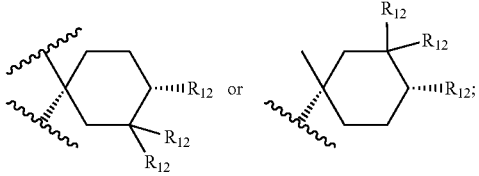

In certain such embodiments, two occurrences of $R_{12}$ bound to the same carbon, taken together with the carbon to which they are attached, form a carbocyclic ring, for example, $R_6$ and $R_7$ form a ring with a structure

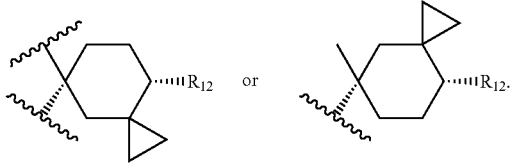

In certain embodiments, A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 0; $R_2$ and $R_3$ both represent protium; and $R_6$ and $R_7$ together with the carbon to which they are attached to form an optionally substituted carbocyclic ring, such as a $C_{3-14}$ membered carbocyclic ring (e.g., a cyclohexyl ring).

In certain embodiments, A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 0; $R_2$ and $R_3$ both represent deuterium; and $R_6$ and $R_7$ together with the carbon to which they are attached to form an optionally substituted carbocyclic ring, such as a $C_{3-14}$ membered carbocyclic ring (e.g., a cyclohexyl ring).

In certain embodiments, A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 1; $R_2$ and $R_3$ both represent protium; and $R_6$ and $R_7$ together with the carbon to which they are attached to form an optionally substituted carbocyclic ring, such as a $C_{3-14}$ membered carbocyclic ring (e.g., a cyclohexyl ring).

In certain embodiments, A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 1; $R_2$ and $R_3$ both represent deuterium; and $R_6$ and $R_7$ together with the carbon to which they are attached to form an optionally substituted carbocyclic ring, such as a $C_{3-14}$ membered carbocyclic ring (e.g., a cyclohexyl ring).

In certain embodiments, the compound of formula (I) can be represented by formula (Ia),

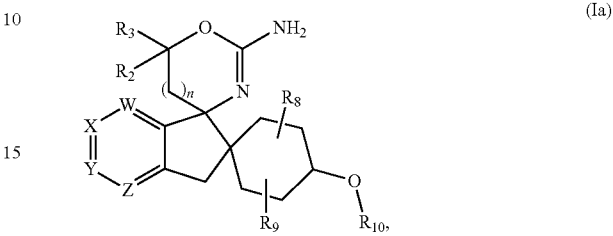

such as a compound of formula (Ia')

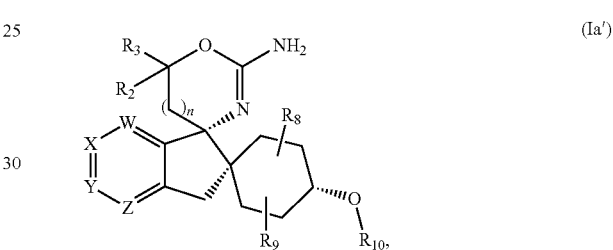

or a prodrug thereof, or a pharmaceutically acceptable salt of the compound of formula (Ia) or (Ia') or its prodrug, wherein:

X, Y, Z, and W each independently represent N or $CR_1$;

n is 0 or 1;

$R_1$, independently for each occurrence, is selected from hydrogen, halogen, CN, and optionally substituted alkyl, alkenyl, alkynyl, alkoxy, aryl, heteroaryl, or oxime;

$R_2$ and $R_3$ are independently selected from protium, deuterium, tritium, and optionally substituted alkyl (e.g., lower alkyl);

$R_8$ and $R_9$, independently for each occurrence, represent hydrogen or optionally substituted alkyl (e.g., lower alkyl, such as methyl or ethyl), or $R_8$ and $R_9$ when bound to the same carbon, taken together with the carbon to which they are attached, form a carbocyclic ring, such as a $C_{3-6}$ carbocyclic ring (e.g., cyclopropyl ring); and $R_{10}$ represents hydrogen or an optionally substituted alkyl (e.g., optionally substituted lower alkyl, such as methyl or $d_3$-methyl).

In certain embodiments, n is 1, and $R_2$ and $R_3$ are independently selected from protium, deuterium, and tritium.

In certain embodiments, both $R_2$ and $R_3$ are deuterium or tritium.

In certain embodiments, the compound of formula (I) can be represented by formula (Ib),

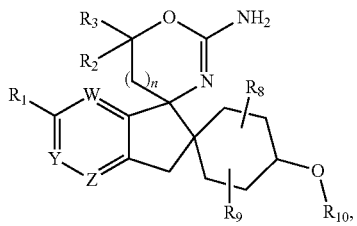

(Ib)

such as a compound of formula (Ib'),

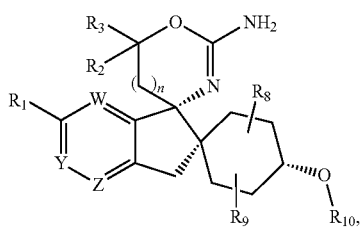

(Ib')

or a prodrug thereof, or a pharmaceutically acceptable salt of the compound of formula (Ib) or (Ib') or its prodrug, wherein:

Y, Z, and W each independently represent N or $CR_1$;
n is 0 or 1;
$R_1$, independently for each occurrence, is selected from hydrogen, halogen, CN, and optionally substituted alkyl, alkenyl, alkynyl, alkoxy, aryl, heteroaryl, or oxime;
$R_2$ and $R_3$ are independently selected from protium, deuterium, tritium, and optionally substituted alkyl (e.g., lower alkyl);
$R_8$ and $R_9$, independently for each occurrence, represent hydrogen or optionally substituted alkyl (e.g., lower alkyl, such as methyl or ethyl), or $R_8$ and $R_9$ when bound to the same carbon, taken together with the carbon to which they are attached, form a carbocyclic ring, such as a $C_{3-6}$ carbocyclic ring (e.g., cyclopropyl ring); and
$R_{10}$ represents hydrogen or an optionally substituted alkyl (e.g., optionally substituted lower alkyl, such as methyl or $d_3$-methyl).

In certain embodiments, n is 1, and $R_2$ and $R_3$ are independently selected from protium, deuterium, and tritium.

In certain embodiments, both $R_2$ and $R_3$ are deuterium or tritium. For example, in certain embodiments, both $R_2$ and $R_3$ are deuterium. In other embodiments, both $R_2$ and $R_3$ are tritium.

In certain embodiments, $R_2$ and $R_3$ are independently selected from protium, deuterium, and tritium, such as deuterium or tritium.

In certain embodiments, Y, Z, and W each represent CH.

In certain embodiments, X is $CR_1$, wherein $R_1$ is selected from halogen, CN, and optionally substituted alkyl, alkenyl, alkynyl, alkoxy, aryl, heteroaryl, or oxime.

In certain embodiments, n is 0. In other embodiments, n is 1.

In certain embodiments, $R_1$, independently for each occurrence, is selected from optionally substituted aryl and heteroaryl, such as optionally substituted phenyl, pyrazine, pyridazine, pyridine, or pyrimidine. In certain such embodiments, the aryl or heteroaryl is optionally substituted with one or more $R_{11}$, wherein $R_{11}$, independently for each occurrence, represents CN, halogen, optionally substituted alkyl (e.g., optionally substituted lower alkyl, such as methyl or 1,1,1-trifluoromethyl), cycloalkyl (e.g., optionally substituted $C_{1-6}$ cycloalkyl, such as cyclopropyl), heterocycloalkyl, alkynyl (e.g., optionally substituted $C_{1-6}$ alkynyl, such as 3-methylbut-1-yn-1-yl), alkenyl, or alkoxy, (e.g., methoxy). For example, in certain embodiments, $R_1$ represents

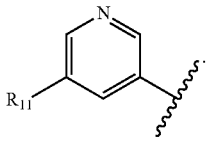

In certain embodiments, $R_1$ is an oxime, wherein the oxime is optionally substituted with optionally substituted $C_{1-6}$ alkyl, such as $C_{1-6}$ haloalkyl, or cycloalkyl, such as $C_{3-6}$ cycloalkyl. In certain embodiments, $R_1$ is selected from one of the following:

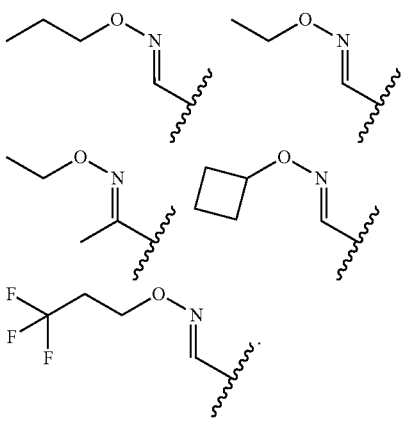

In certain embodiments, $R_1$, independently for each occurrence, is selected from hydrogen and optionally substituted alkyl (e.g., optionally substituted lower alkyl, such as $C_{1-6}$ haloalkyl, or $C_{1-6}$ deuterated alkyl), alkenyl, alkynyl (e.g., optionally substituted $C_{1-6}$ alkynyl, such as 3-methylbut-1-yn-1-yl) or alkoxy (e.g., optionally substituted $C_{1-6}$ alkoxy, such as 3,3,3-trifluoropropoxy).

In certain embodiments, $R_2$ and $R_3$ both represent deuterium.

In certain embodiments, n is 0, and $R_2$ and $R_3$ represent protium.

In certain embodiments, n is 1, $R_2$ and $R_3$ do not represent protium. In certain such embodiments, $R_2$ and $R_3$ both represent deuterium or tritium, such as deuterium.

In certain embodiments, Y, Z, and W each represent CH; n is 0; and $R_2$ and $R_3$ both represent protium.

In certain embodiments, Y, Z, and W each represent CH; n is 0; and $R_2$ and $R_3$ both represent deuterium.

In certain embodiments, Y, Z, and W each represent CH; n is 1; and $R_2$ and $R_3$ both represent protium.

In certain embodiments, Y, Z, and W each represent CH; n is 1; and $R_2$ and $R_3$ both represent deuterium.

In certain embodiments wherein alkyl, alkenyl, alkynyl, alkoxy, aryl, heteroaryl, cycloalkyl, heterocycloalkyl, or oxime are substituted, they are substituted, valency permitting, with one or more substituents selected from substituted or unsubstituted alkyl, such as perfluoroalkyl (e.g., trifluoromethyl), alkenyl, alkoxy, alkoxyalkyl, aryl, aralkyl, arylalkoxy, aryloxy, aryloxyalkyl, hydroxyl, halo, alkoxy, such as perfluoroalkoxy (e.g., trifluoromethoxy), alkoxyalkoxy, hydroxyalkyl, hydroxyalkylamino, hydroxyalkoxy, amino, aminoalkyl, alkylamino, aminoalkylalkoxy, aminoalkoxy, acylamino, acylaminoalkyl, such as perfluoro acylaminoalkyl (e.g., trifluoromethylacylaminoalkyl), acyloxy, cycloalkyl, cycloalkylalkyl, cycloalkylalkoxy, heterocyclyl, heterocyclylalkyl, heterocyclyloxy, heterocyclylalkoxy, heteroaryl, heteroarylalkyl, heteroarylalkoxy, heteroaryloxy, heteroaryloxyalkyl, heterocyclylaminoalkyl, heterocyclylaminoalkoxy, amido, amidoalkyl, amidine, imine, oxo, carbonyl (such as carboxyl, alkoxycarbonyl, formyl, or acyl, including perfluoroacyl (e.g., C(O)CF$_3$)), carbonylalkyl (such as carboxyalkyl, alkoxycarbonylalkyl, formylalkyl, or acylalkyl, including perfluoroacylalkyl (e.g., -alkylC(O) CF$_3$)), carbamate, carbamatealkyl, urea, ureaalkyl, sulfate, sulfonate, sulfamoyl, sulfone, sulfonamide, sulfonamidealkyl, cyano, nitro, azido, sulfhydryl, alkylthio, thiocarbonyl (such as thioester, thioacetate, or thioformate), phosphoryl, phosphate, phosphonate or phosphinate.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used in this application, the term "optionally substituted" means that substitution is optional and therefore it is possible for the designated atom or moiety to be unsubstituted.

In certain embodiments, the compound is selected from any one of compounds 1-43, 45-53, and 56-120. For example, in certain embodiments, the compound is selected from compound 1, compound 2, compound 3, compound 4, compound 5, compound 6, compound 7, compound 8, compound 9, compound 10, compound 11, compound 12, compound 13, compound 14, compound 15, compound 16, compound 17, compound 18, compound 19, compound 20, compound 21, compound 22, compound 23, compound 24, compound 25, compound 26, compound 27, compound 28, compound 29, compound 30, compound 31, compound 32, compound 33, compound 34, compound 35, compound 36, compound 37, compound 38, compound 39, compound 40, compound 41, compound 42, compound 43, compound 45, compound 46, compound 47, compound 48, compound 49, compound 50, compound 51, compound 52, compound 53, compound 56, compound 57, compound 58, compound 59, compound 60, compound 61, compound 62, compound 63, compound 64, compound 65, compound 66, compound 67, compound 68, compound 69, compound 70, compound 71, compound 72, compound 73, compound 74, compound 75, compound 76, compound 77, compound 78, compound 79, compound 80, compound 81, compound 82, compound 83, compound 84, compound 85, compound 86, compound 87, compound 88, compound 89, compound 90, compound 91, compound 92, compound 93, compound 94, compound 95, compound 96, compound 97, compound 98, compound 99, compound 100, compound 101, compound 102, compound 103, compound 104, compound 105, compound 106, compound 107, compound 108, compound 109, compound 110, compound 111, compound 112, compound 113, compound 114, compound 115, compound 116, compound 117, compound 118, compound 119, and compound 120.

Compounds of the present application containing one or multiple asymmetrically substituted atoms may be isolated in optically active or racemic forms. It is well known in the art how to prepare optically active forms, such as by resolution of racemic forms, by synthesis from optically active starting materials, or by synthesis using optically active reagents.

In certain embodiments, compounds of the application may be racemic. In certain embodiments, compounds of the application may be enriched in one enantiomer. For example, a compound of the application may have greater than 30% ee, 40% ee, 50% ee, 60% ee, 70% ee, 80% ee, 90% ee, or even 95% or greater ee.

In certain embodiments, the therapeutic preparation may be enriched to provide predominantly one enantiomer of a compound (e.g., of formula (I), (Ia), such as (Ia'), or (Ib), such as (Ib')). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. For example, a compound of the application may have greater than 30% de, 40% de, 50% de, 60% de, 70% de, 80% de, 90% de, or even 95% or greater de.

In certain embodiments, the therapeutic preparation may be enriched to provide predominantly one diastereomer of a compound (e.g., of formula (I), (Ia), such as (Ia'), or (Ib), such as (Ib')). A diastereomerically enriched mixture may comprise, for example, at least 60 mol percent of one diastereomer, or more preferably at least 75, 90, 95, or even 99 mol percent.

A variety of compounds in the present application may exist in particular geometric or stereoisomeric forms. The present application takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this application. All tautomeric forms are encompassed in the present application. Additional asymmetric carbon atoms may be present in a substituent such as an alkyl group. All such isomers, as well as mixtures thereof, are intended to be included in this application, unless the stereochemistry or isomeric form is specifically indicated.

The present application further includes all pharmaceutically acceptable isotopically labelled compounds (e.g., of formula (I), (Ia), such as (Ia'), or (Ib), such as (Ib')), such as (Ib')). An "isotopically" or "radio-labelled" compound is a compound where one or more atoms are replaced or substituted by an atom having an atomic mass or mass number different from the atomic mass or mass number typically found in nature (i.e., naturally occurring). For example, in certain embodiments, in compounds (e.g., of formula (I), (Ia), such as (Ia'), or (Ib), such as (Ib')), hydrogen atoms are replaced or substituted by one or more deuterium or tritium (e.g., hydrogen atoms on a $C_{1-6}$ alkyl or a $C_{1-6}$ alkoxy are replaced with deuterium, such as $d_3$-methoxy or 1,1,2,2-$d_4$-3-methylbutyl).

Certain isotopically labelled compounds (e.g., of formula (I), (Ia), such as (Ia'), or (Ib), such as (Ib')), in the application, for example, those incorporating a radioactive isotope, are useful in drug and/or substrate tissue distribution studies. The radioactive isotopes tritium, i.e. $^3H$, and carbon 14, i.e., $^{14}C$, are particularly useful for this purpose in view of their ease of incorporation and ready means of detection.

Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically labelled compounds (e.g., of formula (I), (Ia), such as (Ia'), or (Ib), such as (Ib')) or their corresponding prodrugs can generally be prepared by conventional techniques known to those skilled in the art or by processes analogous to those described in the accompanying examples using an appropriate isotopically labelled reagent in place of the non-labelled reagent previously employed. Suitable isotopes that may be incorporated in compounds of the present application include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$.

In certain embodiments, the present application provides a pharmaceutical preparation suitable for use in a human patient, comprising any of the compounds shown above (e.g., a compound of the application, such as a compound of formula (I), (Ia), such as (Ia'), or (Ib), such as (Ib')), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Uses of the Compounds

Compounds of the present application may be administered orally, parenteral, buccal, vaginal, rectal, inhalation, insufflation, sublingually, intramuscularly, subcutaneously, topically, intranasally, intraperitoneally, intrathoracically, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient. The quantity of the compound to be administered will vary for the patient being treated and will vary from about 100 ng/kg of body weight to 100 mg/kg of body weight per day. For instance, dosages can be readily ascertained by those skilled in the art from this disclosure and the knowledge in the art. This, the skilled artisan can readily determine the amount of compound and optional additives, vehicles, and/or carrier in compositions and to be administered in methods of the application. In certain embodiments, the application relates to a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, for use as a medicament, e.g., for treatment or prevention of Aβ-related pathologies.

In certain embodiments, the application relates to a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, for use as a medicament.

In certain embodiments, the application relates to a method of inhibiting activity of BACE with a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug.

In certain embodiments, the application relates to the use of a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, in the manufacture of a medicament for treatment or prevention of Aβ-related pathologies.

In certain embodiments, the application relates to the use of a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, in the manufacture of a medicament for treatment of Aβ-related pathologies, such as, but not limited to, Alzheimer's disease, Down's syndrome, β-amyloid angiopathy, cerebral amyloid angiopathy, hereditary cerebral hemorrhage, a disorder associated with cognitive impairment, MCI ("mild cognitive impairment"), memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy traumatic brain injury and cortical basal degeneration.

In certain embodiments, the application relates to a method of treating or preventing Aβ-related pathologies in a mammal, such as a human being, comprising administering to a mammal in need thereof a therapeutically effective amount of a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug.

In certain embodiments, the application relates to a method of treating or preventing an Aβ-related pathology in a mammal, such as a human being, comprising administering to said patient a therapeutically effective amount of a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, and at least one cognitive enhancing agent, memory enhancing agent, or choline esterase inhibitor.

In certain embodiments, said Aβ-related pathology is, but not limited to, Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration. In certain such embodiments, the Aβ-related pathology is Alzheimer's disease.

In certain embodiments, the application relates to a pharmaceutical composition comprising as active ingredient a therapeutically effective amount of a compound according to formula (I), (Ia), such as (Ia'), or (Ib), such as (Ib'), or a prodrug thereof, or a pharmaceutically acceptable salt of the compound according to formula (I), (Ia), such as (Ia'), or (Ib), such as (Ib'), or its prodrug, in association with at least one pharmaceutically acceptable excipient, carrier or diluent.

In certain embodiments, the application relates to a pharmaceutical composition comprising (1) a compound according to formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug, (2) an additional therapeutic agent, or a pharmaceutically acceptable salt thereof, and (3) pharmaceutically acceptable excipients, carriers or diluents.

In certain embodiments, the application relates to a pharmaceutical composition comprising (1) a compound according to formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug; (2) at least one agent selected from the group consisting of cognitive enhancing agents, memory enhancing agents and choline esterase inhibitors, and (3) pharmaceutically acceptable excipients, carriers or diluents.

In the treatment of Aβ-related pathology defined herein different compounds of the application may be (e.g., conjointly) administered with one or more other compounds of the application. Moreover, compounds of formula (I), (Ia), such as (Ia'), or (Ib), such as (Ib'), or a prodrug thereof, or a pharmaceutically acceptable salt of the compound of formula (I), (Ia), such as (Ia'), or (Ib), such as (Ib'), or its prodrug, or certain combinations thereof, may be conjointly administered with one other conventional therapeutic agents in treating one or more disease conditions referred to herein.

In certain embodiments, compounds of the application may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either simultaneously, sequentially, or by separate dosing of the individual components of the treatment. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the application with one or more additional therapeutic agent(s) provides improved efficacy relative to each individual administration of the compound of the application (e.g., compound of formula (I), (Ia), such as (Ia'), or (Ib), such as (Ib') or a prodrug thereof, or a pharmaceutically acceptable salt of the compound of formula (I), (Ia), such as (Ia'), or (Ib), such as (Ib'), or its prodrug) or the one or more additional therapeutic agent(s). In certain such embodiments, the conjoint administration provides an additive effect, wherein an additive effect refers to the sum of each of the effects of individual administration of the compound of the application and the one or more additional therapeutic agent(s).

Such conventional therapeutics may include one or more of the following categories of agents: acetyl cholinesterase inhibitors, anti-inflammatory agents, cognitive and/or memory enhancing agents or atypical antipsychotic agents. Cognitive enhancing agents, memory enhancing agents and acetyl choline esterase inhibitors includes, but not limited to, donepezil (ARICEPT), galantamine (REMINYL or RAzADYNE), rivastigmine (EXELON), tacrine (COGNEX) and memantine (NAMENDA, AxuRA or EBIXA). Atypical antipsychotic agents includes, but not limited to, olanzapine (marketed as ZYPREXA), aripiprazole (marketed as ABILIFY), risperidone (marketed as RISPERDAL), quetiapine (marketed as SEROQUEL), clozapine (marketed as CLOZARIL), ziprasidone (marketed as GEODON) and olanzapine/fluoxetine (marketed as SYMBYAX).

Additional conventional therapy may include one or more of the following categories of agents:

(1) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, rameltoon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(2) atypical antipsychotics including: for example quetiapine and pharmaceutically active isomer(s) and metabolite(s) thereof.

(3) antipsychotics including: for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(4) anxiolytics including: for example alnespirone, zapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(5) anticonvulsants including: for example carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine, zonisamide and equivalents and pharmaceutically active isomer(s) and metabolite(s) thereof.

(6) Alzheimer's therapies including: for example donepezil, rivastigmine, galantamine, memantine, and equivalents and pharmaceutically active isomer(s) and metabolite(s) thereof.

(7) Parkinson's therapies including: for example deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof.

(8) migraine therapies including: for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof.

(9) stroke therapies including: for example thrombolytic therapy with eg activase and desmoteplase, abciximab, citicoline, clopidogrel, eptifibatide, minocycline, and equivalents and pharmaceutically active isomer(s) and metabolite(s) thereof.

(10) urinary incontinence therapies including: for example darafenacin, falvoxate, oxybutynin, propiverine, robalzotan, solifenacin, tolterodine and equivalents and pharmaceutically active isomer(s) and metabolite(s) thereof.

(11) neuropathic pain therapies including: for example lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof.

(12) nociceptive pain therapies such as paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol, and equivalents and pharmaceutically active isomer(s) and metabolite(s) thereof.

(13) insomnia therapies including: for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(14) mood stabilizers including: for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compounds of this application within the dosage range described herein and the other pharmaceutically active compound or compounds within approved dosage ranges and/or the dosage described in the publication reference.

Definitions

The definitions set forth in this application are intended to clarify terms used throughout this application.

The term "herein" means the entire application.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

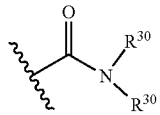

wherein each $R^{30}$ independently represent a hydrogen or hydrocarbyl group, or two $R^{30}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

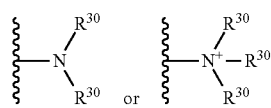

wherein each $R^{30}$ independently represents a hydrogen or a hydrocarbyl group, or two $R^{30}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

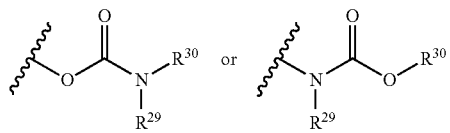

wherein $R^{29}$ and $R^{30}$ independently represent hydrogen or a hydrocarbyl group, such as an alkyl group, or $R^{29}$ and $R^{30}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{30}$, wherein $R^{30}$ represents a hydrocarbyl group.

The term "carboxy", as used herein, refers to a group represented by the formula —CO$_2$H.

The term "ester", as used herein, refers to a group —C(O)OR$^{30}$ wherein R$^{30}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Exemplary heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =OS substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

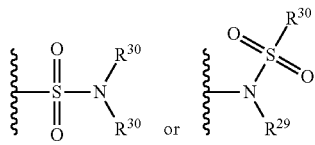

wherein $R^{29}$ and $R^{30}$ independently represents hydrogen or hydrocarbyl, such as alkyl, or $R^{29}$ and $R^{30}$ taken together with the intervening atom(s) complete a heterocycle having from 4 to 8 atoms in the ring structure.

The term "sulfoxide" is art-recognized and refers to the group —S(O)—$R^{30}$, wherein $R^{30}$ represents a hydrocarbyl.

The term "sulfonate" is art-recognized and refers to the group $SO_3H$, or a pharmaceutically acceptable salt thereof.

The term "sulfone" is art-recognized and refers to the group —S(O)$_2$—$R^{30}$, wherein $R^{30}$ represents a hydrocarbyl.

The term "thioalkyl", as used herein, refers to an alkyl group substituted with a thiol group.

The term "thioester", as used herein, refers to a group —C(O)$SR^{30}$ or —SC(O)$R^{30}$ wherein $R^{30}$ represents a hydrocarbyl.

The term "thioether", as used herein, is equivalent to an ether, wherein the oxygen is replaced with a sulfur.

The term "urea" is art-recognized and may be represented by the general formula

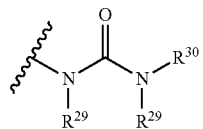

wherein $R^{29}$ and $R^{30}$ independently represent hydrogen or a hydrocarbyl, such as alkyl, or either occurrence of $R^{29}$ taken together with $R^{30}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

The present application includes prodrugs of the compounds of formulae (I), (Ia), such as (Ia'), or (Ib), such as (Ib'), or a pharmaceutically acceptable salt of the compound of formula (I), (Ia), such as (Ia'), or (Ib), such as (Ib'), or its prodrug. The term "prodrug" is intended to encompass compounds which, under physiologic conditions, are converted into the therapeutically active agents of the present application (e.g., a compound of formula (I), (Ia), such as (Ia'), or (Ib), such as (Ib')). A common method for making a prodrug is to include one or more selected moieties which are hydrolyzed under physiologic conditions to yield the desired molecule. In certain embodiments, the prodrug is converted by an enzymatic activity of the host animal. For example, a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds of formula (I), (Ia), such as (Ia'), or (Ib), such as (Ib') in a formulation represented above can be replaced with the corresponding suitable prodrug.

The present application includes metabolites of the compounds of formula (I), (Ia), such as (Ia'), or (Ib), such as (Ib'), or prodrugs thereof, or pharmaceutically acceptable salts of the compounds of formula (I), (Ia), such as (Ia'), or (Ib), such as (Ib'), or their prodrug. The term "metabolite" is intended to encompass compounds that are produced by metabolism/biochemical modification of the parent compound under physiological conditions, e.g. through certain enzymatic pathway. For example, an oxidative metabolite is formed by oxidation of the parent compound during metabolism, such as the oxidation of a pyridine ring to pyridine-N-oxide. In another example, an oxidative metabolite is formed by demethylation of a methoxy group to result in a hydroxyl group.

Pharmaceutical Compositions

The compositions and methods of the present application may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the application and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the application. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the application. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the application, with the carrier and, optionally, one or more accessory ingredients. In general, the formulations are prepared by uniformly and intimately bringing into association a compound of the present application with liquid carriers, or finely divided solid carriers, or both, and then, if necessary, shaping the product.

Formulations of the application suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present application as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this application. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this application, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the application. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the application will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present application, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

This application includes the use of pharmaceutically acceptable salts of compounds of the application in the compositions and methods of the present application. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, such as an amine, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, trifluoroacetic, propionic, isobutyric, maleic, malonic, benzoic, succinic, suberic, fumaric, lactic, mandelic, phthalic, benzensulfonic, p-tolylsulfonic, citric, tartaric, methanesulfonic, camphorsulfonic and the like. In certain embodiments, the pharmaceutically acceptable salt is a hydrochloride salt. In certain embodiments, the pharmaceutically acceptable salt is a camsylate salt. In certain embodiments, contemplated salts of the compounds include, but are not limited to, alkyl, dialkyl, trialkyl or tetra-alkyl ammonium salts. In certain embodiments, contemplated salts of compounds include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of compounds include, but are not limited to, Li, Na, Ca, K, Mg, Zn or other metal salts. Also included are the salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention may contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the application, including their pharmaceutically acceptable salts and prodrugs, can also exist as various solvates, such as with water (also known as hydrates), methanol, ethanol, dimethylformamide, diethyl ether, acetamide, and the like. Mixtures of such solvates can also be prepared. The source of such solvate can be from the solvent of crystallization, inherent in the solvent of preparation or crystallization, or adventitious to such solvent.

The compounds of the application, including their pharmaceutically acceptable salts and prodrugs, can also exist as various polymorphs, pseudo-polymorphs, or in amorphous state. As used herein, the term "polymorph" refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the application comprises a method for conducting a pharmaceutical business, by determining an appropriate formulation and dosage of a compound of the application for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the application relates to a method for conducting a pharmaceutical business by determining an appropriate formulation and dosage of a compound of the application for treating or preventing any of the disease or conditions as described herein, and licensing, to a third party, the rights for further development and sale of the formulation.

EXAMPLES

Example 1: Synthetic Protocols

Below follows a number of non-limiting examples of compounds of the application. Compounds have been named using ChemBioDraw Ultra 13.0.

General Methods

All solvents used were of analytical grade and commercially available anhydrous solvents were routinely used for reactions. Starting materials used were available from commercial sources, or prepared according to literature procedures. Room temperature refers to 20-25° C. Solvent mixture compositions are given as volume percentages or volume ratios.

Microwave heating was performed in a Biotage Creator, Initiator or Smith Synthesizer Single-mode microwave cavity producing continuous irradiation at 2450 MHz. It is understood that microwaves can be used for the heating of reaction mixtures.

Thin layer chromatography (TLC) was performed on Merck TLC-plates (Silica gel 60 $F_{254}$) and spots were UV visualized. Straight phase flash column chromatography was manually performed on Merck Silica gel 60 (0.040-0.063 mm), or automatically using an ISCO Combiflash® Companion™ system using RediSep™ normal-phase flash columns using the solvent system indicated. Phase separation was optionally performed on an Isolute® phase separator.
NMR
NMR spectra were recorded on a 400-600 MHz NMR spectrometer fitted with a probe of suitable configuration. Spectra were recorded at ambient temperature unless otherwise stated. Chemical shifts are given in ppm down- and upfield from TMS (0.00 ppm). The following reference signals were used in $^1$H-NMR: TMS δ 0.00, or the residual solvent signal of DMSO-$d_6$ δ 2.49, $CD_3OD$ δ 3.30, acetone-$d_6$ 2.04 or $CDCl_3$ δ 7.25 (unless otherwise indicated). Resonance multiplicities are denoted s, d, t, q, m, br and app for singlet, doublet, triplet, quartet, multiplet, broad and apparent, respectively. In some cases only diagnostic signals are reported.
HPLC, HPLCMS, and LCMS Analyses:
High pressure liquid chromatography (HPLC) was performed on a reversed phase (RP) column. A linear gradient was applied using for example mobile phase A (10 mM $NH_4OAc$ in 5% $CH_3OH$ or 5% ACN (aq.), or 0.1% $NH_3$ (aq.) or 0.1% formic acid (aq.)) and B ($CH_3OH$ or ACN). Mass spectrometry (MS) analyses were performed in positive and/or negative ion mode using electrospray ionization (ESI+/−) and/or atmospheric pressure chemical ionization (APCI+/−).
GCFID and GCMS Analyses:
Gas chromatography (GC) was performed on a GC equipped with a mass spectrometer (MS) or a flame ionization detector (FID). The MS ion source was either an electron impact (EI) or a chemical ionization (CI, reactant gas methane). For separation a capillary column was used for example DB-5MS, (J&W Scientific). A linear temperature gradient was applied.
Preparative chromatography was run on a Waters FractionLynx system with a Autosampler combined Automated Fraction Collector (Waters 2767), Gradient Pump (Waters 2525), Column Switch (Waters CFO) and PDA (Waters 2996). Column; XBridge® Prep C8 10 μm OBD™ 19×300 mm, with guard column; XTerra® Prep MS C8 10 μm 19×10 mm Cartridge. A gradient of A (95% 0.1 M $NH_4OAc$ in MilliQ water and 5% ACN) in B (100% ACN) or a gradient of A (95% 0.1 M $NH_4OAc$ in MilliQ water and 5% MeOH), A (0.2% $NH_3$ in MilliQ water) or A (0.2% formic acid in MilliQ water) in B (100% MeOH) was applied for LC-separation at flow rate 20 ml/min. Alternatively on a Gilson Unipoint system with Column; XBridge® Prep C18 5 μm OBD™ 19×250 mm, with guard column; A gradient of A (0.1% formic acid or 0.1% TFA or 0.2% $NH_3$ in water) and B (0.1% formic acid or 0.1% TFA or no modifier in ACN) respectively.
SFC Analyses:
Supercritical Fluid Chromatography (SFC) was performed on a straight phase column. A isocratic flow was applied using mobile phase A ($CO_2$) and for example mobile phase B (MeOH, EtOH or IPA).
Straight Phase HPLC Analyses:
High pressure liquid chromatography (HPLC) was performed on a straight phase column. A linear gradient or isocratic flow was applied using for example mobile phase A (Heptane) and B (EtOH or IPA).
Preparative chiral chromatography for separation of enantiomers was run on for example an LaPrep® system using the specified column and mobile phase system.
Terms and Abbreviations:
ACN acetonitrile;
aq aqueous;
Atm atmospheric pressure;
Boc t-butoxycarbonyl;
Borax di-sodium tetraborate or sodium borate or sodium tetraborate;
Cbz benzyloxycarbonyl;
CDI 1,1'-carbonyldiimidazole;
dba dibenzylideneacetone;
DCM dichloromethane;
DEA diethylamine;
DIBAL-H diisobutylaluminium hydride;
DIPEA diisopropylethylamine;
DME 1,2-dimethoxyethane;
DMF N,N-dimethyl formamide;
DMSO dimethyl sulfoxide;
$Et_2O$ diethyl ether;
EtOAc ethyl acetate;
EtOH ethanol;
eq. or equiv. equivalent;
h hour(s);
HATU 2-(7-aza-1H-benzotriazole-1-yl)-1,1,3,3-tetramethyluronium hexafluorophosphate;
HBTU O-benzotriazole-N,N,N',N'-tetramethyluronium hexafluorophosphate
HPLC high performance liquid chromatography;
LCMS liquid chromatography mass spectrometry;
LDA lithium diisopropylamide;
LiHMDS lithium bis(trimethylsilyl)amide;
MeOH methanol;
min minute(s);
MS mass spectrometry;
MW microwave(s);
$NH_4OAc$ ammonium acetate;
NMR nuclear magnetic resonance;
ox oxidation;
Psi pounds per square inch;
quant. quantitative;
RCM ring closing metathesis;
r.t. room temperature;
sat. saturated;
SFC supercritical fluid chromatography;
T3P propylphosphonic anhydride;
TFA trifluoroacetic acid;
THF tetrahydrofuran;
TLC thin layer chromatography;
TMEDA tetramethylethylenediamine;
UPLC ultra performance liquid chromatography.
Synthesis of Compounds (a)-(v)

Compound (a): 6'-Bromo-4-methoxyspiro[cyclohexane-1,2'-inden]-1'(3'H)-one

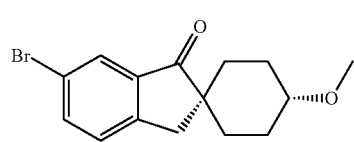 [SMILES: CO[C@H]1CC[C@]2(CC1)Cc1ccc(Br)cc1C2=O]

Step 1: 6'-Bromo-4H-spiro[cyclohexane-1,2'-indene]-1',4(3'H)-dione)

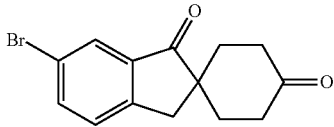 [SMILES: O=C1CCC2(CC1)Cc1ccc(Br)cc1C2=O]

Potassium tert-butoxide (7.50 g, 66.8 mmol) was added in portions to 6-bromo-2,3-dihydro-1H-inden-1-one (11.75 g, 55.67 mmol) and methyl acrylate (11.05 mL, 122.5 mmol) in THF (55 mL) cooled in an ice-bath. The mixture was stirred for 1.5 h at r.t. Water (80 mL) and potassium hydroxide (3.12 g, 55.7 mmol) was added and the mixture was heated to 75° C. and then at 60° C. overnight. The mixture was cooled to 0° C., and the formed precipitate was filtered off and dried in vacuo to give the title compound (11.69 g, 72% yield). $^1$H NMR (500 MHz, CDCl$_3$) δ ppm 1.83-1.92 (m, 2H), 2.15-2.27 (m, 2H), 2.40-2.50 (m, 2H), 2.71 (dt, 2H), 3.17 (s, 2H), 7.39 (d, 1H), 7.75 (dd, 1H), 7.92 (d, 1H); MS (ES+) m/z 293, 295 [M+H]$^+$.

Step 2: 6'-Bromo-4-hydroxyspiro[cyclohexane-1,2'-inden]-1'(3'H)-one

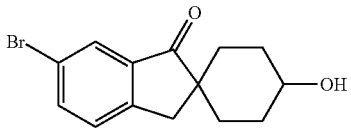 [SMILES: O=C1c2cc(Br)ccc2CC12CCC(O)CC2]

6'-Bromo-4H-spiro[cyclohexane-1,2'-indene]-1',4(3'H)-dione (6.1 g, 20.8 mmol) was dissolved in THF (220 mL) and cooled to −65° C. Sodium borohydride (0.354 g, 9.36 mmol) was added and the cooling bath was removed. The mixture was allowed to reach 0° C. (approx. 30 min). Water (10 mL) was added, and most of the organic solvent was removed by evaporation. The residue was partitioned between EtOAc (100 mL), and brine (50 mL). The organic phase was dried (MgSO$_4$) and evaporated to give a product which was combined with additional product obtained in a similar way starting from 14.6 g of 6'-bromo-4H-spiro[cyclohexane-1,2'-indene]-1',4(3'H)-dione. Purification was done by column chromatography (120 g silica, eluent: DCM to DCM/MeOH, 90:10) affording 13.6 g (66% yield) of the title compound. The obtained material consisted of a 80:20 mixture of isomer 1 and isomer 2. Analytical samples of the isomers were isolated by column chromatography using EtOAc 0% to 100% in heptane to yield:

Isomer 1: (1r,4r)-6'-Bromo-4-hydroxyspiro[cyclohexane-1,2'-inden]-1'(3'H)-one

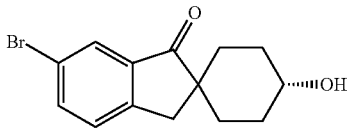

$^1$H NMR (400 MHz, DMSO-d$_6$) δ ppm 1.20-1.43 (m, 4H), 1.49-1.62 (m, 2H), 1.79-1.89 (m, 2H), 2.99 (s, 2H), 3.39-3.50 (m, 1H), 4.68 (d, 1H), 7.56 (d, 1H), 7.76 (d, 1H), 7.85 (dd, 1H); MS (ES+) m/z 317, 319 [M+Na]$^+$ Isomer 2: (1s,4s)-6'-bromo-4-hydroxyspiro[cyclohexane-1,2'-inden]-1'(3'H)-one

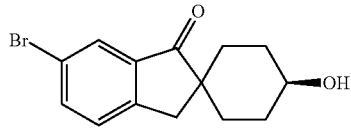

$^1$H NMR (400 MHz, DMSO-d$_6$) δ ppm 1.07-1.20 (m, 2H), 1.51-1.63 (m, 2H), 1.65-1.76 (m, 2H), 1.93 (td, 2H), 2.98 (s, 2H), 3.83 (d, 1H), 4.45 (d, 1H), 7.51-7.55 (m, 1H), 7.76 (d, 1H), 7.84 (dd, 1H); MS (ES+) m/z 317, 319 [M+Na]$^+$.

Step 3: 6'-Bromo-4-methoxyspiro[cyclohexane-1,2'-inden]-1'(3'H)-one

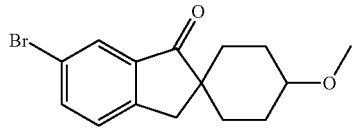 [SMILES: COC1CCC2(CC1)Cc1ccc(Br)cc1C2=O]

A mixture of isomers of 6'-bromo-4-hydroxyspiro[cyclohexane-1,2'-inden]-1'(3'H)-one (12.7 g, 43.0 mmol) was dissolved in THF (210 mL) under N$_2$ and cooled to 0° C. Potassium tert-butoxide (5.79 g, 51.6 mmol) was added portionwise and the mixture was stirred at 0° C. for 25 min. Methyl iodide (4.30 mL, 68.8 mmol) was added. The cooling bath was removed, and the mixture was stirred at r.t. Additional potassium tert-butoxide (0.483 g, 4.30 mmol) was added twice, after 2 h and 3 h respectively, and then the mixture was stirred for 2 h. Water (100 mL) was added and the resulting solution was partitioned between brine (200 mL) and EtOAc (200 mL). The aqueous phase was extracted with another portion of EtOAc (100 mL). The combined organic phases were dried (MgSO$_4$) and evaporated to give 12.5 g (94% yield) of a mixture (approx. 80:20) of:

Isomer 1: (1r,4r)-6'-bromo-4-methoxyspiro[cyclohexane-1,2'-inden]-1'(3'H)-one

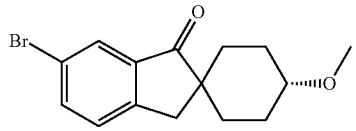

and Isomer 2: (1s,4s)-6'-bromo-4-methoxyspiro[cyclohexane-1,2'-inden]-1'(3'H)-one

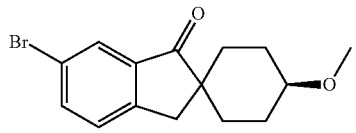

$^1$H NMR (400 MHz, DMSO-d$_6$) δ ppm 1.20-1.32 (m, 2H), 1.40-1.48 (m, 2H), 1.51-1.62 (m, 2H), 1.97-2.07 (m, 2H), 3.00 (s, 2H), 3.15-3.23 (m, 1H), 3.26 (s, 3H), 7.56 (d, 1H), 7.77 (d, 1H), 7.86 (dd, 1H); MS (ES+) m/z 309, 311 [M+H]+.

Compound (b): (1r,4r)-6'-bromo-4-methoxy-3'H,5"H-dispiro[cyclohexane-1,2'-indene-1',4"-oxazol]-2"-amine

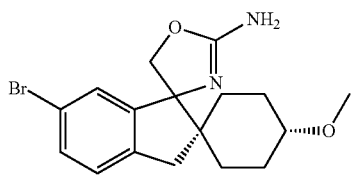

Step 1: (1r,4r)-6'-bromo-4-methoxy-1'-methylene-1',3'-dihydrospiro[cyclohexane-1,2'-indene]

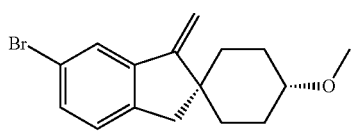 [SMILES: C=C1c2cc(Br)ccc2C[C@]12CC[C@@H](OC)CC2]

To a stirred solution of (1r,4r)-6'-bromo-4-methoxy-spiro[cyclohexane-1,2'-indane]-1'-one (0.31 g, 1 mmol) in THF (10 mL) at −78° C. under nitrogen was added a 1M solution of trimethylsilylmethyllithium (1.33 mL, 1.33 mmol) in pentane over 5 min. The mixture was stirred for 45 min, dropwise treated with acetyl chloride (107 μL, 1.5 mmol), warmed to r.t. and stirred for 3 h. The mixture was quenched with sat. aq. NaHCO₃ (10 mL) and the layers were separated. The aqueous phase was extracted with EtOAc (2×) and the combined organic layers dried (Na₂SO₄), filtered and concentrated to leave a yellow oil (0.4 g). LCMS: rt=3.33 min, m/z=309/311 [M+H]+.

Step 2: (1r,4r)-6'-bromo-4-methoxy-3'H,5"H-dispiro[cyclohexane-1,2'-indene-1',4"-oxazol]-2"-amine

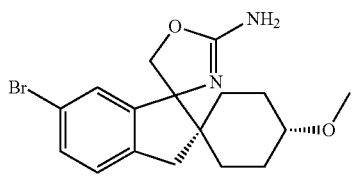

A stirred solution of (1r,4r)-6'-bromo-4-methoxy-1'-methylene-1',3'-dihydrospiro[cyclohexane-1,2'-indene] (0.24 g, 0.78 mmol) in Et₂O (3.3 mL) at 22° C. was treated with isocyanato-silver (0.35 g, 2.34 mmol) followed by iodine (0.20 g, 0.78 mmol). The mixture was stirred at r.t. for 18 h and evaporated to leave a yellow solid (0.6 g). THF (3.3 mL) was added followed by a suspension of iodine (0.3 g, 1.5 eq) in ACN (3.3 mL). The suspension was stirred at r.t. for 18 h, filtered through Celite and concentrated to leave a brown solid (0.5 g) which was dissolved in THF (9 mL) and treated with ammonium hydroxide (1 mL). The mixture was stirred at r.t. for 18 h, concentrated and the residue was partitioned between DCM (20 mL) and water (20 mL). The aqueous layer was extracted with DCM (2×10 mL) and the combined organic extracts were dried (Na₂SO₄), filtered and concentrated to leave a yellow solid (0.4 g). The solid was dissolved in DCM (10 mL) and subjected to flash chromatography (Si 16 g, 5% MeOH (containing 0.1% N ammonia in DCM) afforded a cream solid (0.24 g). ¹H NMR (400 MHz, CD₃OD) δ ppm 1.22-1.36 (m, 3H), 1.44-1.59 (m, 3H), 1.96-2.04 (m, 2H), 2.85 (q, 2H), 3.15-3.19 (m, 1H), 3.35 (s, 3H), 4.21 (d, 1H), 4.64 (d, 1H), 7.14 (d, 1H), 7.35 (dd, 1H) and 7.37 (d, 1H).

Compounds (c) and (d): (1r,1'R,4R)-6'-bromo-4-methoxy-3'H,5"H-dispiro[cyclohexane-1,2'-indene-1',4"-oxazol]-2"-amine (1ˢᵗ Eluting Isomer, c) and (1r,1'S,4S)-6'-bromo-4-methoxy-3'H,5"H-dispiro[cyclohexane-1,2'-indene-1',4"-oxazol]-2"-amine (2ⁿᵈ Eluting Isomer, d)

Enantiomers were separated using preparative supercritical fluid chromatography: column 25 cm×20 mm ChromegaChiral CC4 from ES Industries (West Berlin, N.J.). CO₂ co-solvent (solvent B) CAN/MeOH (3:1), 1% isopropylamine, isocratic method 35% co-solvent at 80 mL/min, system pressure=100 bar, column temperature 25° C., sample diluent MeOH/DCM (9:1).

Compound (e): (1r,4r)-6'-bromo-4-methoxy-3'H,5"H-dispiro[cyclohexane-1,2'-indene-1',4"-oxazol]-5",5"-d₂-2"-amine

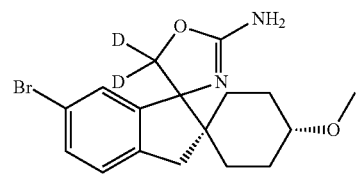

Step 1: (1r,4r)-6'-bromo-4-methoxy-1'-(trideuteriomethyl)spiro[cyclohexane-1,2'-indane]-1'-ol

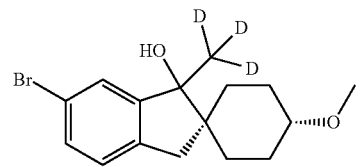

A suspension of magnesium turnings (0.17 g, 6.94 mmol) and one crystal of iodine in Et₂O (5 mL) under N₂ was treated dropwise with iodotrideuteromethane (0.43 mL, 6.94 mmol) over 15 min, stirred at r.t. for 1 h, treated dropwise with a solution of (1r,4r)-6'-bromo-4-methoxy-spiro[cyclohexane-1,2'-indane]-1'-one (1.07 g, 3.47 mmol) in THF (10 mL) and stirred at r.t. for 2 h. The mixture was treated with a saturated ammonium chloride solution and extracted with EtOAc (2×10 mL). The organic layers were dried (Na₂SO₄), filtered and concentrated to leave a brown syrup (1.1 g) which solidified on standing and was used without further purification. ¹H NMR (400 MHz, CDCl₃) δ ppm 1.16-1.33

(2H, m), 1.35-1.46 (2H, m), 1.48-1.56 (2H, m), 1.94-2.02 (2H, m), 2.57 (1H, d), 2.83 (1H, d), 3.02-3.10 (1H, m), 3.30 (3H, s), 7.00 (1H, d), 7.27 (1H, dd) and 7.37 (1H, d).

Step 2: (1r,4r)-6'-bromo-1'-(dideuteriomethylene)-4-methoxy-spiro[cyclohexane-1,2'-indane]

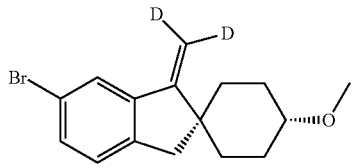 [SMILES: [2H]C([2H])=C1c2cc(Br)ccc2C[C@]12CC[C@@H](OC)CC2]

A solution of (1r,4r)-6'-bromo-4-methoxy-1'-(trideuteriomethyl)spiro[cyclohexane-1,2'-indane]-1'-ol (323. mg, 0.98 mmol) in DCM (10 mL) was treated with p-toluenesulphonic acid monohydrate (18.7 mg, 0.100 mmol) and stirred at r.t. for 40 min. The mixture was washed with water (25 mL), dried (Na$_2$SO$_4$), filtered and concentrated to leave a brown oil (400 mg). Gravity chromatography (Si 4 g, neat DCM) afforded an amber oil which solidified on standing (236 mg). $^1$H NMR (400 MHz, CDCl$_3$) δ ppm 1.32-1.46 (2H, m), 1.48-1.68 (m, 5H), 2.00-2.08 (2H, m), 2.84 (2H, s), 3.18-3.28 (1H, m), 3.38 (3H, s), 4.92 (1.6%), 5.43 (1.6%), 7.09 (1H, d), 7.31 (1H, dd) and 7.56 (1H, d).

Step 3: (1r,4r)-6'-bromo-4-methoxy-3'H,5"H-dispiro[cyclohexane-1,2'-indene-1',4"-oxazol]-5",5"-d$_2$-2"-amine

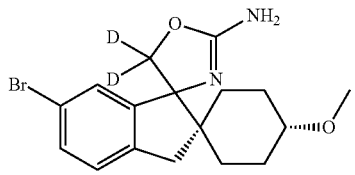

To a stirred solution of (1r,4r)-6'-bromo-1'-(dideuteriomethylene)-4-methoxy-spiro[cyclohexane-1,2'-indane] (8.5 g, 27 mmol) in THF (80 mL) and ACN (80 mL) at r.t. was added isocyanatosilver (12.3 g, 81.9 mmol) followed by a portionwise addition of molecular iodine (10.4 g, 40.9 mmol). The grey mixture was stirred at r.t. for 4 h and the resulting suspension filtered through Celite and concentrated in vacuo to leave a yellow solid. The solid was dissolved in THF (200 mL), treated with ammonium hydroxide (40 mL) and stirred at r.t. for 48 h. The mixture was concentrated and the residue partitioned between EtOAc (500 mL) and water (500 mL). The aqueous layer was separated and extracted with EtOAc (250 mL). The combined organic extracts were dried (Na$_2$SO$_4$), filtered and evaporated to leave a pale yellow solid (11 g). This material was triturated with Et$_2$O (250 mL), filtered and dried to afford a pale yellow solid (8.3 g). $^1$H NMR (400 MHz, CD$_3$OD) δ ppm 1.21-1.38 (3H, m), 1.44-1.59 (3H, m), 1.95-2.04 (2H, m), 2.84 (2H, q), 3.16 (1H, m), 3.35 (3H, s), 7.14 (d, 1H), 7.37 (m, 2H). LCMS: rt=2.54 min, m/z=367/9 [M+H]$^+$.

Compounds (f) & (g): (1r,1'R,4R)-6'-bromo-4-methoxy-3'H,5"H-dispiro[cyclohexane-1,2'-indene-1',4"-oxazol]-5",5"-d2-2"-amine (f) and (1r,1'S,4S)-6'-bromo-4-methoxy-3'H,5"H-dispiro[cyclohexane-1,2'-indene-1',4"-oxazol]-5",5"-d$_2$-2"-amine (g)

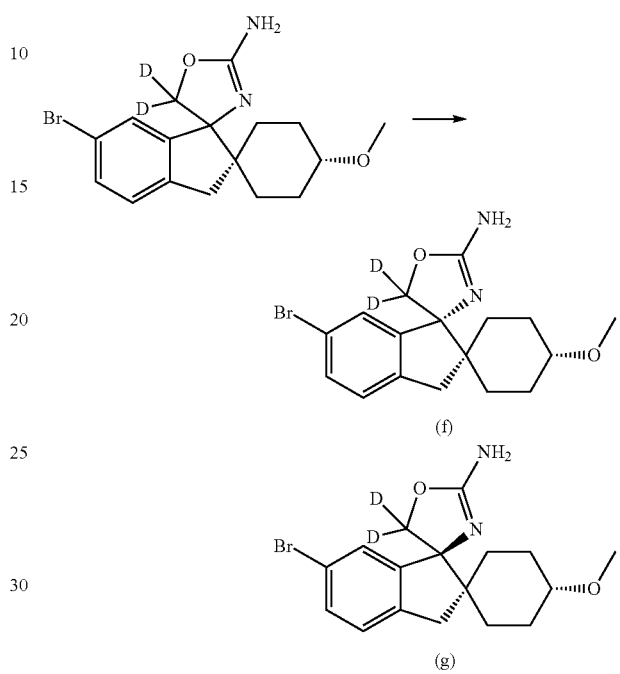

Enantiomers were separated by SFC. For this, the material was dissolved to 50 mg/mL in MeOH. Each injection was 0.5 mL (25 mg). The column used was a Chiralpak AD 20×250 mm 5 um. The eluent was MeOH plus 0.2% DIEA and the flow rate was 50 mL/min.

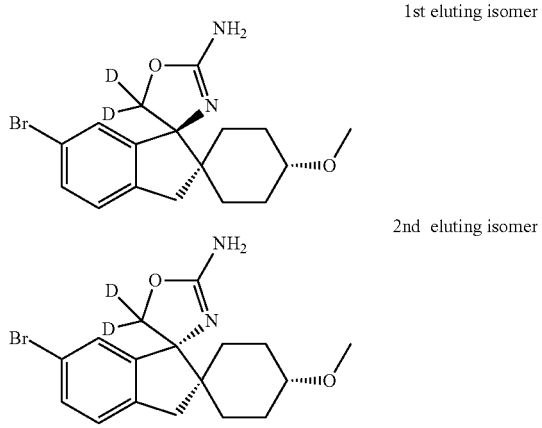

1st eluting isomer

2nd eluting isomer

Isomer 1: solids (2.21 g). $^1$H NMR (400 MHz, CDCl$_3$) δ ppm 1.15-1.60 (6H, m), 1.94-2.03 (2H, m), 2.67 (1H, d), 2.84 (1H, d), 3.04-3.14 (1H, m), 3.33 (3H, s), 4.35 (2H, br, s), 7.03 (1H, d), 7.28 (1H, dd), 7.33 (1H, d). LCMS: rt=2.72 min, m/z=367/369 [M+H]$^+$, purity=99% (e=98%).

Isomer 2: solids (2.08 g). $^1$H NMR (400 MHz, CDCl$_3$) δ ppm 1.15-1.59 (6H, m), 1.92-2.03 (2H, m), 2.66 (1H, d), 2.84 (1H, d), 3.03-3.13 (1H, m), 3.33 (3H, s), 4.35 (2H, br, s), 7.02 (1H, d), 7.28 (1H, dd), 7.32 (1H, d). LCMS: rt=2.72 min, m/z=367/369 [M+H]$^+$, purity=100% (ee=100%).

Compounds (h) & (i): (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (h); (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (i)

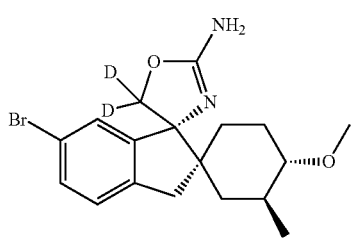

(h)

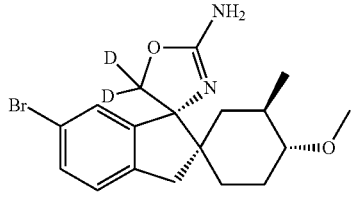

(i)

Step 1: Methyl(1S,5S)-6'-bromo-1-methyl-1',2-dioxo-spiro[cyclohexane-5,2'-indane]-1-carboxylate; methyl(1R,5R)-6'-bromo-1-methyl-1',2-dioxo-spiro[cyclohexane-5,2'-indane]-1-carboxylate

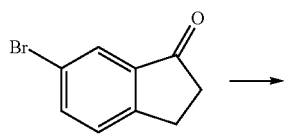

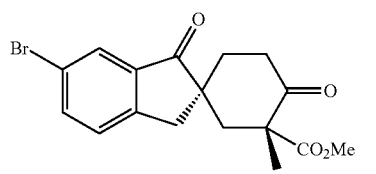

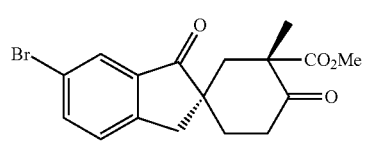

An oven dried 1 L flask was charged with 6-bromoindan-1-one (15 g, 71 mmol), methyl acrylate (13.4 mL, 149 mmol) in THF (150 mL). The mixture was stirred at 0° C. under N$_2$, treated potassium tert-butoxide (50 mg), stirred for 2 min and treated with additional potassium tert-butoxide (9.47 g in small portions over 30 min. The mixture was stirred for 3 h at r.t., treated with DMF (40 mL) followed by iodomethane (8.85 mL, 142 mmol) and stirred at r.t. for 16 h. The suspension was treated with 10% aq. citric acid (100 mL) and concentrated in vacuo to afford an orange oil which was washed with a mixture of H$_2$O/MeOH (9:1). The resulting semi-solid was treated with toluene and evaporated 4×500 mL) and the resulting crude product used for the next step without further purification. $^1$H NMR (400 MHz, CDCl$_3$) δ ppm 1.35 (d, 3H), 1.70-1.82 (m, 1H), 1.90-2.09 (m, 1H), 2.12-2.24 (m, 1H), 2.38-2.48 (m, 1H), 2.76-3.00 (m, 3H), 3.04-3.30 (m, 1H), 3.78-3.82 (m, 3H), 7.26-7.39 (m, 1H), 7.69-7.75 (m, 1H), 7.88 (dd, 1H). LCMS: rt=3.29-3.35 min.

Step 2: (1R,3R,4R)-6'-bromo-4-hydroxy-3-methyl-spiro[cyclohexane-1,2'-indane]-1'-one; (1S,3S,4S)-6'-bromo-4-hydroxy-3-methyl-spiro[cyclohexane-1,2'-indane]-1'-one

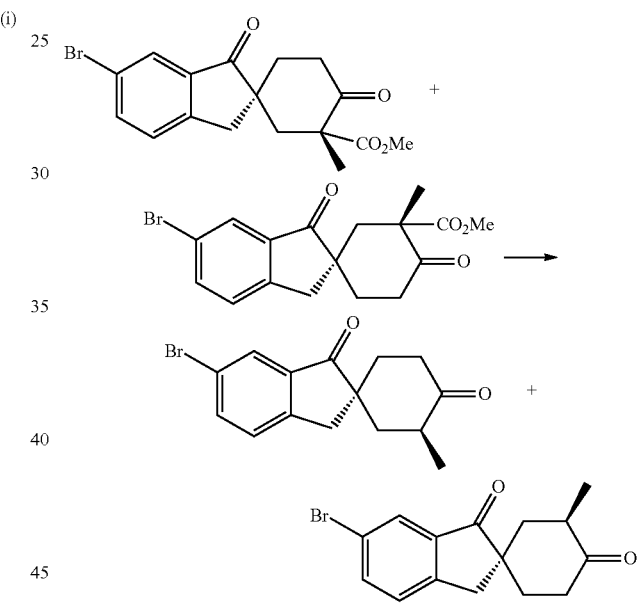

A solution of methyl(1S,5S)-6'-bromo-1-methyl-1',2-dioxo-spiro[cyclohexane-5,2'-indane]-1-carboxylate; methyl(1R,5R)-6'-bromo-1-methyl-1',2-dioxo-spiro[cyclohexane-5,2'-indane]-1-carboxylate (25.9 g, 71.1 mmol) in THF (450 mL) and water (450 mL) was treated with lithium hydroxide monohydrate (11.9 g, 284 mmol) and stirred at r.t. for 55 h. The mixture was heated at 70° C. for 14 h, cooled to r.t. and concentrated in vacuo. The suspension was filtered and the resulting cake was washed with water (400 mL). The isolated solids were washed with MeOH resulting in a white solid (8.42 g). The methanol filtrate was concentrated in vacuo and the resulting residue was stirred in Et$_2$O (50 mL) to give second batch of the desired product (1.25 g): total yield=9.67 g. $^1$H NMR (400 MHz, CDCl$_3$) δ ppm 1.05 (m, 3H), 1.72-1.82 (m, 2H), 1.93 (t, 1H), 2.12-2.24 (m, 1H), 2.46-2.64 (m, 3H), 3.27 (s, 2H), 7.38 (d, 1H), 7.72 (dd, 1H), 7.88 (d, 1H). LCMS: rt=3.26 min, m/z=307/309 [M+H]$^+$.

Step 3: (1R,2R,4R)-6'-bromo-2-methyl-spiro[cyclo-
hexane-4,2'-indane]-1,1'-diol; (1S,2S,4S)-6'-bromo-
2-methyl-spiro[cyclohexane-4,2'-indane]-1,1'-diol

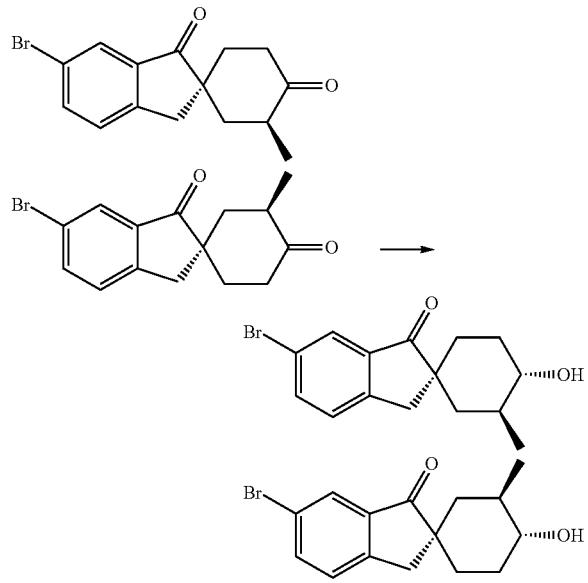

A solution of cerium(III) chloride heptahydrate (1.17 g, 3.15 mmol) in MeOH (140 mL) and under N₂ at r.t was treated with a solution of (2S,4S)-6'-bromo-2-methyl-spiro [cyclohexane-4,2'-indane]-1,1'-dione and (2R,4R)-6'-bromo-2-methyl-spiro[cyclohexane-4,2'-indane]-1,1'-dione (9.67 g, 31.4 mmol) in THF (240 mL), cooled to −70° C., stirred for 30 min and treated with sodium borohydride (0.48 g, 12.6 mmol) in small portions. The mixture was vigorously stirred at this temperature for 2 h and carefully treated with a sat. aq. NH₄Cl (100 mL) and water (200 mL) whilst maintaining the internal temperature below −65° C. The mixture was allowed to warm to r.t. and extracted with EtOAc (3×250 mL). The combined organic layers were dried (Na₂SO₄), filtered and concentrated to give a semi-solid residue (11 g). The crude material was subjected to column chromatography on silica gel, eluting with 10-50% EtOAc in toluene to afford the two title compounds (5.5 g white foam). ¹H NMR (400 MHz, CDCl₃) δ ppm 1.03 (d, 3H), 1.32-1.58 (m, 4H), 1.71 (d, 1H), 1.74-1.86 (m, 1H), 1.98-2.08 (m, 1H), 2.99 (s, 2H), 3.23-3.36 (m, 1H), 7.32 (d, 1H), 7.67 (dd, 1H), 7.85 (d, 1H). LCMS rt=3.10 min; m/z=309/311 [M+H]⁺.

Step 4: (1S,3S,4S)-6'-bromo-4-methoxy-3-methyl-
spiro[cyclohexane-1,2'-indane]-1'-one; (1R,3R,4R)-
6'-bromo-4-methoxy-3-methyl-spiro[cyclohexane-1,
2'-indane]-1'-one

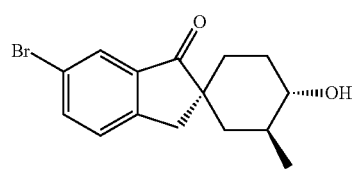

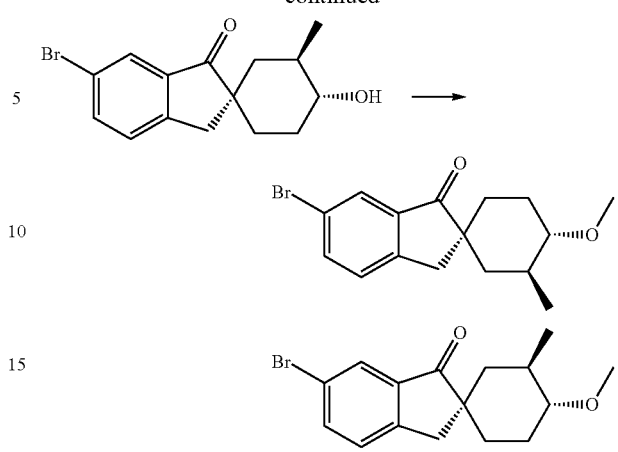

To a stirred solution of (1R,3R,4R)-6'-bromo-4-hydroxy-3-methyl-spiro[cyclohexane-1,2'-indane]-1'-one and (5-bromo-2-methyl-phenyl)-[(1S,3S,4S)-4-hydroxy-1,3-dimethyl-cyclohexyl]methanone (19 g, 62 mmol) in DMF (150 mL) under N₂ was added portionwise NaH (60% dispersion in mineral oil, 2.95 g, 123 mmol) at 0° C. The mixture was stirred for 1 h, treated with iodomethane (10.7 mL, 172 mmol) and allowed to warm to r.t. The mixture was treated with water (100 mL) and EtOAc (250 mL). The organic phase was separated, and further washed with water (2×150 mL), dried over Na₂SO₄, filtered and concentrated in vacuo to afford yellow solid. The crude material (1.77 g) was used without further purification. ¹H NMR (400 MHz, CDCl₃) δ ppm 0.94 (3H, d), 1.14-1.60 (6H, m), 1.69 (1H, td), 2.10-2.19 (1H, m), 2.74 (1H, td), 2.92 (2H, s), 3.34 (3H, s), 7.27 (1H, d), 7.62 (1H, dd), 7.80 (1H, d). LCMS rt=3.49 min; m/z=323/325 [M+H]⁺.

Step 5: (1R,3R,4R)-6'-bromo-1'-(dideuteriomethyl-
ene)-3-ethyl-4-methoxy-spiro[cyclohexane-1,2'-in-
dane]; (1S,3S,4S)-6'-bromo-1'-(dideuteriomethyl-
ene)-3-ethyl-4-methoxy-spiro[cyclohexane-1,2'-
indane]

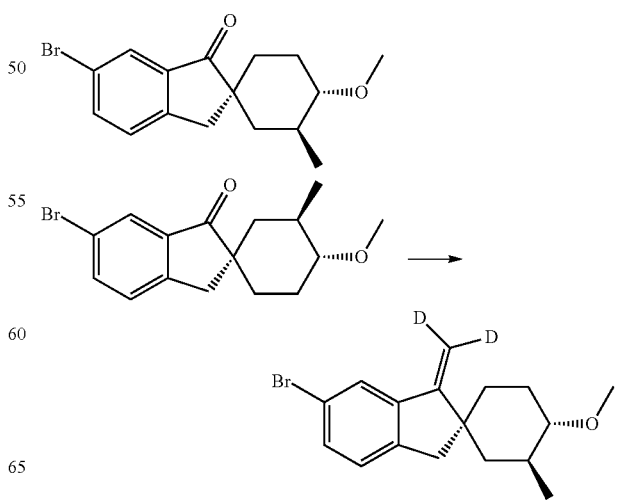

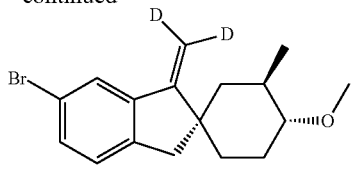

A mixture of n-butyl lithium 2.5 M in hexane (3.14 mL, 7.84 mmol) and THF (50 mL) was treated with a solution of triphenyl(trideuteriomethyl)phosphonium iodide (3.19 g, 7.84 mmol) at −30° C. and stirred for 45 min. A solution of (1S,3S,4S)-6'-bromo-4-methoxy-3-methyl-spiro[cyclohexane-1,2'-indane]-1'-one and (1R,3R,4R)-6'-bromo-4-methoxy-3-methyl-spiro[cyclohexane-1,2'-indane]-1'-one (1.69 g, 5.23 mmol) in THF (20 mL) was added dropwise to the orange solution at −30° C. and the mixture was allowed to warm up to r.t. overnight. The mixture was concentrated in vacuo and the resulting brown oil and absorbed onto silica gel and subjected to column chromatography on silica gel, eluting with 60-80% DCM in hexane to afford the desired product as a clear oil (1.28 g). $^1$H NMR (400 MHz, CDCl$_3$) δ ppm 0.92 (3H, d), 1.16-1.35 (2H, m), 1.40-1.65 (4H, m), 1.98-2.10 (1H, m), 2.71 (1H, td), 2.77 (2H, s), 3.33 (3H, s), 4.86 (1.99%), 5.37 (1.90%), 7.01 (1H, d), 7.24 (1H, dd), 7.51 (1H, d).

Step 6: (1S,1'R,3S,4S)-6'-bromo-4-methoxy-3-methyl-3'H,5"H-dispiro[cyclohexane-1,2'-indene-1',4"-oxazol]-5",5"-d2-2"-amine; (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine

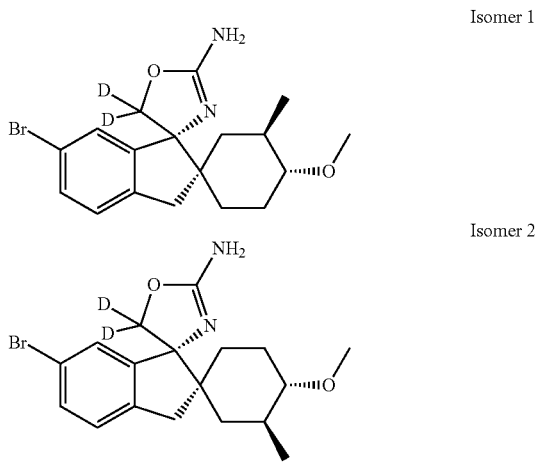

To a stirred solution of (1S,3S,4S)-6'-bromo-1'-(dideuteriomethylene)-4-methoxy-3-methyl-spiro[cyclohexane-1,2'-indane]; (1R,3R,4R)-6'-bromo-1'-(dideuteriomethylene)-4-methoxy-3-methyl-spiro[cyclohexane-1,2'-indane] (1.60 g, 4.95 mmol) in THF (20 mL) and ACN (20 mL) at r.t. was added isocyanatosilver (2.23 g, 14.8 mmol) followed by a portionwise addition of molecular iodine (1.88 g, 7.42 mmol). The mixture was stirred at r.t., filtered through Celite, washed with THF (50 mL) and evaporated to leave a crude yellow semi-solid. This material was dissolved in THF (30 mL), treated with sat. aq. ammonium hydroxide (5 mL), stirred at r.t. for 18 h, and concentrated. The residue was partitioned between EtOAc (250 mL) and sat. aq. NaHCO$_3$ (250 mL). The aqueous layer was extracted with EtOAc (200 mL) and the combined organic extracts were dried (Na$_2$SO$_4$) and evaporated to leave a beige solid (2.4 g).

The crude material was dissolved to 100 mg/mL in MeOH and purified by SFC. Each injection was 0.16 mL (16 mg). The column used was a Lux C4 (250 mm×20 mm, 5 um). The eluent was MeOH/CO$_2$ (40%). The flow rate was 50 mL/min.

Isomer 1: solids (410 mg). $^1$H NMR (400 MHz, CDCl$_3$) δ ppm 0.96 (3H, d), 1.14-1.36 (3H, m), 1.43-1.62 (3H, m), 2.02-2.11 (1H, m), 2.60-2.73 (2H, m), 2.88 (1H, d), 3.36 (3H, s), 7.05 (1H, d), 7.31 (1H, dd), 7.34 (1H, d). LCMS: rt=3.33 min, m/z=381/383 [M+H]$^+$, purity=99% (ee=100%).

Isomer 2: solids (419 mg). $^1$H NMR (400 MHz, CDCl$_3$) δ ppm 0.80-0.92 (4H, m), 1.05-1.58 (6H, m), 1.93-2.03 (1H, m), 2.56-2.67 (1H, m), 2.71 (2H, s), 5.91 (2H, br, s), 7.14 (1H, d), 7.19 (1H, s), 7.28 (1H, d). LCMS: rt=3.33 min, m/z=381/383 [M+H]$^+$, purity=100% (ee=97%).

Isomer 3: solids (398 mg). $^1$H NMR (400 MHz, CDCl$_3$) δ ppm 0.89 (3H, d), 1.10-1.58 (6H, m), 1.94-2.04 (1H, m), 2.54-2.65 (2H, m), 2.78 (1H, d), 3.30 (3H, s), 6.97 (1H, d), 7.23 (1H, dd), 7.27 (1H, d). LCMS: rt=3.36 min, m/z=381/383 [M+H]$^+$, purity=100% (ee=100%).

Isomer 4: solids (505 mg). $^1$H NMR (400 MHz, CDCl$_3$) δ ppm 0.95 (3H, d), 1.12-1.35 (3H, m), 1.41-1.61 (3H, m), 2.01-2.10 (1H, m), 2.60-2.73 (2H, m), 2.86 (1H, d), 3.35 (3H, s), 7.04 (1H, d), 7.29 (1H, dd), 7.33 (1H, d). LCMS: rt=3.35 min, m/z=381/383 [M+H]+, purity=98% (ee=98%).

Compounds (j) & (k): (1S,1'R,3S,4S)-6'-bromo-4-methoxy-3-methyl-3'H,5"H-dispiro[cyclohexane-1,2'-indene-1',4"-oxazol]-2"-amine (j); (1R,1'R,3R,4R)-6'-bromo-4-methoxy-3-methyl-3'H,5"H-dispiro[cyclohexane-1,2'-indene-1',4"-oxazol]-2"-amine (k)

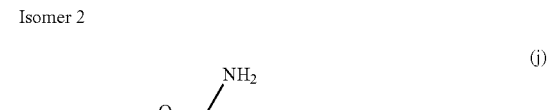

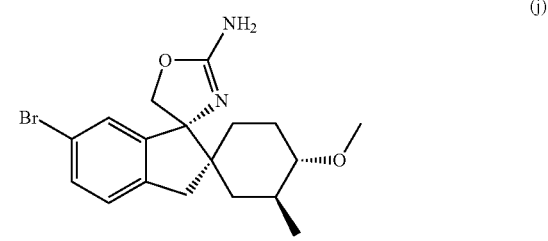

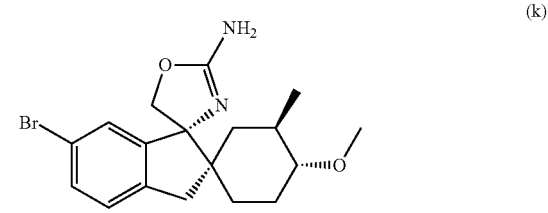

Step 1: (1R,3R,4R)-6'-bromo-1'-(methylene)-3-ethyl-4-methoxy-spiro[cyclohexane-1,2'-indane]; (1S,3S,4S)-6'-bromo-1'-(methylene)-3-ethyl-4-methoxy-spiro[cyclohexane-1,2'-indane]

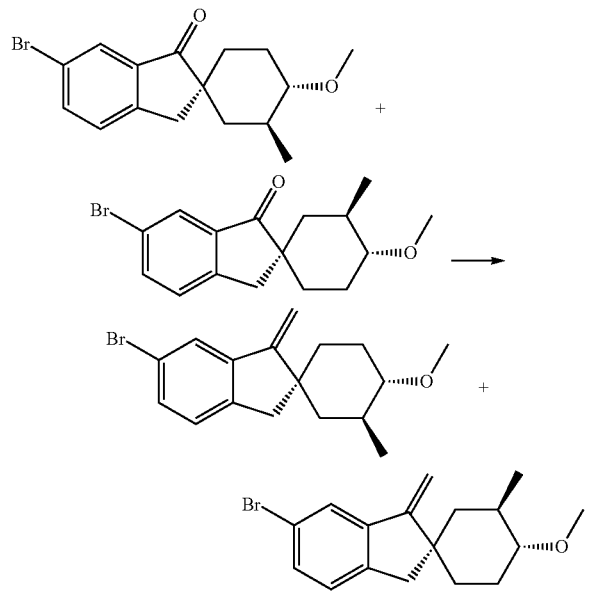

Under N$_2$ at −30° C., a stirred suspension of methyl (triphenyl)phosphonium iodide (2.81 g, 6.96 mmol) in THF (50 mL) was dropwise treated with n-butyllithium (2.5M in hexane, 2.78 mL, 6.96 mmol), stirred for 45 min and treated with a solution of (1S,3S,4S)-6'-bromo-4-methoxy-3-methyl-spiro[cyclohexane-1,2'-indane]-1'-one and (1R,3R,4R)-6'-bromo-4-methoxy-3-methyl-spiro[cyclohexane-1,2'-indane]-1'-one (1.50 g, 4.64 mmol) in THF (20 mL). The mixture was allowed to warm up to r.t. overnight, concentrated in vacuo and the resulting crude orange oil was subjected to column chromatography (silica gel, 30-50% DCM in hexane) to afford the desired product as a pale yellow oil (1.08 g). $^1$H NMR (400 MHz, CDCl$_3$) δ ppm 0.97 (3H, d), 1.22-1.69 (6H, m), 2.06-2.14 (1H, m), 2.76 (1H, td), 2.83 (2H, s), 3.38 (3H, s), 4.92 (1H, s), 5.44 (1H, s), 7.05 (1H, d), 7.29 (1H, dd), 7.55 (1H, d). LCMS: rt=3.89 min.

Step 2: (1S,1'R,3S,4S)-6'-bromo-4-methoxy-3-methyl-3'H,5"H-dispiro[cyclohexane-1,2'-indene-1',4"-oxazol]-2"-amine; (1R,1'R,3R,4R)-6'-bromo-4-methoxy-3-methyl-3'H,5"H-dispiro[cyclohexane-1,2'-indene-1',4"-oxazol]-2"-amine Isomer 1

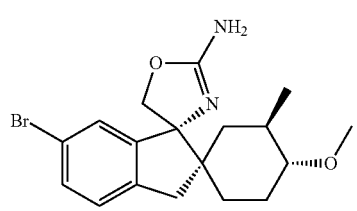

Isomer 2

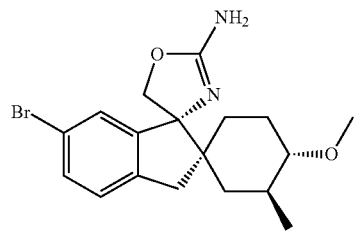

A solution of (1S,3S,4S)-6'-bromo-4-methoxy-3-methyl-1'-methylene-spiro[cyclohexane-1,2'-indane] and (1R,3R,4R)-6'-bromo-4-methoxy-3-methyl-1'-methylene-spiro[cyclohexane-1,2'-indane] (1.08 g, 3.36 mmol) in THF (20 mL) and ACN (20 mL) at r.t. was treated with isocyanatosilver (1.51 g, 10.1 mmol) followed by a portionwise addition of molecular iodine (1.28 g, 5.04 mmol). The grey mixture was stirred at r.t. for 2 h, filtered through Celite, washed with THF (40 mL) and the filtrate was concentrated in vacuo to leave a yellow semi-solid. The solid was dissolved in THF (30 mL) and treated with sat. aq. NH$_4$Cl (5 mL), stirred at r.t. for 48 h and evaporated to afford the desired product as a mixture of 4 diastereoisomers (yellow solid, 1.9 g). The crude material was dissolved to 100 mg/mL in MeOH and was purified by SFC. Each injection was 0.16 mL (16 mg) using a Lux C4 (250 mm x 20 mm, 5 um) column. The eluent was MeOH/CO$_2$ 40% (DEA was added as a modifier). The flow rate was 50 mL/min. The final analysis for isomers 3 and 4 were performed by SFC using a Lux C4 (250 mm×4.6 mm, 5 um) column. The eluent was MeOH 30% (DEA was added as a modifier). The flow rate was 4 mL/min. Peak 1 from the SFC was dissolved to 30 mg/mL in IPA and was then purified by HPLC. Each injection was 0.5 mL (15 mg). The column used was a Lux C1 (250 mm×20 mm, 5 um). The eluent was HEPT/IPA in a 7:3 ratio (DEA was added as a modifier). The flow rate was 21 mL/min.

Isomer 1: solid (133 mg). $^1$H NMR (400 MHz, DMSO-d$_6$) δ ppm 0.88 (3H, m), 1.06-1.25 (3H, m), 1.28-154 (3H, m), 1.94-2.03 (1H, m), 2.63 (1H, td), 2.72 (1H, s), 3.25 (3H, s), 3.98 (1H, d), 4.35 (1H, d), 5.96 (2H, br, s), 7.13 (1H, d), 7.20 (1H, s), 7.31 (1H, m). LCMS: rt=broad peak at 3.34 min, m/z=379/381 [M+H]$^+$, purity=98% (ee=98%).

Isomer 2: solid (78 mg). $^1$H NMR (400 MHz, CDCl$_3$) δ ppm 0.90 (3H, m), 1.11-1.26 (3H, m), 1.31-1.58 (3H, m), 1.90-2.02 (1H, m), 2.54-2.66 (2H, m), 2.76 (1H, s), 3.29 (3H, s), 4.14 (1H, d), 4.53 (1H, d), 7.01 (1H, d), 7.27 (1H, dd), 7.30 (1H, d). LCMS: rt=broad peak at 3.35 min, m/z=379/381 [M+H]$^+$, purity=99% (ee=99%).

Isomer 3: solid (185 mg). $^1$H NMR (400 MHz, CDCl$_3$) δ ppm 0.94 (3H, d), 1.14-1.28 (2H, m), 1.34-1.62 (4H, m), 2.00-2.09 (1H, m), 2.58-2.71 (2H, m), 2.84 (1H, d), 3.34 (3H, s), 4.12 (1H, d), 4.46 (1H, d), 7.02 (1H, d), 7.27 (1H, dd), 7.32 (1H, s). LCMS: rt=broad peak at 3.35 min, m/z=379/381 [M+H]$^+$, purity=95% (ee=96%).

Isomer 4: solid (184 mg). $^1$H NMR (400 MHz, DMSO-d$_6$) δ ppm 0.88 (3H, m), 1.06-1.25 (3H, m), 1.28-154 (3H, m), 1.92-2.03 (1H, m), 2.55-2.65 (1H, m), 2.72 (2H, s), 3.25 (3H, s), 3.98 (1H, dd), 4.35 (1H, dd), 5.94 (2H, br, s), 7.13 (1H, dd), 7.19 (1H, s), 7.29 (1H, m). LCMS: rt=broad peak at 2.71 min, m/z=379/381 [M+H]$^+$, purity=96% (ee=100%).

Compounds (l) & (m): (1S,3S,4S)-6'-bromo-3-ethyl-4-methoxy-3'H,5"H-dispiro[cyclohexane-1,2'-indene-1',4"-oxazol]-5",5"-d$_2$-2"-amine (m); (1R,3R,4R)-6'-bromo-3-ethyl-4-methoxy-3'H,5"H-dispiro[cyclohexane-1,2'-indene-1',4"-oxazol]-5",5"-d$_2$-2"-amine (l)

Isomer 1

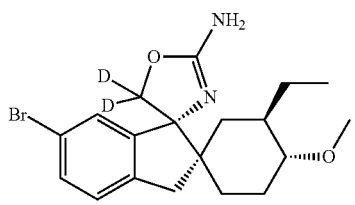
(m)

Isomer 2

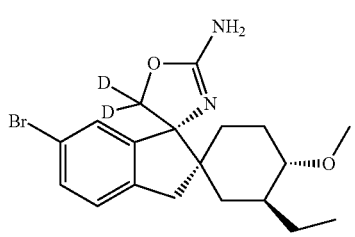
(l)

Step 1: methyl(5R)-6'-bromo-1-ethyl-1',2-dioxo-spiro[cyclohexane-5,2'-indane]-1-carboxylate

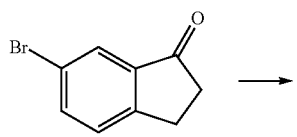

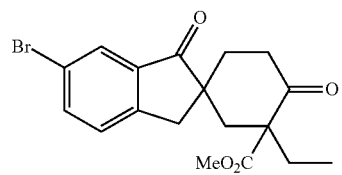

A mixture of 6-bromoindan-1-one (75.0 g, 355 mmol) and methyl acrylate (64 mL, 710 mmol) in THF (1.35 L) was cooled at 0° C. and treated with potassium tert-butoxide (58 mL, 426 mmol in equal portion over 30 min. The mixture was warmed up to r.t. over 1 h, stirred for 40 min at r.t., treated with DMF (300 mL) and iodoethane (57 mL, 711 mmol) and stirred at r.t. for 12 h. The solvent was evaporated and the residue diluted with water (500 mL) and extracted with EtOAc (3×500 mL), dried (Na$_2$SO$_4$) filtered and concentrated in vacuo to give a brown oil (146 g) which was used for the next step without further purification.

Step 2: (2S,4S)-6'-bromo-2-ethyl-spiro[cyclohexane-4,2'-indane]-1,1'-dione; (2R,4R)-6'-bromo-2-ethyl-spiro[cyclohexane-4,2'-indane]-1,1'-dione

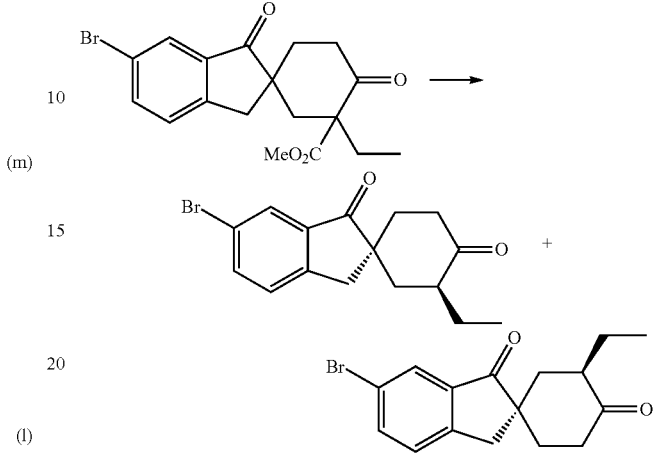

A mixture of methyl (5R)-6'-bromo-1-ethyl-1',2-dioxo-spiro[cyclohexane-5,2'-indane]-1-carboxylate (134 g, 355 mmol) and LiCl (151 g, 3553 mmol) in DMSO (1.35 L) was refluxed for 12 h, cooled and treated with water (3.6 L) and extracted with EtOAc (3×500 mL). The combined organic phases were dried (Na$_2$SO$_4$) and evaporated. Purification (silica, hexane/EtOAc 0-10%) gave the desired product (11.26 g) as a yellow oil. $^1$H NMR (400 MHz, CDCl$_3$) δ ppm 0.81 (3H, t), 1.14-1.23 (2H, m), 1.70-1.86 (4H, m), 2.08-2.18 (1H, m), 2.27-2.36 (1H, m), 2.42-2.48 (2H, m), 3.21 (2H, s), 7.34 (1H, d), 7.68 (1H, dd), 7.84 (1H, d). LCMS: rt=3.34 min, m/z=323 [M+H]$^+$.

Step 3: (1R,3R,4R)-6'-bromo-3-ethyl-4-hydroxy-spiro[cyclohexane-1,2'-indane]-1'-one; (1S,3S,4S)-6'-bromo-3-ethyl-4-hydroxy-spiro[cyclohexane-1,2'-indane]-1'-one

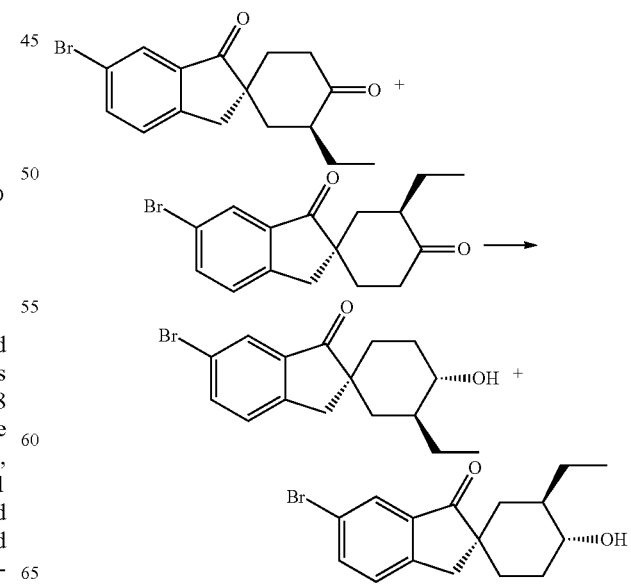

A mixture of (2S,4S)-6'-bromo-2-ethyl-spiro[cyclohexane-4,2'-indane]-1,1'-dione; (2R,4R)-6'-bromo-2-ethyl-spiro[cyclohexane-4,2'-indane]-1,1'-dione (10.9 g, 33.9 mmol) in THF (40 mL) and MeOH (10 mL) was treated with cerium(III) chloride heptahydrate (0.13 g, 0.34 mmol) at −78° C. followed by addition of NaBH$_4$ (0.64 g, 16.9 mmol). The mixture was −78° C. for 20 min, quenched with sat. aq. NH$_4$Cl (100 mL) and extracted with EtOAc (3×500 mL). The combined organic layers were dried (Na$_2$SO$_4$) and evaporated to leave a yellow oil (10.97 g) which was used for the next step without further purification.

Step 4: (1R,3R,4R)-6'-bromo-3-ethyl-4-methoxy-spiro[cyclohexane-1,2'-indane]-1'-one; (1S,3S,4S)-6'-bromo-3-ethyl-4-methoxy-spiro[cyclohexane-1,2'-indane]-1'-one

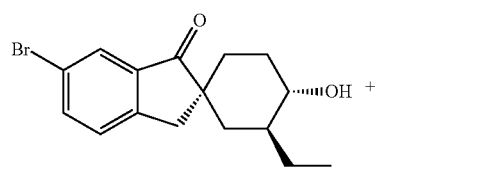

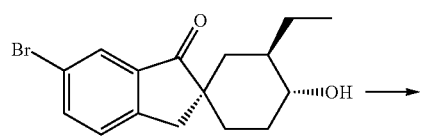

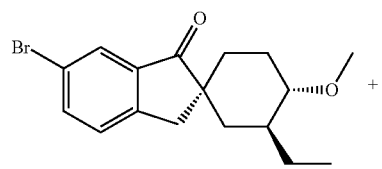

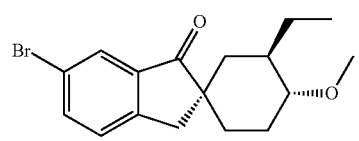

A solution of (1R,3R,4R)-6'-bromo-3-ethyl-4-hydroxy-spiro[cyclohexane-1,2'-indane]-1'-one; (1S,3S,4S)-6'-bromo-3-ethyl-4-hydroxy-spiro[cyclohexane-1,2'-indane]-1'-one (10.9 g, 33.9 mmol) in DMF (170 mL) under N$_2$ at 0° C. was treated with sodium hydride (60% dispersion in mineral oil, 5.43 g, 135.7 mmol), stirred for 30 min, treated with iodomethane (8.45 mL, 135.7 mmol) and allowed to warm up to r.t. After 2 h, the mixture was quenched with water (50 mL), extracted with EtOAc (3×100 mL), dried (Na$_2$SO$_4$) and evaporated. Purification on silica (Hexane/EtOAc 5-10%) gave the title compound as a yellow oil (2.88 g). $^1$H NMR (400 MHz, CDCl$_3$) δ ppm 0.76 (3H, t), 1.07-1.46 (6H, m), 1.63-1.80 (2H, m), 2.14-2.20 (1H, m), 2.81-2.87 (1H, m), 2.91 (2H, s), 3.33 (3H, s), 7.28 (1H, d), 7.63 (1H, dd), 7.81 (1H, s). LCMS: rt=3.62 min, m/z=337 [M+H]$^+$.

Step 5: (1R,3R,4R)-6'-bromo-1'-(dideuteriomethylene)-3-ethyl-4-methoxy-spiro[cyclohexane-1,2'-indane]; (1S,3S,4S)-6'-bromo-1'-(dideuteriomethylene)-3-ethyl-4-methoxy-spiro[cyclohexane-1,2'-indane]

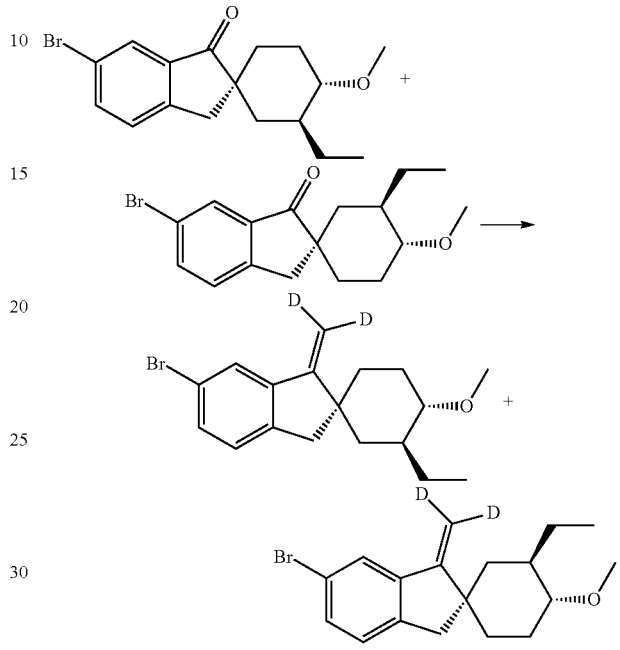

A suspension of triphenyl(trideuteriomethyl)phosphonium iodide (4.31 g, 10.6 mmol) in THF (100 mL) was treated with n-butyllithium (2.5M in hexane, 4.23 mL, 10.59 mmol) at −30° C. under N$_2$. The mixture was stirred for 45 min, treated with a solution of (1R,3R,4R)-6'-bromo-3-ethyl-4-methoxy-spiro[cyclohexane-1,2'-indane]-1'-one; (1S,3S,4S)-6'-bromo-3-ethyl-4-methoxy-spiro[cyclohexane-1,2'-indane]-1'-one (2.38 g, 7.06 mmol) in THF (20 mL) and allowed to warm to r.t. After 3 h, the mixture was concentrated to afford a brown solid. Purification on silica (hexane/DCM 10-60%) gave the desired product as a colorless oil (2.36 g). $^1$H NMR (400 MHz, CDCl$_3$) δ ppm 0.76 (3H, t), 1.00-1.65 (6H, m), 1.72-1.82 (1H, m), 2.04-2.15 (1H, m), 2.76-2.84 (3H, m), 3.32 (3H, s), 7.03 (1H, d), 7.26 (1H, dd), 7.52 (1H, d). LCMS: rt=4.08 min, m/z=339 [M+H]$^+$.

Step 6: (1S,1'R,3S,4S)-6'-bromo-3-ethyl-4-methoxy-3'H,5''H-dispiro[cyclohexane-1,2'-indene-1',4''-oxazol]-5'',5''-d$_2$-2''-amine; (1R,1'R,3R,4R)-6'-bromo-3-ethyl-4-methoxy-3'H,5''H-dispiro[cyclohexane-1,2'-indene-1',4''-oxazol]-5'',5''-d$_2$-2''-amine

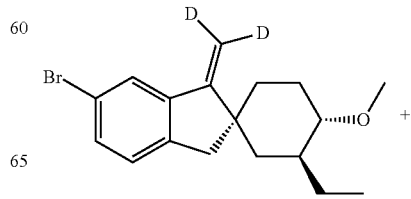

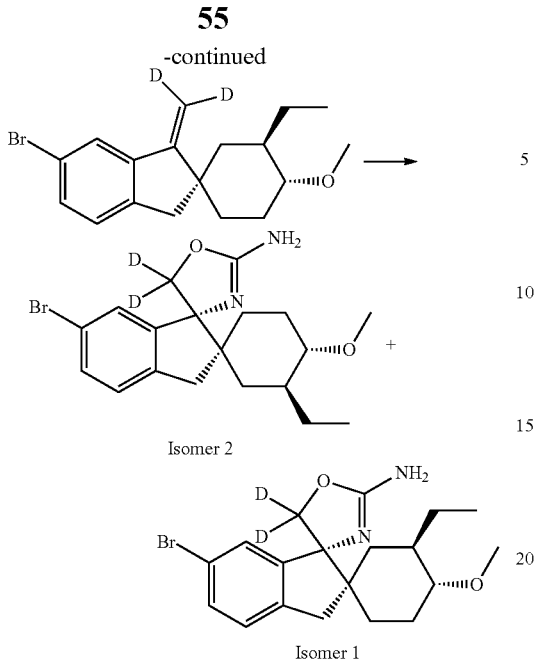

Isomer 2

Isomer 1

A solution of (1R,3R,4R)-6'-bromo-1'-(dideuteriomethylene)-3-ethyl-4-methoxy-spiro[cyclohexane-1,2'-indane]; (1S,3S,4S)-6'-bromo-1'-(dideuteriomethylene)-3-ethyl-4-methoxy-spiro[cyclohexane-1,2'-indane] (2.36 g, 7 mmol) in THF (50 mL) and ACN (50 mL) at r.t. was treated with isocyanatosilver (3.15 g, 21.0 mmol) followed by portion-wise addition of molecular iodine (2.66 g, 10.5 mmol). The grey mixture was stirred at r.t. for 4 h, filtered through Celite and concentrated to leave a yellow solid which was dissolved in THF (20 mL) and sat. aq. NH$_4$Cl (10 mL). The mixture was stirred at r.t. for 18 h concentrated in vacuo, treated with sat. aq. NaHCO$_3$ (25 mL) and extracted with EtOAc (3×50 mL). The combined organic extracts were dried (Na$_2$SO$_4$) and evaporated. The crude material was dissolved to 100 mg/mL in MeOH and purified by SFC. Each injection was 0.16 mL (16 mg) using a Lux C4 (250 mm×20 mm, 5 um) column. The eluent was EtOH/CO$_2$ 40% (DEA was added as a modifier). The flow rate was 50 mL/min. This purification gave a fraction with a mixture of isomer 1 and isomer 2, and isomers 3 and 4 individually. The mixture of isomers 1 and 2 was dissolved to 30 mg/mL in MeOH and purified by HPLC. Each injection was 2 mL (60 mg). The column used was a Lux C1 (250 mm×20 mm, 5 um). The eluent was heptanes/IPA in a 7:3 ratio (DEA was added as a modifier). The flow rate was 21 mL/min. The final analysis of isomers 3 and 4 was performed by SFC using a Lux C4 (250 mm×4.6 mm, 5 um). The eluent was EtOH/CO$_2$ 35% (DEA was added as a modifier). The flow rate was 4 mL/min. The final analysis of isomers 1 and 2 was performed by HPLC using a Lux C1 (250 mm×4.6 mm, 5 um). The eluent was heptane/IPA (DEA was added as a modifier). The flow rate was 1 mL/min.

Isomer 1: solids (302 mg). $^1$H NMR (400 MHz, CDCl$_3$) δ ppm 0.79-0.82 (3H, m), 1.08-1.47 (6H, m), 1.62-1.77 (2H, m), 2.05-2.08 (1H, m), 2.66-2.77 (2H, m), 2.84-2.88 (1H, m), 3.05-3.70 (5H, m), 7.03 (1H, dd), 7.28-7.33 (2H, m). LCMS: rt=2.85 min, m/z=397 [M+H]$^+$, purity=98% (ee=100%).

Isomer 2: solids (313 mg). $^1$H NMR (400 MHz, CDCl$_3$) δ ppm 0.79 (3H, t), 1.04-1.12 (1H, m), 1.17-1.27 (2H, m), 1.32-1.58 (4H, m), 1.72-1.81 (1H, m), 2.04-2.10 (1H, m), 2.64 (1H, d), 2.70-2.76 (1H, m), 2.85 (1H, d), 3.33 (3H, s), 7.03 (1H, d), 7.29 (1H, dd), 7.33 (1H, d), NH$_2$ signals not observed. LCMS: rt=2.89 min, m/z=395 [M+H]$^+$, purity=97.6% (ee=100%).

Isomer 3: solids (492 mg). $^1$H NMR (400 MHz, CDCl$_3$) δ ppm 0.74 (3H, t), 1.00-1.54 (7H, m), 1.66-1.77 (1H, m), 1.98-2.05 (1H, m), 2.60 (1H, d), 2.65-2.71 (1H, m), 2.79 (1H, d), 3.29 (3H, s), 6.98 (1H, d), 7.23 (1H, dd), 7.28 (1H, s), NH$_2$ protons not observed. LCMS: rt=2.98 min, m/z=397 [M+H]$^+$, purity=93.5% (ee=98.3%).

Isomer 4: solids (394 mg). $^1$H NMR (400 MHz, CDCl$_3$) δ ppm 0.75 (3H, t), 1.10-1.42 (6H, m), 1.58 (1H, dd), 1.65-1.75 (1H, m), 1.90-2.05 (1H, m), 2.63 (1H, d), 2.66-2.71 (1H, m), 2.80 (1H, d), 3.29 (3H, s), 6.99 (1H, d), 7.24 (1H, dd), 7.28 (1H, s), NH$_2$ protons not observed. LCMS: rt=2.88 min, m/z=395 [M+H]+, purity=98.6% (ee=98.2%).

Compound (n): (1r,3R,4r,5S)-6'-bromo-4-methoxy-3,5-dimethylspiro[cyclohexane-1,2'-inden]-1'(3'H)-one

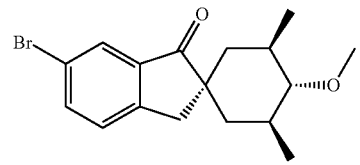 [SMILES: CO[C@H]1[C@H](C)C[C@@]2(Cc3ccc(Br)cc3C2=O)C[C@@H]1C]

Step 1: (1r,3R,5S)-6'-bromo-3,5-dimethylspiro[cyclohexane-1,2'-indene]-1',4(3'H)-dione

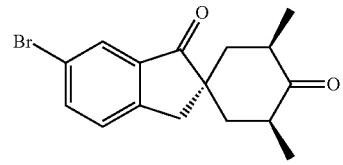 [SMILES: C[C@@H]1C[C@@]2(Cc3ccc(Br)cc3C2=O)C[C@H](C)C1=O]

Under N$_2$ at −5° C., a solution of 6-bromo-indan-1-one (25 g) in THF (250 mL) was treated with potassium tert-butoxide (14.7 g), stirred for 10 min, warmed to r.t., stirred for 10 min and treated with methyl methacrylate (13.4 mL). After 2 h, additional methyl acrylate (13 mL) was added to the mixture at r.t. After 3 h, methyl iodide (11.11 mL) was added and stirring was continued for 16 h at r.t. The mixture was treated with water (250 mL) followed by LiOH monohydrate (20 g) and stirring was continued for 28 h at r.t. The solvent was removed under reduced pressure, the residue diluted with water (250 mL) and the precipitated solid collected by filtration, washed with water until the filtrate was neutral. The solid was further washed with MeOH (3×30 mL) to afford title compound (11.2 g). $^1$H NMR (400 MHz, CDCl$_3$) d ppm 1.06 (d, 6H) 1.77-1.82 (m, 2H) 1.91-1.98 (t, 2H) 2.60-2.67 (m, 2H) 3.34 (s, 2H) 7.415 (d, 1H) 7.74-7.76 (dd, 1H) 7.91 (s, 1H). LCMS: rt=4.49 min; m/z=320.8, 322.8 [M+H]$^+$, purity=96%.

Step 2: (1r,3R,4r,5S)-6'-bromo-4-hydroxy-3,5-dimethylspiro[cyclohexane-1,2'-inden]-1'(3'H)-one

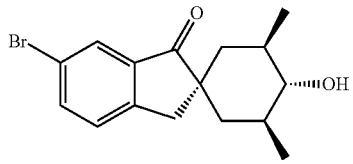 [SMILES: CO[C@H]1[C@H](C)C[C@@]2(Cc3ccc(Br)cc3C2=O)C[C@@H]1C]

A suspension of FeCl₃ (4.1 g) in toluene (41 mL) was cooled to 0° C., treated with a solution of 6'-bromo-2,6-dimethyl-spiro[cyclohexane-4,2'-indane]-1,1'-dione (8.0 g) in THF (30 mL), stirred for 5 min at 0° C., cooled to −10° C., dropwise treated with a solution of t-BuNH₂-BH₃ complex (2.38 g) in THF (11 mL) and stirred for 30 min. The mixture was quenched with 6M aq. HCl solution (8.0 mL) at 0° C., stirred for 30 min and allowed to warm to r.t. for 1 h. The mixture was concentrated and treated with toluene (40 mL). The aqueous layer was separated and the organic phase washed with water (3×25 mL). The organic phase was concentrated to half volume, heated to 110° C. to obtain a solution and cooled to 0° C. over 1 h. The resulting solids were filtered, washed with cold (0° C.) toluene (10 mL) and dried under vacuum to give title compound (6.2 g). ¹H NMR (400 MHz, CDCl₃) d ppm 1.06 (d, 6H) 1.39-1.48 (m, 2H) 1.54-1.62 (m, 4H) 1.68 (d, 1H) 2.89-2.97 (m, 1H), 3.02 (s, 2H) 7.34 (d, 1H) 7.68-7.71 (dd, 1H) 7.88 (d, 1H). HPLC: rt=4.025 min, purity: 91.3%.

Step 3: (3S,5R)-6'-bromo-4-methoxy-3,5-dimethyl-spiro[cyclohexane-1,2'-indane]-1'-one

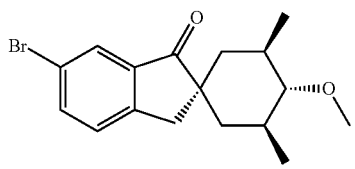

Under N₂ at 0° C., NaH (750 mg) was added to a solution of 6'-bromo-4-hydroxy-3,5-dimethyl-spiro[cyclohexane-1,2'-indane]-1'-one (3.0 g) in DMF (30 mL). The mixture was stirred for 15 min, dropwise treated with methyl iodide (1.16 mL), stirred for 10 min, warmed to r.t. and stirred for 1.5 h. The mixture was quenched with water (100 mL) at 0° C., stirred at 0° C. for 30 min, and then allowed to warm to r.t. for 1 h and extracted with EtOAc (3×50 mL). The combined organic layers were washed with water (2×50 mL), dried (Na₂SO₄) and evaporated to afford crude material (4.1 g). The solids were purified by column chromatography on a pre-packed silica gel cartridge (40 g) eluting with 0 to 20% EtOAc in hexanes, yielding title compound (2.6 g). ¹H NMR (400 MHz, CDCl₃) 1.04 (6H, d), 1.37-1.41 (2H, m), 1.52-1.59 (2H, t), 1.64-1.72 (2H, m), 2.44-2.49 (1H, t), 2.99 (2H, s), 3.49 (3H, s), 7.33 (1H, d), 7.67-7.70 (1H, dd), 7.87 (1H, d). HPLC: rt=5.027 min, purity=96.2%.

Compound (o): (1r,3R,4r,5S)-6'-bromo-4-methoxy-3,5-dimethyl-3'H,5"H-dispiro[cyclohexane-1,2'-indene-1',4"-oxazol]-5",5"-d₂-2"-amine

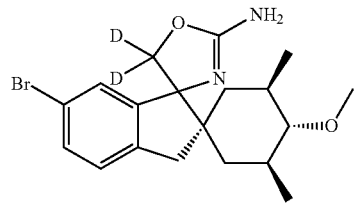

Step 1: (3S,5R)-6'-bromo-1'-(dideuteriomethylene)-4-methoxy-3,5-dimethyl-spiro[cyclohexane-1,2'-indane]

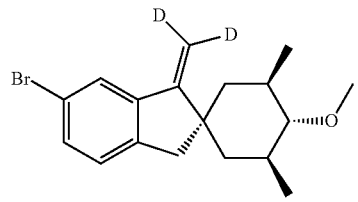 [SMILES: [2H]C([2H])=C1c2cc(Br)ccc2C[C@@]12C[C@@H](C)[C@H](OC)[C@@H](C)C2]

A suspension of triphenyl(trideuteriomethyl)phosphonium iodide (5.0 g) in THF (250 mL) was treated with a solution of n-BuLi (5.0 mL, 2.5 M in hexane) at −30° C. and stirred for 45 min at −30° C. The mixture was dropwise treated with a solution of (3S,5R)-6'-bromo-4-methoxy-3,5-dimethyl-spiro[cyclohexane-1,2'-indane]-1'-one (2.6 g) in THF (30 mL) at −30° C. over 30 min, stirred for 30 min, allowed to warm up to r.t. and stirred for 16 h.

The mixture was concentrated and the resulting brown residue was stirred in Et₂O (250 mL) for 2 h (yellow precipitate formed). The suspension was filtered to remove the yellow precipitate, washed with Et₂O (2×100 mL) and the filtrate concentrated to dryness (4.2 g). The residue was purified by column chromatography on pre-packed silica gel cartridge (120 g) eluting with 100% hexanes to 5% EtOAc in hexane, yielding title compound (2.4 g). The material was re-purified by column chromatography on pre-packed silica gel cartridge (40 g) eluting with 100% hexanes to 5% EtOAc in hexane, yielding (1.84 g). ¹H NMR (400 MHz, CDCl₃) 1.01 (6H, d), 1.31-1.34 (2H, t), 1.55-1.58 (2H, m), 1.69-1.76 (2H, m), 2.42-2.47 (1H, t), 2.85 (2H, s), 3.48 (3H, s) 7.08 (1H, d), 7.31-7.33 (1H, dd), 7.58 (1H, s). HPLC: rt=4.114 min, m/z=336.9, 338.9 [M+H]⁺, purity=96.9%.

Step 2: (1r,3R,4r,5S)-6'-bromo-4-methoxy-3,5-dimethyl-3'H,5"H-dispiro[cyclohexane-1,2'-indene-1',4"-oxazol]-5",5"-d₂-2"-amine

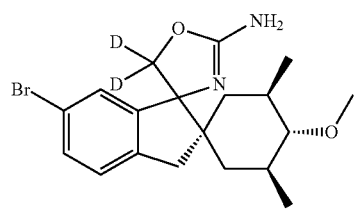

To a stirred solution of (3S,5R)-6'-bromo-1'-(dideuteriomethylene)-4-methoxy-3,5-dimethyl-spiro[cyclohexane-1,2'-indane] (234 mg, 0.69 mmol) in ACN (2.5 mL) and THF (2.5 mL) at r.t. was added isocyanatosilver (312 mg, 2.08 mmol) followed by iodine (264 mg, 1.04 mmol). The brown mixture was stirred at r.t. for 4 h. The resulting yellow suspension was filtered through Celite and rinsed with ACN and THF. The solvent was removed under reduced pressure and the residue dissolved in THF (5 mL). Aqueous $NH_3$ (2 mL) was added and the resulting mixture was stirred at r.t. for 67 h. The solvents were evaporated, the residue dissolved in EtOAc and washed with sat. $NaHCO_3$, dried ($Na_2SO_4$), filtered and concentrated to leave a cream solid (163 mg). $^1$H NMR (400 MHz, $CD_3OD$) δ ppm 0.98 (3H, d), 1.00 (3H, d), 1.20-1.30 (2H, m), 1.38-1.52 (2H, m), 1.57-1.75 (2H, m), 2.38 (1H, t), 2.79 (1H, d), 2.87 (1H, d), 3.44 (3H, s), 7.12 (1H, d) and 7.31-7.36 (2H, m). LCMS: rt=2.98 min, m/z=395/7 $[M+H]^+$.

Compound (p): (1R,3R,4R,5S)-6'-bromo-4-methoxy-3,5-dimethyl-3'H,5"H-dispiro[cyclohexane-1,2'-indene-1',4"-oxazol]-2"-amine

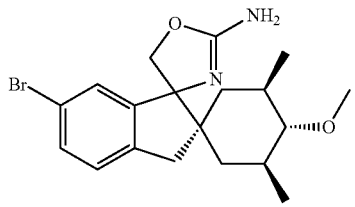

Step 1: (1r,3R,4r,5S)-6'-bromo-4-methoxy-3,5-dimethyl-1'-methylene-1',3'-dihydrospiro[cyclohexane-1,2'-indene]

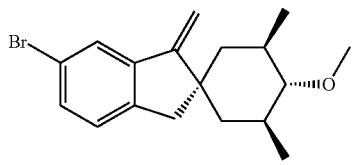

A suspension of triphenyl-methyl-phosphonium iodide (2.2 g) in THF (100 mL) was treated with a solution of n-BuLi (2.5 mL, 2.5 M in hexane) at −30° C. and stirred for 45 min, dropwise treated with a solution of (1r,3R,4r,5S)-6'-bromo-4-methoxy-3,5-dimethyl-spiro[cyclohexane-1,2'-indane]-1'-one (1.2 g) in THF (15 mL) and stirred for 30 min, allowed to warm up to r.t. and stirred for 72 h. The mixture was concentrated and resulting brown residue was stirred in $Et_2O$ (250 mL) for 2 h (yellow precipitate formed). The suspension was filtered to remove the yellow precipitate, washed with $Et_2O$ (2×100 mL) and the filtrate was concentrated to dryness. The resulting residue was purified by column chromatography on pre-packed silica gel cartridge (25 g) eluting with 100% hexanes to 5% EtOAc in hexane, yielding title compound (0.91 g). $^1$H NMR (400 MHz, $CDCl_3$) 1.02 (6H, d), 1.27-1.34 (2H, t), 1.54-1.59 (2H, m), 1.69-1.77 (2H, m), 2.42-2.47 (1H, t), 2.85 (2H, s), 3.47 (3H, s), 4.95 (1H, s), 5.45 (1H, s), 7.09 (1H, d), 7.31-7.33 (1H, d d), 7.57-7.58 (1H, m). LCMS: m/z=334.9, 336.9 $[M+H]^+$.

Step 2: (1r,3R,4r,5S)-6'-bromo-4-methoxy-3,5-dimethyl-3'H,5"H-dispiro[cyclohexane-1,2'-indene-1',4"-oxazol]-2"-amine

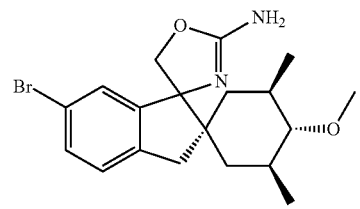

At r.t., to a stirred suspension of (3S,5R)-6'-bromo-4-methoxy-3,5-dimethyl-1'-methylene-spiro[cyclohexane-1,2'-indane] (0.91 g) in THF (10 mL) and ACN (10 mL) was treated with isocyanatosilver (1.23 g) followed by a portionwise addition of iodine (1.03 g). The grey mixture was stirred at r.t. for 16 h, diluted with EtOAc (30 mL) and filtered through Celite. The filtrate was concentrated to leave a yellow solid, which was dissolved in THF (40 mL), treated with sat. aq. ammonium hydroxide (25 mL) and stirred for 24 h at r.t. The solvents were evaporated, the residue dissolved in EtOAc and washed with sat. $NaHCO_3$, dried ($Na_2SO_4$) and evaporated. The resulting solids were purified by column chromatography on pre-packed silica gel cartridge (25 g) eluting with 100% DCM to 5% MeOH in DCM to give the title compound (800 mg). $^1$H NMR (400 MHz, $CDCl_3$): 0.97-1.0 (6H, m), 1.21-1.25 (1H, t), 1.38-1.43 (1H, t d), 1.49-1.55 (1H, t d), 1.60-1.69 (2H, m), 2.29-2.34 (1H, t), 2.69 (1H, d), 2.88 (1H, d), 3.44 (3H, s), 4.11 (1H, d), 4.47 (1H, d), 7.06 (1H, d), 7.3-7.32 (1H, d d), 7.34-7.35 (1H, m). LCMS: m/z=392.9, 394.9 $[M+H]^+$.

Compounds (q) and (r): (1R,3R,4R)-6'-bromo-4-((tert-butyldiphenylsilyl)oxy)-3-methyl-3'H,5"H-dispiro[cyclohexane-1,2'-indene-1',4"-oxazol]-5",5"-$d_2$-2"-amine (q) and (1S,3S,4S)-6'-bromo-4-((tert-butyldiphenylsilyl)oxy)-3-methyl-3'H,5"H-dispiro[cyclohexane-1,2'-indene-1',4"-oxazol]-5",5"-$d_2$-2"-amine (r)

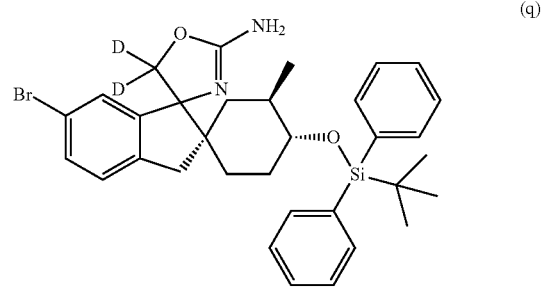

-continued

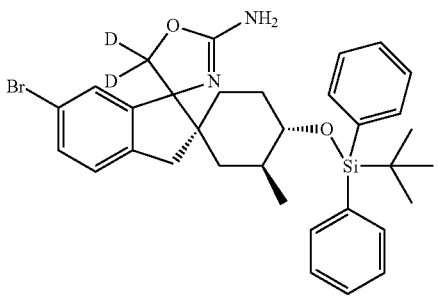

Step 1: (1R,3R,4R)-6'-bromo-4-[tert-butyl(diphenyls)silyl]oxy-3-methyl-spiro[cyclohexane-1,2'-indane]-1'-one and (1S,3S,4S)-6'-bromo-4-[tert-butyl(diphenyl)silyl]oxy-3-methyl-spiro[cyclohexane-1,2'-indane]-1'-one

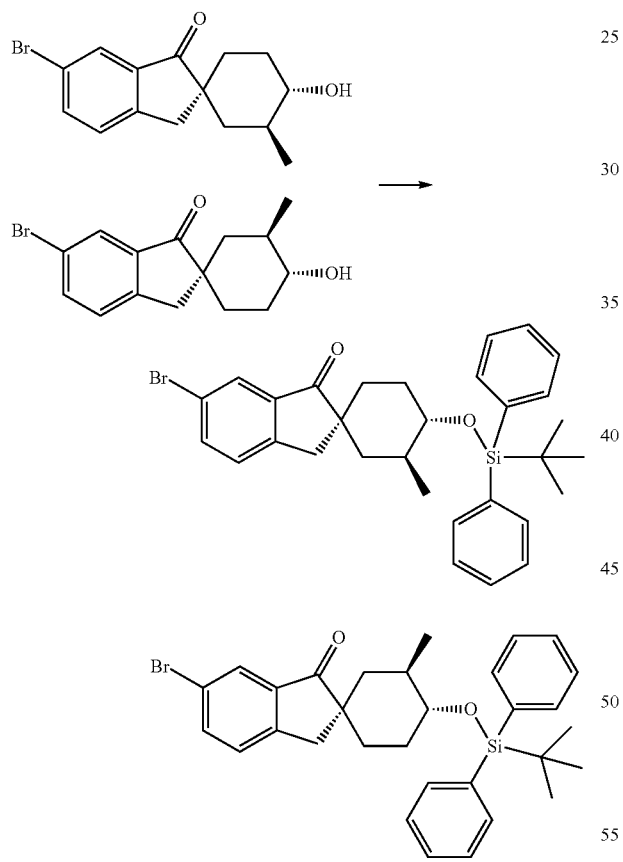

A mixture of (1S,3S,4S)-6'-bromo-4-hydroxy-3-methyl-spiro[cyclohexane-1,2'-indane]-1'-one; (1R,3R,4R)-6'-bromo-4-hydroxy-3-methyl-spiro[cyclohexane-1,2'-indane]-1'-one (2.90 g, 9.38 mmol) and imidazole (2.55 g, 37.5 mmol) in DMF (50 mL) under $N_2$ at r.t. was treated with tert-butyldiphenylchlorosilane (5.37 mL, 20.6 mmol), stirred for 18 h, diluted with EtOAc (600 mL) and washed with water (3×500 mL). The organic phase was dried ($Na_2SO_4$) and concentrated in vacuo to give a pale yellow oil (9.8 g). Purification by column chromatography on silica gel, eluting with 1-3% EtOAc in petroleum ether gave the desired product as a clear oil (3.50 g). $^1$H NMR (400 MHz, CDCl$_3$) δ ppm 0.90 (d, 3H), 0.99 (s, 9H), 1.12-1.52 (m, 5H), 1.56-1.72 (m, 2H), 2.84-2.98 (m, 2H), 3.22-3.32 (m, 1H), 7.24 (d, 1H), 7.27-7.39 (m, 6H), 7.58-7.68 (m, 5H), 7.75 (d, 1H). LCMS: r.t.=7.46 min, m/z=549 [M+H]$^+$.

Step 2: [(1S,2S,4S)-6'-bromo-1'-(dideuteriomethylene)-2-methyl-spiro[cyclohexane-4,2'-indane]-1-yl]oxy-tert-butyl-diphenyl-silane and [(1R,2R,4R)-6'-bromo-1'-(dideuteriomethylene)-2-methyl-spiro[cyclohexane-4,2'-indane]-1-yl]oxy-tert-butyl-diphenyl-silane

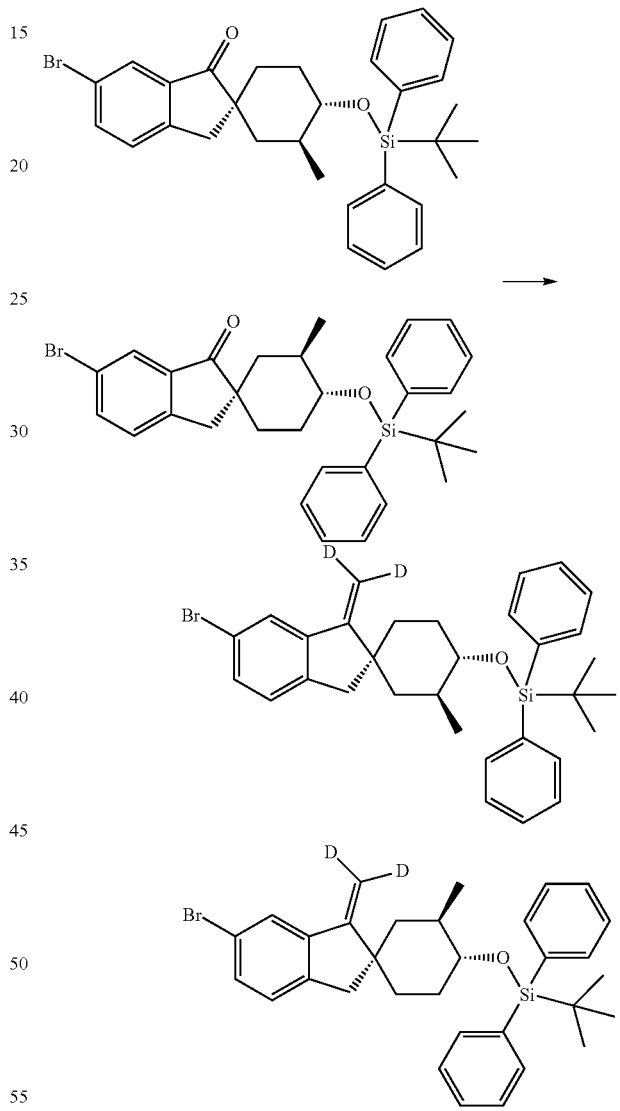

A suspension of triphenyl(trideuteriomethyl)phosphonium iodide (3.90 g, 9.59 mmol) in THF (50 mL) at −30° C. was treated dropwise with n-butyllithium (2.5M in hexane, 3.83 mL, 9.59 mmol), stirred for 45 min whilst maintaining the internal temperature at −30° C. A solution of (1R,3R,4R)-6'-bromo-4-[tert-butyl(diphenyl)silyl]oxy-3-methyl-spiro[cyclohexane-1,2'-indane]-1'-one; (1S,3S,4S)-6'-bromo-4-[tert-butyl(diphenyl)silyl]oxy-3-methyl-spiro[cyclohexane-1,2'-indane]-1'-one (3.50 g, 6.39 mmol) in THF (20 mL) was added dropwise to the orange solution at −30° C. and upon completion, the mixture was allowed to stir at r.t for 4 h. The mixture was concentrated and the resulting brown residue absorbed on to silica gel and subjected to column chromatography on silica gel, eluting with 5-20% DCM in hexane to afford the desired product a clear oil (2.89 g). ¹H NMR (400 MHz, CDCl₃) δ ppm 0.97 (d, 3H), 1.06 (s, 9H), 1.10-1.44 (m, 5H), 1.44-1.58 (m, 2H), 2.76-2.90 (m, 2H), 3.27-3.37 (m, 1H), 4.82 (2%), 5.36 (2%), 7.07 (d, 1H), 7.29 (dd, 1H), 7.34-7.49 (m, 6H), 7.52 (d, 1H), 7.66-7.76 (m, 4H). LCMS: rt=5.79 min.

Step 3: (1R,3R,4R)-6'-bromo-4-((tert-butyldiphenylsilyl)oxy)-3-methyl-3'H,5"H-dispiro[cyclohexane-1, 2'-indene-1',4"-oxazol]-5",5"-d₂-2"-amine and (1S, 3S,4S)-6'-bromo-4-((tert-butyldiphenylsilyl)oxy)-3-methyl-3'H,5"H-dispiro[cyclohexane-1,2'-indene-1', 4"-oxazol]-5",5"-d₂-2"-amine

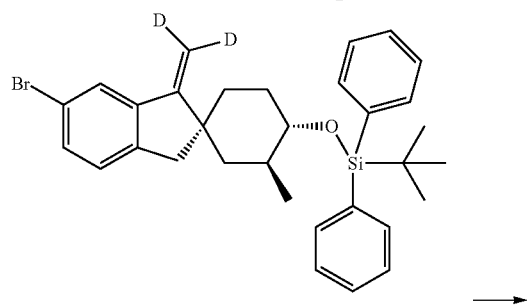

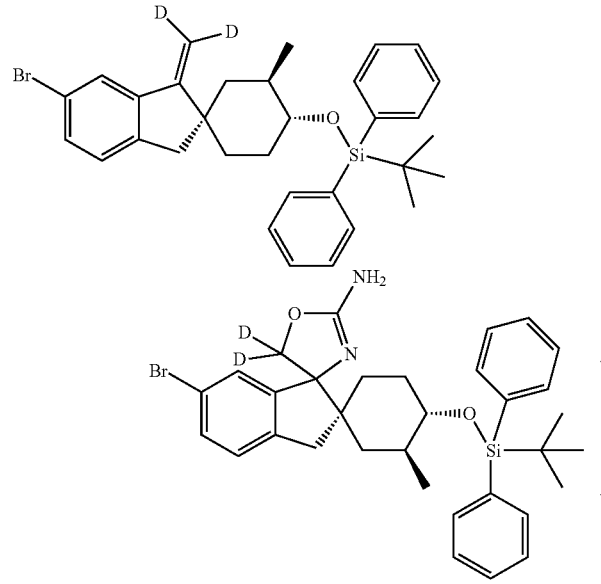

A solution of [(1S,2S,4S)-6'-bromo-1'-(dideuteriomethylene)-2-methyl-spiro[cyclohexane-4,2'-indane]-1-yl]oxy-tert-butyl-diphenyl-silane; [(1R,2R,4R)-6'-bromo-1'-(dideuteriomethylene)-2-methyl-spiro[cyclohexane-4,2'-indane]-1-yl]oxy-tert-butyl-diphenyl-silane (2.80 g, 5.11 mmol) in THF (40 mL) and ACN (40 mL) at r.t. was treated with isocyanatosilver (2.30 g, 15.3 mmol) followed by a portion-wise addition of iodine (1.95 g, 7.67 mmol). The grey mixture was stirred at for 4 h, filtered through Celite and concentrated to leave a yellow residue which was dissolved in THF (20 mL) and sat. aq. ammonium hydroxide (4 mL). The mixture was stirred at r.t. for 18 h concentrated in vacuo and the residue was partitioned between EtOAc (200 mL) and water (200 mL). The aqueous layer was separated and further extracted with EtOAc (200 mL). The combined organic extracts were dried (Na₂SO₄) and evaporated to leave a pale yellow foam (3.8 g). The residue dissolved in Et₂O (250 mL) and washed with sat. NaHCO₃ (2×100 mL). The organic phase was dried (Na₂SO₄) and evaporated to give the desired product as a foam/solid (2.95 g). ¹H NMR (400 MHz, CD₃OD) δ ppm 0.90-0.99 (3H, m), 1.06 (9H, s), 1.12-1.52 (5H, m), 1.52-1.76 (2H, m), 2.69 (1H, dd), 2.86 (1H, dd), 3.13-3.26 (1H, m), 4.30 (2H, br) 7.01-7.06 (1H, m), 7.27-7.31 (2H, m), 7.33-7.46 (6H, m), 7.65-7.73 (4H, m). LCMS: rt=5.12 min, m/z=605/608 [M+H]⁺.

Compounds (s) and (t): (1S,1'R,3S,4S)-6'-bromo-4-(methoxy-d3)-3-methyl-3'H,5"H-dispiro[cyclohexane-1,2'-indene-1',4"-oxazol]-5",5"-d2-2"-amine (t); (1R,1'R,3R,4R)-6'-bromo-4-(methoxy-d3)-3-methyl-3'H,5"H-dispiro[cyclohexane-1,2'-indene-1', 4"-oxazol]-5",5"-d₂-2"-amine (s)

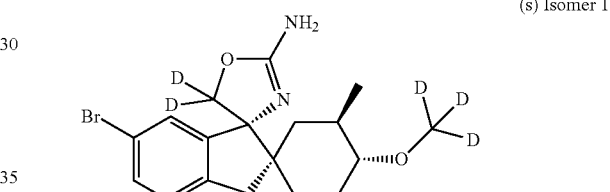

(s) Isomer 1

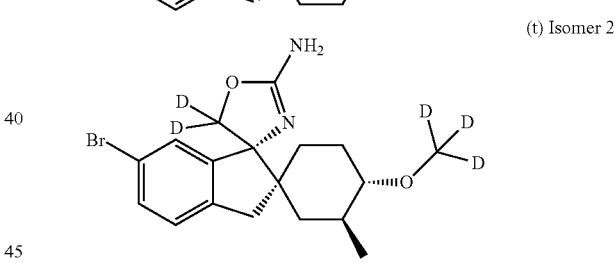

(t) Isomer 2

Step 1: (1S,3S,4S)-6'-bromo-3-methyl-4-(trideuteriomethoxy)spiro[cyclohexane-1,2'-indane]-1'-one; (1R,3R,4R)-6'-bromo-3-methyl-4-(trideuteriomethoxy)spiro[cyclohexane-1,2'-indane]-1'-one

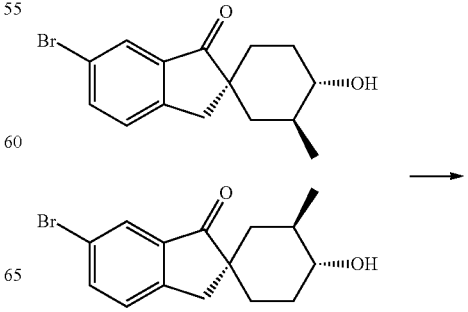

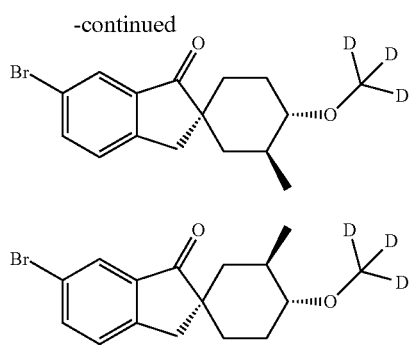

A solution of (1R,3R,4R)-6'-bromo-4-hydroxy-3-methyl-spiro[cyclohexane-1,2'-indane]-1'-one; (5-bromo-2-methylphenyl)-[(1S,3S,4S)-4-hydroxy-1,3-dimethyl-cyclohexyl]methanone (5.0 g, 16 mmol) in DMF (60 mL) under $N_2$ at 0° C. was treated portionwise with NaH (60% dispersion in mineral oil, 0.78 g, 32.3 mmol), stirred for 1 h, treated with iodomethane-$d_3$ (2.82 mL, 45.3 mmol), allowed to warm up to r.t. and stirred for 12 h. The mixture was suspended between water (500 mL) and EtOAc (600 mL). The organic phase was separated, washed with water (2×250 mL), dried ($Na_2SO_4$) and concentrated to afford a yellow oil (5.80 g). The crude material was subjected to column chromatography on silica gel, eluting with 5-20% EtOAc in hexane to afford the desired product as an off-white solid (3.88 g). $^1$H NMR (400 MHz, CDCl$_3$) δ ppm 0.94 (3H, d), 1.15-1.60 (5H, m), 1.69 (1H, td), 2.10-2.19 (1H, m), 2.74 (1H, td), 2.92 (2H, s), 7.27 (1H, d), 7.62 (1H, dd), 7.80 (1H, d). LCMS: rt=3.56 min, m/z=326/328 [M+H]$^+$.

Step 2: (1S,3S,4S)-6'-bromo-1'-(dideuteriomethylene)-3-methyl-4-(trideuteriomethoxy)spiro[cyclohexane-1,2'-indane]; (1R,3R,4R)-6'-bromo-1'-(dideuteriomethylene)-3-methyl-4-(trideuteriomethoxy)spiro[cyclohexane-1,2'-indane]

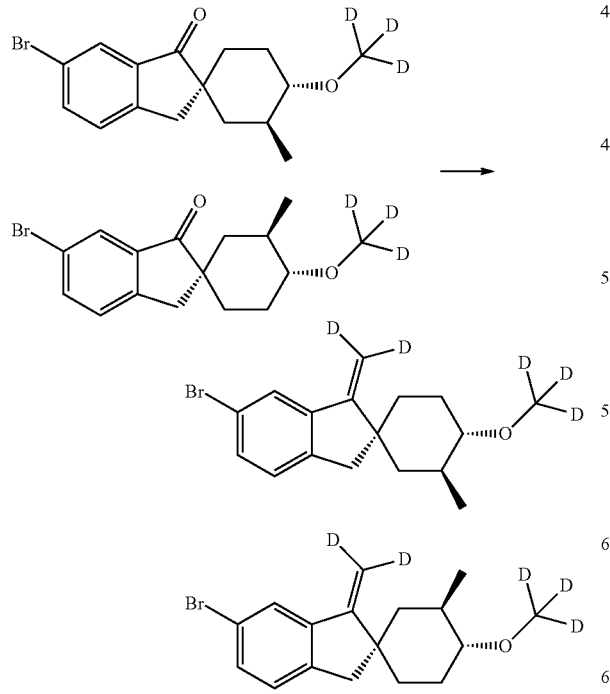

Under $N_2$ at −30° C., a suspension of triphenyl(trideuteriomethyl)phosphonium iodide (7.12 g, 17.5 mmol) in THF (80 mL) was added n-butyllithium (2.5M in hexane, 6.99 mL, 17.4 mmol), stirred for 45 min and treated with a solution of (1S,3S,4S)-6'-bromo-3-methyl-4-(trideuteriomethoxy)spiro[cyclohexane-1,2'-indane]-1'-one; (1R,3R,4R)-6'-bromo-3-methyl-4-(trideuteriomethoxy)spiro[cyclohexane-1,2'-indane]-1'-one (3.80 g, 11.6 mmol) in THF (20 mL). The mixture was allowed to stir at r.t. for 3 h and concentrated in vacuo to afford a brown solid. Purification of the crude residue by column chromatography on silica gel, eluting with 10-60% DCM in hexane gave the desired product as a pale yellow oil (3.51 g). $^1$H NMR (400 MHz, CDCl$_3$) δ ppm 0.92 (3H, d), 1.13-1.66 (6H, m), 1.99-2.09 (1H, m), 2.71 (1H, td), 2.77 (2H, s), 4.86 (3%), 5.37 (3%), 7.01 (1H, d), 7.24 (1H, dd), 7.50 (1H, d). LCMS: rt=4.15 min, purity=97%+3% DH/HH product.

Step 3: (1S,1'R,3S,4S)-6'-bromo-4-(methoxy-d3)-3-methyl-3'H,5"H-dispiro[cyclohexane-1,2'-indene-1', 4"-oxazol]-5",5"-$d_2$-2"-amine; (1R,1'R,3R,4R)-6'-bromo-4-(methoxy-d3)-3-methyl-3'H,5"H-dispiro[cyclohexane-1,2'-indene-1',4"-oxazol]-5",5"-$d_2$-2"-amine

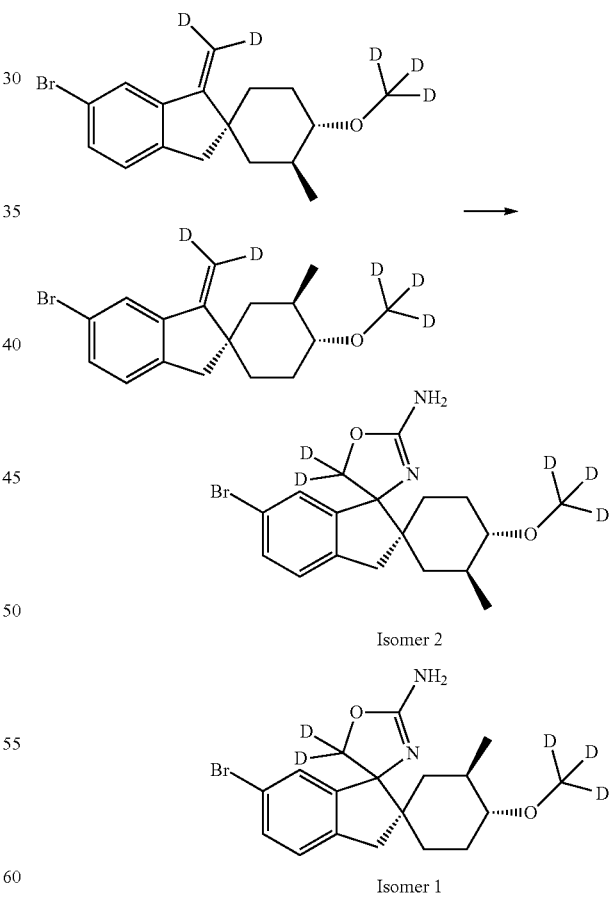

A solution of (1S,3S,4S)-6'-bromo-1'-(dideuteriomethylene)-3-methyl-4-(trideuteriomethoxy)spiro[cyclohexane-1,2'-indane]; (1R,3R,4R)-6'-bromo-1'-(dideuteriomethylene)-3-methyl-4-(trideuteriomethoxy)spiro[cyclohexane-1,2'-indane] (3.51 g, 10.7 mmol) in THF (40 mL) and ACN (40 mL) at r.t. was treated with isocyanatosilver (4.84 g, 32.3 mmol) followed by portionwise addition of iodine (4.1 g, 16 mmol). The grey mixture was stirred at r.t. for 4 h, filtered through Celite, washed with THF (50 mL) and concentrated to leave a yellow solid. This residue was dissolved in THF (50 mL) and sat. aq. ammonium hydroxide (10 mL), stirred at r.t. for 18 h and concentrated to give a beige foam (5.3 g). This material was partitioned between EtOAc (500 mL) and aq. sat. NaHCO$_3$ (500 mL). The aqueous layer was separated and further extracted with EtOAc (200 mL) and the combined organic extracts were dried (Na$_2$SO$_4$) and evaporated to leave a beige solid (4.2 g). The crude material was dissolved to 45 mg/mL in MeOH and purified by SFC. Each injection was 0.4 mL (18 mg) using a Lux C4 column (250 mm×20 mm, 5 um). The eluent was MeOH/CO$_2$ 40% (DEA was added as a modifier). The flow rate was 50 mL/min. Peak 1 a mixture of isomer 1 & 2, peak 2 isomer 3 and peak 3 isomer 4. Isomer 3 required a second pass on this method to reach the desired enantio-purity. Peak 1 which containing isomer 1 and 2 was dissolved 50 mg/mL in MeOH/IPA and purified by HPLC. The column used was a Lux C1 (250 mm×20 mm, 5 um). The eluent was heptanes/IPA (70:30) (DEA was added as a modifier). The flow rate was 21 mL/min.

Isomer 1: solids (982 mg). $^1$H NMR (400 MHz, DMSO-d$_6$) δ ppm 0.88 (3H, m), 1.06-1.24 (3H, m), 1.28-1.52 (3H, m), 1.96 (1H, m), 2.55-2.65 (1H, m), 2.71 (1H, s), 5.94 (2H, br, s), 7.11-7.17 (1H, m), 7.20 (1H, s), 7.27-7.34 (1H, m). LCMS: rt=broad peak 3.36 min, m/z=384/386 [M+H]$^+$, purity=98% (ee=100%).

Isomer 2: solids (914 mg). $^1$H NMR (400 MHz, DMSO-d$_6$) δ ppm 0.80 (4H, m), 0.99-1.12 (1H, m), 1.23 (1H, dd), 1.32-1.49 (3H, m), 1.86-1.96 (1H, m), 2.54 (1H, td), 2.66 (2H, s), 5.88 (2H, br, s), 7.07 (1H, d), 7.13 (1H, d), 7.24 (1H, dd). LCMS: rt=broad peak at 3.25 min, m/z=384/386 [M+H]$^+$, purity=100% (ee=100%).

Isomer 3: solids (920 mg). $^1$H NMR (400 MHz, DMSO-d$_6$) δ ppm 0.80 (4H, m), 0.99-1.12 (1H, m), 1.23 (1H, dd), 1.32-1.49 (3H, m), 1.86-1.95 (1H, m), 2.54 (1H, td), 2.65 (2H, s), 5.88 (2H, br, s), 7.06 (1H, d), 7.13 (1H, d), 7.24 (1H, dd). LCMS: rt=broad peak at 3.27 min, m/z=384/386 [M+H]$^+$, purity=97% (ee=98%).

Isomer 4: solids (1.07 g). $^1$H NMR (400 MHz, DMSO-d$_6$) δ ppm 0.88 (3H, m), 1.06-1.24 (3H, m), 1.30-1.52 (3H, m), 1.94-2.02 (1H, m), 2.62 (1H, td), 2.72 (1H, s), 5.94 (2H, br. s), 7.13 (1H, d), 7.20 (1H, d), 7.30 (1H, dd). LCMS: rt=broad peak 3.36 min, m/z=384/386 [M+H]$^+$, purity=100% (ee=96%).

Compound (u): (1r,4r)-6'-bromo-4-methoxy-5'',6''-dihydro-3'H-dispiro[cyclohexane-1,2'-indene-1',4''-[1,3]oxazin]-6'',6''-d$_2$-2''-amine

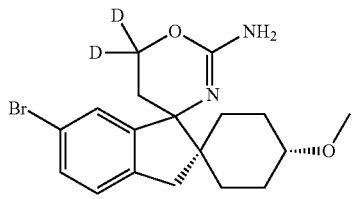

Step 1: N-((1r,4r)-5'-bromo-4-methoxyspiro[cyclohexane-1,2'-inden]-3'(1H)-ylidene)-2-methylpropane-2-sulfinamide

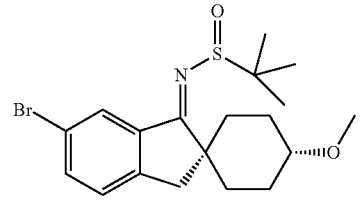 [SMILES: CO[C@H]1CC[C@]2(CC1)Cc1ccc(Br)cc1/C2=N/S(=O)C(C)(C)C]

Titanium (IV) ethoxide (8.30 g, 36.4 mmol) was added to a solution of 2-methylpropane-2-sulfinamide (2.90 g, 23.9 mmol) and (1r,4r)-6'-bromo-4-methoxy-spiro[cyclohexane-1,2'-indane]-1'-one (5.30 g, 17.1 mmol) in THF (100 mL) under N$_2$ at r.t. The mixture was heated at reflux for 12 h, treated with additional titanium ethoxide (5.50 g) and 2-methylpropane-2-sulfinamide (1.50 g), stirred for 48 h at reflux temperature, cooled to r.t., treated with TBME (200 mL) and sat. NaHCO$_3$ (~100 mL). The resulting precipitates were removed by filtration through Celite. The filtrate was dried (Na$_2$SO$_4$) and evaporated. Purification on silica (500 g, eluting petrol+EtOAc 10-50%) gave the desired product as a yellow solid (5.40 g). $^1$H NMR (400 MHz, CDCl$_3$) δ ppm 0.8 (1H, m), 1.2-1.8 (14H, m), 2.1 (2H, m), 2.95 (2H, br. s), 3.26 (1H, m), 3.40 (3H, s), 7.2-7.3 (2H, s), 7.58 (1H, dd).

Step 2: Ethyl 2-((1r,4r)-6'-bromo-1'-((tert-butylsulfinyl)amino)-4-methoxy-1',3'-dihydrospiro[cyclohexane-1,2'-inden]-1'-yl)acetate

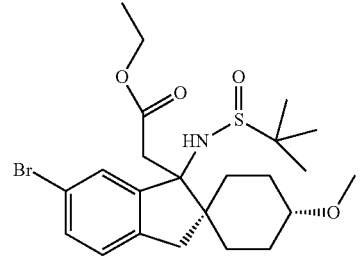

Under N$_2$ at −78° C., a solution of diisopropylamine (4.0 mL, 28 mmol) in THF (100 mL) was treated with nBuLi (2.5M hexanes, 11.5 mL, 28.7 mmol), warmed to stir at 0° C. for 30 min, cooled to −78° C., treated with EtOAc (3.0 mL, 30 mmol), stirred at −78° C. for 30 min, treated with a solution of N-((1r,4r)-5'-bromo-4-methoxyspiro[cyclohexane-1,2'-inden]-3'(1'H)-ylidene)-2-methylpropane-2-sulfinamide (5.6 g, 13.58 mmol) in THF (50 mL) and stirred at −78° C. for 1 h. The mixture was allowed to warm to r.t. and poured onto sat. aq. NaHCO$_3$ (300 mL) and extracted with TBME (300 mL). The organic layer was washed with brine, dried (Na$_2$SO$_4$) and evaporated to give a yellow oil. Purification on silica (500 g, eluting petrol+EtOAc 25, 35, 45, 55, 80, 100%) gave the desired product (1.7 g). $^1$H NMR (400 MHz, CDCl$_3$) δ ppm 0.8-1.8 (20H, m), 2.0 (2H, br. s), 2.7-2.9 (2H, m), 3.07 (1H, m), 3.33 (3H, s), 4.1 (2H, m), 7.08 (1H, d), 7.37 (1H, dd), 7.50 (1H, d), NH not observed. LCMS: rt=3.42 min, m/z=522/524 [M+Na]$^+$.

Step 3: N-((1r,4r)-6'-bromo-1'-(2-hydroxyethyl-2,2-d₂)-4-methoxy-1',3'-dihydrospiro[cyclohexane-1,2'-inden]-1'-yl)-2-methylpropane-2-sulfinamide

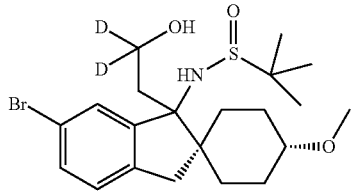

Lithium aluminium deuteride (1M THF) (10 mL, 10 mmol) was added to an ice-cooled solution of ethyl 2-((1r,4r)-6'-bromo-1'-((tert-butylsulfinyl)amino)-4-methoxy-1',3'-dihydrospiro[cyclohexane-1,2'-inden]-1'-yl)acetate (4.20 g, 8.39 mmol) in THF (80 mL) under N₂. The mixture was stirred for 1 h, treated with water (300 uL), 1M NaOH aq (300 uL), and water (600 uL). The mixture was diluted with EtOAc, layers were separated, the organic phase was dried (Na₂SO₄) and evaporated to give a viscous oil. Purification on silica (40 g cartridge, eluting petrol+EtOAc 50, 60, 70, 100%, then EtOAc+5% MeOH) gave the desired product (2.25 g). LCMS: rt=3.0 min, m/z=460/462 [M+H]⁺ and 482/484 [M+Na]⁺.

Step 4: 2-((1r,4r)-1'-amino-6'-bromo-4-methoxy-1',3'-dihydrospiro[cyclohexane-1,2'-inden]-1'-yl)ethan-1,1-d₂-1-ol hydrochloride

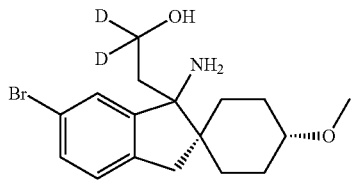

At r.t., a mixture of N-((1r,4r)-6'-bromo-1'-(2-hydroxyethyl-2,2-d₂)-4-methoxy-1',3'-dihydrospiro[cyclohexane-1,2'-inden]-1'-yl)-2-methylpropane-2-sulfinamide (2.25 g, 4.89 mmol) in TBME (30 mL) was treated with HCl (4M in dioxane, 5 mL, 20 mmol). After 10 min, the formed precipitate was collected by filtration, washed with TBME (2×30 mL) and dried to give a pink solid (1.5 g). ¹H NMR (400 MHz, CD₃OD, 35° C.) δ ppm 1.3-1.5 (4H, m), 1.7-1.85 (2H, m), 1.90 (1H, d), 2.0-2.2 (3H, m), 2.80 (1H, d), 3.17 (1H, d), 3.20 (1H, m), 3.36 (3H, s), 7.27 (1H, d), 7.52 (1H, dd), 7.63 (1H, d), 4H not observed. LCMS: rt=2.45 min, m/z=339/341 [M+H—NH₃]⁺.

Step 5: (1r,4r)-6'-Bromo-4-methoxy-5",6"-dihydro-3'H-dispiro[cyclohexane-1,2'-indene-1',4"-[1,3]oxazin]-6",6"-d₂-2"-amine

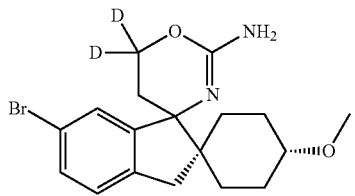

2-((1r,4r)-1'-amino-6'-bromo-4-methoxy-1',3'-dihydrospiro[cyclohexane-1,2'-inden]-1'-yl)ethan-1,1-d₂-1-ol hydrochloride (1.40 g, 3.56 mmol) was partitioned between EtOAc and sat. aq. NaHCO₃. The layers were separated and the organic phase washed with brine, dried (Na₂SO₄) and evaporated to give the freebase (660 mg) which was suspended in THF (25 mL). The resulting suspension was treated with NaOAc (160 mg, 1.95 mmol) and cyanogen bromide (260 mg, 2.45 mmol) and heated at 80° C. for 48 h. The mixture was poured onto sat. aq. NaHCO₃ and extracted into EtOAc. The organic phase was dried (Na₂SO₄) and evaporated. Purification on silica (20 g cartridge, eluting DCM/7M NH₃ in MeOH 0, 1, 2, 4%) gave the desired product as solids (200 mg). ¹H NMR (400 MHz, CD₃OD, 35° C.) δ ppm 1.0-2.2 (10H, m), 2.70 (1H, d), 3.0 (1H, d), 3.12 (1H, m), 3.3 (3H, s), 7.11 (1H, d), 7.20 (1H, d), 7.30 (1H, dd).

Compound (v): Mixture of (1'R,4'S)-6"-bromo-4'-methoxy-3"H,5'''H-trispiro[cyclopropane-1,3'-cyclohexane-1',2"-indene-1",4'''-oxazol]-5''',5'''-d₂-2'''-amine and (1'S,4'R)-6"-bromo-4'-methoxy-3"H,5'''H-trispiro[cyclopropane-1,3'-cyclohexane-1',2"-indene-1",4'''-oxazol]-5''',5'''-d₂-2'''-amine

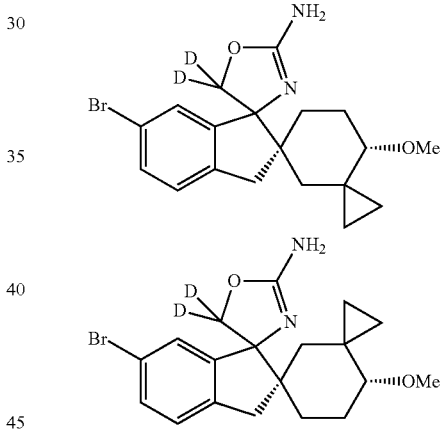

Step 1: (R)-6"-bromodispiro[cyclopropane-1,3'-cyclohexane-1',2"-indene]-1",4'(3"H)-dione; (S)-6"-bromodispiro[cyclopropane-1,3'-cyclohexane-1',2"-indene]-1",4'(3"H)-dione

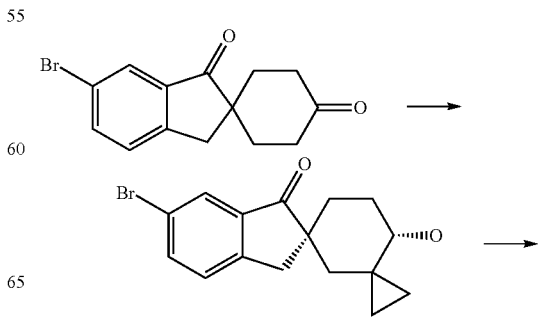

-continued

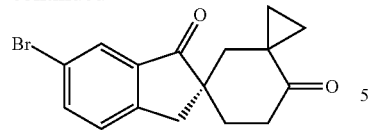

To a solution of 6'-bromospiro[cyclohexane-4,2'-indane]-1,1'-dione (19.4 g, 66.4 mmol) in tert-butanol (220 mL) was added NaI (1.99 g, 13.3 mmol) and NaH (60% in oil, 5.31 g, 132.8 mmol). The mixture was stirred at r.t. for 20 min, treated with 2-chloroethyl(dimethyl)sulfonium iodide (17.6 g, 69.7 mmol) (portionwise over 1 h). The mixture was stirred at r.t. for 12 h, treated with water (100 mL), stirred for 5 min and extracted with EtOAc (2×150 mL). The combined organic extracts were dried (Na$_2$SO$_4$) and evaporated. Purification on silica (eluting with hexane+EtOAc 0-10%) gave the desired compound (2.88 g) as a white solid. $^1$H NMR (400 MHz, CDCl$_3$) δ ppm 0.52-0.59 (1H, m), 0.71-0.76 (1H, m), 1.12-1.17 (1H, m), 1.23-1.31 (1H, m), 1.56-1.63 (1H, m), 1.79-1.87 (1H, m), 2.27-2.35 (1H, m), 2.44-2.53 (2H, m), 2.65-2.72 (1H, m), 3.20 (2H, dd), 7.35 (1H, d), 7.10 (1H, dd), 7.88 (1H, d). LCMS: rt=3.33 min, m/z=321 [M+H]$^+$.

Step 2: (1'R,4'S)-6"-bromo-4'-hydroxydispiro[cyclopropane-1,3'-cyclohexane-1',2"-inden]-1"(3"H)-one; (1'S,4'R)-6"-bromo-4'-hydroxydispiro[cyclopropane-1,3'-cyclohexane-1',2"-inden]-1"(3"H)-one

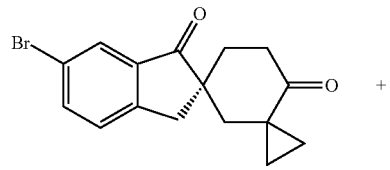

-continued

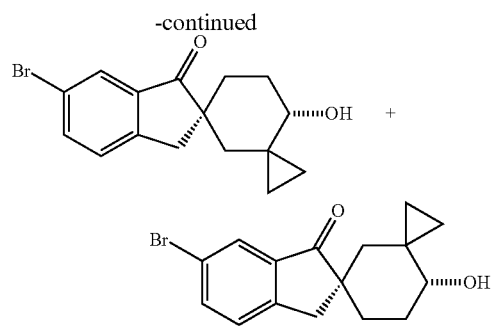

A mixture of (R)-6"-bromodispiro[cyclopropane-1,3'-cyclohexane-1',2"-indene]-1",4'(3"H)-dione; (S)-6"-bromodispiro[cyclopropane-1,3'-cyclohexane-1',2"-indene]-1",4'(3"H)-dione (2.18 g, 6.83 mmol) in THF (10 mL) and MeOH (2.5 mL) was treated with cerium(III) chloride heptahydrate (0.025 g, 0.070 mmol) at −78° C. followed by addition of NaBH$_4$ (0.13 g, 3.41 mmol). The mixture was stirred at −78° C. for 20 min, treated with sat. aq. NH$_4$Cl (100 mL) and extracted with EtOAc (3×500 mL). The organic layers were dried (Na$_2$SO$_4$) and evaporated. Purification on silica (hexane+EtOAc 0-20%) gave a yellow oil (0.88 g). $^1$H NMR (400 MHz, CDCl$_3$) δ ppm 0.046-0.093 (1H, m), 0.023-0.27 (1H, m), 0.58-0.63 (1H, m), 0.69-1.55 (5H, m), 1.75-1.83 (1H, m), 1.98-2.10 (2H, m), 2.93 (1H, d), 3.08 (1H, d), 3.71-3.75 (1H, m), 7.26 (1H, d), 7.61 (1H, d), 7.79 (1H, s).

Step 3: (1'R,4'S)-6"-bromo-4'-methoxydispiro[cyclopropane-1,3'-cyclohexane-1',2"-inden]-1"(3"H)-one; (1'S,4'R)-6"-bromo-4'-methoxydispiro[cyclopropane-1,3'-cyclohexane-1',2"-inden]-1"(3"H)-one

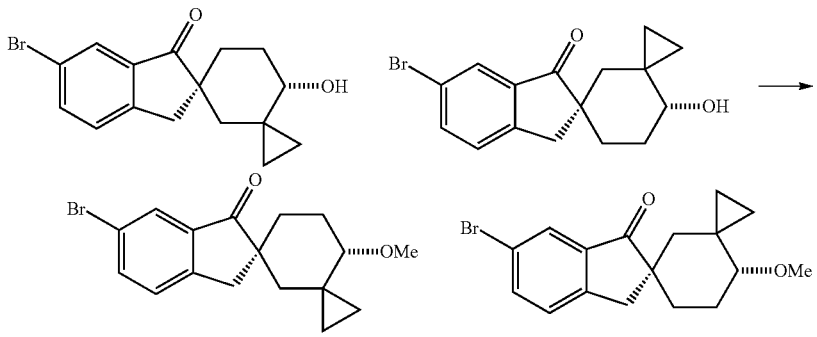

-continued

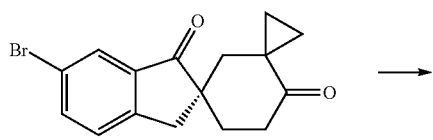

Under N$_2$ at 0° C., a solution of (1'R,4'S)-6"-bromo-4'-hydroxydispiro[cyclopropane-1,3'-cyclohexane-1',2"-inden]-1"(3"H)-one; (1'S,4'R)-6"-bromo-4'-hydroxydispiro[cyclopropane-1,3'-cyclohexane-1',2"-inden]-1"(3"H)-one (0.78 g, 2.43 mmol) in DMF (25 mL) was treated with NaH (60% dispersion in mineral oil, 0.39 g, 9.71 mmol). The mixture was stirred for 30 min, treated with iodomethane (0.60 mL, 9.71 mmol), allowed to warm up to r.t. and stirred for 2 h. The mixture was quenched with water (25 mL), extracted with EtOAc (3×100 mL), dried (Na$_2$SO$_4$) and evaporated. Purification on silica (hexane/EtOAc 5-10%) gave the desired product as a yellow oil (0.80 g). ¹H NMR (400 MHz, CDCl₃) δ ppm 0.00-0.02 (1H, m), 0.18-0.21 (1H, m), 0.55-0.60 (1H, m), 0.67-0.71 (1H, m), 0.97-1.04 (1H, m), 1.35-1.45 (1H, m), 1.50-1.57 (1H, m), 1.68-1.77 (1H, m), 1.97-2.02 (1H, m), 2.11-2.18 (1H, m), 2.91 (1H, d), 3.05 (1H, d), 3.13-3.17 (1H, m), 3.26 (3H, s), 7.24 (1H, d), 7.59 (1H, dd), 7.76 (1H, d). LCMS: rt=5.44 min, m/z=337 [M+H]⁺.

Step 4: (1'R,4'S)-6"-bromo-4'-methoxy-1"-(methylene-d₂)-1",3"-dihydrodispiro[cyclopropane-1,3'-cyclohexane-1',2"-indene]; (1'S,4'R)-6"-bromo-4'-methoxy-1"-(methylene-d₂)-1",3"-dihydrodispiro[cyclopropane-1,3'-cyclohexane-1',2"-indene]

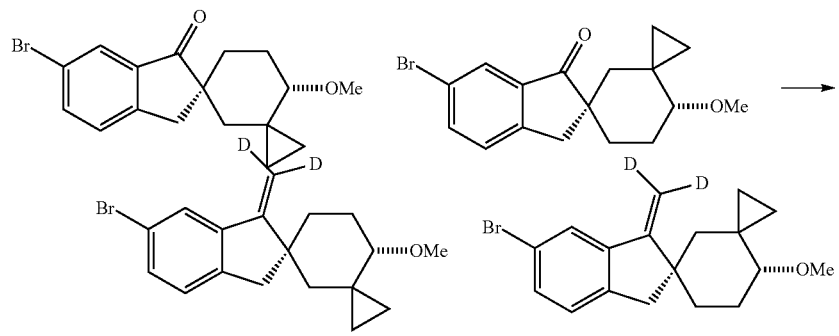

To a stirred suspension of triphenyl(trideuteriomethyl)phosphonium iodide (0.95 g, 2.33 mmol) in THF (20 mL) was added n-butyllithium (2.5M in hexane, 0.93 mL, 2.33 mmol) at −30° C. under N₂. The mixture was stirred for 45 min, treated with a solution of (1'R,4'S)-6"-bromo-4'-methoxydispiro[cyclopropane-1,3'-cyclohexane-1',2"-inden]-1"(3"H)-one; (1'S,4'R)-6"-bromo-4'-methoxydispiro[cyclopropane-1,3'-cyclohexane-1',2"-inden]-1"(3"H)-one (1.04 g, 1.55 mmol) in THF (20 mL) and upon completion, the mixture was allowed to stir at r.t. for 3 h. The mixture was concentrated in vacuo to afford a brown residue. Purification on silica (hexane+DCM 0-10%) gave the title compound as a yellow oil (0.365 g). ¹H NMR (400 MHz, CDCl₃) δ ppm 0.00-0.02 (1H, m), 0.28-0.33 (1H, m), 0.58-0.63 (1H, m), 0.78-0.83 (1H, m), 1.04-1.07 (1H, m), 1.43-1.53 (1H, m), 1.58-1.65 (1H, m), 1.69-1.75 (1H, m), 2.01-2.12 (2H, m), 2.85 (1H, d), 3.05 (1H, d), 3.27-3.34 (4H, m), 7.09 (1H, d), 7.31 (1H, dd), 7.56 (1H, d). LCMS: rt=6.38 min.

Step 5: (1'R,4'S)-6"-bromo-4'-methoxy-3"H,5'''H-trispiro[cyclopropane-1,3'-cyclohexane-1',2"-indene-1",4'''-oxazol]-5''',5'''-d₂-2'''-amine; (1'S,4'R)-6"-bromo-4'-methoxy-3"H,5'''H-trispiro[cyclopropane-1,3'-cyclohexane-1',2"-indene-1",4'''-oxazol]-5''',5'''-d₂-2'''-amine

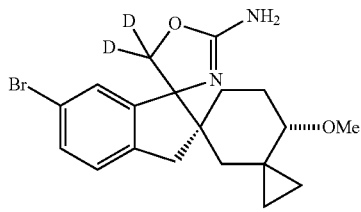

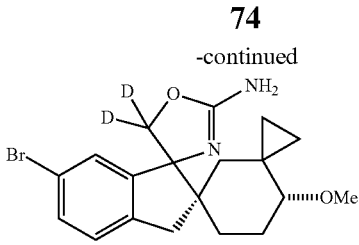

To a stirred solution of (1'R,4'S)-6"-bromo-4'-methoxy-1"-(methylene-d₂)-1",3"-dihydrodispiro[cyclopropane-1,3'-cyclohexane-1',2"-indene]; (1'S,4'R)-6"-bromo-4'-methoxy-1"-(methylene-d₂)-1",3"-dihydrodispiro[cyclopropane-1,3'-cyclohexane-1',2"-indene] (0.36 g, 1.09 mmol) in THF (8 mL) and ACN (8 mL) at r.t. was added isocyanatosilver (0.49 g, 3.27 mmol) followed by a portionwise addition of iodine (0.41 g, 1.63 mmol). The grey mixture was stirred at r.t. for 4 h, filtered through Celite and concentrated in vacuo to leave a yellow solid which was dissolved in THF (8 mL) and sat. aq. NH₄Cl (4 mL). The mixture was stirred at r.t. for 18 h, concentrated, treated with sat. aq. NaHCO₃ (25 mL) and extracted with EtOAc (3×50 mL). The combined organic extracts were dried (Na₂SO₄) and evaporated to give title compound which was used for the next step without further purification (0.457 g). ¹H NMR (400 MHz, CD₃OD) δ ppm −0.09-0.01 (1H, m), 0.10-0.25 (1H, m), 0.56-0.63 (1H, m), 0.71-0.79 (1H, m), 1.20-1.70 (5H, m), 1.90-2.10 (1H, m), 2.70-3.28 (3H, m), 3.29 (3H, d), 7.07 (1H, dd), 7.25-7.35 (2H, m). LCMS: rt=2.24 min, m/z=393/395 [M+H]⁺.

Synthesis of Compounds 1-120

General Procedure 1:

Under nitrogen at r.t., a mixture of arylbromide (1 eq), boronic acid (2 eq), 1,1-bis(di-tert-butylphosphino)ferrocene palladium dichloride (0.1 eq) in 1,4-dioxane (3 mL) was treated with a solution of K₂CO₃ (3 eq) in H₂O (1 mL) and heated at 100° C. for 2-4 h. The mixture was cooled to r.t., treated with Deloxan (Pd scavenger resin), stirred for 15 min and concentrated in vacuo. The residue was suspended in DCM, filtered and concentrated which was purified by HPLC (Gilson, 0.2% NH₃ or 0.1% formic acid or 0.1% TFA in water/CAN or 0.2% NH₄OH/ACN). Evaporation, then freeze drying afforded the title compound.

Compound 1: {(1R,1'R,3R,4R)-6'-(5-cyclopropylpyridin-3-yl)-4-methoxy-3-methyl-3'H,5"H-dispiro[cyclohexane-1,2'-indene-1',4"-oxazol]-5",5"-d₂-2"-amine formate Salt}

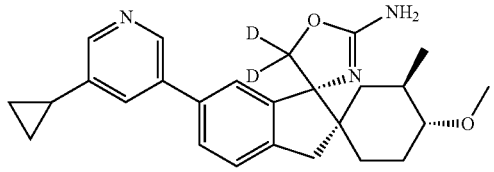 [SMILES: [2H]C1([2H])OC(N)=N[C@]12c1cc(-c3cncc(C4CC4)c3)ccc1C[C@]21CC[C@@H](OC)[C@H](C)C1]

The title compound (27 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-cyclopropyl-3-pyridyl)boronic acid (29.9 mg, 0.180 mmol). ¹H NMR (400 MHz, CD₃OD) δ ppm 0.82-0.92 (2H, m), 0.98 (3H, d), 1.05-1.15 (3H, m), 1.25-1.41 (3H, m), 1.48-1.70 (2H, m), 2.02-2.18 (2H, m), 2.72-2.80 (1H, m), 2.98 (2H, AB q), 3.38 (3H, s), 7.37 (1H, d), 7.54-7.60 (2H, m), 7.69 (1H, d), 8.30 (1H, s) and 8.54 (1H, s). LCMS: rt=3.00 min, m/z=420 [M+H]⁺, purity=100%.

Compound 2: {(1R,1'R,3R,4R)-4-methoxy-3-methyl-6'-(5-(prop-1-yn-1-yl)pyridin-3-yl)-3'H,5"H-dispiro[cyclohexane-1,2'-indene-1',4"-oxazol]-5",5"-d₂-2"-amine}

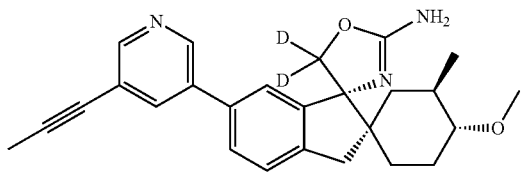 [SMILES: [2H]C1([2H])OC(N)=N[C@]12c1cc(-c3cncc(C#CC)c3)ccc1C[C@]21CC[C@@H](OC)[C@H](C)C1]

The title compound (26 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-prop-1-ynyl-3-pyridyl)boronic acid (17.7 mg, 0.110 mmol). ¹H NMR (400 MHz, CD₃OD) δ ppm 0.96 (3H, d), 1.22-1.34 (3H, m), 1.50-1.60 (3H, m), 2.03-2.12 (1H, m), 2.09 (3H, s), 2.68-2.74 (1H, m), 2.87 (1H, d), 2.98 (1H, d), 3.37 (3H, s), 7.32 (1H, d), 7.44-7.48 (2H, m), 7.99 (1H, s), 8.45 (1H, s) and 8.65 (1H, s). LCMS: rt=3.42 min, m/z=418 [M+H]⁺, purity=96.2%.

Compound 3: {(1S,1'R,3S,4S)-4-methoxy-3-methyl-6'-(5-(prop-1-yn-1-yl)pyridin-3-yl)-3'H,5"H-dispiro[cyclohexane-1,2'-indene-1',4"-oxazol]-5",5"-d₂-2"-amine}

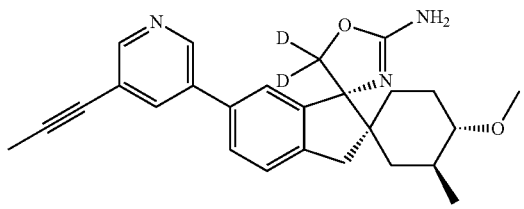 [SMILES: [2H]C1([2H])OC(N)=N[C@]12c1cc(-c3cncc(C#CC)c3)ccc1C[C@@]21CC[C@H](OC)[C@@H](C)C1]

The title compound (27 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-prop-1-ynyl-3-pyridyl)boronic acid (30 mg, 0.19 mmol). ¹H NMR (400 MHz, CD₃OD, 35° C.) δ ppm 0.96 (3H, d), 1.03 (1H, t), 1.30 (1H, qd), 1.45-1.7 (4H, m), 2.05-2.15 (4H, m), 2.71 (1H, td), 2.95 (2H, ABq), 3.38 (3H, s), 7.34 (1H, d), 7.4-7.5 (2H, m), 7.98 (1H, s), 8.45 (1H, s), 8.65 (1H, s). 2H not observed. LCMS: rt 3.35 min, m/z 418 [M+H]⁺, purity=97.1%.

Compound 4: {(1S,1'R,3S,4S)-6'-(5-chloropyridin-3-yl)-4-methoxy-3-methyl-3'H,5"H-dispiro[cyclohexane-1,2'-indene-1',4"-oxazol]-5",5"-d₂-2"-amine}

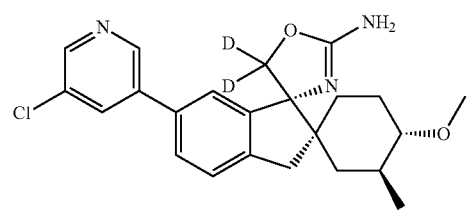 [SMILES: [2H]C1([2H])OC(N)=N[C@]12c1cc(-c3cncc(Cl)c3)ccc1C[C@@]21CC[C@H](OC)[C@@H](C)C1]

The title compound (8 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-chloro-3-pyridyl)boronic acid (30 mg, 0.190 mmol). ¹H NMR (400 MHz, CD₃OD, 35° C.) δ ppm 0.96 (3H, d), 1.03 (1H, t), 1.30 (1H, qd), 1.5-1.7 (4H, m), 2.05-2.15 (1H, m), 2.74 (1H, td), 2.95 (2H, ABq), 3.37 (3H, s), 7.36 (1H, d), 7.50-7.55 (2H, m), 8.08 (1H, s), 8.49 (1H, s), 8.71 (1H, s). 2H not observed. LCMS: rt=3.33 min, m/z 414/416 [M+H]⁺, purity=98.8%.

Compound 5: {(1S,1'R,3S,4S)-6'-(2-fluoropyridin-3-yl)-4-methoxy-3-methyl-3'H,5"H-dispiro[cyclohexane-1,2'-indene-1',4"-oxazol]-5",5"-d₂-2"-amine}

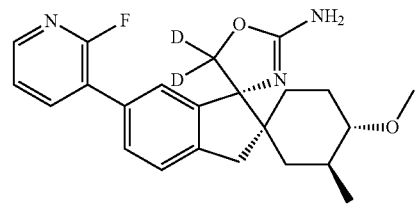 [SMILES: [2H]C1([2H])OC(N)=N[C@]12c1cc(-c3cccnc3F)ccc1C[C@@]21CC[C@H](OC)[C@@H](C)C1]

The title compound was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and 2-fluoropyridine-3-boronic acid (20 mg, 0.14 mmol). ¹H NMR (400 MHz, CDCl₃) δ ppm 0.94 (3H, d), 1.1-1.3 (2H, m), 1.4-1.5 (2H, m), 1.5-1.6 (2H, m), 2.0-2.1 (1H, m), 2.63 (1H, td), 2.74 (1H, d), 2.95 (1H, d), 3.30 (3H, s), 7.2-7.3 (2H, m), 7.3-7.4 (2H, m), 7.80 (1H, td), 8.11 (1H, d), 2H not observed. LCMS: rt=3.30 min, m/z 398 [M+H]⁺, purity=99.3%.

Compound 6: {(1S,1'R,3S,4S)-6'-(5-cyclopropylpyridin-3-yl)-4-methoxy-3-methyl-3'H,5"H-dispiro[cyclohexane-1,2'-indene-1',4"-oxazol]-5",5"-d₂-2"-amine}

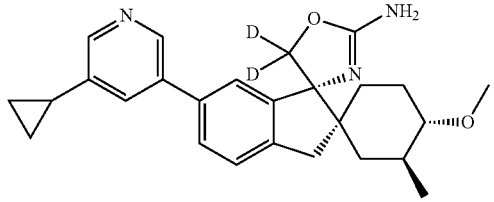 [SMILES: [2H]C1([2H])OC(N)=N[C@]12c1cc(-c3cncc(C4CC4)c3)ccc1C[C@@]21CC[C@H](OC)[C@@H](C)C1]

The title compound (14 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-cyclopropyl-3-pyridyl)boronic acid (35 mg, 0.21 mmol). ¹H NMR (400 MHz, CD₃OD, 35° C.) δ ppm 0.80-0.90 (2H, m), 0.96 (3H, d), 1.03 (1H, t), 1.05-1.15 (2H, m), 1.20-1.40 (1H, m), 1.45-1.7 (4H, m), 2.03 (1H, quin), 2.08 (1H, dq), 2.71 (1H, td), 2.95 (2H, ABq), 3.38 (3H, s), 7.31 (1H, d), 7.45-7.55 (2H, m), 7.65 (1H, s), 8.28 (1H, s), 8.51 (1H, s). LCMS: rt=2.99 min, m/z 420 [M+H]⁺, purity=99.5%.

Compound 7: {(1R,1'R,3R,4R)-6'-(5-chloropyridin-3-yl)-4-methoxy-3-methyl-3'H,5"H-dispiro[cyclohexane-1,2'-indene-1',4"-oxazol]-5",5"-d₂-2"-amine}

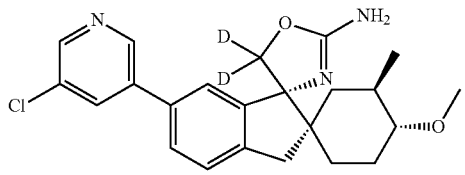 [SMILES: [2H]C1([2H])OC(N)=N[C@]12c1cc(-c3cncc(Cl)c3)ccc1C[C@]21CC[C@@H](OC)[C@H](C)C1]

The title compound (9 mg, solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and (5-chloro-3-pyridyl)boronic acid (28.9 mg, 0.180 mmol). ¹H NMR (400 MHz, CD₃OD) δ ppm 0.97 (3H, d), 1.24-1.36 (3H, m), 1.50-1.62 (3H, m), 2.08-2.14 (1H, m), 2.69-2.76 (1H, m), 2.94 (2H, AB q), 3.38 (3H, s), 7.35 (1H, d), 7.49-7.53 (2H, m), 8.12 (1H, t), 8.50 (1H, d) and 8.72 (1H, d). LCMS: rt=2.85 min, m/z=414/416 [M+H]⁺, purity=97.8%.

Compound 8: {(1S,1'R,3S,4S)-4-methoxy-3-methyl-6'-(pyridin-3-yl)-3'H,5"H-dispiro[cyclohexane-1,2'-indene-1',4"-oxazol]-5",5"-d₂-2"-amine}

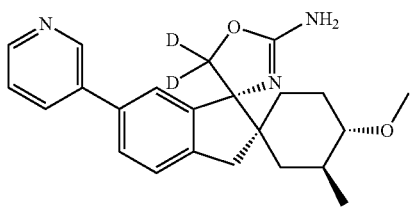 [SMILES: [2H]C1([2H])OC(N)=N[C@]12c1cc(-c3cccnc3)ccc1C[C@@]21CC[C@H](OC)[C@@H](C)C1]

The title compound (white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.090 mmol) and 3-pyridylboronic acid (25 mg, 0.20 mmol). ¹H NMR (400 MHz, CD₃OD, 35° C.) δ ppm 0.96 (3H, d), 1.03 (1H, t), 1.30 (1H, qd), 1.5-1.7 (4H, m), 2.05-2.15 (1H, m), 2.74 (1H, td), 2.95 (2H, ABq), 3.38 (3H, s), 7.34 (1H, d), 7.4-7.5 (3H, m), 8.04 (1H, dt), 8.48 (1H, dd), 8.76 (1H, d). 2H not observed. LCMS: rt=2.79 min, m/z 380 [M+H]⁺, purity=99.3%.

Compound 9: {(1S,1'R,3S,4S)-6'-(5-fluoropyridin-3-yl)-4-methoxy-3-methyl-3'H,5"H-dispiro[cyclohexane-1,2'-indene-1',4"-oxazol]-5",5"-d₂-2"-amine}

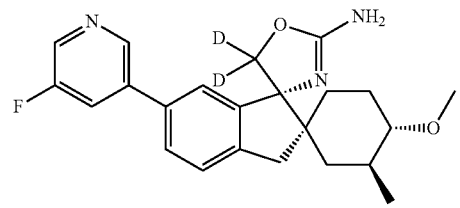 [SMILES: [2H]C1([2H])OC(N)=N[C@]12c1cc(-c3cncc(F)c3)ccc1C[C@@]21CC[C@H](OC)[C@@H](C)C1]

The title compound (27 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (38 mg, 0.10 mmol) and 5-fluoropyridine-3-boronic acid (30 mg, 0.21 mmol). ¹H NMR (400 MHz, CD₃OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 3.38 (3H, s), 7.34 (1H, d), 7.50-7.55 (2H, m), 7.85 (1H, dt), 8.40 (1H, s), 8.65 (1H, s), 2H not observed. LCMS: rt=3.25 min, m/z 398 [M+H]⁺, purity=98.3%.

Compound 10: {(1R,1'R,3R,4R)-4-methoxy-3-methyl-6'-(pyrimidin-5-yl)-3'H,5"H-dispiro[cyclohexane-1,2'-indene-1',4"-oxazol]-5",5"-d₂-2"-amine TFA Salt}

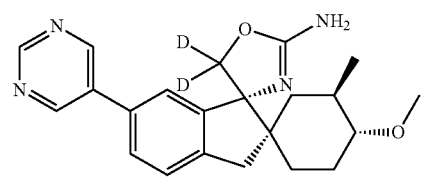 [SMILES: [2H]C1([2H])OC(N)=N[C@]12c1cc(-c3cncnc3)ccc1C[C@]21CC[C@@H](OC)[C@H](C)C1]

The title compound (28 mg, white solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (27 mg, 0.07 mmol) and pyrimidin-5-ylboronic acid (20 mg, 0.16 mmol). ¹H NMR (400 MHz, CD₃OD, 35° C.) δ ppm 1.01 (3H, d), 1.2-1.5 (3H, m), 1.55 (1H, dt), 1.60-1.70 (2H, m), 2.15-2.20 (1H, m), 2.75-2.80 (1H, m), 3.07 (2H, ABq (very close)), 3.38 (3H, s), 7.50 (1H, d), 7.71 (1H, dd), 7.79 (1H, d), 9.07 (2H, brs), 9.13 (1H, br. s), 3H observed. LCMS: rt=2.85 min, m/z 381 [M+H]⁺, purity=98.9%.

Compound 11: Four Isomers {(1S,3S,4S)-2"-amino-3-methyl-6'-(3-methylbut-1-yn-1-yl)-3'H,5"H-dispiro[cyclohexane-1,2'-indene-1',4"-oxazol]-5",5"-d$_2$-4-ol} and {(1R,3R,4R)-2"-amino-3-methyl-6'-(3-methylbut-1-yn-1-yl)-3'H,5"H-dispiro[cyclohexane-1,2'-indene-1',4"-oxazol]-5",5"-d$_2$-4-ol TFA Salt}

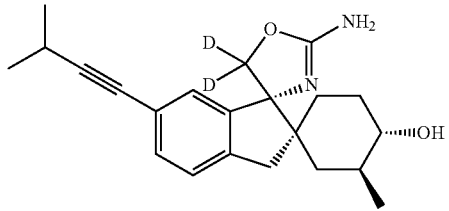 [SMILES: [2H]C1([2H])OC(N)=N[C@]12c1cc(C#CC(C)C)ccc1C[C@@]21CC[C@H](O)[C@@H](C)C1]

A solution of (1S,3S,4S)-4-((tert-butyldiphenylsilyl)oxy)-3-methyl-6'-(3-methylbut-1-yn-1-yl)-3'H,5"H-dispiro[cyclohexane-1,2'-indene-1',4"-oxazol]-5",5"-d$_2$-2"-amine and (1R,3R,4R)-4-((tert-butyldiphenylsilyl)oxy)-3-methyl-6'-(3-methylbut-1-yn-1-yl)-3'H,5"H-dispiro[cyclohexane-1,2'-indene-1',4"-oxazol]-5",5"-d$_2$-2"-amine (108 mg, 0.050 mmol) in THF (5 mL) was treated with TBAF (1M THF) (0.54 mL, 0.54 mmol), stirred at 40° C. for 24 h, cooled and evaporated. Purification of the residue by HPLC (ACN (10-70%)/water+0.1% TFA) yielded two pairs of diastereomersv (white solid, 13 mg). $^1$H NMR (400 MHz, CDCl$_3$) δ ppm 0.9-1.1 (4H, m), 1.23 (6H, d), 1.3-1.7 (5H, m), 1.9-2.0 (1H, m), 2.74 (1H, septet), 2.99 (2H, s), 3.0-3.1 (1H, m), 7.25 (1H, d), 7.33 (1H, dd), 7.39 (1H, d). 4H not observed. LCMS: rt=3.32 min, m/z=355 [M+H]$^+$, purity 98.6% (mixture of 4 isomers).

Compound 12: {(1r,4r)-4-methoxy-6'-(3-methylbut-1-yn-1-yl)-3'H,5"H-dispiro[cyclohexane-1,2'-indene-1',4"-oxazol]-2"-amine}

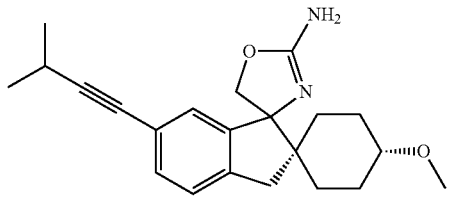

A mixture of (1r,4r)-6'-bromo-4-methoxy-3'H,5"H-dispiro[cyclohexane-1,2'-indene-1',4"-oxazol]-2"-amine (182 mg, 0.50 mmol), tetrakis(triphenylphosphine)palladium(0) (58 mg, 0.050 mmol) in DMF (2 mL) under nitrogen at r.t. was treated with 3-methylbut-1-yne (102 mg, 1.50 mmol) and triethylamine (2.1 mL, 15 mmol). The mixture was stirred for 5 min, treated with CuI (24 mg, 0.13 mmol), heated at 65° C. for 15 h. The mixture was cooled to r.t., diluted with TBME (30 mL), washed with sat. aq. NaHCO$_3$ solution (2×10 mL), brine (10 mL), dried (Na$_2$SO$_4$) and evaporated to leave a dark gum (~300 mg). Purification by HPLC (0.1% formic/ACN) afforded a white flocculent solid (97 mg). $^1$H NMR (400 MHz, CD$_3$OD) δ ppm 1.24 (6H, d), 1.25-1.42 (3H, m), 1.45-1.60 (3H, m), 1.95- 2.09 (2H, m), 2.76 (1H, septet), 2.94 (2H, t), 3.13-3.23 (1H, m), 3.36 (3H, s), 4.55 (1H, d), 4.93 (1H, d), 7.21 (1H, d), 7.29 (1H, dd), 7.34 (1H, d). LCMS: rt=2.82 min, m/z=353 [M+H]$^+$.

Compound 13: {(1R,1'R,3R,4R)-4-methoxy-3-methyl-6'-(pyridin-3-yl)-3'H,5"H-dispiro[cyclohexane-1,2'-indene-1',4"-oxazol]-5",5"-d$_2$-2"-amine}

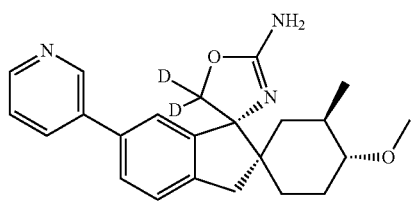 [SMILES: [2H]C1([2H])OC(N)=N[C@]12c1cc(-c3cccnc3)ccc1C[C@]21CC[C@@H](OC)[C@H](C)C1]

The title compound (24 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and 3-pyridylboronic acid (22.5 mg, 0.180 mmol). $^1$H NMR (400 MHz, CD$_3$OD) δ ppm 0.97 (3H, d), 1.24-1.38 (3H, m), 1.50-1.62 (3H, m), 2.08-2.14 (1H, m), 2.69-2.76 (1H, m), 2.88 (1H, d), 2.99 (1H, d), 3.37 (3H, s), 7.35 (1H, d), 7.48-7.52 (3H, m), 8.08 (1H, dd), 8.49 (1H, d) and 8.77 (1H, s). LCMS: rt=2.26 min, m/z=380 [M+H]$^+$, purity=97.6%.

Compound 14: {(1S,1R,3S,4S)-4-methoxy-3-methyl-6'-(pyrimidin-5-yl)-3'H,5"H-dispiro[cyclohexane-1,2'-indene-1',4"-oxazol]-5",5"-d$_2$-2"-amine TFA Salt}

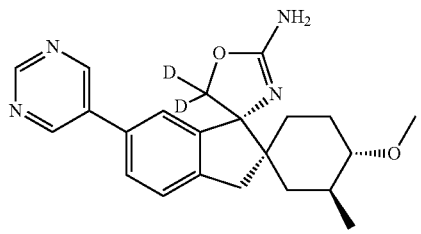 [SMILES: [2H]C1([2H])OC(N)=N[C@]12c1cc(-c3cncnc3)ccc1C[C@@]21CC[C@H](OC)[C@@H](C)C1]

The title compound (22 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (27 mg, 0.07 mmol) and pyrimidin-5-ylboronic acid (30 mg, 0.24 mmol). $^1$H NMR (400 MHz, CD$_3$OD, 35° C.) δ ppm 1.00 (3H, d), 1.12 (1H, t), 1.40 (1H, dt), 1.50-1.70 (4H, m), 2.15-2.20 (1H, m), 2.75-2.80 (1H, m), 3.07 (2H, ABq (very close)), 3.38 (3H, s), 7.50 (1H, d), 7.71 (1H, dd), 7.79 (1H, d), 9.07 (2H, s), 9.13 (1H, s), 3H not observed. LCMS: rt=2.95 min, m/z 381 [M+H]$^+$, purity=98.4%.

Compound 15: {(1r,4r)-4-methoxy-6'-(5-(prop-1-yn-1-yl)pyridin-3-yl)-3'H,5"H-dispiro[cyclohexane-1,2'-indene-1',4"-oxazol]-2"-amine formate Salt}

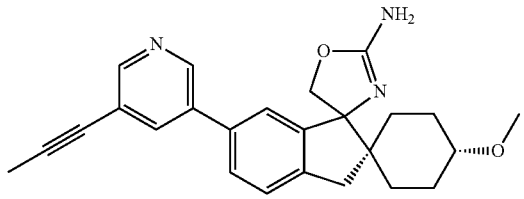

The title compound (34 mg, floculent solid) was prepared according to General Procedure 1 using (1r,4r)-6'-bromo-4-methoxy-3-methyl-3'H,5"H-dispiro[cyclohexane-1,2'-indene-1',4"-oxazol]-amine (122 mg, 0.33 mmol) and (5-prop-1-ynyl-3-pyridyl)boronic acid (54 mg, 0.33 mmol). $^1$H NMR (400 MHz, CD$_3$OD) δ ppm 1.24-1.42 (3H, m), 1.50-1.62 (3H, m), 2.00-2.08 (2H, m), 2.09 (3H, s), 2.97 (2H, q), 3.14-3.25 (1H, m), 3.36 (3H, s), 4.43 (1H, d), 4.82 (1H, d), 7.38 (1H, d), 7.55 (1H, dd), 7.56 (1H, s), 8.03 (1H, t), 8.47 (1H, d) and 8.67 (1H, d). LCMS: rt=2.64 min, m/z=402 [M+H]$^+$, purity=100%.

Compound 16: {(1r,4r)-6'-(5-chloropyridin-3-yl)-4-methoxy-3'H,5"H-dispiro[cyclohexane-1,2'-indene-1',4"-oxazol]-5",5"-d$_2$-2"-amine}

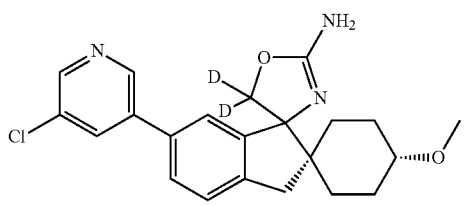

The title compound (52 mg, brown solid) was prepared according to General Procedure 1 using (1r,4r)-6'-bromo-4-methoxy-3-methyl-3'H,5"H-dispiro[cyclohexane-1,2'-indene-1',4"-oxazol]-5",5"-d$_2$-2"-amine (22 mg, 0.030 mmol) and (5-chloro-3-pyridyl)boronic acid (53 mg, 0.33 mmol). $^1$H NMR (400 MHz, CD$_3$OD) δ ppm 1.30-1.45 (m, 3H), 1.54-1.64 (m, 3H), 2.00-2.09 (m, 2H), 3.00 (q, 2H), 3.15-3.23 (m, 1H), 3.36 (s, 3H), 4.48 (d, 1H), 4.86 (d, 1H), 7.42 (d, 1H), 7.60 (dd, 1H), 8.14 (d, 1H), 8.52 (d, 1H) and 8.74 (d, 1H). LCMS: rt=2.50 min, m/z=398/400 [M+H]$^+$, purity=100%.

Compound 17: {3-((1R,1'R,3R,4R)-2"-amino-4-methoxy-3-methyl-3'H,5"H-dispiro[cyclohexane-1,2'-indene-1',4"-oxazol]-6'-yl-5",5"-d$_2$)-5-fluorobenzonitrile formate Salt}

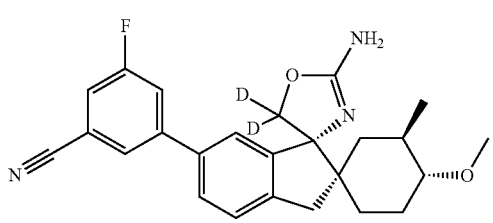 [SMILES: [2H]C1([2H])OC(N)=N[C@]12c1cc(-c3cc(F)cc(C#N)c3)ccc1C[C@]21CC[C@@H](OC)[C@H](C)C1]

The title compound (21 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and (3-cyano-5-fluoro-phenyl)boronic acid (30 mg, 0.18 mmol). $^1$H NMR (400 MHz, CD$_3$OD) δ ppm 0.98 (3H, d), 1.23-1.39 (3H, m), 1.48-1.68 (3H, m), 2.10-2.18 (1H, m), 2.71-2.79 (1H, m), 2.98 (2H, ABq), 3.38 (3H, s), 7.38 (1H, d), 7.51-7.54 (1H, m), 7.58-7.60 (2H, m), 7.73-7.76 (1H, m) and 7.86 (1H, s). LCMS: rt=3.67 min, m/z=422 [M+H]$^+$, purity=98.7%.

Compound 18: {3-((1r,4r)-2"-amino-4-methoxy-3'H,5"H-dispiro[cyclohexane-1,2'-indene-1',4"-oxazol]-6'-yl-5",5"-d$_2$)-5-chlorobenzonitrile formate Salt}

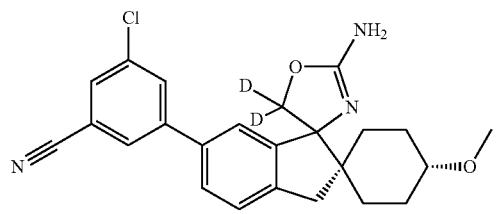

The title compound (60 mg, solid) was prepared according to General Procedure 1 using (1r,4r)-6'-bromo-4-methoxy-3-methyl-3'H,5"H-dispiro[cyclohexane-1,2'-indene-1',4"-oxazol]-5",5"-d$_2$-2"-amine (22 mg, 0.03 mmol) and 3-chloro-5-(4,4,5,5-tetramethyl-1,3,2-dioxaborolan-2-yl)benzonitrile (88 mg, 0.33 mmol). $^1$H NMR (400 MHz, CD$_3$OD) δ ppm 1.29-1.45 (m, 3H), 1.50-1.68 (m, 3H), 2.02-2.12 (m, 2H), 3.03 (q, 2H), 3.16-3.27 (m, 1H), 3.37 (s, 3H), 4.69 (d, 1H), 5.07 (d, 1H), 7.43 (d, 1H), 7.66 (dd, 1H), 7.70 (d, 1H), 7.78 (d, 1H) and 7.97-8.01 (m, 2H). LCMS: rt=2.75 min, m/z=422/4 [M+H]$^+$, purity=99.3%.

Compound 19: {3-((1S,1'R,3S,4S)-2"-amino-4-methoxy-3-methyl-3'H,5"H-dispiro[cyclohexane-1,2'-indene-1',4"-oxazol]-6'-yl-5",5"-d$_2$)-5-fluorobenzonitrile}

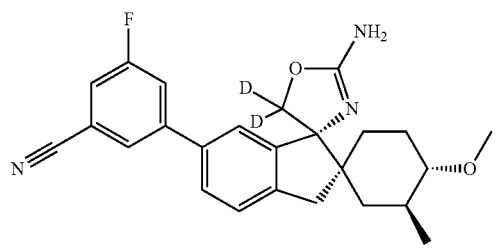 [SMILES: [2H]C1([2H])OC(N)=N[C@]12c1cc(-c3cc(F)cc(C#N)c3)ccc1C[C@@]21CC[C@H](OC)[C@@H](C)C1]

The title compound (20 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and (3-cyano-5-fluoro-phenyl)boronic acid (30 mg, 0.18 mmol). $^1$H NMR (400 MHz, CD$_3$OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 3.38 (3H, s), 7.34 (1H, d), 7.4-7.5 (3H, m), 7.70 (1H, dt), 7.81 (1H, t), 2H not observed. LCMS: rt=3.65 min, m/z 422 [M+H]$^+$, purity=98.9%

Compound 20: {(1R,1'R,3R,4R)-4-methoxy-3-methyl-6'-(5-methylpyridin-3-yl)-3'H,5"H-dispiro[cyclohexane-1,2'-indene-1',4"-oxazol]-5",5"-d₂-2"-amine formate Salt}

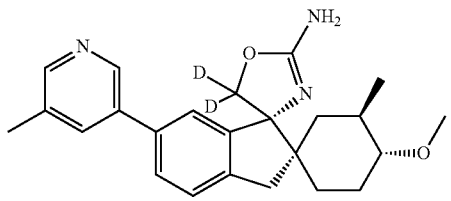

The title compound (30 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.09 mmol) and (5-methyl-3-pyridyl)boronic acid (25 mg, 0.18 mmol). ¹H NMR (400 MHz, CD₃OD) δ ppm 1.01 (3H, d), 1.24-1.42 (3H, m), 1.49-1.69 (3H, m), 2.13-2.20 (1H, m), 2.44 (3H, s), 2.74-2.82 (1H, m), 3.03 (2H, AB q), 3.39 (3H, s), 7.43 (1H, d), 7.62 (1H, dd), 7.68 (1H, s), 7.95 (1H, s), 8.37 (1H, s) and 8.60 (1H, s). LCMS: rt=2.82 min, m/z=394 [M+H]⁺, purity=100%.

Compound 21: {(1S,3S,4S)-4-methoxy-3-methyl-6'-(5-methylpyridin-3-yl)-3'H,5"H-dispiro[cyclohexane-1,2'-indene-1',4"-oxazol]-5",5"-d₂-2"-amine}

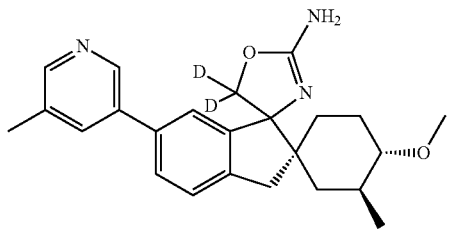

The title compound (23 mg, white solid) was prepared according to General Procedure 1 using (1S,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.09 mmol) and (5-methyl-3-pyridyl)boronic acid (46 mg, 0.33 mmol). ¹H NMR (400 MHz, CD₃OD) δ ppm 1.31-1.44 (m, 3H), 1.51-1.67 (m, 3H), 2.00-2.10 (m, 2H), 2.43 (s, 3H), 3.00 (q, 2H), 3.15-3.24 (m, 1H), 3.36 (s, 3H), 4.61 (d, 1H), 5.02 (d, 1H), 7.41 (d, 1H), 7.60 (dd, 1H), 7.64 (d, 1H), 7.93 (s, 1H), 8.35 (s, 1H) and 8.59 (s, 1H). LCMS: rt=2.18 min, m/z=378 [M+H]⁺, purity=100%.

Compound 22: {(1r,3R,4r,5S)-4-methoxy-3,5-dimethyl-6'-(pyrimidin-5-yl)-3'H,5"H-dispiro[cyclohexane-1,2'-indene-1',4"-oxazol]-5",5"-d₂-2"-amine}

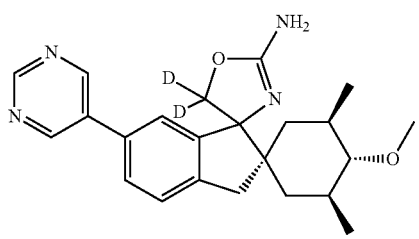

The title compound (29 mg, solid) was prepared according to General Procedure 1 using (1r,3R,4r,5S)-6'-bromo-4-methoxy-3,5-dimethyl-3'H,5"H-dispiro[cyclohexane-1,2'-indene-1',4"-oxazol]-5",5"-d₂-2"-amine (150 mg) and pyrimidin-5-ylboronic acid (95 mg). ¹H NMR (400 MHz, CDCl₃): 0.99-1.033 (6H, m), 1.25-1.35 (2H, m), 1.46-1.59 (2H, m), 1.63-1.70 (2H, m), 2.32-2.37 (1H, t), 2.80 (1H, d), 3.02 (1H, d), 3.45 (3H, s), 4.25 (2H, br), 7.33 (1H, d), 7.41-7.43 (1H, m), 8.93 (2H, s), 7.18 (1H, s). LCMS: rt=3.518 min, m/z=395.0 [M+H]⁺, purity=96.8%.

Compound 23: {3-((1S,1'R,3S,4S)-2"-amino-4-methoxy-3-methyl-3'H,5"H-dispiro[cyclohexane-1,2'-indene-1',4"-oxazol]-6'-yl-5",5"-d₂)-5-methoxybenzonitrile TFA Salt}

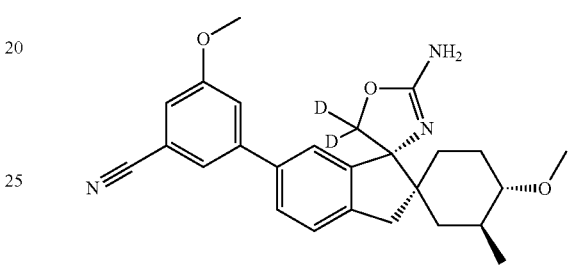

The title compound (12 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (27 mg, 0.07 mmol) and 3-methoxy-5-(4,4,5,5-tetramethyl-1,3,2-dioxaborolan-2-yl)benzonitrile (36 mg, 0.14 mmol). ¹H NMR (400 MHz, CD₃OD, 35° C.) δ ppm 1.00 (3H, d), 1.11 (1H, t), 1.40 (1H, qd), 1.50-1.70 (4H, m), 2.20 (1H, dq), 2.78 (1H, td), 3.05 (2H, ABq (very close)), 3.39 (3H, s), 3.90 (3H, s), 7.28 (1H, dd), 7.43 (1H, d), 7.46 (1H, t), 7.57 (1H, t), 7.66 (1H, dd), 7.70 (1H, d), 3H not observed. LCMS: rt=3.53 min, m/z=434 [M+H]⁺, purity=99.2%.

Compound 24: {3-((1R,1'R,3R,4R)-2"-amino-4-methoxy-3-methyl-3'H,5"H-dispiro[cyclohexane-1,2'-indene-1',4"-oxazol]-6'-yl-5",5"-d₂)-5-methoxybenzonitrile TFA Salt}

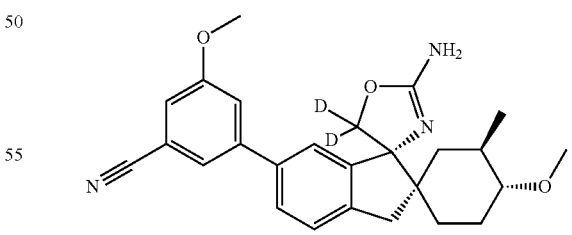

The title compound (12 mg, white solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (27 mg, 0.07 mmol) and 3-methoxy-5-(4,4,5,5-tetramethyl-1,3,2-dioxaborolan-2-yl)benzonitrile (36 mg, 0.140 mmol). ¹H NMR (400 MHz, CD₃OD, 35° C.) δ ppm 1.00 (3H, d), 1.11 (1H, t), 1.40 (1H, qd), 1.50-1.70 (4H, m), 2.20 (1H, dq), 2.78 (1H, td), 3.05 (2H, ABq (very close)), 3.39 (3H, s), 3.90 (3H, s), 7.28 (1H, dd), 7.43 (1H, d), 7.46 (1H, t), 7.57 (1H, t), 7.66 (1H, dd), 7.70 (1H, d), 3H not observed. LCMS rt=3.53 min, m/z=434 [M+H]$^+$, purity=99.2%.

Compound 25: {(1R,1'R,3R,4R)-6'-(5-fluoropyridin-3-yl)-4-methoxy-3-methyl-3'H,5"H-dispiro[cyclohexane-1,2'-indene-1',4"-oxazol]-5",5"-d$_2$-2"-amine}

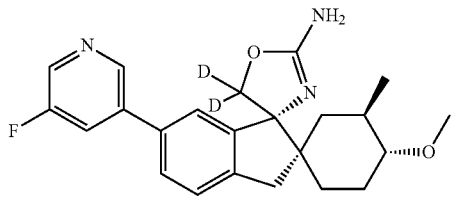 [SMILES: [2H]C1([2H])OC(N)=N[C@]12c1cc(-c3cncc(F)c3)ccc1C[C@]21CC[C@@H](OC)[C@H](C)C1]

The title compound (26 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and 5-fluoropyridine-3-boronic acid (26 mg, 0.18 mmol). $^1$H NMR (400 MHz, CD$_3$OD) δ ppm 0.97 (3H, d), 1.24-1.36 (3H, m), 1.50-1.62 (3H, m), 2.10-2.14 (1H, m), 2.68-2.76 (1H, m), 2.88 (1H, d), 3.00 (1H, d), 3.36 (3H, s), 7.38 (1H, d), 7.52-7.56 (2H, m), 7.90 (1H, dt), 8.42 (1H, s) and 8.66 (1H, s). LCMS: rt=2.54 min, m/z=398 [M+H]$^+$, purity=98.9%.

Compound 26: {((1S,1'R,3S,4S)-4-methoxy-3-methyl-6'-(5-(trifluoromethyl)pyridin-3-yl)-3'H,5"H-dispiro[cyclohexane-1,2'-indene-1',4"-oxazol]-5",5"-d$_2$-2"-amine bis TFA Salt}

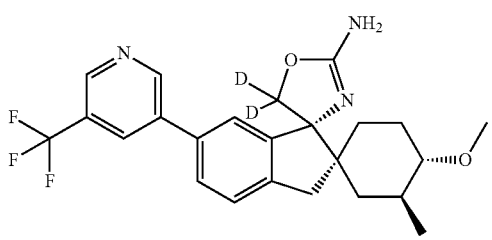 [SMILES: [2H]C1([2H])OC(N)=N[C@]12c1cc(-c3cncc(C(F)(F)F)c3)ccc1C[C@@]21CC[C@H](OC)[C@@H](C)C1]

The title compound (33 mg, sticky brown solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and 3-(4,4,5,5-tetramethyl-1,3,2-dioxaborolan-2-yl)-5-(trifluoromethyl)pyridine (55 mg, 0.20 mmol). $^1$H NMR (400 MHz, CD$_3$OD, 35° C.) δ ppm 0.99 (3H, d), 1.13 (1H, t), 1.30 (1H, qd), 1.45-1.7 (4H, m), 2.18 (1H, dq), 2.80 (1H, td), 3.06 (2H, ABq), 3.39 (3H, s), 7.50 (1H, d), 7.73 (1H, d), 7.81 (1H, s), 8.37 (1H, s), 8.87 (1H, s), 9.09 (1H, s), 4H not observed. LCMS rt=3.56 min, m/z=448 [M+H]$^+$, purity=98.5%.

Compound 27: {((1S,1'R,3S,4S)-6'-(3-chlorophenyl)-4-methoxy-3-methyl-3'H,5"H-dispiro[cyclohexane-1,2'-indene-1',4"-oxazol]-5",5"-d$_2$-2"-amine}

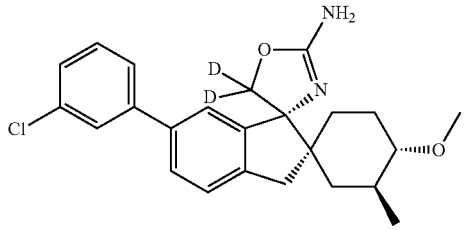 [SMILES: [2H]C1([2H])OC(N)=N[C@]12c1cc(-c3cccc(Cl)c3)ccc1C[C@@]21CC[C@H](OC)[C@@H](C)C1]

The title compound (21 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and 3-chlorophenylboronic acid (30 mg, 0.19 mmol). $^1$H NMR (400 MHz, CD$_3$OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 3.38 (3H, s), 7.29 (2H, t), 7.39 (1H, t), 7.40-7.50 (2H, m), 7.51 (1H, dt), 7.57 (1H, s), 2H not observed. LCMS: rt=3.75 min, m/z=413/415 [M+H]$^+$, purity=97.4%.

Compound 28: {((1S,1'R,3S,4S)-4-methoxy-3-methyl-6'-(5-methylpyridin-3-yl)-3'H,5"H-dispiro[cyclohexane-1,2'-indene-1',4"-oxazol]-5",5"-d$_2$-2"-amine}

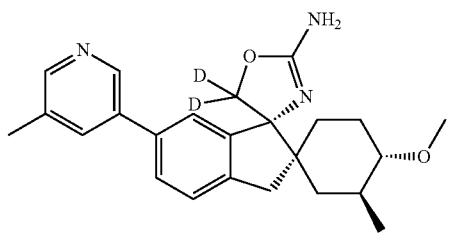

The title compound (off-white solids) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and (5-methyl-3-pyridyl)boronic acid (25 mg, 0.18 mmol). $^1$H NMR (400 MHz, CD$_3$OD, 35° C.) δ ppm 0.96 (3H, d), 1.03 (1H, t), 1.30 (1H, qd), 1.5-1.7 (4H, m), 2.05-2.15 (1H, m), 2.42 (3H, s), 2.74 (1H, td), 2.95 (2H, ABq), 3.42 (3H, s), 7.31 (1H, d), 7.4-7.5 (2H, m), 7.88 (1H, s), 8.33 (1H, s), 8.55 (1H, s), 2H not observed. LCMS: rt=2.79 min, m/z=394 [M+H]$^+$, purity=98.8%.

Compound 29: {(1R,1'R,3R,4R)-4-methoxy-3-methyl-6'-(5-(trifluoromethyl)pyridin-3-yl)-3'H,5"H-dispiro[cyclohexane-1,2'-indene-1',4"-oxazol]-5",5"-d$_2$-2"-amine formate Salt}

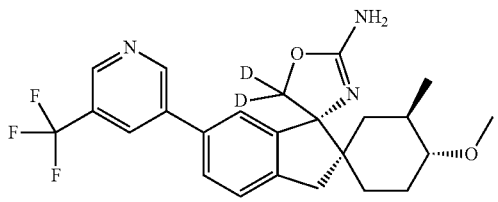 [SMILES: [2H]C1([2H])OC(N)=N[C@]12c1cc(-c3cncc(C(F)(F)F)c3)ccc1C[C@]21CC[C@@H](OC)[C@H](C)C1]

The title compound (31 mg, floculent solids) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and 3-(4,4,5,5-tetramethyl-1,3,2-dioxaborolan-2-yl)-5-(trifluoromethyl)pyridine (50 mg, 0.18 mmol). $^1$H NMR (400 MHz, CD$_3$OD) δ ppm 1.00 (3H, d), 1.22-1.42 (3H, m), 1.47-1.55 (1H, m), 1.58-1.68 (2H, m), 2.12-2.18 (1H, m), 2.72-2.80 (1H, m), 3.03 (2H, ABq), 3.39 (3H, s), 7.46 (1H, d), 7.70 (1H, d), 7.74 (1H, s), 8.39 (1H, s), 8.86 (1H, s) and 9.09 (1H, s). LCMS: rt=3.60 min, m/z=448 [M+H]$^+$, purity=97.4%.

Compound 30: {(1r,3R,4r,5S)-4-methoxy-3,5-dimethyl-6'-(5-(trifluoromethyl)pyridin-3-yl)-3'H,5"H-dispiro[cyclohexane-1,2'-indene-1',4"-oxazol]-2"-amine}

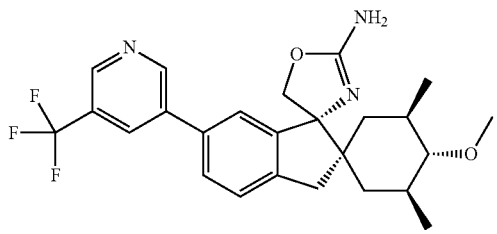 [SMILES: CO[C@H]1[C@H](C)C[C@@]2(Cc3ccc(-c4cncc(C(F)(F)F)c4)cc3[C@@]23COC(N)=N3)C[C@@H]1C]

The title compound (29 mg, solids) was prepared according to General Procedure 1 using (1r,3R,4r,5S)-6'-bromo-4-methoxy-3,5-dimethyl-3'H,5"H-dispiro[cyclohexane-1,2'-indene-1',4"-oxazol]-2"-amine (400 mg) and), [5-(trifluoromethyl)-3-pyridyl]boronic (292 mg), tri-potassium phosphate (650 mg). $^1$H NMR (400 MHz, CDCl$_3$): 0.94-1.01 (6H, m), 1.22-1.29 (2H, m), 1.41-1.47 (1H, m), 1.51-1.57 (1H, m), 1.62-1.71 (2H, m), 2.32-2.35 (1H, t), 2.75 (1H, d), 2.94 (1H, d), 3.44 (3H, s), 4.12 (1H, d), 4.11-4.17 (2H, br), 4.49 (1H, d), 7.18-7.24 (4H, d). LCMS: rt=7.283 min, m/z=315.0 [M+H]$^+$, purity=97.3%.

Compound 31: {5-((1r,3R,4r,5S)-2"-amino-4-methoxy-3,5-dimethyl-3'H,5"H-dispiro[cyclohexane-1,2'-indene-1',4"-oxazol]-6'-yl)nicotinonitrile}

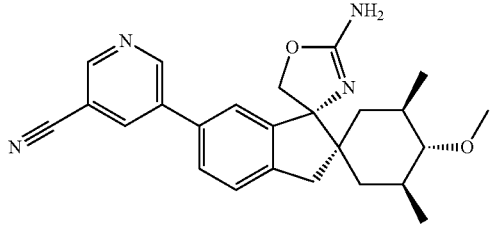 [SMILES: CO[C@H]1[C@H](C)C[C@@]2(Cc3ccc(-c4cncc(C#N)c4)cc3[C@@]23COC(N)=N3)C[C@@H]1C]

The title compound (14 mg, solids) was prepared according to General Procedure 1 using (1r,3R,4r,5S)-6'-bromo-4-methoxy-3,5-dimethyl-3'H,5"H-dispiro[cyclohexane-1,2'-indene-1',4"-oxazol]-2"-amine (400 mg) and (5-cyano-3-pyridyl)boronic acid (225 mg), tri-potassium phosphate (650 mg). $^1$H NMR (400 MHz, CDCl$_3$): 1.00-1.02 (6H, m), 1.25-1.35 (2H, m), 1.46-1.57 (2H, m), 1.64-1.73 (2H, m), 2.32-2.37 (1H, t), 2.82 (1H, d), 3.03 (1H, d), 3.46 (3H, s), 4.19 (1H, d), 4.29 (2H, br), 4.59 (1H, d), 7.34 (1H, d), 7.42-7.44 (2H, m), 8.10 (1H, d), 8.83 (1H, d), 9.01 (1H, d). LCMS: rt=6.578 min, m/z=417.0 [M+H]$^+$, purity=96.2%.

Compound 32: {3-((1r,3R,4r,5S)-2"-amino-4-methoxy-3,5-dimethyl-3'H,5"H-dispiro[cyclohexane-1,2'-indene-1',4"-oxazol]-6'-yl-5",5"-d$_2$)-5-methoxybenzonitrile}

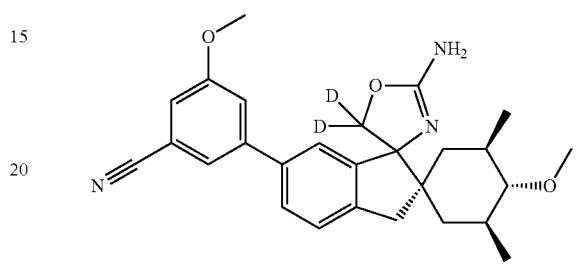

The title compound (23 mg, solids) was prepared according to General Procedure 1 using (1r,3R,4r,5S)-6'-bromo-4-methoxy-3,5-dimethyl-3'H,5"H-dispiro[cyclohexane-1,2'-indene-1',4"-oxazol]-2"-amine (150 mg) and 3-methoxy-5-(4,4,5,5-tetramethyl-1,3,2-dioxaborolan-2-yl)benzonitrile (196 mg). $^1$H NMR (400 MHz, CDCl$_3$): 0.99-1.02 (6H, d d), 1.24-1.35 (2H, m), 1.46-1.49 (1H, t d), 1.53-1.57 (1H, t d), 1.62-1.68 (2H, m), 2.32-2.37 (1H, t), 2.78 (1H, d), 3.09 (1H, d), 3.45 (3H, s), 3.88 (3H, s), 4.22 (2H, br), 7.08-7.09 (1H, m), 7.29-7.32 (2H, m), 7.38-7.39 (2H, m), 7.44-7.51 (1H, m). LCMS: rt=3.490 min, m/z=448.0 [M+H]$^+$, purity=94.2%.

Compound 33: {(1R,1'R,3R,4R)-4-methoxy-3-methyl-6'-(pyrimidin-5-yl)-3'H,5"H-dispiro[cyclohexane-1,2'-indene-1',4"-oxazol]-2"-amine}

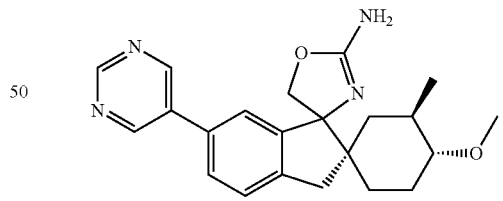

The title compound (22 mg, white solids) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-2"-amine (35 mg, 0.09 mmol) and pyrimidin-5-ylboronic acid (40 mg, 0.32 mmol). $^1$H NMR (400 MHz, CD$_3$OD, 35° C.) δ ppm 0.96 (3H, d), 1.2-1.4 (3H, m), 1.5-1.7 (3H, m), 2.05-2.15 (1H, m), 2.74 (1H, td), 2.95 (2H, ABq), 3.37 (3H, s), 4.25 (1H, d), 4.65 (1H, d), 7.40 (1H, d), 7.55 (2H, brs), 9.03 (2H, s), 9.10 (1H, s), 2H not observed. LCMS: rt=2.95 min, m/z=379 [M+H]$^+$, purity=99.1%.

Compound 34: {(1R,1'R,3R,4R)-6'-(5-chloropyridin-3-yl)-4-methoxy-3-methyl-3'H,5"H-dispiro[cyclohexane-1,2'-indene-1',4"-oxazol]-5",5"-d₂-2"-amine}

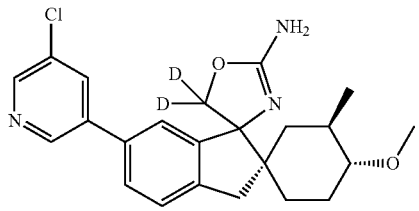

The title compound (9 mg, floculent solids) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.09 mmol) and (5-chloro-3-pyridyl)boronic acid (28.9 mg, 0.180 mmol). ¹H NMR (400 MHz, CD₃OD) δ ppm 0.97 (3H, d), 1.24-1.36 (3H, m), 1.50-1.62 (3H, m), 2.08-2.14 (1H, m), 2.69-2.76 (1H, m), 2.94 (2H, AB q), 3.38 (3H, s), 7.35 (1H, d), 7.49-7.53 (2H, m), 8.12 (1H, t), 8.50 (1H, d) and 8.72 (1H, d). LCMS: rt=2.85 min, m/z=414/6 [M+H]⁺, purity=97.8%.

Compound 35: {3-((1r,1'R,4R)-2"-amino-4-methoxy-3'H,5"H-dispiro[cyclohexane-1,2'-indene-1',4"-oxazol]-6'-yl-5",5"-d₂)-5-chlorobenzonitrile formate Salt}

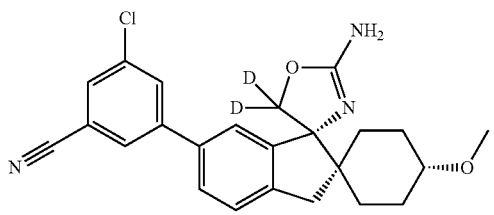 [SMILES: [2H]C1([2H])OC(N)=N[C@]12c1cc(-c3cc(Cl)cc(C#N)c3)ccc1C[C@]21CC[C@@H](OC)CC1]

The title compound (65 mg, white solids) was prepared according to General Procedure 1 using (1r,1'R,4R)-6'-bromo-4-methoxy-3-methyl-3'H,5"H-dispiro[cyclohexane-1,2'-indene-1',4"-oxazol]-5",5"-d₂-2"-amine (250 mg, 0.68 mmol) and 3-chloro-5-(4,4,5,5-tetramethyl-1,3,2-dioxaborolan-2-yl)benzonitrile (360. mg, 1.37 mmol). ¹H NMR (400 MHz, CD₃OD) δ ppm 1.28-1.47 (m, 3H), 1.50-1.68 (m, 3H), 2.02-2.13 (m, 2H), 3.04 (ABq, 2H), 3.18-3.26 (m, 1H), 3.37 (s, 3H), 7.45 (d, 1H), 7.68 (dd, 1H), 7.74 (d, 1H), 7.79 (d, 1H) and 7.99-8.01 (m, 2H), 2H not observed, 0.18 eq formic acid. LCMS: rt=3.55 min, m/z=424/426 [M+H]⁺, purity=100%.

Compound 36: {3-((1r,4r)-2"-amino-4-methoxy-3'H,5"H-dispiro[cyclohexane-1,2'-indene-1',4"-oxazol]-6'-yl-5",5"-d₂)-5-methoxybenzonitrile formate Salt}

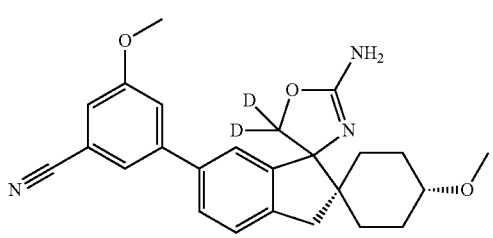

The title compound (28 mg, white solids) was prepared according to General Procedure 1 using (1r,4r)-6'-bromo-4-methoxy-3-methyl-3'H,5"H-dispiro[cyclohexane-1,2'-indene-1',4"-oxazol]-5",5"-d₂-2"-amine (83 mg, 0.23 mmol) and 3-methoxy-5-(4,4,5,5-tetramethyl-1,3,2-dioxaborolan-2-yl)benzonitrile (59 mg, 0.23 mmol). ¹H NMR (400 MHz, CD₃OD) δ ppm 1.32-1.48 (3H, m), 1.50-1.70 (3H, m), 2.02-2.12 (2H, m), 3.03 (2H, q), 3.18-3.28 (1H, m), 3.37 (3H, s), 3.90 (3H, s), 7.28 (1H, d), 7.39 (1H, d), 7.45 (1H, d), 7.58 (1H, s), 7.63 (1H, dd) and 7.68 (1H, d). LCMS: rt=2.89 min, m/z=420 [M+H]⁺, purity=100%.

Compound 37: {(1R,1'R,3R,4R)-6'-(3-chlorophenyl)-4-methoxy-3-methyl-3'H,5"H-dispiro[cyclohexane-1,2'-indene-1',4"-oxazol]-5",5"-d₂-2"-amine}

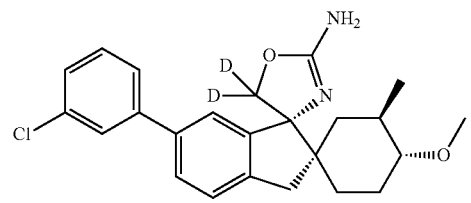 [SMILES: [2H]C1([2H])OC(N)=N[C@]12c1cc(-c3cccc(Cl)c3)ccc1C[C@]21CC[C@@H](OC)[C@H](C)C1]

The title compound (25 mg, floculent solids) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.09 mmol) and 3-chlorophenylboronic acid (17 mg, 0.11 mmol). ¹H NMR (400 MHz, CD₃OD) δ ppm 0.97 (3H, d), 1.24-1.35 (3H, m), 1.50-1.62 (3H, m), 2.08-2.16 (1H, m), 2.68-2.76 (1H, m), 2.86 (1H, d), 2.97 (1H, d), 3.37 (3H, s), 7.26-7.33 (2H, m), 7.38-7.48 (3H, m), 7.52 (1H, d) and 7.58 (1H, s). LCMS: rt=2.90 min, m/z=413/5 [M+H]⁺, purity=98.0%.

Compound 38: {5-((1r,1'R,4R)-2"-amino-4-methoxy-3'H,5"H-dispiro[cyclohexane-1,2'-indene-1',4"-oxazol]-6'-yl)nicotinonitrile formate Salt}

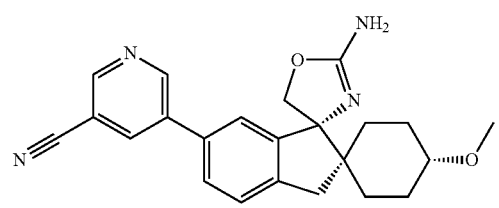 [SMILES: CO[C@H]1CC[C@]2(CC1)Cc1ccc(-c3cncc(C#N)c3)cc1[C@@]21COC(N)=N1]

The title compound (52 mg, floculent solids) was prepared according to General Procedure 1 using (1r,1'R,4R)-6'-bromo-4-methoxy-3-methyl-3'H,5"H-dispiro[cyclohexane-1,2'-indene-1',4"-oxazol]-2"-amine (61 mg, 0.17 mmol) and (5-cyano-3-pyridyl)boronic acid (49 mg, 0.33 mmol). ¹H NMR (400 MHz, CD₃OD) δ ppm 1.32-1.47 (3H, m), 1.54-1.68 (3H, m), 2.02-2.13 (2H, m), 3.05 (2H, q), 3.17-3.27 (1H, m), 3.37 (3H, s), 4.76 (1H, d), 5.12 (1H, d), 7.48 (1H, d), 7.72 (1H, dd), 7.78 (1H, d), 8.50 (1H, t), 8.89 (1H, d) and 9.09 (1H, d). LCMS: rt=2.49 min, m/z=389 [M+H]⁺, purity=100%.

Compound 39: {3-((1r,3R,4r,5S)-2"-amino-4-methoxy-3,5-dimethyl-3'H,5"H-dispiro[cyclohexane-1,2'-indene-1',4"-oxazol]-6'-yl-5",5"-d$_2$)-5-chlorobenzonitrile}

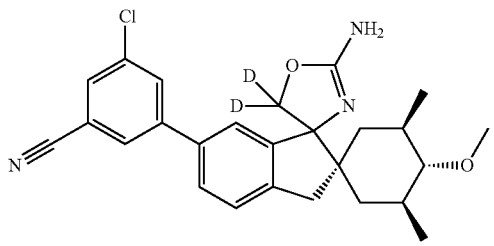

The title compound (14 mg, solid) was prepared according to General Procedure 1 using (1r,3R,4r,5S)-6'-bromo-4-methoxy-3,5-dimethyl-3'H,5"H-dispiro[cyclohexane-1,2'-indene-1',4"-oxazol]-5",5"-d$_2$-2"-amine (150 mg) and 3-chloro-5-(4,4,5,5-tetramethyl-1,3,2-dioxaborolan-2-yl)benzonitrile (200 mg). $^1$H NMR (400 MHz, CDCl$_3$): 0.99-1.02 (6H, d d), 1.25-1.34 (2H, dd), 1.45-1.59 (2H, m), 1.63-1.69 (2H, m), 2.32-2.37 (1H, t), 2.79 (1H, d), 3.00 (1H, d), 3.45 (3H, s), 4.25 (2H, br), 7.29 (1H, d), 7.37-7.39 (2H, m), 7.56-7.57 (1H, t), 7.73-7.74 (1H, t), 7.77-7.79 (1H, t). LCMS: rt=7.767 min, m/z=452.0 [M+H]$^+$, purity=98.0%.

Compound 40: {(1r,3R,4r,5S)-4-methoxy-3,5-dimethyl-6'-(3-methylbutyl-1,1,2,2-d$_4$)-3'H,5"H-dispiro[cyclohexane-1,2'-indene-1',4"-oxazol]-5",5"-d$_2$-2"-amine}

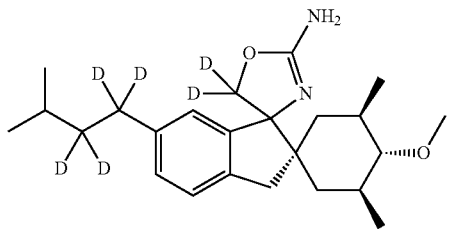

A solution of (1r,3R,4r,5S)-4-methoxy-3,5-dimethyl-6'-(3-methylbut-1-yn-1-yl)-3'H,5"H-dispiro[cyclohexane-1,2'-indene-1',4"-oxazol]-5",5"-d$_2$-2"-amine (116 mg, 0.300 mmol) in EtOH (10 mL) was treated with Pd—C (50 mg), purged with N$_2$ (3×) and then D$_2$ (g). The suspension was vigorously stirred under at r.t. for 24 h, heated to 40° C., stirred for 5 h, cooled to r.t., filtered through Celite and evaporated. Purification by HPLC (Gilson, 0.2% NH$_4$OH/ACN) afforded a white floculent solid (48 mg). $^1$H NMR (400 MHz, CD$_3$OD) δ ppm 0.92 (6H, d), 0.96 (3H, d), 0.98 (3H, d), 1.24 (1H, t), 1.45-1.58 (3H, m), 1.60-1.75 (2H, m), 2.38 (1H, t), 2.76 (1H, d), 3.13-3.23 (1H, m), 3.36 (3H, s), 4.08 (1H, s, <5%), 4.54 (1H, s, <5%), 7.00 (1H, dd), 7.03 (1H, d) and 7.07 (1H, d). LCMS: rt=3.03 min, m/z=391 [M+H]$^+$, purity=98.3%.

Compound 41: {(1r,4r)-4-methoxy-6'-(5-methylpyridin-3-yl)-3'H,5"H-dispiro[cyclohexane-1,2'-indene-1',4"-oxazol]-2"-amine formate Salt}

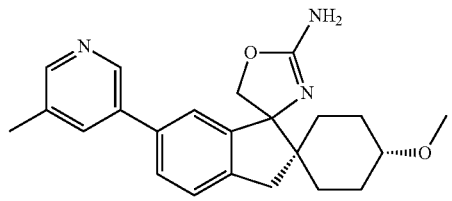

The title compound (23 mg, white solids) was prepared according to General Procedure 1 using (1r,4r)-6'-bromo-4-methoxy-3-methyl-3'H,5"H-dispiro[cyclohexane-1,2'-indene-1',4"-oxazol]-2"-amine (35 mg, 0.09 mmol) and (5-methyl-3-pyridyl)boronic acid (46 mg, 0.33 mmol). $^1$H NMR (400 MHz, CD$_3$OD) δ ppm 1.31-1.44 (m, 3H), 1.51-1.67 (m, 3H), 2.00-2.10 (m, 2H), 2.43 (s, 3H), 3.00 (q, 2H), 3.15-3.24 (m, 1H), 3.36 (s, 3H), 4.61 (d, 1H), 5.02 (d, 1H), 7.41 (d, 1H), 7.60 (dd, 1H), 7.64 (d, 1H), 7.93 (s, 1H), 8.35 (s, 1H) and 8.59 (s, 1H). LCMS: rt=2.18 min, m/z=378 [M+H]$^+$, purity=100%.

Compound 42: {(1r,4r)-4-methoxy-6'-(5-(trifluoromethyl)pyridin-3-yl)-3'H,5"H-dispiro[cyclohexane-1,2'-indene-1',4"-oxazol]-2"-amine formate Salt}

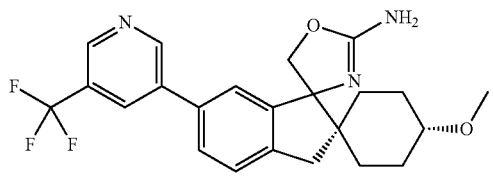

The title compound (85 mg, beige solids) was prepared according to General Procedure 1 using (1r,4r)-6'-bromo-4-methoxy-3-methyl-3'H,5"H-dispiro[cyclohexane-1,2'-indene-1',4"-oxazol]-2"-amine (35 mg, 0.09 mmol) and 3-(4,4,5,5-tetramethyl-1,3,2-dioxaborolan-2-yl)-5-(trifluoromethyl)pyridine (91 mg, 0.33 mmol). $^1$H NMR (400 MHz, CD$_3$OD) δ ppm 1.30-1.46 (m, 3H), 1.50-1.68 (m, 3H), 2.02-2.12 (m, 2H), 3.03 (q, 2H), 3.15-3.28 (m, 1H), 3.37 (s, 3H), 4.65 (d, 1H), 5.03 (d, 1H), 7.46 (d, 1H), 7.69 (dd, 1H), 7.75 (d, 1H), 8.38 (s, 1H), 8.86 (s, 1H) and 9.09 (s, 1H). LCMS: rt=2.53 min, m/z=432 [M+H]$^+$, purity=100%.

Compound 43: {(1r,3R,4r,5S)-6'-isopentyl-4-methoxy-3,5-dimethyl-3'H,5"H-dispiro[cyclohexane-1,2'-indene-1',4"-oxazol]-5",5"-d$_2$-2"-amine}

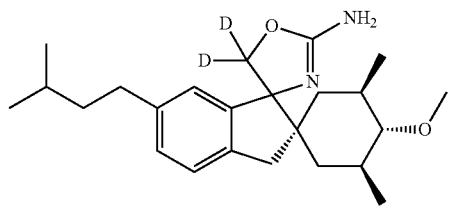

Step 1: bis-N-tert-butoxycarbonyl-{(1r,3R,4r,5S)-6'-bromo-4-methoxy-3,5-dimethyl-3'H,5"H-dispiro[cyclohexane-1,2'-indene-1',4"-oxazol]-5",5"-d$_2$-2"-amine}

Di-tert-butyl dicarbonate (1.5 g), triethyl amine (1.6 mL) and DMAP (30 mg) were added to a solution of 6'-bromo-{(1r,3R,4r,5S)-4-methoxy-3,5-dimethyl-3'H,5"H-dispiro[cyclohexane-1,2'-indene-1',4"-oxazol]-5",5"-d$_2$-2"-amine} (900 mg) in DCM (30 mL) at r.t. The mixture was stirred for 24 h at r.t. and diluted with DCM (50 mL). The organic layer was washed with water (3×25 mL), sat. aq. NaHCO$_3$ (2×25 mL) and brine (2×25 mL), dried (Na$_2$SO$_4$) and evaporated to give title compound (1.1 g). $^1$H NMR (400 MHz, CDCl$_3$): 0.91 (3H, d d), 1.02 (3H, m), 1.18-1.26 (4H, m), 1.48 (18H, s), 1.67-1.79 (2H, m), 2.28-2.33 (1H, t), 2.85 (1H, d), 2.98 (1H, d), 3.44 (3H, s), 7.11 (1H, d), 7.34-7.35 (1H, m), 7.36-7.38 (1H, m). MS: m/z=595.0, 597.0 [M+H]$^+$. HPLC: rt=5.152 min, purity=94.9%.

Step 2: bis-N-tert-butoxycarbonyl-{(1r,3R,4r,5S)-6'-isopentyl-4-methoxy-3,5-dimethyl-3'H,5"H-dispiro[cyclohexane-1,2'-indene-1',4"-oxazol]-5",5"-d$_2$-2"-amine}

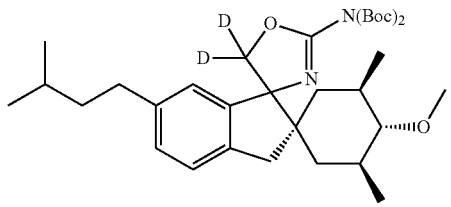

A mixture of bis-N-tert-butoxycarbonyl-6'-bromo-{(1r,3R,4r,5S)-4-methoxy-3,5-dimethyl-3'H,5"H-dispiro[cyclohexane-1,2'-indene-1',4"-oxazol]-5",5"-d$_2$-2"-amine} (300 mg), t-BuOK (170 mg) in THF (3 mL) was degassed with N$_2$ for 10 min at r.t., treated with Pd(t-Bu$_3$P)$_2$ (52 mg) followed by a solution of 0.5 M bromo(isoopentyl)zinc in THF (3 mL) and degassed for another 10 min. The mixture was heated 75° C. for 45 min using microwave, cooled to r.t., diluted with EtOAc (25 mL) and filtered through Celite. The filtrate was washed with water (2×10 mL), the organic layer dried (Na$_2$SO$_4$) and evaporated to give the title compound which was used without further purification (1.0 g). MS: m/z=487.1 [M+H]$^+$ (mono Boc product), 387.0 [M+H]$^+$.

Step 3: {(1r,3R,4r,5S)-6'-isopentyl-4-methoxy-3,5-dimethyl-3'H,5"H-dispiro[cyclohexane-1,2'-indene-1',4"-oxazol]-5",5"-d$_2$-2"-amine}

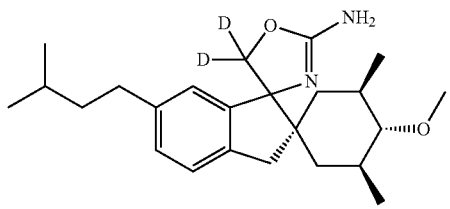

A solution of bis-N-tert-butoxycarbonyl-{(1r,3R,4r,5S)-6'-isopentyl-4-methoxy-3,5-dimethyl-3'H,5"H-dispiro[cyclohexane-1,2'-indene-1',4"-oxazol]-5",5"-d$_2$-2"-amine} (1.0 g) in 7M NH$_3$ in MeOH (25 mL) and water (2 mL) was heated at 85° C. for 16 h, cooled to r.t. and evaporated. The residue was dissolved in DCM (5 mL), treated with TFA (0.2 mL) and stirred for 3 h at r.t. The mixture was diluted with DCM (25 mL) and washed with sat. aq. NaHCO$_3$ (2×10 mL), dried over K$_2$CO$_3$ and filtered through Celite. The filtrate was evaporated and purified by prep. TLC (5% MeOH in DCM), followed by HPLC (11 mg). $^1$H NMR (400 MHz, CDCl$_3$): 0.92 (6H, d), 0.96-1.00 (6H, t), 1.25-1.30 (2H, m), 1.44-1.51 (4H, m), 1.54-1.60 (1H, m), 1.63-1.71 (2H, m), 2.29-3.34 (1H, t), 2.55-2.59 (2H, t), 2.68 (1H, d), 2.89 (1H, d), 2.99 (2H, s), 3.43 (3H, s), 4.3 (2H, br), 7.00-7.08 (3H, m). $^{13}$C NMR (400 MHz, CDCl$_3$): 18.92, 19.10, 22.55, 22.59, 27.84, 29.70, 33.83, 34.48, 34.82, 37.83, 38.42, 39.49, 41.09, 50.19, 58.98, 82.82, 91.79, 122.62, 124.80, 127.69, 137.84, 142.03, 147.14, 159.45. LCMS: rt=8.043 min, m/z=387.1 [M+H]$^+$, purity=95.0%.

Compound 45: {(1r,4r)-4-methoxy-6'-(3,3,3-trifluoropropoxy)-3'H,5"H-dispiro[cyclohexane-1,2'-indene-1',4"-oxazol]-5",5"-d$_2$-2"-amine}

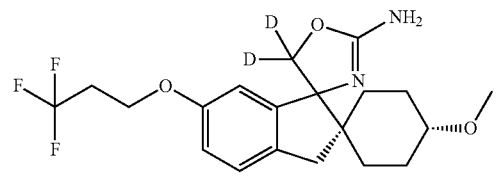

Step 1

A mixture of 6'-bromo-4-methoxy-spiro[cyclohexane-1,2'-indane]-1'-one (185 mg, 0.60 mmol), allylpalladium chloride dimer (11 mg, 0.030 mmol), Rockphos (28 mg, 0.060 mmol), 3,3,3-trifluoropropan-1-ol (274 mg, 2.40 mmol), cesium carbonate (391 mg, 1.20 mmol) in toluene (5 mL) was heated at 100° C. for 18 h, cooled to r.t. and filtered through cotton wool. The filtrate was concentrated to leave a brown gum (305 mg). Gravity chromatography (Si 4 g cartridge, 0-5% EtOAc in DCM) afforded a pale yellow solid (197 mg). $^1$H NMR (400 MHz, CDCl$_3$) δ ppm 1.30-1.40 (2H, m), 1.45-1.52 (2H, m), 1.72-1.80 (2H, m), 2.10-2.18 (2H, m), 2.63 (2H, sextet), 2.95 (2H, s), 3.20-3.30 (1H, m), 3.38 (3H, s), 4.21 (2H, t), 7.15 (1H, d), 7.19 (1H, dd), 7.35 (1H, d).

Step 2

Under N$_2$ at r.t., a suspension of magnesium turnings (55 mg, 2.3 mmol) in Et$_2$O (2.5 mL) was treated with iodine and stirred until the brown colour disappeared. A solution iodomethane-d$_3$ (0.14 mL, 2.28 mmol) in Et$_2$O (2.5 mL) was added dropwise over 15 min. The resulting solution was stirred for 1 h, treated with a solution of 4-methoxy-6'-(3,3,3-trifluoropropoxy)spiro[cyclohexane-1,2'-indane]-1'-one (390 mg, 1.14 mmol) in Et$_2$O (5 mL) and stirred at r.t. for 18 h. The mixture was treated with sat. aq. NH$_4$Cl, the layers were separated and the aqueous phase was extracted with Et$_2$O (2×10 mL). The combined organic layers were dried (Na$_2$SO$_4$), filtered and evaporated to leave a yellow syrup (420 mg) which was used for the next step without further purification. LCMS: rt=3.21 min, m/z=312 [M+H]+ (desired product minus H₂O minus MeOH, ie, 361−50=311).

Step 3

A solution of 4-methoxy-1'-(trideuteriomethyl)-6'-(3,3,3-trifluoropropoxy)spiro[cyclohexane-1,2'-indane]-1'-ol (412 mg, 1.14 mmol) in DCM (10 mL) at r.t. was treated with p-toluenesulphonic acid (22 mg, 0.11 mmol), stirred for 15 min, treated with water (10 mL) and the layers were separated. The aqueous phase was extracted with DCM (2×5 mL) and the combined organic layers were dried (Na₂SO₄), filtered and evaporated to leave a yellow oil (500 mg). Gravity chromatography (Si 10 g cartridge, 0-5% EtOAc in DCM) afforded a yellow oil (373 mg). ¹H NMR (400 MHz, CDCl₃) δ ppm 1.33-1.46 (2H, m), 1.50-1.67 (4H, m), 2.01-2.08 (2H, m), 2.55-2.68 (2H, m), 2.83 (2H, s), 3.20-3.28 (1H, m), 3.38 (3H, s), 4.19 (2H, t), 4.90 (1H, s, 22%), 4.92 (1H, s, 6%), 5.42 (1H, s, 22%), 5.43 (1H, 6%), 6.80 (1H, dd), 6.95 (1H, d) and 7.13 (1H, d).

Step 4

A solution of 1'-(dideuteriomethylene)-4-methoxy-6'-(3,3,3-trifluoropropoxy)spiro[cyclohexane-1,2'-indane] (373 mg, 1.09 mmol) in THF (3.75 mL) and ACN (3.75 mL) at 22° C. was treated with isocyanatosilver (489 mg, 3.27 mmol) and molecular iodine (415 mg, 1.63 mmol). The resulting suspension was stirred for 1 h, filtered through Celite and concentrated to leave a yellow solid. The solid was redissolved in THF (5 mL) and ammonium hydroxide (1 mL) was added. The mixture was stirred at r.t. for 18 h, concentrated and the residue partitioned between EtOAc (20 mL) and H₂O (20 mL). The organic layer was washed with sat. aq. NaHCO₃ (10 mL), dried (Na₂SO₄) and evaporated to leave a yellow gum (440 mg). Flash chromatography [10 g Si cartridge, 0-10% of (0.1M NH₃ in MeOH) and DCM afforded a yellow gum (390 mg) which was further purified by flash chromatography to yield a white foam (290 mg). ¹H NMR (400 MHz, CDCl₃) δ ppm 1.12-1.33 (3H, m), 1.37-1.53 (3H, m), 1.88-1.96 (2H, m), 2.47-2.59 (2H, m), 2.61 (1H, d), 2.81 (1H, d), 3.00-3.09 (1H, m), 3.25 (3H, s), 3.59 (2H, bd s), 4.02 (1H, s, 22%), 4.05 (1H, s, 6%), 4.10 (2H, t), 4.45 (1H, s, 22%), 4.48 (1H, s, 6%), 6.67 (1H, dd), 6.71 (1H, d) and 7.02 (1H, d). LCMS: rt=2.84 min, m/z=399/400/401 [M+H]+.

Compound 46: {5-((1r,4r)-2"-amino-4-methoxy-3'H,5"H-dispiro[cyclohexane-1,2'-indene-1',4"-oxazol]-6'-yl)nicotinonitrile formate Salt}

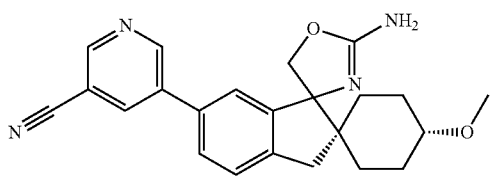

The title compound (49 mg, white solids) was prepared according to General Procedure 1 using (1r,4r)-6'-bromo-4-methoxy-3-methyl-3'H,5"H-dispiro[cyclohexane-1,2'-indene-1',4"-oxazol]-2"-amine (122 mg, 0.33 mmol) and (5-cyano-3-pyridyl)boronic acid (49 mg, 0.33 mmol). ¹H NMR (400 MHz, CD₃OD) δ ppm 1.31-1.45 (3H, m), 1.50-1.66 (3H, m), 2.02-2.12 (2H, m), 3.05 (2H, q), 3.16-3.27 (m, 1H), 3.37 (3H, s), 4.67 (1H, d), 5.04 (1H, d), 7.46 (1H, d), 7.68 (1H, dd), 7.74 (1H, d), 8.49 (1H, s), 8.88 (1H, s) and 9.08 (1H, s). LCMS: rt=2.54 min, m/z=389 [M+H]+, purity=100%.

Compound 47: {(1r,1'R,4R)-4-methoxy-6'-(pyrimidin-5-yl)-3'H,5"H-dispiro[cyclohexane-1,2'-indene-1',4"-oxazol]-2"-amine formate Salt}

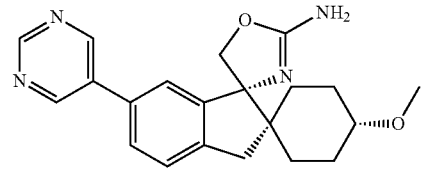

The title compound (57 mg, white solids) was prepared according to General Procedure 1 using (1r,1'R,4R)-6'-bromo-4-methoxy-3-methyl-3'H,5"H-dispiro[cyclohexane-1,2'-indene-1',4"-oxazol]-2"-amine (61 mg, 0.17 mmol) and pyrimidin-5-ylboronic acid (41 mg, 0.33 mmol). ¹H NMR (400 MHz, CD₃OD) δ ppm 1.30-1.46 (3H, m), 1.52-1.70 (3H, m), 2.02-2.13 (2H, m), 3.06 (2H, q), 3.16-3.27 (1H, m), 3.37 (3H, s), 4.75 (1H, d), 5.12 (1H, d), 7.49 (1H, d), 7.72 (1H dd), 7.78 (1H, d), 9.09 (2H, d) and 9.14 (1H, d). LCMS: rt=2.40 min, m/z=365 [M+H]+, purity=100%.

Compound 48: {(1r,4r)-4-methoxy-6'-(5-methylpyridin-3-yl)-3'H,5"H-dispiro[cyclohexane-1,2'-indene-1',4"-oxazol]-5",5"-d₂-2"-amine formate Salt}

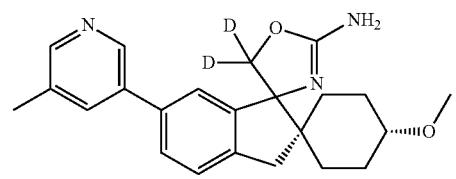

The title compound (14 mg, white solids) was prepared according to General Procedure 1 using (1r,4r)-6'-bromo-4-methoxy-3-methyl-3'H,5"H-dispiro[cyclohexane-1,2'-indene-1',4"-oxazol]-5",5"-d₂-2"-amine (83 mg, 0.23 mmol) and (5-methyl-3-pyridyl)boronic acid (31 mg, 0.23 mmol). ¹H NMR (400 MHz, CD₃OD) δ ppm 1.31-1.46 (3H, m), 1.51-1.69 (3H, m), 2.02-2.12 (2H, m), 2.43 (3H, s), 3.03 (2H, q), 3.15-3.26 (1H, m), 3.37 (3H, s), 7.42 (1H, d), 7.63 (1H, d), 7.68 (1H, s), 7.94 (1H, s), 8.36 (1H, s) and 8.59 (1H, s). LCMS: rt=2.24 min, m/z=380 [M+H]+, 98.9%.

Compound 49: Mixture of 4 diastereomers {3-((1S,3S,4S)-2"-amino-4-hydroxy-3-methyl-3'H,5"H-dispiro[cyclohexane-1,2'-indene-1',4"-oxazol]-6'-yl-5",5"-d₂)-5-methoxybenzonitrile TFA Salt}

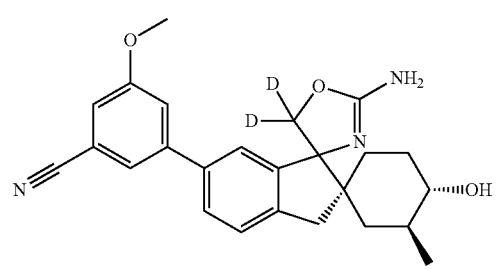

Step 1: 3-((1S,3S,4S)-2"-amino-4-((tert-butyldiphenylsilyl)oxy)-3-methyl-3'H,5"H-dispiro[cyclohexane-1,2'-indene-1',4"-oxazol]-6'-yl-5",5"-d2)-5-methoxybenzonitrile Under N$_2$ at r.t., a mixture of (1S,3S,4S)-6'-bromo-4-((tert-butyldiphenylsilyl)oxy)-3-methyl-3'H,5"H-dispiro[cyclohexane-1,2'-indene-1',4"-oxazol]-5",5"-d2-2"-amine (200 mg, 0.080 mmol), 1,1-bis(di-tert-butylphosphino)ferrocene palladium dichloride (22 mg, 0.030 mmol) and 3-methoxy-5-(4,4,5,5-tetramethyl-1,3,2-dioxaborolan-2-yl)benzonitrile (86 mg, 0.33 mmol) in 1,4-dioxane (6 mL) was treated with a solution of K$_2$CO$_3$ (137 mg, 0.99 mmol) in water (1 mL), heated at 100° C. for 20 h and cooled to r.t. Deloxan (Pd scavenger resin) was added (spatula end) and the mixture was stirred for 30 min. The suspension was filtered and washed with DCM (30 mL). The dark brown filtrate was concentrated to leave a black residue (338 mg) which was purified by flash column chromatography (20-100% EtOAc in petroleum ether) to give a yellow oil (150 mg). $^1$H NMR (400 MHz, CDCl$_3$) δ ppm 0.76-1.32 (15H, m), 1.33-1.79 (4H, m), 2.80 (1H, t), 2.99 (1H, t), 3.14-3.26 (1H, m), 3.85 (3H, s), 7.04-7.07 (1H, m), 7.25-7.43 (10H, m), 7.64-7.71 (5H, m). LCMS: rt=5.68 min, m/z=658/659 [M+H]$^+$.

Step 2: Mixture of 4 diastereomers {3-((1S,3S,4S)-2"-amino-4-hydroxy-3-methyl-3'H,5"H-dispiro[cyclohexane-1,2'-indene-1',4"-oxazol]-6'-yl-5",5"-d$_2$)-5-methoxybenzonitrile}

A solution of 3-((1S,3S,4S)-2"-amino-4-((tert-butyldiphenylsilyl)oxy)-3-methyl-3'H,5"H-dispiro[cyclohexane-1,2'-indene-1',4"-oxazol]-6'-yl-5",5"-d$_2$)-5-methoxybenzonitrile (150 mg, 0.060 mmol) in THF (5 mL) was treated with tetrabutylammonium fluoride (1M in THF) (0.63 mL, 0.63 mmol), stirred under N$_2$ r.t. for 24 h, treated with additional tetrabutylammonium fluoride (1.0M in THF) (1.26 mL, 1.26 mmol) was added to the mixture and stirring was continued at 40° C. for 24 h. The mixture was cooled to r.t., treated with H$_2$O (80 mL) and extracted with DCM (2×100 mL). The combined organic layers were dried over Na$_2$SO$_4$ and evaporated give a dark brown oil. Purification on silica (40 g cartridge, eluting DCM+MeOH 2-5%) yielded two products.

1$^{st}$ product (racemate): further purified by HPLC (ACN/H$_2$O+0.1% TFA) to give first diastereomer (14 mg). $^1$H NMR (400 MHz, CD$_3$OD) δ ppm 1.03 (3H, d), 1.24 (1H, t), 1.39-1.68 (5H, m), 1.91-1.97 (1H, m), 3.01-3.13 (3H, m), 3.90 (3H, s), 7.28 (1H, dd), 7.43 (1H, d), 7.47 (1H, dd), 7.59 (1H, dd), 7.66 (1H, dd), 7.71 (1H, d). LCMS: rt=3.30 min, m/z=420 [M+H]$^+$, purity=98%.

2$^{nd}$ product (racemate): further purified by HPLC (ACN/H$_2$O+0.1% TFA) to give first diastereomer (8 mg). $^1$H NMR (400 MHz, CD$_3$OD) δ ppm 0.97-1.14 (4H, m), 1.47-1.65 (5H, m) 1.91-1.98 (1H, m), 2.99-3.16 (3H, m), 3.90 (3H, s), 7.28 (1H, dd), 7.43 (1H, d), 7.47 (1H, dd), 7.59 (1H, dd), 7.66 (1H, dd), 7.72 (1H, d). LCMS: rt=3.37 min, m/z=420 [M+H]$^+$, purity=100%.

Compound 50: {(1r,4r)-4-methoxy-6'-(pyrimidin-5-yl)-3'H,5"H-dispiro[cyclohexane-1,2'-indene-1',4"-oxazol]-2"-amine formate Salt}

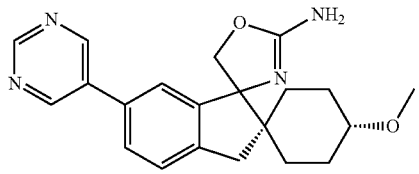

The title compound (85 mg, floculent solids) was prepared according to General Procedure 1 using (1r,4r)-6'-bromo-4-methoxy-3'H,5"H-dispiro[cyclohexane-1,2'-indene-1',4"-oxazol]-2"-amine (122 mg, 0.33 mmol) and pyrimidin-5-ylboronic acid (42 mg, 0.33 mmol). $^1$H NMR (400 MHz, CD$_3$OD) δ ppm 1.32-1.46 (3H, m), 1.51-1.68 (3H, m), 2.02-2.12 (2H, m), 3.05 (2H, q), 3.17-3.27 (1H, m), 3.37 (3H, s), 4.70 (1H, d), 5.07 (1H, d), 7.48 (1H,), 7.69 (1H, dd), 7.76 (1H, d), 9.08 (2H, s) and 9.12 (1H, s). LCMS: rt=2.35 min, m/z=365 [M+H]$^+$, purity=100%.

Compound 51: {(1r,4r)-6'-isopentyl-4-methoxy-3'H,5"H-dispiro[cyclohexane-1,2'-indene-1',4"-oxazol]-2"-amine}

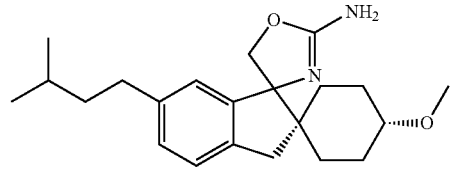

A solution of (1r,4r)-4-methoxy-6'-(3-methylbut-1-yn-1-yl)-3'H,5"H-dispiro[cyclohexane-1,2'-indene-1',4"-oxazol]-2"-amine (67 mg, 0.19 mmol) in MeOH (10 mL) was treated with 10% Pd—C (20 mg), stirred at r.t. under H$_2$ at atmospheric pressure for 2 h, treated with 10% Pd—C (20 mg), stirred at r.t. for additional 18 h, filtered and concentrated. Purification by HPLC (FractionLynx, 0.1% formic, ACN) yielded title compound as a white solid (41 mg). $^1$H NMR (400 MHz, CD$_3$OD) δ ppm 0.93 (6H, d), 1.21-1.40 (3H, m), 1.42-1.60 (6H, m), 1.95-2.05 (2H, m), 2.59 (2H, t), 2.84 (2H, q), 3.10-3.19 (1H, m), 3.35 (3H, s), 4.22 (1H, d), 4.65 (1H, d), 7.01-7.12 (4H, m). LCMS: rt=2.84 min, m/z=357 [M+H]$^+$, purity=100%.

Compound 52: {3-((1r,3R,4r,5S)-2"-amino-4-methoxy-3,5-dimethyl-3'H,5"H-dispiro[cyclohexane-1,2'-indene-1',4"-oxazol]-6'-yl-5",5"-d$_2$)-5-chlorobenzonitrile}

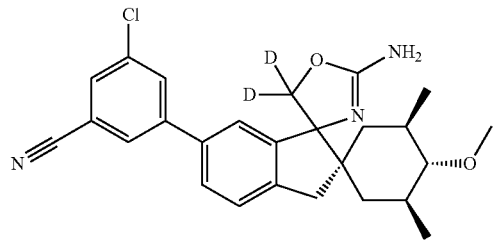

Under N$_2$, a mixture of (1r,3R,4r,5S)-6'-bromo-4-methoxy-3,5-dimethyl-3'H,5"H-dispiro[cyclohexane-1,2'-indene-1',4"-oxazol]-5",5"-d$_2$-2"-amine (150 mg), 3-chloro-5-(4,4,5,5-tetramethyl-1,3,2-dioxaborolan-2-yl)benzonitrile (200 mg), cesium carbonate (371 mg), tetrakis(triphenylphosphine) palladium (66 mg) and DMF (3 mL) was heated in microwave reactor at 130° C. for 1 h. The mixture was cooled to r.t., filtered through Celite and evaporated. The crude product was purified by prep-TLC (5% MeOH in DCM) and HPLC to give title compound (14 mg, solid). $^1$H NMR (400 MHz, CDCl$_3$): 0.99-1.02 (6H, dd), 1.25-1.34

(2H, dd), 1.45-1.59 (2H, m), 1.63-1.69 (2H, m), 2.32-2.37 (1H, t), 2.79 (1H, d), 3.00 (1H, d), 3.45 (3H, s), 4.25 (2H, br), 7.29 (1H, d), 7.37-7.39 (2H, m), 7.56-7.57 (1H, t), 7.73-7.74 (1H, t), 7.77-7.79 (1H, t). LCMS: rt=7.76 min, m/z=452.0 [M+H]$^+$, purity=98.0%.

Compound 53: {(E)-2"-amino-4-methoxy-3'H,5"H-dispiro[cyclohexane-1,2'-indene-1',4"-oxazole]-5",5"-d$_2$-6'-carbaldehyde O-propyl oxime}

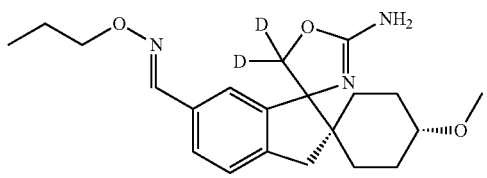

A solution of (1r,4r)-2"-amino-4-methoxy-3'H,5"H-dispiro[cyclohexane-1,2'-indene-1',4"-oxazole]-5",5"-d$_2$-6'-carbaldehyde (0.10 g, 0.32 mmol) in EtOH (10 mL) was treated with 1-(aminooxy)propane hydrochloride (0.07 g, 0.65 mmol) and triethylamine (0.14 mL, 1.0 mmol) and stirred at r.t. for 5 h. The mixture was concentrated, treated with DCM (50 ml), washed with water (3×25 mL), dried (Na$_2$SO$_4$ and evaporated. Purification on silica (12 g cartridge, eluting DCM+MeOH 0-6%) followed by purification by prep. RP-HPLC (eluting ACN/water+0.1% TFA) yielded the title compound (20 mg, dry film). $^1$H NMR (400 MHz, CDCl$_3$) δ ppm 0.95 (3H, t), 1.21-1.38 (3H, m), 1.44-1.53 (2H, m), 1.59-1.65 (1H, m), 1.68-1.75 (2H, m), 1.99-2.07 (2H, m), 2.75 (1H, d), 2.97 (1H, d), 3.08-3.16 (1H, m), 3.34 (3H, s), 4.09 (2H, t), 7.18 (1H, d), 7.37 (1H, d), 7.51 (1H, s), 8.03 (1H, s). LCMS: rt=2.89 min, m/z=374 [M+H]$^+$.

Compound 56: {(E)-2"-amino-4-methoxy-3'H,5"H-dispiro[cyclohexane-1,2'-indene-1',4"-oxazole]-5",5"-d$_2$-6'-carbaldehyde O-ethyl oxime}

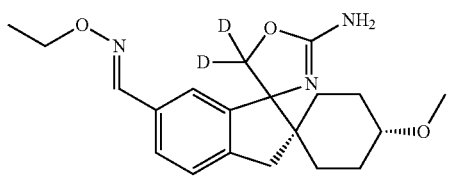

At r.t., a solution of (1r,4r)-2"-amino-4-methoxy-3'H,5"H-dispiro[cyclohexane-1,2'-indene-1',4"-oxazole]-5",5"-d$_2$-6'-carbaldehyde (0.10 g, 0.32 mmol) in EtOH (10 mL) was treated with ethoxyamine hydrochloride (0.06 g, 0.65 mmol) and triethylamine (0.14 mL, 1.0 mmol) and stirred for 5 h. The mixture was concentrated in vacuo, treated with DCM (50 mL) and washed with water (3×25 mL). The organic phase was dried (Na$_2$SO$_4$), filtered and evaporated. Purification on silica (12 g cartridge, DCM+MeOH 0-6%) followed by purification by HPLC (Xterra, ACN/water+0.1% TFA) and HPLC (Xterra, ACN/water+0.2% NH$_4$OH) gave the title compound as a dry film (20 mg). $^1$H NMR (400 MHz, CDCl$_3$) δ ppm 1.20-1.65 (9H, m), 1.95-2.07 (2H, m), 2.76 (1H, dd), 2.96 (1H, dd), 3.06-3.16 (1H, m), 3.33-3.36 (3H, m), 4.16-4.22 (2H, m), 7.17-7.25 (1H, m), 7.36-7.39 (1H, m), 7.50 (1H, d), 8.02 (1H, d). LCMS: rt=2.96 min, m/z=360 [M+H]$^+$.

Compound 57: {(1R,3R,4R)-2"-amino-3-methyl-6'-(pyrimidin-5-yl)-3'H,5"H-dispiro[cyclohexane-1,2'-indene-1',4"-oxazol]-5",5"-d$_2$-4-ol TFA Salt}

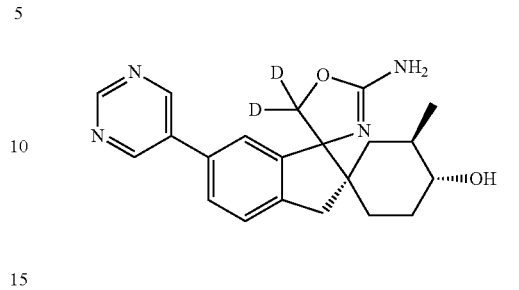

Step 1: (1R,3R,4R)-4-((tert-butyldiphenylsilyl)oxy)-3-methyl-6'-(pyrimidin-5-yl)-3'H,5"H-dispiro[cyclohexane-1,2'-indene-1',4"-oxazol]-5",5"-d2-2"-amine The title compounds (198 mg, brown oil, mixture of 4 diastereomers) were prepared according to General Procedure 1 using (1R,3R,4R)-6'-bromo-4-((tert-butyldiphenylsilyl)oxy)-3-methyl-3'H,5"H-dispiro[cyclohexane-1,2'-indene-1',4"-oxazol]-5",5"-d2-2"-amine and (1S,3S,4S)-6'-bromo-4-((tert-butyldiphenylsilyl)oxy)-3-methyl-3'H,5"H-dispiro[cyclohexane-1,2'-indene-1',4"-oxazol]-5",5"-d2-2"-amine (200 mg, 0.082 mmol) and .pyrimidin-5-ylboronic acid (81 mg, 0.66 mmol). $^1$H NMR (400 MHz, CDCl$_3$) δ ppm 0.76-1.78 (22H, m), 2.81 (1H, t), 3.02 (1H, t), 3.16-3.28 (1H, m), 7.26-7.44 (10H, m), 7.60-7.72 (3H, m), 8.88 (2H, s), 9.13 (1H, s). LCMS: rt=4.81 min, m/z=605 [M+H]$^+$.

Step 2: {(1R,3R,4R)-2"-amino-3-methyl-6'-(pyrimidin-5-yl)-3'H,5"H-dispiro[cyclohexane-1,2'-indene-1',4"-oxazol]-5",5"-d2-4-ol}

A solution of the (1R,3R,4R)-4-((tert-butyldiphenylsilyl)oxy)-3-methyl-6'-(pyrimidin-5-yl)-3'H,5"H-dispiro[cyclohexane-1,2'-indene-1',4"-oxazol]-5",5"-d$_2$-2"-amine (198 mg, 0.080 mmol) in THF (5 mL) was treated with tetrabutylammonium fluoride (1.0M in THF) (0.76 mL, 2.62 mmol), stirred under N$_2$ at 40° C. for 18 h, treated with additional tetrabutylammonium fluoride (1.0M in THF) (0.76 mL, 2.62 mmol) and stirred for 48 h. The mixture was treated with water (80 mL) and extracted with DCM (2×100 mL). The combined organic layers were dried (Na$_2$SO$_4$) and evaporated to give a dark brown oil. Purification on silica (40 g cartridge, DCM+MeOH 2-6%) gave the desired product as a mixture of diasteresoisomers. Further purification by HPLC (Xterra, ACN/water+0.1% TFA) gave 2 products.

1$^{st}$ product: clear oil (51 mg). $^1$H NMR (400 MHz, CD$_3$OD) δ ppm 0.96-1.07 (3H, m), 1.21-1.31 (1H, m), 1.39-1.84 (5H, m), 1.90-1.99 (1H, m), 3.02-3.18 (3H, m), 7.49 (1H, m), 7.72-7.85 (2H, m), 9.09 (2H, br, s), 9.15 (1H, br, s). LCMS rt=2.62 min, m/z=367 [M+H]$^+$, purity=98%.

2$^{nd}$ product: white solid (26 mg). $^1$H NMR (400 MHz, CD$_3$OD) δ ppm 0.99-1.15 (4H, m), 1.50-1.65 (5H, m) 1.91-2.00 (1H, m), 3.05-3.18 (3H, m), 7.48-7.53 (1H, m), 7.72-7.85 (2H, m), 9.09 (1H, br, s), 9.16 (1H, br, s). LCMS: rt=2.69 min, m/z=367 [M+H]$^+$, purity=98%.

Compound 58: {3-((1R,3R,4R)-2"-amino-4-hydroxy-3-methyl-3'H,5"H-dispiro[cyclohexane-1,2'-indene-1',4"-oxazol]-6'-yl-5",5"-d₂)-5-methoxybenzonitrile TFA Salt}

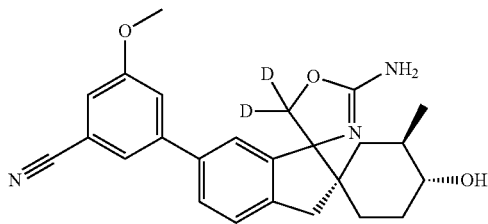

A solution of 3-((1R,3R,4R)-2"-amino-4-((tert-butyldiphenylsilyl)oxy)-3-methyl-3'H,5"H-dispiro[cyclohexane-1,2'-indene-1',4"-oxazol]-6'-yl-5",5"-d₂)-5-methoxybenzonitrile (150 mg, 0.060 mmol) in THF (5 mL) was treated with tetrabutylammonium fluoride (1.0M in THF, 0.63 mL, 0.63 mmol) stirred under N₂ at r.t. for 24 h, treated with additional tetrabutylammonium fluoride (1.0M in THF, 0.63 mL, 0.63 mmol), stirred for 12 h, treated with tetrabutylammonium fluoride (1.0M in THF, 0.63 mL, 0.6300 mmol) and stirred at 40° C. for 12 h. The mixture was treated with water (80 mL) and extracted with DCM (2×100 mL). The combined organic layers were dried (Na₂SO₄) and evaporated to give a dark brown oil. Purification on silica (40 g cartridge, DCM+MeOH 2-5%) gave two products.

1ˢᵗ product: Purification by HPLC (Xterra, ACN/water+ 0.1% TFA) gave a white solid (14 mg). ¹H NMR (400 MHz, CD₃OD) δ ppm 1.03 (3H, d), 1.24 (1H, t), 1.39-1.68 (5H, m), 1.91-1.97 (1H, m), 3.01-3.13 (3H, m), 3.90 (3H, s), 7.28 (1H, dd), 7.43 (1H, d), 7.47 (1H, dd), 7.59 (1H, dd), 7.66 (1H, dd), 7.71 (1H, d). LCMS: rt=3.30 min, m/z=420 [M+H]⁺, purity=98%.

2ⁿᵈ product: Purification by HPLC (Xterra, ACN/water+ 0.1% TFA) gave a dry film (8 mg).
¹H NMR (400 MHz, CD₃OD) δ ppm 0.97-1.14 (4H, m), 1.47-1.65 (5H, m) 1.91-1.98 (1H, m), 2.99-3.16 (3H, m), 3.90 (3H, s), 7.28 (1H, dd), 7.43 (1H, d), 7.47 (1H, dd), 7.59 (1H, dd), 7.66 (1H, dd), 7.72 (1H, d). LCMS: rt=3.37 min, m/z=420 [M+H]⁺, purity=100%.

Compound 59: (1r,4r)-4-methoxy-6'-(pyridazin-3-yl)-3'H,5"H-dispiro[cyclohexane-1,2'-indene-1',4"-oxazol]-2"-amine

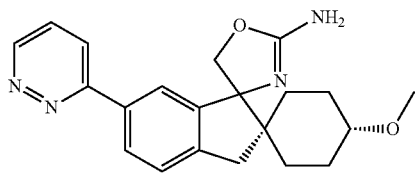

Step 1: tert-butyl((1r,4r)-6'-(6-chloropyridazin-3-yl)-4-methoxy-3'H,5"H-dispiro[cyclohexane-1,2'-indene-1',4"-oxazol]-2"-yl)carbamate A mixture of tert-butyl ((1r,4r)-6'-bromo-4-methoxy-3'H,5"H-dispiro[cyclohexane-1,2'-indene-1',4"-oxazol]-2"-yl) carbamate (232 mg, 0.50 mmol), (dppf)PdCl₂ (33 mg, 0.050 mmol), potassium acetate (147 mg, 1.50 mmol) and 4,4,5,5-tetramethyl-2-(4,4,5,5-tetramethyl-1,3,2-dioxaborolan-2-yl)-1,3,2-dioxaborolane (253 mg, 1.0 mmol) in DMF (5 mL) was degassed with N₂, heated at 60° C. for 18 h and cooled to r.t. The mixture was treated with 3,6-dichloropyridazine (111 mg, 0.75 mmol) and a solution of Cs₂CO₃ (488 mg, 1.50 mmol) in water (2 mL), heated at 60° C. for 8 h and cooled to r.t. The mixture was treated with additional 3,6-dichloropyridazine (111 mg, 0.75 mmol), (dppf)PdCl₂ (33 mg, 0.050 mmol) and Cs₂CO₃ (244 mg, 0.75 mmol), heated at 60° C. for 18 hours and cooled to r.t. The mixture was evaporated and the residue dissolved in DCM (30 mL) and washed with water (30 mL). The organic layer was separated, dried (Na₂SO₄) and evaporated to leave a black oil (630 mg). Flash chromatography (12 g Si cartridge, 2.5% (0.1N NH₃ (MeOH/DCM) afforded a pale brown gum (165 mg) which was used for the next step. ¹H NMR (400 MHz, CDCl₃) δ ppm 1.25-1.55 (5H, m), 1.44 (9H, s), 1.62-1.70 (1H, m), 1.98-2.08 (2H, m), 2.82 (1H, d), 3.04 (1H, s), 3.04 (1H, d), 3.04-3.14 (1H, m), 3.32 (3H, s), 4.22 (1H, d), 4.68 (1H, d), 7.35 (1H, d), 7.55 (1H, d), 8.00 (1H, d) and 7.92-7.98 (2H, m). LCMS: rt=3.02 min, m/z=499/501 [M+H]⁺ (mono-Boc).

Step 2: (1r,4r)-4-methoxy-6'-(pyridazin-3-yl)-3'H,5"H-dispiro[cyclohexane-1,2'-indene-1',4"-oxazol]-2"-amine A suspension of 10% Pd on CaCO₃ (111 mg, 0.050 mmol) and tert-butyl ((1r,4r)-6'-(6-chloropyridazin-3-O-4-methoxy-3'H,5"H-dispiro[cyclohexane-1,2'-indene-1',4"-oxazol]-2"-yl)carbamate (131 mg, 0.26 mmol) in MeOH (10 mL) was vigorously stirred under H₂ for 2 h, filtered through Celite and washed with MeOH (5 mL). The filtrate was evaporated to leave a dark red gum (121 mg) which was dissolved in DCM (2 mL) and TFA (0.2 mL). The mixture was stirred at r.t. for 5 h and evaporated to leave a dark brown gum (240 mg) which was subjected to HPLC (aq. 0.1% formic acid/ACN). Further purification by flash chromatography (Si 4 g cartridge, 10% 0.1M NH₃ in MeOH/ DCM) afforded a cream solid (35 mg). ¹H NMR (400 MHz, CDCl₃) δ ppm 1.12-1.38 (3H, m), 1.40-1.52 (2H, m), 1.58-1.67 (1H, m), 1.90-2.04 (2H, m), 2.79 (1H, d), 2.98 (1H, d), 3.02-3.13 (1H, m), 3.30 (3H, s), 4.29 (1H, d), 4.54 (1H, d), 7.29 (1H, d), 7.45 (1H, dd), 7.76-7.84 (2H, m), 7.98 (1H, d) and 9.06 (1H, d). LCMS: rt=2.31 min, m/z=365 [M+H]⁺, purity=100%.

Compound 60: {(E)-1-((1r,4r)-2"-amino-4-methoxy-3'H,5"H-dispiro[cyclohexane-1,2'-indene-1',4"-oxazol]-6'-yl-5",5"-d₂)ethan-1-one O-(3,3,3-trifluoropropyl)oxime}

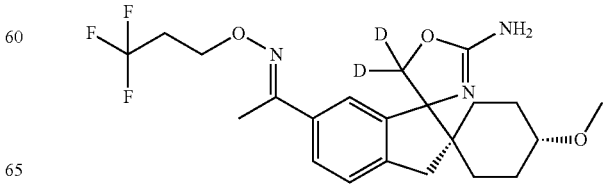

Step 1

A solution of 1-((1r,4r)-2"-amino-4-methoxy-3'H,5"H-dispiro[cyclohexane-1,2'-indene-1',4"-oxazol]-6'-yl-5",5"-d$_2$)ethan-1-one (0.11 g, 0.17 mmol) in EtOH (10 mL) was treated with O-(3,3,3-trifuoropropyl)hydroxylamine hydrochloride (0.06 g, 0.35 mmol) and triethylamine (0.08 mL, 0.54 mmol) and stirred at r.t. for 5 h. The mixture was evaporated and the residue dissolved in DCM (50 mL), washed with water (3×25 mL), dried (Na$_2$SO$_4$) and evaporated. Purification by HPLC (Xterra, ACN/water+0.2% NH$_4$OH) gave the tile compound as a dry film (30 mg). $^1$H NMR (400 MHz, CDCl$_3$) δ ppm 1.20-1.65 (6H, m), 1.95-2.02 (2H, m), 2.15 (3H, s), 2.40-3.30 (2H, m), 2.44-2.56 (2H, m), 2.71 (1H, d), 2.97 (1H, d), 3.05-3.11 (1H, m), 3.29 (3H, s), 4.34 (2H, t), 7.16 (1H, d), 7.46 (1H, d). LCMS: rt=3.13 min, m/z=442 [M+H]$^+$.

Compound 61: {(E)-2"-amino-4-methoxy-3'H,5"H-dispiro[cyclohexane-1,2'-indene-1',4"-oxazole]-5",5"-d$_2$-6'-carbaldehyde O-cyclobutyl oxime}

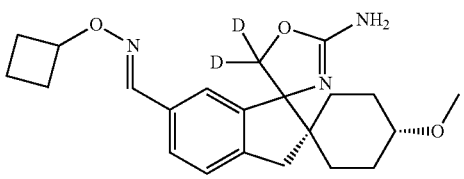

Step 1

A solution of (1r,4r)-2"-amino-4-methoxy-3'H,5"H-dispiro[cyclohexane-1,2'-indene-1',4"-oxazole]-5",5"-d$_2$-6'-carbaldehyde (0.10 g, 0.32 mmol) in EtOH (10 mL) was treated with O-cyclobutylhydroxyalmine hydrochloride (0.08 g, 0.65 mmol) and triethylamine (0.14 mL, 1 mmol) and stirred at r.t. for 5 h. The mixture was concentrated in vacuo, treated with DCM (50 mL) and washed with water (3×25 mL). The organic phase was dried (Na$_2$SO$_4$) and evaporated. Purification by HPLC (Xterra, eluting ACN/water+0.2% NH$_4$OH) gave the title compound as a dry film (40 mg). $^1$H NMR (400 MHz, CDCl$_3$) δ ppm 1.13-1.33 (3H, m), 1.38-1.46 (2H, m), 1.48-1.59 (2H, m), 1.67-1.77 (1H, m), 1.90-2.00 (2H, m), 2.02-2.13 (2H, m), 2.21-2.29 (2H, m), 2.35-3.15 (2H, m), 2.69 (1H, d), 2.87 (1H, d), 3.01-3.10 (1H, m), 3.29 (3H, s), 4.68 (1H, q), 7.11 (1H, d), 7.30 (1H, dd), 7.42 (1H, d), 7.99 (1H, s). LCMS: rt=3.06 min, m/z=386 [M+H]$^+$.

Compound 62: {(1r,4r)-4-methoxy-6'-(pyridazin-4-yl)-3'H,5"H-dispiro[cyclohexane-1,2'-indene-1',4"-oxazol]-2"-amine formate Salt}

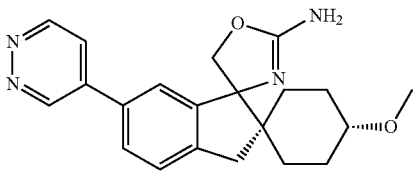

The title compound (49 mg, white solids) was prepared according to General Procedure 1 using (1r,4r)-6'-bromo-4-methoxy-3'H,5"H-dispiro[cyclohexane-1,2'-indene-1',4"-oxazol]-2"-amine (122 mg, 0.33 mmol) and 4-(4,4,5,5-tetramethyl-1,3,2-dioxaborolan-2-yl)pyridazine (68 mg, 0.33 mmol). $^1$H NMR (400 MHz, CD$_3$OD) δ ppm 1.29-1.45 (3H, m), 1.50-1.65 (3H, m), 2.02-2.12 (2H, m), 3.05 (2H, q), 3.16-3.27 (1H, m), 3.37 (3H, s), 4.67 (1H, d), 5.05 (1H, d), 7.51 (1H, d), 7.83 (1H, dd), 7.88 (1H, d), 8.02 (1H, dd), 9.20 (1H, d) and 9.56 (1H, d). LCMS: rt=2.31 min, m/z=365 [M+H]$^+$, 729 [2M+H]$^+$, purity=100%.

Compound 63: {(1S,3S,4S)-2"-amino-3-methyl-6'-(pyrimidin-5-yl)-3'H,5"H-dispiro[cyclohexane-1,2'-indene-1',4"-oxazol]-5",5"-d$_2$-4-ol TFA Salt}

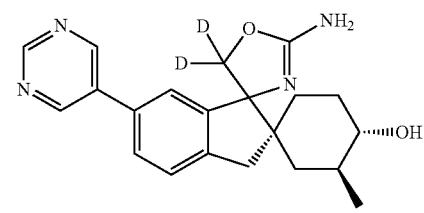

A solution of (1S,3S,4S)-4-((tert-butyldiphenylsilyl)oxy)-3-methyl-6'-(pyrimidin-5-yl)-3'H,5"H-dispiro[cyclohexane-1,2'-indene-1',4"-oxazol]-5",5"-d$_2$-2"-amine (198 mg, 0.080 mmol) in THF (5 mL) was treated with tetrabutylammonium fluoride (1.0M in THF, 0.76 mL, 2.62 mmol), stirred under N$_2$ at 40° C. 24 h, treated with additional tetrabutylammonium fluoride (1.0M in THF, 0.76 mL, 2.62 mmol) and stirred for 48 h. The mixture was treated with water (80 mL) and extracted with DCM (2×100 mL). The combined organic layers were dried (Na$_2$SO$_4$) and evaporated to give a dark brown oil. Purification on silica (40 g cartridge, DCM+MeOH 2-6%) gave the desired product as a mixture of diasteresoisomers. This mixture was purified by HPLC (Xterra, ACN/water+0.1% TFA) to afford two products.

1$^{st}$ product: clear oil (51 mg). $^1$H NMR (400 MHz, CD$_3$OD) δ ppm 0.96-1.07 (3H, m), 1.21-1.31 (1H, m), 1.39-1.84 (5H, m), 1.90-1.99 (1H, m), 3.02-3.18 (3H, m), 7.49 (1H, m), 7.72-7.85 (2H, m), 9.09 (2H, br, s), 9.15 (1H, br, s). LCMS: rt=2.62 min, m/z=367 [M+H]$^+$, purity=98%.

2$^{nd}$ product: white solid (26 mg). $^1$H NMR (400 MHz, CD$_3$OD) δ ppm 0.99-1.15 (4H, m), 1.50-1.65 (5H, m) 1.91-2.00 (1H, m), 3.05-3.18 (3H, m), 7.48-7.53 (1H, m), 7.72-7.85 (2H, m), 9.09 (1H, br, s), 9.16 (1H, br, s). LCMS: rt=2.69 min, m/z=367 [M+H]$^+$, purity=98%.

Compound 64: {(1r,4r)-4-methoxy-3'H,5"H-dispiro[cyclohexane-1,2'-indene-1',4"-oxazole]-2"-amine formate Salt}

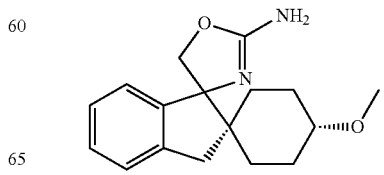

A solution of (1r,4r)-6'-bromo-4-methoxy-3'H,5"H-dispiro[cyclohexane-1,2'-indene-1',4"-oxazol]-2"-amine (100 mg, 0.27 mmol) in MeOH (10 mL) was treated with 10% Pd on carbon (29 mg, 0.030 mmol) and stirred at r.t. under $H_2$ for 21 h. The mixture was filtered through Celite and evaporated. Purification by HPLC (FractionLynx, 0.1% formic, ACN) gave a white solid (38 mg). $^1$H NMR (400 MHz, CD$_3$OD) δ ppm 1.28-1.43 (m, 3H), 1.48-1.63 (m, 3H), 2.00-2.10 (m, 2H), 2.97 (q, 2H), 3.15-3.25 (m, 1H), 3.36 (s, 3H), 4.59 (d, 1H), 4.98 (d, 1H), 7.25-7.40 (m, 4H). LCMS: rt=2.53 min, m/z=287 [M+H]$^+$, purity=100%.

Compound 65: {(E)-1-((1r,4r)-2"-amino-4-methoxy-3'H,5"H-dispiro[cyclohexane-1,2'-indene-1',4"-oxazol]-6'-yl-5",5"-d$_2$)ethan-1-one O-ethyl oxime}

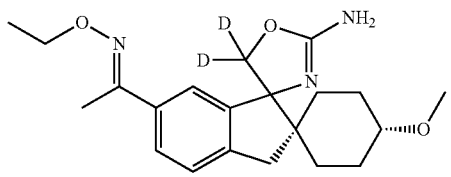

A solution of 1-((1r,4r)-2"-amino-4-methoxy-3'H,5"H-dispiro[cyclohexane-1,2'-indene-1',4"-oxazol]-6'-yl-5",5"-d$_2$)ethan-1-one (0.11 g, 0.17 mmol) in EtOH (10 mL) was treated with ethoxyamine hydrochloride (0.03 g, 0.35 mmol) and triethylamine (0.08 mL, 0.54 mmol) and stirred at r.t. for 5 h. The mixture was concentrated in vacuo, treated with DCM (50 mL) and washed with water (3×25 mL). The organic phase was dried (Na$_2$SO$_4$) and evaporated. Purification HPLC Xterra, ACN/water+0.2% NH$_4$OH) gave the title compound as a dry film (40 mg). $^1$H NMR (400 MHz, CDCl$_3$) δ ppm 1.15-1.61 (9H, m), 1.70-2.50 (2H, m), 1.95-2.03 (2H, m), 2.12 (3H, s), 2.70 (2H, d), 2.96 (2H, d), 3.04-3.12 (1H, m), 3.29 (3H, s), 4.02 (2H, t), 7.16-7.18 (1H, m), 7.36-7.39 (2H, m). LCMS: rt=2.74 min, m/z=374 [M+H]$^+$.

Compound 66: {(1S,1'R,3S,4S)-6'-(5-fluoropyridin-3-yl)-4-(methoxy-d$_3$)-3-methyl-3'H,5"H-dispiro[cyclohexane-1,2'-indene-1',4"-oxazol]-5",5"-d$_2$-2"-amine}

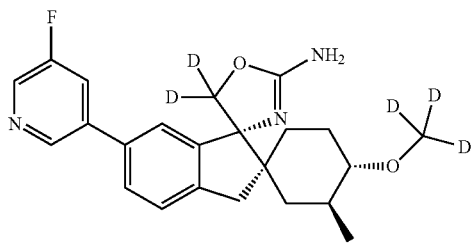 [SMILES: [2H]C([2H])([2H])O[C@H]1CC[C@@]2(Cc3ccc(-c4cncc(F)c4)cc3[C@]23N=C(N)OC3([2H])[2H])C[C@@H]1C]

The title compound (22 mg, solids) was prepared according to General Procedure 1 using (1S,1'R,3S,4S)-6'-bromo-4-(methoxy-d3)-3-methyl-3'H,5"H-dispiro[cyclohexane-1,2'-indene-1',4"-oxazol]-5",5"-d2-2"-amine (35 mg, 0.09 mmol) and 5-fluoropyridine-3-boronic acid (50 mg, 0.18 mmol). $^1$H NMR (400 MHz, CD$_3$OD, 35° C.) δ ppm 0.94 (3H, d), 1.05 (1H, t), 1.27 (1H, m), 1.5-1.7 (4H, m), 2.08 (1H, dq), 2.73 (1H, td), 2.95 (2H, ABq), 7.33 (1H, d), 7.52 (2H, br. s), 7.90 (1H, dt), 8.41 (1H, s), 8.65 (1H, s), 2H not observed. LCMS: rt=3.18 min, m/z=401 [M+H]$^+$, purity=97.5%.

Compound 67: {(1R,1'R,3R,4R)-6'-(2-fluoropyridin-3-yl)-4-methoxy-3-methyl-3'H,5"H-dispiro[cyclohexane-1,2'-indene-1',4"-oxazol]-5",5"-d$_2$-2"-amine}

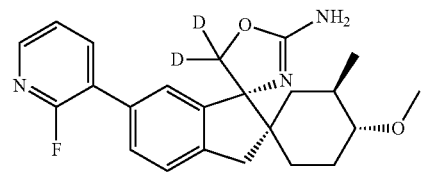 [SMILES: [2H]C1([2H])OC(N)=N[C@]12c1cc(-c3cccnc3F)ccc1C[C@]21CC[C@@H](OC)[C@H](C)C1]

The title compound (42 mg, solids) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d2-2"-amine (57 mg, 0.15 mmol) and 2-fluoropyridine-3-boronic acid (42 mg, 0.30 mmol). $^1$H NMR (400 MHz, CD$_3$OD) δ ppm 0.97 (3H, d), 1.24-1.38 (3H, m), 1.52-1.64 (3H, m), 2.08-2.16 (1H, m), 2.69-2.76 (1H, m), 2.94 (2H, AB q), 3.37 (3H, s), 7.33 (1H, d), 7.36-7.48 (3H, m), 8.03 (1H, t) and 8.15 (1H, d). LCMS: rt=3.25 min, m/z=398 [M+H]$^+$, purity=98.3%.

Compound 68: {(1S,1'R,3S,4S)-3-ethyl-4-methoxy-6'-(pyrimidin-5-yl)-3'H,5"H-dispiro[cyclohexane-1,2'-indene-1',4"-oxazol]-5",5"-d$_2$-2"-amine}

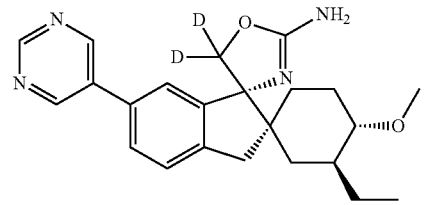 [SMILES: [2H]C1([2H])OC(N)=N[C@]12c1cc(-c3cncnc3)ccc1C[C@@]21CC[C@H](OC)[C@@H](CC)C1]

The title compound (22 mg, white solids) was prepared according to General Procedure 1 using (1S,1'R,3S,4S)-6'-bromo-3-ethyl-4-methoxy-3'H,5"H-dispiro[cyclohexane-1,2'-indene-1',4"-oxazol]-5",5"-d$_2$-2"-amine (35 mg, 0.090 mmol) and pyrimidin-5-ylboronic acid (30 mg, 0.24 mmol). $^1$H NMR (400 MHz, CD$_3$OD, 35° C.) δ ppm 0.82 (3H, t), 0.97 (1H, t), 1.10-1.20 (1H, m), 1.20-1.35 (1H, m), 1.35-1.65 (4H, m), 1.70-1.80 (1H, m), 2.11 (1H, dt), 2.82 (1H, td), 2.95 (2H, ABq), 3.37 (3H, s), 7.39 (1H, d), 7.55 (2H, m), 9.04 (2H, s), 9.10 (1H, s), 2H not observed. LCMS: rt=3.19 min, m/z=395 [M+H]$^+$, purity=100%.

Compound 69: {(1R,1'R,3R,4R)-4-methoxy-3-methyl-6'-(pyrazin-2-yl)-3'H,5"H-dispiro[cyclohexane-1,2'-indene-1',4"-oxazol]-5",5"-d$_2$-2"-amine}

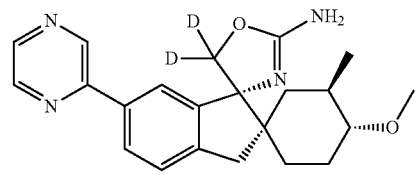 [SMILES: [2H]C1([2H])OC(N)=N[C@]12c1cc(-c3cnccn3)ccc1C[C@]21CC[C@@H](OC)[C@H](C)C1]

A solution of (1R,1'R,3R,4R)-6'-bromo-4-methoxy-3-methyl-3'H,5"H-dispiro[cyclohexane-1,2'-indene-1',4"-oxazol]-5",5"-d₂-2"-amine (35 mg, 0.09 mmol) in 1,4-dioxane (3 mL) under N₂ was treated at r.t. with Pd(PPh₃)₄ (10.6 mg, 0.0100 mmol) followed by tributyl(pyrazin-2-yl)stannane (68 mg, 0.18 mmol), heated at 100° C. for 18 h and cooled to r.t. Deloxan (Pd scavenger) was added and the mixture was stirred at r.t., for 1 h, filtered and evaporated to leave a brown oil (160 mg). Purification by HPLC (Gilson, 0.2% NH₃/ACN) gave title compound as a floculent white solid (2 mg). ¹H NMR (400 MHz, CD₃OD) δ ppm 0.98 (3H, d), 1.24-1.38 (3H, m), 1.50-1.62 (3H, m), 2.08-2.14 (1H, m), 2.70-2.76 (1H, m), 2.97 (2H, AB q), 3.37 (3H, s), 7.38 (1H, d), 7.94 (1H, dd), 7.96 (1H, s), 8.50 (1H, d), 8.65 (1H, d) and 9.09 (1H, s). LCMS: rt=3.10 min, m/z=381 [M+H]⁺, purity=100%.

Compound 70: (1S,1'R,3S,4S)-4-methoxy-3-methyl-6'-(4-methylpyrimidin-5-yl)-3'H,5"H-dispiro[cyclohexane-1,2'-indene-1',4"-oxazol]-5",5"-d₂-2"-amine}

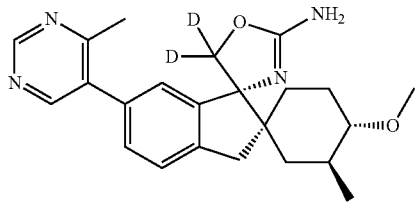 [SMILES: [2H]C1([2H])OC(N)=N[C@]12c1cc(-c3cncnc3C)ccc1C[C@@]21CC[C@H](OC)[C@@H](C)C1]

The title compound (12 mg, white solids) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (19 mg, 0.05 mmol) and 4-methyl-5-(4,4,5,5-tetramethyl-1,3,2-dioxaborolan-2-yl)pyrimidine (65 mg, 0.15 mmol). ¹H NMR (400 MHz, CD₃OD, 35° C.) δ ppm 0.96 (3H, d), 1.03 (1H, t), 1.25-1.30 (1H, m), 1.45-1.7 (4H, m), 2.05-2.15 (1H, m), 2.50 (3H, s), 2.73 (1H, td), 2.98 (2H, ABq), 3.38 (3H, s), 7.24 (2H, brs), 7.38 (1H, d), 8.53 (1H, s), 8.97 (1H, s), 2H not observed. LCMS: rt=3.03 min, m/z=395 [M+H]⁺, purity=98.2%.

Compound 71: {(1S,1'R,3S,4S)-4-(methoxy-d₃)-3-methyl-6'-(pyrimidin-5-yl)-3'H,5"H-dispiro[cyclohexane-1,2'-indene-1',4"-oxazol]-5",5"-d₂-2"-amine}

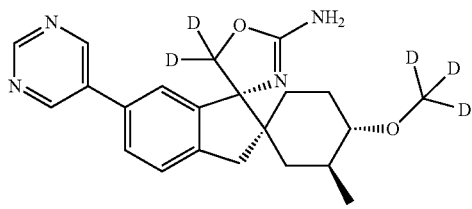 [SMILES: [2H]C([2H])([2H])O[C@H]1CC[C@@]2(Cc3ccc(-c4cncnc4)cc3[C@]23N=C(N)OC3([2H])[2H])C[C@@H]1C]

The title compound (22 mg, floculent solids) was prepared according to General Procedure 1 using (1S,1'R,3S,4S)-6'-bromo-4-(methoxy-d₃)-3-methyl-3'H,5"H-dispiro[cyclohexane-1,2'-indene-1',4"-oxazol]-5",5"-d₂-2"-amine (35 mg, 0.09 mmol) and pyrimidin-5-ylboronic acid (23 mg, 0.18 mmol). ¹H NMR (400 MHz, CD₃OD) δ ppm 0.96 (3H, d), 1.04 (1H, t), 1.22-1.34 (1H, m), 1.47-1.68 (4H, m), 2.08-2.14 (1H, m), 2.69-2.78 (1H, m), 2.95 (2H, AB q), 7.39 (1H, d), 7.55-7.59 (2H, m), 9.05 (2H, s) and 9.10 (1H, s). LCMS: rt=2.97 min, m/z=384 [M+H]⁺, purity=98.5%.

Compound 72: {(1S,1'R,3S,4S)-4-(methoxy-d₃)-3-methyl-6'-(pyrazin-2-yl)-3'H,5"H-dispiro[cyclohexane-1,2'-indene-1',4"-oxazol]-5",5"-d₂-2"-amine}

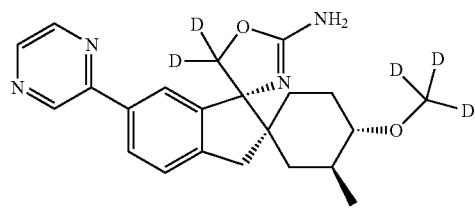 [SMILES: [2H]C([2H])([2H])O[C@H]1CC[C@@]2(Cc3ccc(-c4cnccn4)cc3[C@]23N=C(N)OC3([2H])[2H])C[C@@H]1C]

A mixture of 2-tributylstannyl)pyrazine (192 mg, 0.26 mmol), (1S,1'R,3S,4S)-6'-bromo-4-(methoxy-d₃)-3-methyl-3'H,5"H-dispiro[cyclohexane-1,2'-indene-1',4"-oxazol]-5",5"-d₂-2"-amine (50 mg, 0.13 mmol), Pd(Ph₃P)₄ (15 mg, 0.01 mmol) in 1,4-dioxane (3 mL) was flushed with N₂ and heated at 100° C. for 12 h, cooled to r.t., treated with Deloxan (Pd scavenger) and MeOH, stirred for 1 h at r.t., filtered and evaporated. Purification by HPLC (Xbridge, ACN (30-95%)/water+0.2% NH₃) gave the title compound (9 mg). ¹H NMR (400 MHz, CD₃OD, 35° C.) δ ppm 0.94 (3H, d), 1.05 (1H, t), 1.32 (1H, qd), 1.5-1.7 (4H, m), 2.08 (1H, dq), 2.73 (1H, td), 2.95 (2H, ABq), 7.36 (1H, d), 7.90-7.95 (2H, m), 8.48 (1H, d), 8.63 (1H, d), 9.06 (1H, s), 2H not observed. LCMS: rt=3.06 min, m/z=384 [M+H]⁺, purity=97.5%.

Compound 73: {(1R,1'R,3R,4R)-4-(methoxy-d₃)-3-methyl-6'-(pyrimidin-5-yl)-3'H,5"H-dispiro[cyclohexane-1,2'-indene-1',4"-oxazol]-5",5"-d₂-2"-amine}

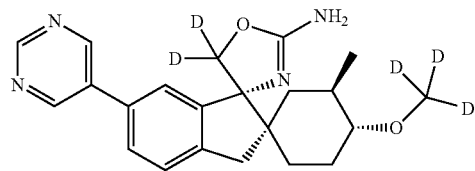 [SMILES: [2H]C([2H])([2H])O[C@@H]1CC[C@]2(Cc3ccc(-c4cncnc4)cc3[C@]23N=C(N)OC3([2H])[2H])C[C@H]1C]

The title compound (29 mg, floculent solids) was prepared according to General Procedure 1 using (1R,1'R,3R,4R)-6'-bromo-4-(methoxy-d3)-3-methyl-3'H,5"H-dispiro[cyclohexane-1,2'-indene-1',4"-oxazol]-5",5"-d2-2"-amine (35 mg, 0.09 mmol) and pyrimidin-5-ylboronic acid (23 mg, 0.18 mmol). ¹H NMR (400 MHz, CD₃OD) δ ppm 0.97 (3H, d), 1.24-1.38 (3H, m), 1.50-1.64 (3H, m), 2.08-2.16 (1H, m), 2.69-2.76 (1H, m), 2.95 (2H, AB q), 7.39 (1H, d), 7.55 (1H, s), 7.56 (1H, m), 9.05 (1H, s) and 9.10 (1H, s). LCMS: rt=3.00 min, m/z=384 [M+H]⁺, purity=98.6%.

Compound 74: {(1S,1'R,3S,4S)-6'-(2-fluoropyridin-3-yl)-4-(methoxy-d₃)-3-methyl-3'H,5"H-dispiro[cyclohexane-1,2'-indene-1',4"-oxazol]-5",5"-d₂-2"-amine}

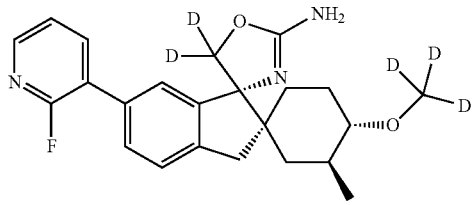 [SMILES: [2H]C([2H])([2H])O[C@H]1CC[C@@]2(Cc3ccc(-c4cccnc4F)cc3[C@]23N=C(N)OC3([2H])[2H])C[C@@H]1C]

The title compound (20 mg, solids) was prepared according to General Procedure 1 using (1S,1'R,3S,4S)-6'-bromo-4-(methoxy-d3)-3-methyl-3'H,5"H-dispiro[cyclohexane-1,2'-indene-1',4"-oxazol]-5",5"-d2-2"-amine (35 mg, 0.09 mmol) and 2-fluoropyridine-3-boronic acid (50 mg, 0.18 mmol). ¹H NMR (400 MHz, CD₃OD, 35° C.) δ ppm 0.94 (3H, d), 1.05-1.30 (1H, t), 1.32 (1H, qd), 1.50-1.70 (4H, m), 2.08 (1H, dq), 2.73 (1H, td), 2.95 (2H, ABq), 7.33 (1H, d), 7.38 (1H, m), 7.42 (2H, s), 8.01 (1H, t), 8.14 (1H, d), 2H not observed. LCMS: rt=3.22 min, m/z=401 [M+H]⁺, purity=98.1%.

Compound 75: {(1R,1'R,3R,4R)-3-ethyl-4-methoxy-6'-(pyrimidin-5-yl)-3'H,5"H-dispiro[cyclohexane-1,2'-indene-1',4"-oxazol]-5",5"-d₂-2"-amine}

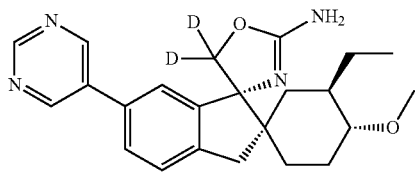 [SMILES: [2H]C1([2H])OC(N)=N[C@]12c1cc(-c3cncnc3)ccc1C[C@]21CC[C@@H](OC)[C@H](CC)C1]

The title compound (20 mg, solids) was prepared according to General Procedure 1 using (1R,1'R,3R,4R)-6'-bromo-3-ethyl-4-methoxy-3'H,5"H-dispiro[cyclohexane-1,2'-indene-1',4"-oxazol]-5",5"-d2-2"-amine (35 mg, 0.09 mmol) and pyrimidin-5-ylboronic acid (40 mg, 0.32 mmol). ¹H NMR (400 MHz, CD₃OD, 35° C.) δ ppm 0.83 (3H, t), 1.10-1.50 (5H, m), 1.55 (1H, d), 1.66 (1H, d), 1.75-1.85 (1H, m), 2.13 (1H, d), 2.82 (1H, td), 2.95 (2H, ABq), 3.37 (3H, s), 7.39 (1H, d), 7.55 (2H, m), 9.04 (2H, s), 9.10 (1H, s), 2H not observed. LCMS: rt=3.11 min, m/z=395 [M+H]⁺, purity=99.1%.

Compound 76: (1S,1'R,3S,4S)-6'-(2,5-difluoropyridin-3-yl)-4-methoxy-3-methyl-3'H,5"H-dispiro[cyclohexane-1,2'-indene-1',4"-oxazol]-5",5"-d2-2"-amine

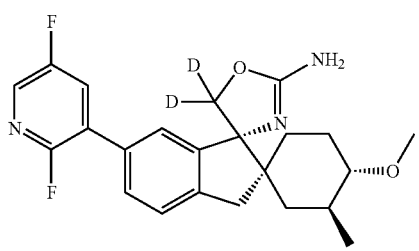 [SMILES: [2H]C1([2H])OC(N)=N[C@]12c1cc(-c3cc(F)cnc3F)ccc1C[C@@]21CC[C@H](OC)[C@@H](C)C1]

A mixture of K₂CO₃ (25 mg, 0.18 mmol), 1,1-bis(di-tert-butylphosphino)ferrocene palladium dichloride (10 mg, 0.02 mmol), (2,5-difluoro-3-pyridyl)boronic acid (45 mg, 0.14 mmol) and (1S,1'R,3S,4S)-6'-bromo-4-methoxy-3-methyl-3'H,5"H-dispiro[cyclohexane-1,2'-indene-1',4"-oxazol]-5",5"-d2-2"-amine (19 mg, 0.05 mmol) in 1,4-dioxane (3 mL) was treated with water (0.5 mL) and stirred under N₂ at 100° C. for 1 h. The mixture was cooled to r.t. diluted with MeOH, treated with Deloxan (Pd scavenge), filtered and evaporated. Purification by HPLC (Xbridge, ACN (30-70%)/water+0.2% NH₃) gave the title compound as a white solid (10 mg). ¹H NMR (400 MHz, CD₃OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 3.38 (3H, s), 7.34 (1H, d), 7.44 (2H, br. s), 7.86 (1H, td), 8.03 (1H, s), 2H not observed. LCMS: rt=3.44 min, m/z=416 [M+H]⁺, purity=100%.

Compound 77: (1r,1'R,4R)-4-methoxy-6'-(5-methylpyridin-3-yl)-3'H,5"H-dispiro[cyclohexane-1,2'-indene-1',4"-oxazol]-2"-amine formate Salt

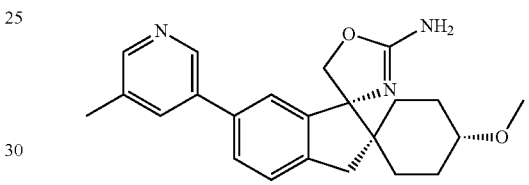

The title compound (25 mg, floculent white solids) was prepared according to General Procedure 1 using (1r,1'R,4R)-6'-bromo-4-methoxy-3'H,5"H-dispiro[cyclohexane-1,2'-indene-1',4"-oxazol]-2"-amine (61 mg, 0.17 mmol) and (5-methyl-3-pyridyl)boronic acid (46 mg, 0.33 mmol). ¹H NMR (400 MHz, CD₃OD) δ ppm 1.25-1.44 (3H, m), 1.50-1.66 (3H, m), 2.00-2.11 (2H, m), 2.43 (3H, s), 2.99 (2H, q), 3.12-3.24 (1H, m), 3.36 (3H, s), 4.64 (1H, d), 4.95 (1H, d), 7.40 (1H, d), 7.59 (1H, dd), 7.61 (1H, s), 7.93 (1H, s), 8.35 (1H, d) and 8.58 (1H, d). LCMS: rt=2.22 min, m/z=378 [M+H]⁺, purity 99.1%.

Compound 78: (1R,1'R,3R,4R)-6'-(2-fluoropyridin-3-yl)-4-(methoxy-d₃)-3-methyl-3'H,5"H-dispiro[cyclohexane-1,2'-indene-1',4"-oxazol]-5",5"-d₂-2"-amine

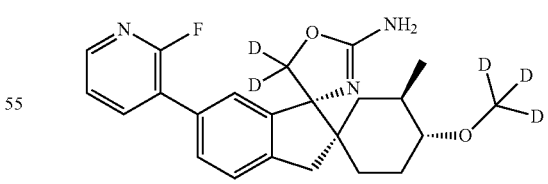

The title compound (26 mg, floculent solid) was prepared according to General Procedure 1 using (1R,1'R,3R,4R)-6'-bromo-4-(methoxy-d3)-3-methyl-3'H,5"H-dispiro[cyclohexane-1,2'-indene-1',4"-oxazol]-5",5"-d2-2"-amine (35 mg, 0.090 mmol) and 2-fluoropyridine-3-boronic acid (26 mg, 0.18 mmol). ¹H NMR (400 MHz, CD₃OD) δ ppm 0.97 (3H, d), 1.22-1.38 (3H, m), 1.50-1.63 (3H, m), 2.08-2.14 (1H, m), 2.68-2.76 (1H, m), 2.94 (2H, AB q), 7.33 (1H, d), 7.38-7.46 (3H, m), 8.04 (1H, td) and 8.15 (1H, dd). LCMS: rt=3.26 min, m/z=401 [M+H]+, purity 99.4%.

Compound 79: (1R,1'R,3R,4R)-6'-(5-fluoropyridin-3-yl)-4-(methoxy-d₃)-3-methyl-3'H,5"H-dispiro[cyclohexane-1,2'-indene-1',4"-oxazol]-5",5"-d₂-2"-amine

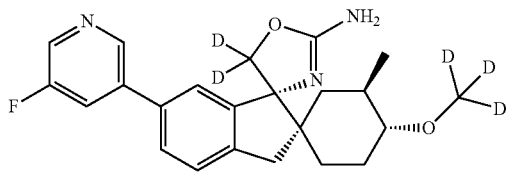 [SMILES: [2H]C([2H])([2H])O[C@@H]1CC[C@]2(Cc3ccc(-c4cncc(F)c4)cc3[C@]23N=C(N)OC3([2H])[2H])C[C@H]1C]

The title compound (25 mg, floculent solid) was prepared according to General Procedure 1 using (1R,1'R,3R,4R)-6'-bromo-4-(methoxy-d3)-3-methyl-3'H,5"H-dispiro[cyclohexane-1,2'-indene-1',4"-oxazol]-5",5"-d2-2"-amine (35 mg, 0.090 mmol) and 5-fluoropyridine-3-boronic acid (26 mg, 0.18 mmol). ¹H NMR (400 MHz, CD₃OD) δ ppm 0.97 (3H, d), 1.24-1.36 (3H, m), 1.48-1.62 (3H, m), 2.08-2.14 (1H, m), 2.69-2.76 (1H, m), 2.94 (2H, AB q), 7.35 (1H, d), 7.52 (1H, d), 7.53 (1H, dd), 7.90 (1H, dt), 8.42 (1H, d) and 8.66 (1H, d). LCMS: rt=3.26 min, m/z=401 [M+H]+, purity=99.2%.

Compound 80: (1R,1'R,3R,4R)-4-(methoxy-d₃)-3-methyl-6'-(pyridin-3-yl)-3'H,5"H-dispiro[cyclohexane-1,2'-indene-1',4"-oxazol]-5",5"-d₂-2"-amine

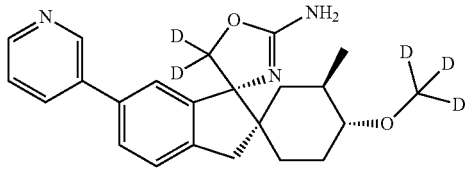 [SMILES: [2H]C([2H])([2H])O[C@@H]1CC[C@]2(Cc3ccc(-c4cccnc4)cc3[C@]23N=C(N)OC3([2H])[2H])C[C@H]1C]

The title compound (25 mg, floculent solid) was prepared according to General Procedure 1 using (1R,1'R,3R,4R)-6'-bromo-4-(methoxy-d3)-3-methyl-3'H,5"H-dispiro[cyclohexane-1,2'-indene-1',4"-oxazol]-5",5"-d2-2"-amine (35 mg, 0.090 mmol) and 3-pyridylboronic acid (22 mg, 0.18 mmol). ¹H NMR (400 MHz, CD₃OD) δ ppm 0.97 (3H, d), 1.22-1.36 (3H, m), 1.50-1.62 (3H, m), 2.08-2.14 (1H, m), 2.69-2.76 (1H, m), 2.93 (2H, AB q), 7.34 (1H, d), 7.49-7.53 (2H, m), 8.07 (1H, dd), 8.48 (1H, d) and 8.76 (1H, d). LCMS: rt=2.74 min, m/z=383 [M+H]+, purity=98.7%.

Compound 81: (1R,1'R,3R,4R)-4-(methoxy-d₃)-3-methyl-6'-(pyrazin-2-yl)-3'H,5"H-dispiro[cyclohexane-1,2'-indene-1',4"-oxazol]-5",5"-d₂-2"-amine

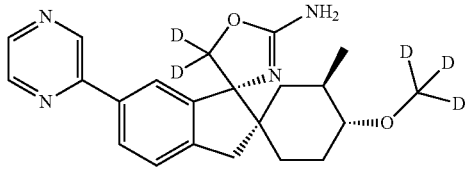 [SMILES: [2H]C([2H])([2H])O[C@@H]1CC[C@]2(Cc3ccc(-c4cnccn4)cc3[C@]23N=C(N)OC3([2H])[2H])C[C@H]1C]

A solution of (1R,1'R,3R,4R)-6'-bromo-4-(methoxy-d3)-3-methyl-3'H,5"H-dispiro[cyclohexane-1,2'-indene-1',4"-oxazol]-5",5"-d2-2"-amine (35 mg, 0.09 mmol) in 1,4-dioxane (3 mL) under N₂ was treated with Pd(PPh₃)₄ (15 mg, 0.010 mmol) followed by tributyl(pyrazin-2-yl)stannane (96 mg, 0.26 mmol). The mixture was heated at 100° C. for 18 h, cooled to r.t. treated with Deloxan (Pd scavenger) and stirred at r.t. for 1h. The mixture was filtered and evaporated to leave a brown oil (~160 mg). Purification by HPLC (Gilson, 0.2% NH₃/ACN) afforded a floculent white solid (7 mg). ¹H NMR (400 MHz, CD₃OD) δ ppm 0.98 (3H, d), 1.22-1.38 (3H, m), 1.48-1.62 (3H, m), 2.06-2.12 (1H, m), 2.68-2.76 (1H, m), 2.96 (2H, AB q), 7.38 (1H, d), 7.94 (1H, dd), 7.96 (1H, s), 8.50 (1H, d), 8.65 (1H, dd), 9.08 (1H, d). LCMS: rt=3.11 min, m/z=384 [M+H]+, purity=98.2%.

Compound 82: (1r,4r)-4-methoxy-6'-(pyrimidin-5-yl)-5",6"-dihydro-3'H-dispiro[cyclohexane-1,2'-indene-1',4"-[1,3]oxazin]-6",6"-d₂-2"-amine TFA salt

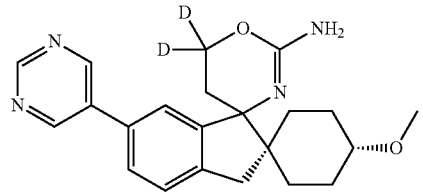

A mixture of (1r,4r)-6'-bromo-4-methoxy-5",6"-dihydro-3'H-dispiro[cyclohexane-1,2'-indene-1',4"-[1,3]oxazin]-6",6"-d2-2"-amine (35 mg, 0.090 mmol) and pyrimidin-5-ylboronic acid (25 mg, 0.20 mmol) in 1,4-dioxane (5 mL) was treated with 1,1-bis(di-tert-butylphosphino)ferrocene palladium dichloride (16 mg, 0.020 mmol) and K₂CO₃ (60 mg, 0.43 mmol) in water (1 mL). The mixture was heated under N₂ at 100° C. for 3 h, cooled to r.t., acidified with 1M aq. HCl. Purification by HPLC (Xterra, ACN (10-70%)/water+0.1% TFA) gave the title compound as a hygroscopic solid (14 mg). ¹H NMR (400 MHz, CD₃OD, 35° C.) δ ppm 1.4-1.6 (4H, m), 1.7 (1H, td), 1.8 (1H, d), 2.1 (2H, brt), 2.24 (1H, d), 2.58 (1H, d), 3.00 (1H, d), 3.16 (1H, d), 3.20 (1H, m), 3.37 (3H, s), 7.50 (1H, d), 7.70 (1H, dd), 7.73 (1H, d), 9.08 (2H, s), 9.14 (1H, s), 3H not observed. LCMS: rt=2.4 min, m/z=381 [M+H]+, purity=100%.

Compound 83: 3-((1r,4r)-2"-amino-4-methoxy-5",6"-dihydro-3'H-dispiro[cyclohexane-1,2'-indene-1',4"-[1,3]oxazin]-6'-yl-6",6"-d₂)-5-chlorobenzonitrile TFA Salt

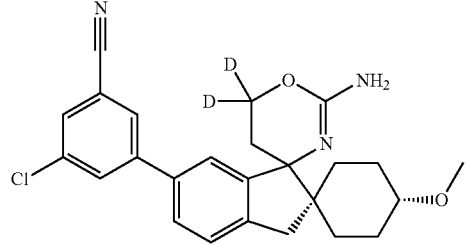

A mixture of 1,1-bis(di-tert-butylphosphino)ferrocene palladium dichloride (15 mg, 0.020 mmol), (1r,4r)-6'-bromo-4-methoxy-5",6"-dihydro-3'H-dispiro[cyclohexane-1,2'-indene-1',4"-[1,3]oxazin]-6",6"-d$_2$-2"-amine (65 mg, 0.17 mmol) and 3-chloro-5-(4,4,5,5-tetramethyl-1,3,2-dioxaborolan-2-yl)benzonitrile (110 mg, 0.42 mmol) in 1,4-dioxane (10 mL) under an N$_2$ was treated with a solution of K$_2$CO$_3$ (80 mg, 0.58 mmol) in water (1 mL), heated at 100° C. for 18 h and treated with Deloxan (Pd scavenger resin). The mixture was stirred for 30 min, filtered and evaporated to leave a brown residue. Purification by HPLC (Xterra, ACN (10-70%)/water+0.1% TFA) gave the title compound as a solid (3 mg). $^1$H NMR (400 MHz, CD$_3$OD) δ ppm 1.28-1.55 (4H, m), 1.60 (1H, td), 1.68 (1H, brd), 2.00-2.15 (2H, m), 2.22 (1H, d), 2.58 (1H, d), 3.00 (1H, d), 3.18 (1H, d), 3.20 (1H, m), 3.37 (3H, s), 7.45 (1H, d), 7.68 (1H, d), 7.70 (1H, s), 7.77 (1H, s), 7.99 (2H, m), 3H not observed. LCMS: rt=3.55 min, m/z=346/348 [M+H]$^+$, purity=100%.

Compound 84: 5-((1r,4r)-2"-amino-4-methoxy-5", 6"-dihydro-3'H-dispiro[cyclohexane-1,2'-indene-1', 4"-[1,3]oxazin]-6'-yl-6",6"-d$_2$)nicotinonitrile bis TFA Salt

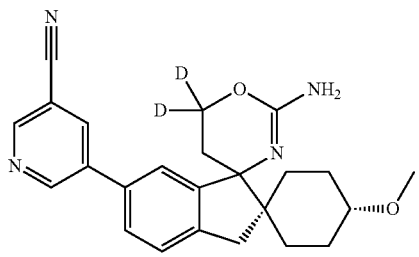

The title compound (25 mg, solids) was prepared according to General Procedure 1 using (1r,4r)-6'-bromo-4-methoxy-5",6"-dihydro-3'H-dispiro[cyclohexane-1,2'-indene-1',4"-[1,3]oxazin]-6",6"-d2-2"-amine (110 mg, 0.29 mmol) and (5-cyano-3-pyridyl)boronic acid (85 mg, 0.57 mmol). $^1$H NMR (400 MHz, CD$_3$OD) δ ppm 1.30-1.55 (4H, m), 1.60 (1H, td), 1.70 (1H, brd), 2.00-2.15 (2H, brt), 2.24 (1H, d), 2.59 (1H, d), 3.00 (1H, d), 3.16 (1H, d), 3.20 (1H, m), 3.37 (3H, s), 7.49 (1H, d), 7.70 (1H, d), 7.72 (1H, s), 8.50 (1H, s), 8.88 (1H, br. s), 9.09 (1H, br. s), 4H not observed. LCMS: rt=3.10 min, m/z=405 [M+H]$^+$, purity=95.1%.

Compound 85: 3-((1r,4r)-2"-amino-4-methoxy-5", 6"-dihydro-3'H-dispiro[cyclohexane-1,2'-indene-1', 4"-[1,3]oxazin]-6'-yl-6",6"-d$_2$)-5-methoxybenzonitrile TFA Salt

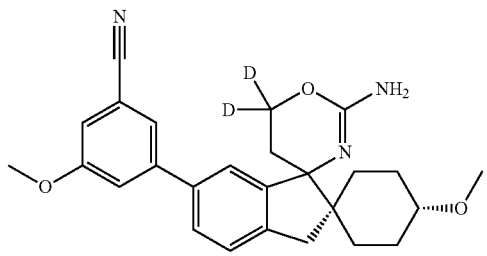

The title compound (22 mg, white solids) was prepared according to General Procedure 1 using (1r,4r)-6'-bromo-4-methoxy-5",6"-dihydro-3'H-dispiro[cyclohexane-1,2'-indene-1',4"-[1,3]oxazin]-6",6"-d2-2"-amine (100 mg, 0.17 mmol) and 3-methoxy-5-(4,4,5,5-tetramethyl-1,3,2-dioxaborolan-2-yl)benzonitrile (80 mg, 0.31 mmol). $^1$H NMR (400 MHz, CD$_3$OD, 35° C.) δ ppm 1.35-1.55 (4H, m), 1.60 (1H, td), 1.70 (1H, brd), 2.00-2.20 (2H, m), 2.27 (1H, d), 2.56 (1H, d), 3.00 (1H, d), 3.20 (1H, d), 3.25 (1H, m), 3.37 (3H, s), 3.90 (3H, s), 7.26 (1H, dd), 7.42 (1H, d), 7.46 (1H, t), 7.58 (1H, t), 7.61 (1H, s), 7.62 (1H, dd), 3H not observed. LCMS: rt=3.47 min, m/z=434 [M+H]$^+$.

Compound 86: Mixture of (1'R,4'S)-4'-methoxy-6"-(pyrimidin-5-yl)-3"H,5'''H-trispiro[cyclopropane-1, 3'-cyclohexane-1',2"-indene-1",4'''-oxazol]-5''',5'''-d2-2'''-amine and (1'S,4'R)-4'-methoxy-6"-(pyrimidin-5-yl)-3"H,5'''H-trispiro[cyclopropane-1, 3'-cyclohexane-1',2"-indene-1",4'''-oxazol]-5''',5'''-d$_2$-2'''-amine

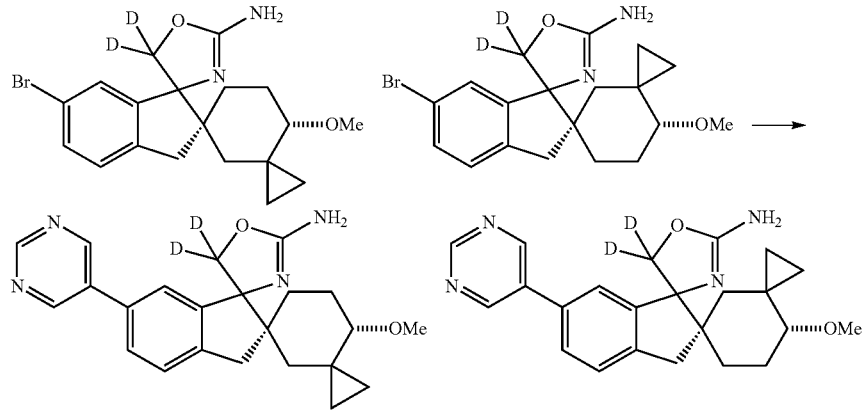

The title compound (22 mg, flocculent solids) was prepared according to General Procedure 1 using (1'R,4'S)-6"-bromo-4'-methoxy-3"H,5'''H-trispiro[cyclopropane-1,3'-cyclohexane-1',2"-indene-1",4'''-oxazol]-5''',5'''-d2-2'''-amine; (1'S,4'R)-6"-bromo-4'-methoxy-3"H,5'''H-trispiro[cyclopropane-1,3'-cyclohexane-1',2"-indene-1",4'''-oxazol]-5''',5'''-d$_2$-2'''-amine (35 mg, 0.09 mmol) and pyrimidin-5-ylboronic acid (22 mg, 0.18 mmol). ¹H NMR (400 MHz, CD₃OD) δ ppm −0.09 to −0.01 (1H, m), 0.20-0.29 (1H, m), 0.56-0.63 (1H, m), 0.71-0.79 (1H, m), 0.88-0.96 (1H, m), 1.23-1.47 (2.5H, m), 1.51-1.71 (1.5H, m), 1.83-1.89 (0.5H, m), 2.01-2.10 (1.5H, m), 2.91-3.20 (2H, m), 3.21-3.28 (1H, m), 3.29 (3H, d), 7.38 (1H, dd), 7.53-7.58 (2H, m), 9.04 (2H, s), 9.10 (1H, s). LCMS: rt=3.16 min, m/z=383 [M+H]⁺, purity=99.2%.

Compound 87: Mixture of (1'R,4'S)-4'-methoxy-6"-(pyridin-3-yl)-3"H,5"'H-trispiro[cyclopropane-1,3'-cyclohexane-1',2"-indene-1",4'''-oxazol]-5''',5'''-d₂-2'''-amine and (1'S,4'R)-4'-methoxy-6"-(pyridin-3-yl)-3"H,5'''H-trispiro[cyclopropane-1,3'-cyclohexane-1',2"-indene-1",4'''-oxazol]-5''',5'''-d₂-2'''-amine

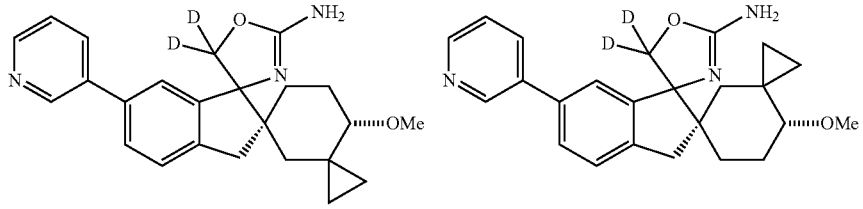

The title compound (24 mg, flocculent solids) was prepared according to General Procedure 1 using (1'R,4'S)-6"-bromo-4'-methoxy-3"H,5'''H-trispiro[cyclopropane-1,3'-cyclohexane-1',2"-indene-1",4'''-oxazol]-5''',5'''-d₂-2'''-amine; (1'S,4'R)-6"-bromo-4'-methoxy-3"H,5'''H-trispiro[cyclopropane-1,3'-cyclohexane-1',2"-indene-1",4'''-oxazol]-5''',5'''-d₂-2'''-amine (35 mg, 0.090 mmol) and 3-pyridylboronic acid (22 mg, 0.18 mmol). ¹H NMR (400 MHz, CD₃OD) δ ppm −0.09 to −0.01 (1H, m), 0.20-0.28 (1H, m), 0.55-0.62 (1H, m), 0.71-0.79 (1H, m), 0.89-0.96 (1H, m), 1.26-1.47 (1.5H, m), 1.51-1.70 (1.5H, m), 1.82-1.88 (0.5H, m), 2.00-2.10 (1.5H, m), 2.89-3.18 (2H, m), 3.20-3.26 (1H, m), 3.28 (3H, d), 7.33 (1H, dd), 7.46-7.52 (3H, m), 8.07 (1H, dt), 8.48 (1H, dd), 8.76 (1H, t). LCMS: rt=2.94 min, m/z=382 [M+H]⁺, purity=99.1%.

Compound 88: 3-(2'-amino-2-(3-methoxypropyl)-2-methyl-2,3-dihydro-5'H-spiro[indene-1,4'-oxazol]-6-yl)-5-methoxybenzonitrile

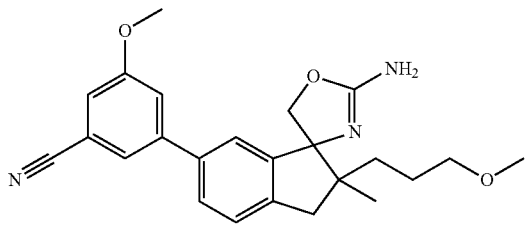 [SMILES: COCCCC1(C)Cc2ccc(-c3cc(C#N)cc(OC)c3)cc2C12COC(N)=N2]

Step 1: 2-(6-bromo-2,3-dihydro-1H-inden-1-ylidene)-1,1-dimethylhydrazine

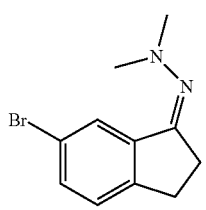

A suspension of 6-bromoindan-1-one (5.00 g, 23 mmol) in MeOH (35 mL) and THF (35 mL) was treated with 1,1-dimethylhydrazine (2.7 mL, 35 mmol) and acetic acid (0.7 mL, 12 mmol) and stirred under reflux for 16 h. The mixture was cooled to r.t., evaporated and the residue dissolved in DCM, washed by aq. sat. NaHCO₃ and extracted with DCM. The layers were separated and the aqueous phase extracted with DCM. The combined organic extracts were washed with brine, dried (Na₂SO₄) and evaporated. Purification by column chromatography (0-25% EtOAc in hexane) afforded the title compound (4.1 g, 68%). ¹H NMR (400 MHz, CDCl₃) δ ppm 2.66 (6H, s), 2.87-2.91 (2H, m), 2.97-3.01 (2H, m), 7.15-7.17 (1H, m), 7.41-7.44 (1H, m), 7.88 (1H, s). MS: m/z=252.8 [M+H]⁺.

Step 2: 2-(6-bromo-2-(3-methoxypropyl)-2,3-dihydro-1H-inden-1-ylidene)-1,1-dimethylhydrazine

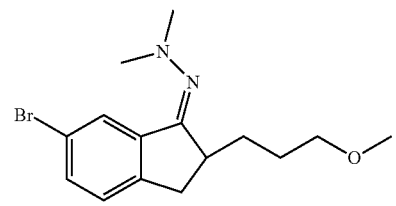 [SMILES: COCCCC1Cc2ccc(Br)cc2/C1=N\N(C)C]

At −78° C. under N₂, a solution of 2-(6-bromo-2,3-dihydro-1H-inden-1-ylidene)-1,1-dimethylhydrazine (506 mg, 2 mmol) in THF (5 mL) was treated with lithium bis(trimethylsilyl)amide (1 M in THF, 2.2 mL, 2.2 mmol). The mixture was stirred for 1 h, treated with a solution of 1-bromo-3-methoxypropane (0.3 mL, 2.7 mmol) in THF (5 mL), stirred for 1 h and allowed to warm up to r.t. and stirred for 12 h. The mixture was evaporated and the residue dissolved in EtOAc, washed with sat. aq. NH₄Cl and extracted with EtOAc (3×). The combined organic extracts were washed with brine, dried (Na₂SO₄) and evaporated. The crude product (540 mg, 83%) was used for next step without other purification. ¹H NMR (400 MHz, CDCl₃) δ ppm 1.43-1.98 (3H, m), 2.51-2.72 (8H, m), 2.87-3.01 (2H, m), 3.09-3.16 (1H, m), 3.30-3.41 (4H, m), 7.11-7.19 (1H, m), 7.39-7.48 (1H, m), 7.85-7.88 (1H, d). MS: m/z=324.9 [M+H]⁺.

Step 3: 6-bromo-2-(3-methoxypropyl)-2-methyl-2,3-dihydro-1H-inden-1-one

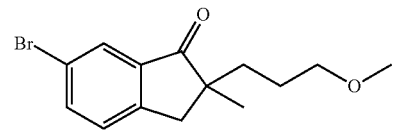 [SMILES: COCCCC1(C)Cc2ccc(Br)cc2C1=O]

A solution of 2-(6-bromo-2-(3-methoxypropyl)-2,3-dihydro-1H-inden-1-ylidene)-1,1-dimethylhydrazine (540 mg, 1.66 mmol) in THF (5 mL) was treated with HCl (2.5M solution in H$_2$O, 10 mL, 25 mmol), heated to 50° C. and stirred for 2 h. The mixture was cooled to r.t., treated with H$_2$O and extracted with EtOAc (3×). The combined organic layers were dried (Na$_2$SO$_4$) and evaporated. The residue was dissolved in THF (5 mL) and added to an ice-cooled solution of NaH (95%, 50 mg, 1.98 mmol) in THF (5 mL). The mixture was stirred under N$_2$ at 0° C. for 30 min, dropwise treated with methyl iodide (0.30 mL, 4.82 mmol), allowed to warm up to r.t. and stirred for 12 h. The solvent was evaporated under reduced pressure and the residue dissolved in EtOAc and washed with H$_2$O. The aqueous phase was extracted with EtOAc. The combined organic extracts were washed with brine, dried (Na$_2$SO$_4$) and evaporated to yield the crude product. Purification by column chromatography (0-10% EtOAc in hexane) afforded the title compound (110 mg, 22%). $^1$H NMR (400 MHz, CDCl$_3$) δ ppm 1.21 (3H, s), 1.35-1.39 (1H, m), 1.41-1.54 (1H, m), 1.62-1.68 (2H, m), 2.81-3.08 (2H, dd), 3.28-3.32 (5H, m), 7.31-7.33 (1H, m), 7.67-7.69 (1H, m), 7.86 (1H, d). MS: m/z=296.8 [M+H]$^+$.

Step 4: 6-bromo-2-(3-methoxypropyl)-2-methyl-1-methylene-2,3-dihydro-1H-indene

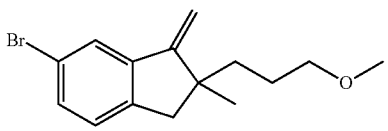 [SMILES: C=C1c2cc(Br)ccc2CC1(C)CCCOC]

Under N$_2$, a mixture of methyl(triphenyl)phosphonium iodide (250 mg, 0.62 mmol) in THF (5 mL) was treated with n-butyllithium (2.5 M solution in hexanes, 0.25 mL, 0.63 mmol) at −30° C., stirred for 45 min and dropwise treated with a solution of 6-bromo-2-(3-methoxypropyl)-2-methyl-2,3-dihydro-1H-inden-1-one (110 mg, 0.37 mmol) in THF (5 mL). Upon completion, the mixture was allowed to warm up to r.t. and stirred for 12 h and quenched with a sat. aq. NH$_4$Cl solution. The organic phase was separated and the aqueous phase extracted with EtOAc. The combined organic extracts were washed with brine, dried (Na$_2$SO$_4$) and evaporated. Purification of the residue by column chromatography (0 to 5% EtOAc in hexanes) gave the title compound (96 mg, 87%). $^1$H NMR (400 MHz, CDCl$_3$) δ ppm 1.21 (3H, s), 1.43-1.56 (4H, m), 2.66-2.87 (2H, dd), 3.29-3.32 (5H, m), 4.93 (1H, s), 5.49 (1H, s), 7.07 (1H, d), 7.31 (1H, d), 7.57 (1H, s). MS: m/z=216.8 [M−Br]$^+$.

Step 5: 6-bromo-2-(3-methoxypropyl)-2-methyl-2,3-dihydro-5'H-spiro[indene-1,4'-oxazol]-2'-amine

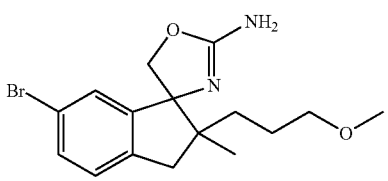 [SMILES: COCCCC1(C)Cc2ccc(Br)cc2C12COC(N)=N2]

At r.t., a solution of 6-bromo-2-(3-methoxypropyl)-2-methyl-1-methylene-2,3-dihydro-1H-indene (96 mg, 0.33 mmol) in THF (2 mL) and ACN (2 mL) was treated with isocyanatosilver (146 mg, 0.97 mmol) followed by iodine (124 mg, 0.49 mmol). The mixture was stirred at r.t. for 4 h, filtered through Celite and concentrated in vacuo. The residue was dissolved in THF (2 mL), treated with ammonium hydroxide (1 mL) and stirred at r.t. for 48 h. The mixture extracted with EtOAc. The layers were separated and the aqueous phase extracted with EtOAc. The combined organic extracts were washed with brine, dried over Na$_2$SO$_4$ and evaporated. Purification of the residue by column chromatography (0-5% MeOH in DCM) afforded the title compound (76 mg, 66%). $^1$H NMR (400 MHz, CD$_3$OD) δ ppm 0.87-1.00 (3H, s), 1.35-1.65 (4H, m), 2.49-2.88 (2H, m), 3.30-3.40 (5H, m), 4.03-4.52 (2H, m), 4.93 (2H, br), 7.00-7.05 (1H, m), 7.27-7.34 (2H, m). MS: m/z=352.9 [M+H]$^+$.

Step 6: 3-(2'-amino-2-(3-methoxypropyl)-2-methyl-2,3-dihydro-5'H-spiro[indene-1,4'-oxazole]-6-yl)-5-methoxybenzonitrile

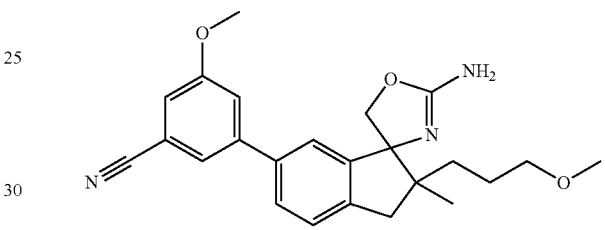

Under N$_2$ at r.t., a mixture of 6-bromo-2-(3-methoxypropyl)-2-methyl-2,3-dihydro-5'H-spiro[indene-1,4'-oxazol]-2'-amine (76 mg, 0.22 mmol), 3-methoxy-5-chlorophenylboronic acid pinacol ester (84 mg, 0.32 mmol) and potassium phosphate (138 mg, 0.65 mmol) in 1,4-dioxane (2 mL) and H$_2$O (0.2 mL) was treated with tetrakis(triphenylphosphine)palladium(0) (38 mg, 0.03 mmol). The reaction mixture was degassed (nitrogen bubbling) for 15 min and heated to 100° C. for 24 h. The mixture was cooled to r.t., filtered through Celite and evaporated. Purification of the residue by column chromatography (0-5% MeOH in DCM) afforded the title compound (30 mg, 34%). $^1$H NMR (400 MHz, CDCl$_3$) δ ppm 0.92-1.06 (3H, s), 1.41-1.69 (4H, m), 2.60-3.02 (2H, m), 3.31-3.42 (5H, m), 3.87 (3H, s), 4.11-4.61 (2H, m), 4.81 (2H, br. s), 7.08 (1H, s), 7.22-7.30 (2H, m), 7.35-7.38 (2H, m), 7.43 (1H, m). LCMS: m/z=406.0 [M+H]$^+$, purity=98.4%.

Compound 89: 3-(2'-amino-2-methyl-2-(tetrahydro-2H-pyran-4-yl)-2,3-dihydro-5'H-spiro[indene-1,4'-oxazol]-6-yl-5',5'-d$_2$)-5-methoxybenzonitrile

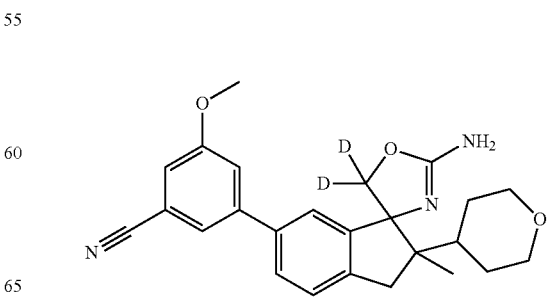

Step 1: 6-bromo-2-(4-hydroxytetrahydro-2H-pyran-4-yl)-2,3-dihydro-1H-inden-1-one

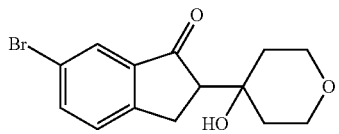

To a stirred solution of lithium bis(trimethylsilyl)amide (5 mL, 5 mmol) in THF (5 mL) at −70° C. was added a solution of 6-bromo-2,3-dihydro-1H-inden-1-one (1.06 g, 5.00 mmol) in THF (5 mL). The mixture was stirred at −70° C. for 3 h, dropwise treated with tetrahydro-4H-pyran-4-one (0.46 mL, 5.0 mmol), stirred at −70° C. for 3 h and poured into sat. aq. ammonium chloride solution (20 mL). The layers were separated and the aqueous layer was extracted with EtOAc (20 mL). The combined organic layers were dried ($Na_2SO_4$) and concentrated in vacuo to leave a golden syrup (1.6 g, used for the next step without further purification). LCMS: rt=2.82 m, m/z=263/265 [M+H−$H_2O$)]$^+$.

Step 2: 6-bromo-2-(tetrahydro-4H-pyran-4-ylidene)-2,3-dihydro-1H-inden-1-one

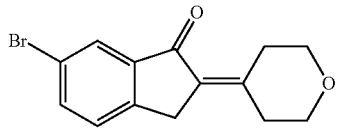 [SMILES: O=C1C(=C2CCOCC2)Cc2ccc(Br)cc21]

To a stirred solution of crude 6-bromo-2-(4-hydroxytetrahydro-2H-pyran-4-yl)-2,3-dihydro-1H-inden-1-one (1.56 g, 5.0 mmol) in pyridine (16 mL) at 0° C. was added thionyl chloride (0.4 mL, 5.5 mmol) dropwise over 5 min. The mixture was allowed to warm up to r.t. over a period of 12 h and poured into 1M aqueous HCl solution (100 mL). The dark brown mixture was extracted with DCM (2×50 mL), dried ($Na_2SO_4$) and evaporated to leave a brown solid (1.55 g). Flash chromatography (40 g Si cartridge, 2.5% EtOAc in DCM) gave a yellow solid (1.01 g). $^1$H NMR (400 MHz, CDCl$_3$) δ ppm 2.46 (2H, t), 3.34 (2H, t), 3.60 (2H, s) 3.78 (2H, t), 3.84 (2H, t), 7.34 (1H, d), 7.65 (1H, dd) and 7.90 (1H, d). LCMS: rt=3.29 min, m/z=293/295 [M+H]$^+$.

Step 3: 3-methoxy-5-(3-oxo-2-(tetrahydro-4H-pyran-4-ylidene)-2,3-dihydro-1H-inden-5-yl)benzonitrile

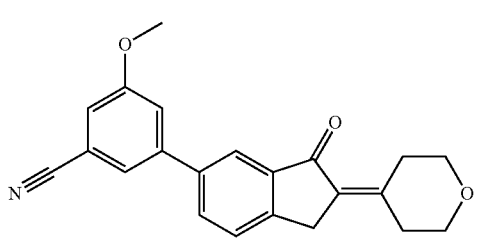 [SMILES: COc1cc(C#N)cc(-c2ccc3c(c2)C(=O)C(=C2CCOCC2)C3)c1]

Under $N_2$, a mixture of 6-bromo-2-(tetrahydro-4H-pyran-4-ylidene)-2,3-dihydro-1H-inden-1-one (703 mg, 2.40 mmol), 1,1-bis(di-tert-butylphosphino)ferrocene palladium dichloride (78 mg, 0.12 mmol) and 3-methoxy-5-(4,4,5,5-tetramethyl-1,3,2-dioxaborolan-2-yl)benzonitrile (621 mg, 2.40 mmol) in 1,4-dioxane (9 mL) was treated with a solution of $K_2CO_3$ (995 mg, 7.20 mmol) in $H_2O$ (3 mL), at 100° C. for 1 h and cooled to r.t. Deloxan (Pd scavenger resin) was added, the mixture was stirred for 30 min and concentrated in vacuo. The residue was suspended in DCM (60 mL), filtered and evaporated to leave a black residue (1.3 g). Flash chromatography (20 g Si cartridge, 2.5-5% EtOAc in DCM) gave a pale yellow solid (624 mg). $^1$H NMR (400 MHz, CDCl$_3$) δ ppm 2.44 (2H, t), 3.34 (2H, t), 3.67 (2H, s), 3.76 (2H, t), 3.82 (2H, t), 3.83 (3H, s), 7.08 (1H, dd), 7.29 (1H, dd), 7.42 (1H, dd), 7.52 (1H, d), 7.70 (1H, dd) and 7.91 (1H, d). LCMS: rt=3.37 min, m/z=346 [M+H]$^+$.

Step 4: 3-methoxy-5-(3-oxo-2-(tetrahydro-2H-pyran-4-yl)-2,3-dihydro-1H-inden-5-yl)benzonitrile

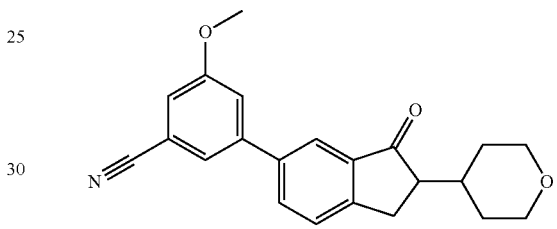

To a stirred solution of 3-methoxy-5-(3-oxo-2-(tetrahydro-4H-pyran-4-ylidene)-2,3-dihydro-1H-inden-5-yl)benzonitrile (846 mg, 2.45 mmol) in THF (35 mL) was added palladium on charcoal (85 mg, 0.040 mmol). The mixture was stirred under an atmosphere of $H_2$ (balloon) at 22° C. for 66 h, filtered through Celite and concentrated in vacuo to leave a gum (1.3 g). Flash chromatography (12 g Si cartridge, 5-10% EtOAc in DCM) afforded a pale brown solid (547 mg). $^1$H NMR (400 MHz, CDCl$_3$) δ ppm 1.25 (1H, dq), 1.37 (1H, qd), 1.55 (1H, qd), 1.66 (1H, dq), 2.21-2.31 (1H, m), 2.70 (1H, quin), 2.98 (1H, dd), 3.19 (1H, dd), 3.33-3.43 (2H, m), 3.83 (3H, s), 3.87 (1H, dd), 3.96 (1H, dd), 7.08 (1H, dd), 7.26 (1H, dd), 7.39 (1H, t), 7.52 (1H, dd), 7.72 (1H, dd) and 7.84 (1H, d). LCMS: rt=3.34 m, m/z=348 [M+H]$^+$.

Step 5: 3-methoxy-5-(2-methyl-3-oxo-2-(tetrahydro-2H-pyran-4-yl)-2,3-dihydro-1H-inden-5-yl)benzonitrile

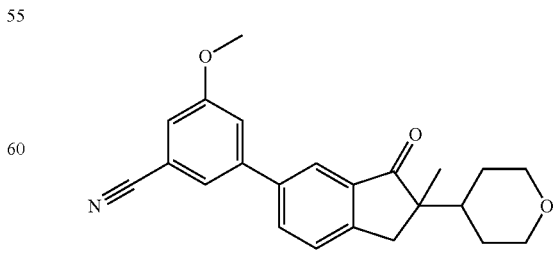

A stirred solution of 3-methoxy-5-(3-oxo-2-(tetrahydro-2H-pyran-4-yl)-2,3-dihydro-1H-inden-5-yl)benzonitrile (200 mg, 0.580 mmol) in THF (5 mL) at −78° C. under N₂ was dropwise treated with lithium bis(trimethylsilyl)amide (0.11 mL, 0.58 mmol), stirred at −78° C. for 1 h, treated with iodomethane (0.04 mL, 0.58 mmol) and warmed to r.t. The mixture was quenched with sat. aq. ammonium chloride solution (5 mL) and extracted with EtOAc (2×10 mL). The combined organic layers were dried (Na₂SO₄), filtered and concentrated in vacuo to leave a pale yellow oil (205 mg). ¹H NMR (400 MHz, CDCl₃) δ ppm 1.12-1.28 (1H, m), 1.17 (3H, s), 1.30-1.44 (1H, m), 1.60-1.70 (1H, m), 1.90-1.98 (1H, m), 2.72 (1H, d), 3.21 (1H, d), 3.23-3.39 (2H, m), 3.76-3.80 (1H, m), 3.81 (3H, s), 3.94-4.00 (1H, dd), 7.08 (1H, dd), 7.26 (1H, dd), 7.39 (1H, d), 7.50 (1H, d), 7.71 (1H, dd) and 7.83 (1H, d). LCMS: rt=3.37 min, m/z=362 [M+H]⁺.

Step 6: 3-methoxy-5-(2-methyl-3-(methylene-d₂)-2-(tetrahydro-2H-pyran-4-yl)-2,3-dihydro-1H-inden-5-yl)benzonitrile

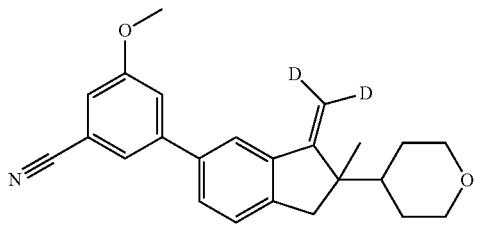 [SMILES: [2H]C([2H])=C1c2cc(-c3cc(C#N)cc(OC)c3)ccc2CC1(C)C1CCOCC1]

A stirred suspension of triphenyl(trideuteriomethyl)phosphonium iodide (0.35 g, 0.86 mmol) in THF (10 mL) under N₂ at −78° C. was treated with a solution of n-Butyllithium 2.5M in hexane (0.35 mL, 0.86 mmol), stirred for 45 min, treated with a solution of 3-methoxy-5-(2-methyl-3-oxo-2-(tetrahydro-2H-pyran-4-yl)-2,3-dihydro-1H-inden-5-yl)benzonitrile (208 mg, 0.58 mmol) in THF (5 mL), warmed to −40° C., then to r.t. The mixture was concentrated in vacuo and the resulting brown oil (190 mg) purified by flash column chromatography (4 g Si cartridge, 100% DCM) to give a yellow oil (62 mg). ¹H NMR (400 MHz, CDCl₃) δ ppm 1.09-1.25 (1H, m), 1.17 (3H, s), 1.30-1.40 (2H, m), 1.51-1.65 (2H, m), 2.57 (1H, d), 3.01 (1H, d), 3.22 (1H, td), 3.29 (1H, td), 3.81 (3H, s), 3.83 (1H, dt), 3.95 (1H, dt), 4.88 (12%), 5.58 (12%), 7.03 (1H, dd), 7.22 (1H, d), 7.25 (1H, dd), 7.32 (1H, dd), 7.38 (1H, dd) and 7.52 (1H, d). LCMS: rt=3.79 min, m/z=362 [M+H]⁺.

Step 7: 3-(2'-amino-2-methyl-2-(tetrahydro-2H-pyran-4-yl)-2,3-dihydro-5'H-spiro[indene-1,4'-oxazol]-6-yl-5',5'-d₂)-5-methoxybenzonitrile

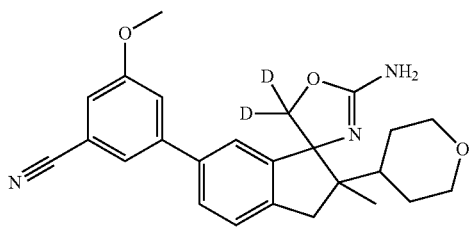 [SMILES: [2H]C1([2H])OC(N)=NC12c1cc(-c3cc(C#N)cc(OC)c3)ccc1CC2(C)C1CCOCC1]

To a stirred solution of 3-methoxy-5-(2-methyl-3-(methylene-d₂)-2-(tetrahydro-2H-pyran-4-yl)-2,3-dihydro-1H-inden-5-yl)benzonitrile (61 mg, 0.17 mmol) in THF (2 mL) and ACN (2 mL) at 22° C. was added isocyanatosilver (76 mg, 0.51 mmol) followed by molecular iodine (64 mg, 0.26 mmol). The mixture was stirred at r.t. for 2 h, filtered through Celite and concentrated in vacuo to leave a crude yellow solid. The solid was dissolved in THF (4 mL) and sat. aq. ammonium hydroxide (1 mL), stirred at r.t. for 18 h and concentrated in vacuo. The residue was purified by HPLC (ACN/H₂O+0.1% TFA) to afford a flocculent white solid (69 mg) as the TFA salt. ¹H NMR (400 MHz, CD₃OD, 2 pairs of diastereomers) δ ppm 1.03 and 1.07 (3H, s), 1.32-1.61 (3H, m), 1.63-1.84 (1H, m), 1.98-2.23 (1H, m), 2.79-2.90 (1H, m), 2.92-3.13 (1H, m), 3.39-3.55 (2H, m), 3.91 (3H, s), 3.94-4.10 (2H, m), 4.63 (1H, s, 10%), 5.40 (1H, s, 10%), 7.27-7.30 (1H, m), 7.36-7.46 (1H, m), 7.47-7.50 (1H, m), 7.59-7.62 (1H, m), 7.63-7.68 (1H, m) and 7.69-7.78 (1H, m). LCMS: rt=2.70 min, m/z=367/369 [M+H]⁺.

Compound 90: 3-(2'-amino-2-(3-methoxypropyl)-2,3-dihydro-5'H-spiro[indene-1,4'-oxazol]-6-yl)-5-methoxybenzonitrile

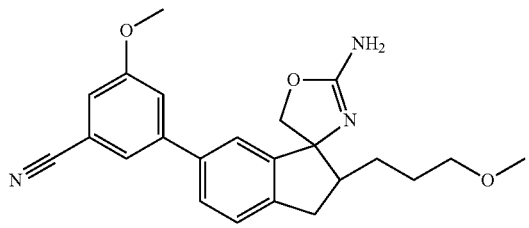 [SMILES: COCCCC1Cc2ccc(-c3cc(C#N)cc(OC)c3)cc2C12COC(N)=N2]

Step 1: 6-bromo-2-(3-methoxypropyl)-2,3-dihydro-1H-inden-1-one

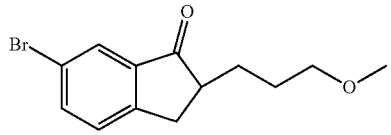 [SMILES: COCCCC1Cc2ccc(Br)cc2C1=O]

Under N₂, a stirred and cooled (~78° C.) solution of 2-(6-bromo-2,3-dihydro-1H-inden-1-ylidene)-1,1-dimethylhydrazine (1.35 g, 5.32 mmol) in THF (5 mL) was treated with LiHMDS (1.0 M in THF, 5.85 mL, 5.85 mmol), stirred at −78° C. for 1 h and dropwise treated with a solution of 1-bromo-3-methoxypropane (0.77 mL, 6.91 mmol) in THF (3 mL). The mixture was stirred for 1 h, allowed to warm up to r.t., stirred for 16 h, treated with 2.5 M aqueous HCl solution (25 mL) and stirred for 2 h at 50° C. The mixture was cooled and evaporated. The residue was diluted with EtOAc (40 mL), the layers were separated and the aqueous phase extracted with EtOAc (2×30 mL). The combined organic layers were dried over Na₂SO₄ and evaporated. Flash chromatography of the residue over silica gel (hexane/EtOAc 4:1) gave the title compound (703 mg, 47%) as a brown solid. ¹H NMR (CDCl₃, 400 MHz, 25° C.) δ ppm 1.55-1.61 (m, 1H), 1.67-1.74 (m, 2H), 1.94-2.03 (m, 1H), 2.69-2.80 (m, 2H), 3.29 (dd, 1H), 3.26 (s, 3H), 3.36-3.46 (m, 2H), 7.3.4 (d, 1H), 7.68 (dd, 1H), 7.87 (d, 1H). MS: m/z=282.9, 284.8 [M+H]⁺.

Step 2: 6-bromo-2-(3-methoxypropyl)-1-methylene-2,3-dihydro-1H-indene

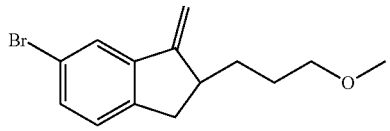 [SMILES: C=C1c2cc(Br)ccc2CC1CCCOC]

Under N₂ at −42° C., a suspension of methyltriphenylphosphonium bromide (1.03 g, 2.54 mmol) in THF (15 mL) was dropwise treated with a solution of n-BuLi (2.5M in hexane, 1.02 mL, 2.54 mmol) and stirred for 1 h. The mixture was then treated with a solution of 6-bromo-2-(3-methoxypropyl)-2,3-dihydro-1H-inden-1-one (360 mg, 1.27 mmol) in THF (10 mL), stirred for 1 h, allowed to warm to r.t. and stirred for 16 h. The mixture was diluted with EtOAc (50 mL) and sat. aq. NH₄Cl (100 mL). The layers were separated and the aqueous layer extracted with EtOAc (2×30 mL). The combined organic layers were washed with brine (100 mL), dried over Na₂SO₄ and evaporated. Flash chromatography of the residue over silica gel (hexane/EtOAc 9:1 to 4:1) gave the title compound (65 mg, 18%). ¹H NMR (CDCl₃, 400 MHz) δ ppm 1.46-1.53 (m, 1H), 1.61-1.78 (m, 3H), 2.58 (dd, 1H), 2.95-2.99 (m, 1H), 3.09 (dd, 1H), 3.33 (s, 3H), 3.40 (t, 2H), 5.03 (d, 1H), 5.48 (d, 1H), 7.09 (d, 1H), 7.30 (dd, 1H), 7.58 (d, 1H). ¹³C NMR (CDCl₃, 100 MHz) δ ppm 27.1, 31.9, 36.5, 43.2, 58.6, 72.8, 104.2, 120.5, 123.9, 126.8, 131.1, 143.2, 143.7, 153.0.

Step 3: 6-bromo-2-(3-methoxypropyl)-2,3-dihydro-5'H-spiro[indene-1,4'-oxazol]-2'-amine

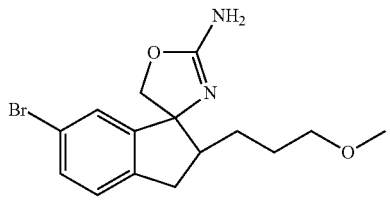 [SMILES: COCCCC1Cc2ccc(Br)cc2C12COC(N)=N2]

At r.t. under N₂, a solution of 6-bromo-2-(3-methoxypropyl)-1-methylene-2,3-dihydro-1H-indene (120 mg, 0.43 mmol) in THF and ACN (each 2 mL) was treated with isocyanatosilver (192 mg, 1.28 mmol) and iodine (163 mg, 0.64 mmol) and stirred for 18 h. The mixture was diluted with EtOAc (40 mL) and filtered through Celite. The cake was washed with EtOAc (20 mL) and the filtrate was evaporated. The residue was dissolved in THF (5 mL), cooled (0° C.), treated with aq. NH₃ (5 mL) and stirred for 72 h. The mixture was concentrated in vacuo, diluted with EtOAc (20 mL) and washed with H₂O (25 mL). The aqueous phase was extracted with EtOAc (2×25 mL) and the combined organic layers dried over Na₂SO₄ and evaporated. Purification of the residue by prep. TLC (2 mm thickness, 20×20 cm, EtOAc/MeOH 20:1) gave the desired product (62 mg, 43%). ¹H NMR (CDCl₃, 400 MHz) δ ppm 1.41-1.92 (m, 4H), 2.11-2.68 (m, 1H), 2.90-3.49 (m, 7H), 4.21-4.65 (m, 2H), 5.21-5.61 (m, 2H), 7.02-7.60 (m, 3H). MS: m/z=338.8, 340.8 [M+H]⁺.

Step 4: 3-(2'-amino-2-(3-methoxypropyl)-2,3-dihydro-5'H-spiro[indene-1,4'-oxazole]-6-yl)-5-methoxybenzonitrile

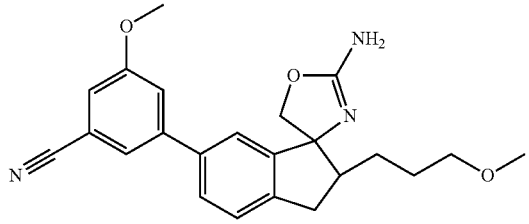 [SMILES: COCCCC1Cc2ccc(-c3cc(C#N)cc(OC)c3)cc2C12COC(N)=N2]

A suspension of 6-bromo-2-(3-methoxypropyl)-2,3-dihydro-5'H-spiro[indene-1,4'-oxazol]-2'-amine (62 mg, 0.18 mmol), 3-cyano-5-methoxyphenylboronic acid pinacol ester (142 mg, 0.54 mmol) and K₃PO₄ (232 mg, 1.09 mmol) in 1,4-dioxane (3 mL) and H₂O (0.3 mL) was purged with N₂ for 15 min, treated with Pd(PPh₃)₄ (42 mg, 0.04 mmol) and stirred under reflux for 16 h. The mixture was evaporated and the residue dissolved in DCM (20 mL), washed with H₂O (50 mL) and extracted with DCM (2×20 mL). The combined organic layers were dried over Na₂SO₄ and evaporated. Purification of the residue by prep. TLC (3×; 2 mm thickness, 20×20 cm, EtOAc/MeOH=20:1) gave the title compound as a brown solid (35 mg). ¹H NMR (CDCl₃, 400 MHz) δ ppm 1.50-1.57 (m, 2H), 1.78-1.86 (m, 2H), 3.08 (d, 1H), 3.29-3.41 (m, 5H), 3.60 (d, 1H), 3.80 (s, 3H), 4.46 (s, 2H), 5.21 (s, 1H), 5.52 (s, 1H), 5.72 (s, 1H), 7.11-7.61 (m, 6H). MS: m/z=392.0 [M+H]⁺.

Compound 91: 3-(2'-Amino-2-(tetrahydro-2H-pyran-4-yl)-2,3-dihydro-5'H-spiro[indene-1,4'-oxazol]-6-yl)-5-methoxybenzonitrile

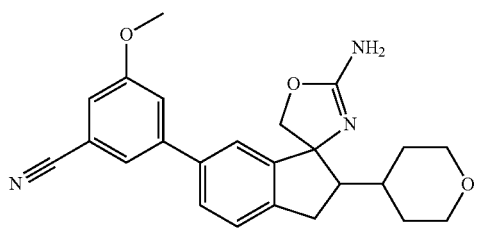 [SMILES: COc1cc(C#N)cc(-c2ccc3c(c2)C2(COC(N)=N2)C(C2CCOCC2)C3)c1]

Step 1: 3-methoxy-5-(3-methylene-2-(tetrahydro-2H-pyran-4-yl)-2,3-dihydro-1H-inden-5-yl)benzonitrile

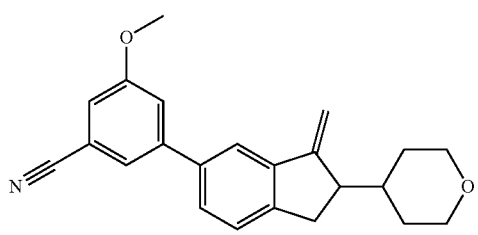 [SMILES: C=C1c2cc(-c3cc(C#N)cc(OC)c3)ccc2CC1C1CCOCC1]

To a stirred solution of 3-methoxy-5-(3-oxo-2-(tetrahydro-2H-pyran-4-yl)-2,3-dihydro-1H-inden-5-yl)benzonitrile (125 mg, 0.36 mmol) in THF (5 mL) at 0° C. under N₂ was added a 0.5M solution of Tebbe's reagent (0.79 mL, 0.40 mmol) in toluene over 5 min. The mixture was warmed to r.t., stirred for 15 h, treated with 0.1N aq. NaOH solution (2 mL), stirred for 15 min and treated with MgSO₄. The mixture was filtered through Celite and washed with THF (20 mL). The filtrate was concentrated in vacuo to leave a red gum (0.6 g). Flash chromatography (Si 10 g, DCM) afforded a pale yellow gum (21 mg). ¹H NMR (400 MHz, CDCl₃) δ ppm 1.14-1.20 (1H, m), 1.22-1.31 (1H, m), 1.34-1.42 (1H, m), 1.44-1.54 (1H, m), 1.70-1.80 (1H, m), 2.80 (1H, dd), 2.87-2.94 (1H, m), 3.00 (1H, dd), 3.22-3.36 (2H, m), 3.81 (3H, s), 3.84-3.96 (2H, m), 5.00 (1H, s), 5.60 (1H, s), 7.04 (1H, dd), 7.23-7.28 (2H, m), 7.32 (1H, dd), 7.39 (1H, dd) and 7.58 (1H, dd). LCMS: rt=3.66 mins, m/z=346 [M+H]⁺.

Step 2: 3-(2'-amino-2-(tetrahydro-2H-pyran-4-yl)-2,3-dihydro-5'H-spiro[indene-1,4'-oxazol]-6-yl)-5-methoxybenzonitrile

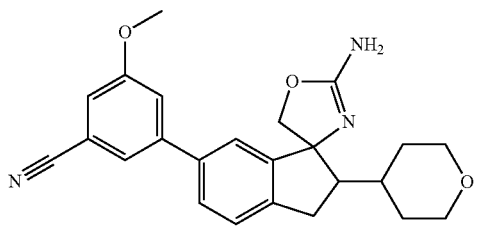

To a stirred solution of 3-methoxy-5-(3-methylene-2-(tetrahydro-2H-pyran-4-yl)-2,3-dihydro-1H-inden-5-yl)benzonitrile (20.7 mg, 0.06 mmol) in THF (1 mL) and ACN (1 mL) at 22° C. was added isocyanatosilver (27 mg, 0.18 mmol) followed by molecular iodine (23 mg, 0.090 mmol). The mixture was stirred at r.t. for 1 h, filtered through Celite and concentrated in vacuo to leave a grey gum, which was dissolved in THF (2 mL) and sat. aq. ammonium hydroxide (1 mL). The mixture was stirred at r.t. for 1 h, concentrated in vacuo and the residue (30 mg) was purified by HPLC (ACN/H₂O+0.1% TFA) to give a yellow gum (8 mg). ¹H NMR (400 MHz, CD₃OD, 2 pairs of diastereoisomers) δ ppm 1.44-1.79 (4H, m), 1.85-2.17 (1H, m), 2.40-3.21 (3H, m), 3.41-3.58 (2H, m), 3.91 (3H, s), 3.92-4.03 (2H, m), 4.59 (d) and 5.03 (d) (1H), 5.27 (d) and 5.29 (d) (1H), 7.28-7.30 (1H, m), 7.38-7.45 (1H, m), 7.47-7.50 (1H, m), 7.59-7.62 (1H, m), 7.65-7.70 (1H, m) and 7.72-7.80 (1H, m). LCMS: rt=3.41 min, m/z=406 [M+H]⁺, purity=93.4%.

Compound 92: 3-(2'-amino-2-(2-methoxyethyl)-2,3-dihydro-5'H-spiro[indene-1,4'-oxazol]-6-yl)-5-methoxybenzonitrile

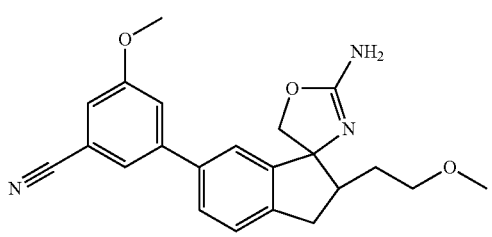 [SMILES: COCCC1Cc2ccc(-c3cc(C#N)cc(OC)c3)cc2C12COC(N)=N2]

Step 1: 6-bromo-2-(2-methoxyethyl)-2,3-dihydro-1H-inden-1-one

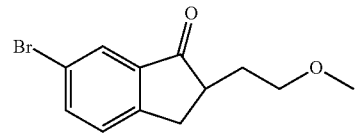

Under N₂ at −78° C., a solution of 2-(6-bromo-2,3-dihydro-1H-inden-1-ylidene)-1,1-dimethylhydrazine (3.29 g, 13.0 mmol) in THF (25 mL) was treated with a solution of LiHMDS (1.0 M in THF, 16.9 mL, 16.9 mmol), stirred for 1 h, dropwise treated with 2-bromoethyl methyl ether (1.83 mL, 19.5 mmol) and stirred for 1 h. The mixture was allowed to warm up to r.t. and stirring was continued for 16 h. The mixture was quenched with 4.0M aq. HCl (50 mL), stirred at 50° C. for 2 h and cooled to r.t. The mixture was extracted with EtOAc (3×40 mL) and the combined organic layers were washed with brine, dried over Na₂SO₄ and evaporated. Flash chromatography of the residue over silica gel (Hex/EtOAc 9:1 to 6:1) gave the title compound (1.70 g, 49%) as a brown solid. ¹H NMR (CDCl₃, 400 MHz) δ ppm 1.71-1.77 (m, 1H), 2.22-2.26 (m, 1H), 2.80-2.86 (m, 2H), 3.28-3.35 (m, 4H), 3.54-3.58 (m, 2H), 7.35 (d, 1H), 7.68 (dd, 1H), 7.87 (d, 1H).

Step 2: 6-bromo-2-(2-methoxyethyl)-1-methylene-2,3-dihydro-1H-indene

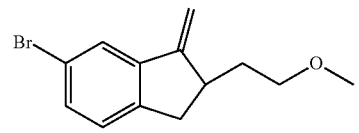

At r.t. under N₂, a stirred solution of 6-bromo-2-(2-methoxyethyl)-2,3-dihydro-1H-inden-1-one (1.70 g, 6.32 mmol) in THF (12 mL) was treated Tebbe's reagent (19 mL, 9.5 mmol) and stirred for 16 h. The mixture was quenched with 0.5M aq. NaOH (50 mL) and extracted with EtOAc (3×25 mL). The combined organic layers were dried over Na₂SO₄ and evaporated. Flash chromatography of the residue over silica gel (Hex/EtOAc 6:1) gave the title compound (929 mg, 55%) as a off-white solid. ¹H NMR (CDCl₃, 400 MHz) δ ppm 1.65-1.73 (m, 1H), 1.93-2.00 (m, 1H), 2.59-2.65 (m, 1H), 3.09-3.14 (m, 2H), 3.36 (s, 3H), 3.43-3.54 (m, 2H), 5.04 (s, 1H), 5.49 (s, 1H), 7.10 (d, 1H), 7.32 (d, 1H), 7.59 (s, 1H). MS: m/z=266.9, 268.8 [M+H]⁺.

Step 3: 6-bromo-2-(2-methoxyethyl)-2,3-dihydro-5'H-spiro[indene-1,4'-oxazol]-2'-amine

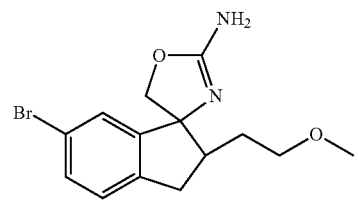 [SMILES: COCCC1Cc2ccc(Br)cc2C12COC(N)=N2]

At r.t. under N$_2$, a stirred solution of 6-bromo-2-(2-methoxyethyl)-1-methylene-2,3-dihydro-1H-indene (120 mg, 0.43 mmol) in THF (6 mL) and ACN (5 mL) was treated with isocyanatosilver (1.55 g, 10.3 mmol) and iodine (1.31 g, 5.16 mmol) and stirred for 4 h. The mixture was diluted with EtOAc (60 mL) and filtered through Celite. The filtrate was evaporated, the residue dissolved in THF (5 mL), cooled (0° C.), treated with NH$_3$.H$_2$O (5 mL) and stirred for 16 h. The mixture was evaporated and the residue dissolved in EtOAc (20 mL), washed with H$_2$O (25 mL) and extracted with EtOAc (2×25 mL). The combined organic layers were dried over Na$_2$SO$_4$ and evaporated. Flash chromatography of the residue over silica gel (DCM/MeOH 20:1) gave the title compound (353 mg, 32%) a off-white solid. $^1$H NMR (CDCl$_3$, 400 MHz) δ ppm 1.73-1.93 (m, 1H), 2.42-2.54 (m, 1H), 2.71-2.80 (m, 1H), 2.99-3.04 (m, 1H), 3.31-3.42 (m, 3H), 3.56-3.60 (m, 1H), 4.07-4.17 (m, 1H), 4.58-4.763 (m, 1H), 6.60 (br. s, 2H), 7.06-7.48 (m, 3H). MS: m/z=324.8, 326.8 [M+H]$^+$.

Step 4: 3-(2'-amino-2-(2-methoxyethyl)-2,3-dihydro-5'H-spiro[indene-1,4'-oxazol]-6-yl)-5-methoxybenzonitrile

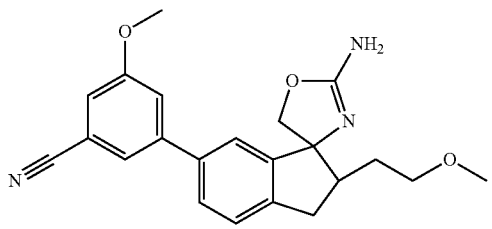 [SMILES: COCCC1Cc2ccc(-c3cc(C#N)cc(OC)c3)cc2C12COC(N)=N2]

A suspension of 6-bromo-2-(2-methoxyethyl)-2,3-dihydro-5'H-spiro[indene-1,4'-oxazol]-2'-amine (350 mg, 1.08 mmol), 3-cyano-5-methoxyphenylboronic acid pinacol ester (418 mg, 1.61 mmol) and K$_3$PO$_4$ (685 mg, 3.23 mmol) in 1,4-dioxane (10 mL) and H$_2$O (1 mL) was purged with N$_2$ for 15 min, treated with Pd(PPh$_3$)$_4$ (248 mg, 0.22 mmol) and stirred at reflux temperature for 16 h. The mixture was evaporated and the residue dissolved in DCM (25 mL), washed with H$_2$O (50 mL) and extracted with DCM (2×25 mL). The combined organic layers were dried over Na$_2$SO$_4$ and evaporated. Flash chromatography of the residue over silica gel (DCM/MeOH 20:1) gave crude material (85 mg). Purification by prep. TLC (2×2 mm thickness, 20×20 cm, DCM/MeOH 20:1) gave the title compound (62 mg) as a brown solid. $^1$H NMR (CDCl$_3$, 400 MHz) δ ppm 1.73-2.00 (m, 2H), 2.47-2.88 (m, 2H), 3.05-3.12 (m, 1H), 3.34-3.38 (m, 3H), 3.45-3.56 (m, 2H), 3.89 (s, 3H), 4.11-4.83 (m, 2H), 7.10-7.56 (m, 6H). MS: m/z=377.9 [M+H]$^+$. HPLC (column: BEH_C18_2_1×50 mm_1_7 um; Method: ACQ_IS_PDA3): rt=3.125 min, purity=96.8%.

Compound 93: 3-(2'-amino-2-(2-methoxyethyl)-2-methyl-2,3-dihydro-5'H-spiro[indene-1,4'-oxazol]-6-yl)-5-methoxybenzonitrile

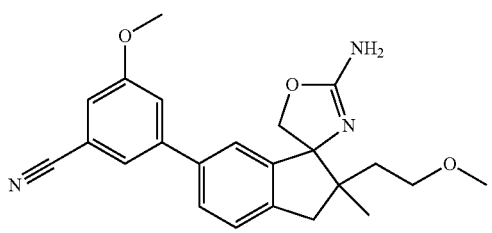 [SMILES: COCCC1(C)Cc2ccc(-c3cc(C#N)cc(OC)c3)cc2C12COC(N)=N2]

Step 1: 6-bromo-2-(2-methoxyethyl)-2-methyl-2,3-dihydro-1H-inden-1-one

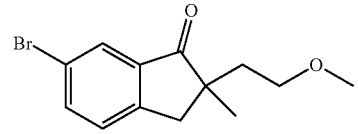 [SMILES: COCCC1(C)Cc2ccc(Br)cc2C1=O]

At 0° C. under N$_2$, a solution sodium hydride (95%, 50 mg, 1.98 mmol) in THF (5 mL) was treated with 6-bromo-2-(2-methoxyethyl)-2,3-dihydro-1H-inden-1-one (150 mg, 0.56 mmol) in THF (5 mL), stirred for 30 min, treated with methyl iodide (0.30 mL, 4.8 mmol) and stirred at r.t. for 12 h. Solvent was evaporated under reduced pressure. The residue was dissolved in EtOAc and washed with an aq. sat. NH$_4$Cl solution and extracted with EtOAc. The combined organic phases were washed with brine, dried with Na$_2$SO$_4$ and evaporated. Purification by column chromatography (0-10% EtOAc in hexane) afforded the title compound (86 mg, 54%). $^1$H NMR (400 MHz, CDCl$_3$) δ ppm 1.22 (3H, s), 1.79-1.86 (1H, m), 1.97-2.04 (1H, m), 2.81-2.85 (1H, m), 3.14-3.24 (4H, m), 3.33-3.37 (2H, m), 7.32 (1H, d), 7.68 (1H, d), 7.87 (1H, s). MS: m/z=282.8 [M+H]$^+$.

Step 2: 6-bromo-2-(2-methoxyethyl)-2-methyl-1-methylene-2,3-dihydro-1H-indene

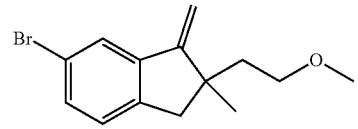

Under N$_2$ at −30° C., a mixture of methyl(triphenyl)phosphonium iodide (200 mg, 0.49 mmol) in THF (5 mL) was treated with n-butyllithium (2.5M solution in hexanes, 0.2 mL, 0.5 mmol), stirred for 45 min, dropwise treated with a solution of 6-bromo-2-(2-methoxyethyl)-2-methyl-2,3-dihydro-1H-inden-1-one (86 mg, 0.30 mmol) in THF (5 mL) and stirred at r.t. for 12 h. The mixture was quenched with a sat. aq. NH$_4$Cl solution. The organic phase was separated and the aqueous phase was extracted with EtOAc. The combined organic extracts were washed with brine, dried over Na$_2$SO$_4$ and evaporated. Purification by column chromatography (0-5% EtOAc in hexane) afforded the title compound (78 mg, 91%). $^1$H NMR (400 MHz, CDCl$_3$) δ ppm 1.22 (3H, s), 1.80-1.84 (2H, m), 2.66-2.97 (2H, dd), 3.23 (3H, s), 3.26-3.33 (2H, m), 4.95 (1H, s), 5.49 (1H, s), 7.07 (1H, d), 7.32 (1H, d), 7.58 (1H, s). MS: m/z=280.8 [M+H]$^+$.

Step 3: 6-bromo-2-(2-methoxyethyl)-2-methyl-2,3-dihydro-5'H-spiro[indene-1,4'-oxazol]-2'-amine

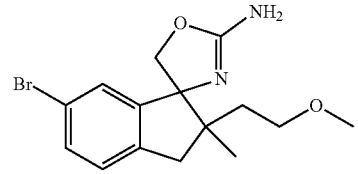 [SMILES: COCCC1(C)Cc2ccc(Br)cc2C12COC(N)=N2]

At r.t. under N₂, a solution of 6-bromo-2-(2-methoxy-ethyl)-2-methyl-1-methylene-2,3-dihydro-1H-indene (78 mg, 0.28 mmol) in THF (2 mL) and ACN (2 mL) was treated with isocyanatosilver (125 mg, 0.83 mmol) followed by iodine (105 mg, 0.41 mmol) and stirred at r.t. for 4 h. The mixture was filtered through Celite and the filtrate evaporated. The residual solids were dissolved in THF (2 mL) and aq. ammonium hydroxide (1 mL) was added. The mixture was stirred at r.t. for 48 h, concentrated in vacuo and the residue was extracted with EtOAc. The organic phase was separated and the aqueous phase was extracted with EtOAc. The combined organic extracts were washed with brine, dried over Na₂SO₄ and evaporated. Purification by column chromatography (0-5% MeOH in DCM) afforded the title compound (61 mg). ¹H NMR (400 MHz, CDCl₃) δ ppm 0.94-1.08 (3H, s), 1.66-1.95 (2H, m), 2.57-2.95 (2H, m), 3.24-3.28 (3H, s), 3.32-3.49 (2H, m), 4.14-4.69 (2H, m), 6.12 (2H, br. s), 7.04-7.08 (1H, m), 7.27-7.37 (2H, m). MS: m/z=338.8 [M+H]⁺.

Step 4: 3-(2'-amino-2-(2-methoxyethyl)-2-methyl-2,3-dihydro-5'H-spiro[indene-1,4'-oxazol]-6-yl)-5-methoxybenzonitrile

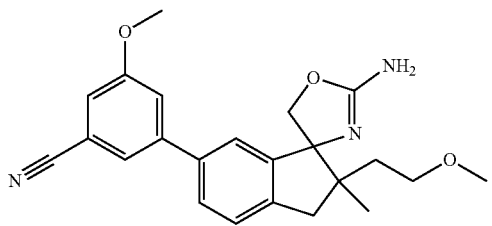 [SMILES: COCCC1(C)Cc2ccc(-c3cc(C#N)cc(OC)c3)cc2C12COC(N)=N2]

A degassed (15 min of N₂ bubbling) mixture of 6-bromo-2-(2-methoxyethyl)-2-methyl-2,3-dihydro-5'H-spiro[indene-1,4'-oxazol]-2'-amine (61 mg, 0.18 mmol), 3-methoxy-5-chlorophenylboronic acid pinacol ester (70 mg, 0.27 mmol), potassium phosphate (115 mg, 0.54 mmol), 1,4-dioxane (2 mL) and H₂O (0.2 mL) was treated with tetrakis(triphenylphosphine)palladium(0) (32 mg, 0.03 mmol) and stirred at 100° C. for 24 h. The mixture was cooled to r.t., filtered through Celite and evaporated. Purification of the residue by column chromatography (0-5% MeOH in DCM) afforded the title compound (10.3 mg). ¹H NMR (400 MHz, CDCl₃) δ ppm 0.95-1.07 (3H, s), 1.74-2.01 (2H, m), 2.64-3.11 (2H, m), 3.29-3.52 (5H, m), 3.88 (3H, s), 4.11-4.64 (4H, m), 7.08 (1H, s), 7.26-7.30 (2H, m), 7.37-7.39 (2H, m), 7.43 (1H, m). MS: m/z=392.0 [M+H]⁺. HPLC: purity=95.6%.

Compound 94: 6-(pyrimidin-5-yl)-2-(tetrahydro-2H-pyran-4-yl)-2,3-dihydro-5'H-spiro[indene-1,4'-oxazol]-2'-amine

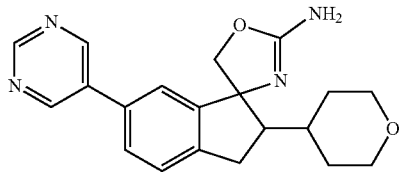 [SMILES: NC1=NC2(CO1)c1cc(-c3cncnc3)ccc1CC2C1CCOCC1]

Step 1: 6-bromo-2-(4-hydroxytetrahydro-2H-pyran-4-yl)-2,3-dihydro-1H-inden-1-one

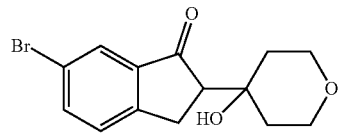 [SMILES: O=C1c2cc(Br)ccc2CC1C1(O)CCOCC1]

To a stirred solution of lithium bis(trimethylsilyl)amide (1M THF) (50 mL, 50 mmol) at −70° C. was added a solution of 6-bromo-2,3-dihydro-1H-inden-1-one (10 g, 47 mmol) in THF (70 mL) over 5 min. The mixture was stirred at −70° C. for 1.5 h, treated with tetrahydro-4H-pyran-4-one (4.8 mL, 52 mmol), stirred at −70° C. for 1 h and warmed up to r.t. and stirred for 30 min. The mixture was diluted with TBME, washed with 1M aq. HCl (2×), brine (1×), dried over Na₂SO₄ and evaporated to give a dark oil (~20 g). Purification on silica (500, eluting DCM/MeOH 0 to 8%) gave the desired material as a dark oil (12.5 g). ¹H NMR (400 MHz, CDCl₃) δ ppm 1.25 (1H, dd), 1.6-1.8 (4H, m (incl. H₂O in CDCl₃)), 2.85-2.95 (2H, m), 3.2 (1H, dd), 3.7-3.9 (4H, m), 7.38 (1H, d), 7.70 (1H, dd), 7.85 (1H, d). LCMS: rt=2.82 min, m/z=275/277 [M+H]⁺.

Step 2: 6-bromo-2-(tetrahydro-4H-pyran-4-ylidene)-2,3-dihydro-1H-inden-1-one

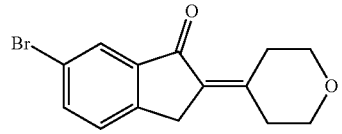 [SMILES: O=C1C(=C2CCOCC2)Cc2ccc(Br)cc21]

Trifluoroacetic acid (4.0 mL, 52 mmol) was added to a solution of 6-bromo-2-(4-hydroxytetrahydro-2H-pyran-4-yl)-2,3-dihydro-1H-inden-1-one (10.7 g, 34.39 mmol) in DCM (30 mL). The mixture was stirred at 40° C. for 16 h and evaporated. Trituration with isohexane gave a precipitate which was collected by filtration and dried in vacuo at 45° C. to give final product as a solid (8.6 g). ¹H NMR (400 MHz, CDCl₃) δ ppm 2.46 (2H, t), 3.34 (2H, t), 3.60 (2H, s), 3.77 (2H, t), 3.86 (2H, t), 7.34 (1H, d), 7.65 (1H, dd), 7.90 (1H, d).

Step 3: 6-(pyrimidin-5-yl)-2-(tetrahydro-4H-pyran-4-ylidene)-2,3-dihydro-1H-inden-1-one

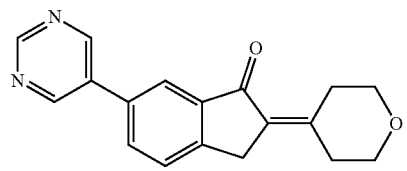 [SMILES: O=C1C(=C2CCOCC2)Cc2ccc(-c3cncnc3)cc21]

A mixture of 6-bromo-2-(tetrahydro-4H-pyran-4-ylidene)-2,3-dihydro-1H-inden-1-one (2.10 g, 7.16 mmol), 1,1-bis(di-tert-butylphosphino)ferrocene palladium dichloride (490 mg, 0.75 mmol), pyrimidin-5-ylboronic acid (1.00 g, 8.07 mmol) and K$_2$CO$_3$ (3.20 g, 23.1 mmol) under N$_2$ was suspended in 1,4-dioxane (25 mL) and H$_2$O (5 mL), heat at 100° C. for 4 h, treated with Deloxan (Pd scavenger) and stirred at r.t. for 12 h. The mixture was diluted with DCM and dried (Na$_2$SO$_4$), filtered and evaporated to give a dark solid (~2 g). Purification by chromatography (silica, 20 g cartridge, eluting DCM+MeOH, 0-1%) provided the desired product as a cream solid (1.5 g). $^1$H NMR (400 MHz, CDCl$_3$, 50° C.) δ 2.52 (2H, t), 3.39 (2H, t), 3.76 (2H, s), 3.80 (2H, t), 3.88 (2H, t), 7.63 (1H, d), 7.78 (1H, dd), 8.01 (1H, d), 8.8-9.5 (3H, br. s). $^1$H NMR (400 MHz, DMSO, 50° C.) δ 2.48 (2H, t), 3.27 (2H, t), 3.68 (2H, t), 3.78 (4H, m), 7.74 (1H, d), 8.04 (1H, d), 8.07 (1H, dd), 9.17 (2H, s), 9.18 (1H, s). LCMS: rt=2.85 min, m/z=293 [M+H]$^+$.

Step 4: 6-(pyrimidin-5-yl)-2-(tetrahydro-2H-pyran-4-yl)-2,3-dihydro-1H-inden-1-one

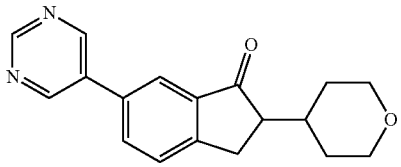 [SMILES: O=C1c2cc(-c3cncnc3)ccc2CC1C1CCOCC1]

Under N$_2$ at 30° C., a solution of 6-(pyrimidin-5-yl)-2-(tetrahydro-4H-pyran-4-ylidene)-2,3-dihydro-1H-inden-1-one (1.50 g, 5.13 mmol) in THF (50 mL) was treated with a suspension of Pd/C (220 mg, 5.13 mmol) in THF (10 mL) and stirred under H$_2$ (1 atm) for 6 h. The mixture was purged with N2, solids were filtered off (Celite) and the filtrate was evaporated to give the crude product (ca. 1.5 g) which was used without further purification. $^1$H NMR (400 MHz, CDCl$_3$) δ ppm 1.30 (1H, dq), 1.40 (1H, qd), 1.60 (1H, qd), 1.70 (1H, dq), 2.30 (1H, tq), 2.75 (1H, dt), 3.04 (1H, dd), 3.22 (1H, dd), 3.38 (1H, td), 3.43 (1H, td), 3.90 (1H, dd), 4.0 (1H, dd), 7.63 (1H, d), 7.79 (1H, dd), 7.93 (1H, d), 8.95 (2H, s), 9.22 (1H, s). LCMS: rt=2.75 min.

Step 5: 5-(3-methylene-2-(tetrahydro-2H-pyran-4-yl)-2,3-dihydro-1H-inden-5-yl)pyrimidine

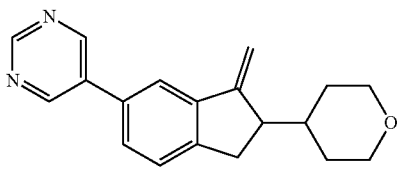

A solution of 6-(pyrimidin-5-yl)-2-(tetrahydro-2H-pyran-4-yl)-2,3-dihydro-1H-inden-1-one (0.20 g, 0.68 mmol) in THF (10 mL) at 0° C. was treated with Tebbe's reagent (0.5M in toluene, 2 mL, 1 mmol) via syringe, warmed to r.t. and stirred for 6 h. The mixture was carefully treated with 0.1M aq. NaOH solution (2 mL, 0.2 mmol), stirred for 15 min and treated with Na$_2$SO$_4$. The mixture was filtered through Celite and the cake washed with THF (2×10 mL) and DCM. The filtrate was concentrated in vacuo to leave a red gum. Purification on silica (10 g cartridge, eluting DCM+0-1% MeOH) gave the title compound (~30 mg). $^1$H NMR (400 MHz, CDCl$_3$) δ ppm 0.8-1.9 (5H, m), 2.90 (1H, dd), 3.0 (1H, m), 3.06 (1H, dd), 3.3-3.4 (2H, m), 3.9-4.0 (2H, m), 5.09 (1H, d), 5.68 (1H, d), 7.39 (1H d), 7.40 (1H, dd), 7.63 (1H, d), 8.94 (2H, s), 9.19 (1H, s). LCMS: rt=3.35 min, m/z=293 [M+H]$^+$.

Step 6: 6-(pyrimidin-5-yl)-2-(tetrahydro-2H-pyran-4-yl)-2,3-dihydro-5'H-spiro[indene-1,4'-oxazol]-2'-amine

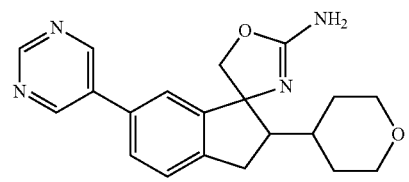 [SMILES: NC1=NC2(CO1)c1cc(-c3cncnc3)ccc1CC2C1CCOCC1]

At 22° C., a stirred solution of 5-(3-methylene-2-(tetrahydro-2H-pyran-4-yl)-2,3-dihydro-1H-inden-5-yl)pyrimidine (30 mg, 0.10 mmol) in THF (2 mL) and ACN (2 mL) was treated with isocyanatosilver (45 mg, 0.30 mmol) and iodine (40 mg, 0.16 mmol) and stirred at r.t. for 1 h. The suspension was filtered through Celite, washed with THF (5 mL) and treated with sat. aq. ammonium hydroxide (1 mL). The mixture was stirred at r.t. for 1 h and evaporated. Purification by HPLC (Xbridge, eluting ACN 10-70%/H$_2$O+ 0.1% TFA) gave the desired material as a white solid (3 mg). $^1$H NMR (400 MHz, CD$_3$OD, 35° C., 2:1 mixture of diastereomers) δ ppm 1.40-2.20 (4H, m), 2.5-3.2 (4H, m), 3.40-3.60 (2H, septet), 3.98 (2H, overlapping pair br. d), 4.60 and 5.06 (1H, d), 5.28 (1H, pair d), 7.50 (1H, pair d), 7.75 (1H, pair dd), 7.88 (1H, s), 9.08 (2H, pair s), 9.14 (1H, s). LCMS: rt=2.33 min, m/z=351 [M+H]$^+$, purity=100%.

Compound 95: 2-methyl-6-(pyrimidin-5-yl)-2-(tetrahydro-2H-pyran-4-yl)-2,3-dihydro-5'H-spiro[indene-1,4'-oxazol]-2'-amine

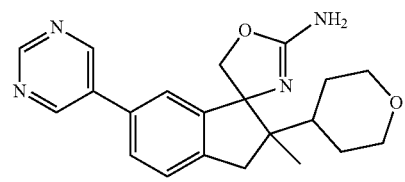 [SMILES: CC1(C2CCOCC2)Cc2ccc(-c3cncnc3)cc2C12COC(N)=N2]

Step 1: 2-methyl-6-(pyrimidin-5-yl)-2-(tetrahydro-2H-pyran-4-yl)-2,3-dihydro-1H-inden-1-one

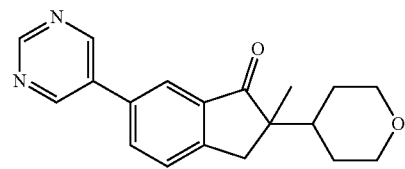 [SMILES: CC1(C2CCOCC2)Cc2ccc(-c3cncnc3)cc2C1=O]

Sodium hydride (60% in oil, 180 mg, 4.50 mmol) was added to a solution of 6-pyrimidin-5-yl-2-tetrahydropyran-4-yl-indan-1-one (518 mg, 1.76 mmol) in THF (20 mL) at r.t. The mixture was stirred for 10 min, treated with iodomethane (0.35 mL, 5.62 mmol), stirred for 12 h, treated H₂O (1 mL) and extracted with EtOAc. The layers were separated and the organic layer dried (Na₂SO₄) and evaporated to give crude material (750 mg). Purification on silica (10 g cartridge, eluting DCM+MeOH 0-3%) gave the desired compound as a cream solid (400 mg). ¹H NMR (400 MHz, CD₃OD, 35° C.) δ ppm 1.23 (3H, s), 1.25 (1H, brd), 1.34 (1H, qd), 1.41 (1H, qd), 1.72 (1H, brd), 1.96 (1H, tt), 2.87 (1H, d), 3.34 (1H, d), 3.34 (1H, td), 3.42 (1H, td), 3.83 (1H, dd), 3.98 (1H, dd), 7.72 (1H, d), 8.01 (1H, d), 8.02 (1H, dd), 9.10 (2H, s), 9.16 (1H, s). LCMS: rt=2.86 min, m/z=309 [M+H]⁺.

Step 2: 5-(2-methyl-3-methylene-2-(tetrahydro-2H-pyran-4-yl)-2,3-dihydro-1H-inden-5-yl)pyrimidine

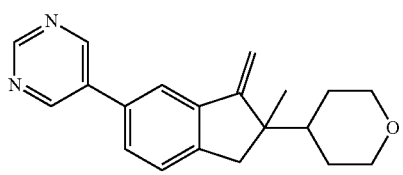 [SMILES: C=C1c2cc(-c3cncnc3)ccc2CC1(C)C1CCOCC1]

At r.t. under N₂, a stirred solution of 2-methyl-6-(pyrimidin-5-yl)-2-(tetrahydro-2H-pyran-4-yl)-2,3-dihydro-1H-inden-1-one (185 mg, 0.60 mmol) in THF (25 mL) was treated with methylmagnesium iodide (3M in Et₂O, 0.4 mL, 1.2 mmol), stirred for 2 h, treated with additional methylmagnesium iodide (3M Et₂O, 1.6 mL) and stirred for 12 h. The mixture was carefully treated with 1M HCl (aqueous, 20 mL) and extracted with EtOAc (2×). The combined organic layers were dried (Na₂SO₄) and evaporated to give a dark residue (~0.5 g). Purification by chromatography (silica, 10 g cartridge, eluting DCM+MeOH 0-2%) gave the desired compound (120 mg) which was used for the next step without further purification. ¹H NMR (400 MHz, CDCl₃) δ ppm 1.20-1.35 (5H, m), 1.45-1.55 (2H, m), 1.65-1.75 (1H, m), 2.70 (1H, d), 3.10 (1H, d), 3.39 (1H, td), 3.45 (1H, td), 4.01 (1H, dt), 4.15 (1H, dt), 5.02 (1H, s), 5.71 (1H, s), 7.42 (1H, d), 7.45 (1H, dd), 7.66 (1H, d), 9.19 (2H, s), 9.31 (1H, s). LCMS: rt=3.41 min, m/z=307 [M+H]⁺.

Step 3: 2-methyl-6-(pyrimidin-5-yl)-2-(tetrahydro-2H-pyran-4-yl)-2,3-dihydro-5'H-spiro[indene-1,4'-oxazol]-2'-amine

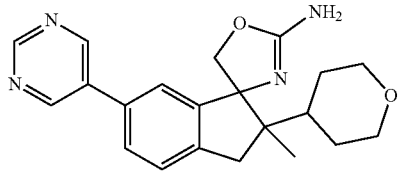 [SMILES: CC1(C2CCOCC2)Cc2ccc(-c3cncnc3)cc2C12COC(N)=N2]

At r.t., a stirred solution of 5-(2-methyl-3-methylene-2-(tetrahydro-2H-pyran-4-yl)-2,3-dihydro-1H-inden-5-yl)pyrimidine (120 mg, 0.39 mmol) in THF (5 mL) and ACN (5 mL) was treated with MP-carbonate resin, agitated for 30 min and filtered. The filtrate was treated with isocyanatosilver (140 mg, 0.93 mmol) followed by iodine (120 mg, 0.47 mmol). The mixture was stirred at r.t. for 1 h, filtered through Celite and evaporated. The residue was dissolved in THF (10 nmL), treated with ammonium hydroxide 880 (2 mL), stirred at r.t. for 12 h and evaporated. The residue was dissolved in MeOH and acidified with TFA, filtered through a cottonwool plug and evaporated. Purification by HPLC (Xbridge, eluting ACN 20-60%/H₂O+0.1% TFA) gave the desired compound as a white solid (14 mg). ¹H NMR (400 MHz, CD₃OD, 35° C.) δ ppm mix of diastereomers dr 85:15: major diastereomer 1.09 (3H, s), 1.3-1.4 (2H, br. t), 1.50 (1H, qd), 1.7 (1H, qd), 2.18 (1H, tt), 2.85 (1H, d), 2.99 (1H, d), 3.50 (2H, t), 3.97 (2H, d), 4.67 (1H, d), 5.44 (1H, d), 7.45 (1H, d), 7.70 (1H, dd), 7.76 (1H, d), 9.08 (2H, s), 9.14 (1H, s), 3H not observed; minor diastereomer 1.04 (3H, s), 1.3-1.8 (4H, m), 2.08 (1H, tt), 2.45 (1H, d), 2.94 (1H, d), 3.48 (2H, t), 4.03 (2H, d), 5.23 (2H, ABq), 7.50 (1H, d), 7.85 (1H, m), 7.97 (1H, s), 9.09 (2H, s), 9.14 (1H, s), 3H not observed. LCMS: rt=2.46 min, m/z=365 [M+H]⁺.

Compound 96: 2-(4-methyltetrahydro-2H-pyran-4-yl)-6-(pyrimidin-5-yl)-2,3-dihydro-5'H-spiro[indene-1,4'-oxazol]-2'-amine

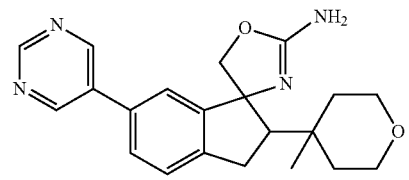 [SMILES: CC1(C2Cc3ccc(-c4cncnc4)cc3C23COC(N)=N3)CCOCC1]

Step 1: 6-bromo-2-(4-methyltetrahydro-2H-pyran-4-yl)-2,3-dihydro-1H-inden-1-one

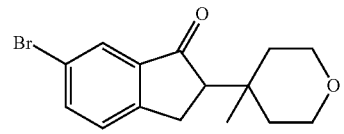 [SMILES: CC1(C2Cc3ccc(Br)cc3C2=O)CCOCC1]

At ca. −10° C. under N₂, copper(I)chloride anhydrous (1.0 g, 10 mmol) was treated with methylmagnesium iodide (3M in Et₂O, 10 mL, 30 mmol). The solvent was evaporated in vacuo and THF (30 mL) was added followed by a solution of 6-bromo-2-(tetrahydro-4H-pyran-4-ylidene)-2,3-dihydro-1H-inden-1-one (4.00 g, 13.6 mmol) in THF (60 mL). The mixture was stirred for 18 h at r.t., treated with 1M aq. HCl solution (400 mL) and extracted with EtOAc (400 mL). The organic phase was separated, washed with 1M aq. HCl solution (2×), brine, dried (Na₂SO₄) and evaporated to give a grey solid (4.3 g) which was used for the next step without further purification. ¹H NMR (400 MHz, CDCl₃) δ ppm 0.94 (3H, s), 1.36 (1H, dq), 1.69 (1H, ddd), 1.86 (1H, dq), 2.0 (1H, ddd), 2.74 (1H, dd), 2.92 (1H, dd), 3.09 (1H, dd), 3.6-3.7 (2H, m), 3.75 (1H, dt), 3.80 (1H, dt), 7.34 (1H, d), 7.65 (1H, dd), 7.81 (1H, d). LCMS: rt=3.34 min, m/z=309/311 [M+H]⁺.

Step 2: 4-(6-bromo-1-methylene-2,3-dihydro-1H-inden-2-yl)-4-methyltetrahydro-2H-pyran

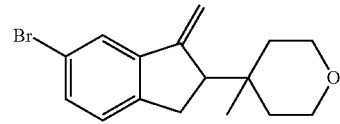 [SMILES: C=C1c2cc(Br)ccc2CC1C1(C)CCOCC1]

At 0° C. under N₂, a stirred solution of 6-bromo-2-(4-methyltetrahydro-2H-pyran-4-yl)-2,3-dihydro-1H-inden-1-one (3.30 g, 10.6 mmol) in THF (100 mL) was treated with a solution of Tebbe's reagent (0.5 M in toluene, 25 mL, 12.5 mmol). The mixture was warmed to r.t. for 5 h, treated with additional Tebbe's reagent (0.5M in toluene, 5 mL, 2.5 mmol) and stirred for 12 h. The mixture was carefully quenched with aq. NaOH solution (0.1M, 6 mL, 0.6 mmol), stirred for 15 min, treated with Na₂SO₄ and filtered through Celite. The cake was washed with THF (100 mL) and DCM (200 mL) and the filtrate concentrated in vacuo to leave a red gum (7.6 g). Purification on silica (40 g cartridge, eluting DCM) gave the desired compound as an orange oil (2.7 g). ¹H NMR (400 MHz, CDCl₃) δ ppm 0.73 (3H, s), 1.33 (1H, dq), 1.49 (1H, dq), 1.5-1.70 (2H, m), 2.80 (1H, dd), 2.83 (1H, dd), 2.93 (1H, dd), 3.55 (2H, tq), 3.75-3.85 (2H, m), 5.05 (1H, d), 5.59 (1H, d), 7.08 (1H, d), 7.28 (1H, dd), 7.54 (1H, d). LCMS: rt=3.70 min.

Step 3: 6-bromo-2-(4-methyltetrahydro-2H-pyran-4-yl)-2,3-dihydro-5'H-spiro[indene-1,4'-oxazol]-2'-amine

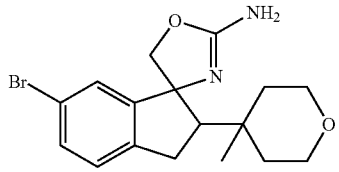 [SMILES: CC1(C2Cc3ccc(Br)cc3C23COC(N)=N3)CCOCC1]

At 22° C. under N₂, a solution of 4-(6-bromo-1-methylene-2,3-dihydro-1H-inden-2-yl)-4-methyltetrahydro-2H-pyran (2.50 g, 8.14 mmol) in THF (25 mL) and ACN (25 mL) was treated with isocyanatosilver (3.66 g, 24.4 mmol) followed by iodine (3.10 g, 12.2 mmol). The mixture was stirred at r.t. for 1 h and the resulting suspension filtered through Celite and concentrated in vacuo to leave an orange gum. The gum was dissolved in THF (20 mL) and treated with ammonium hydroxide 880 (5 mL), stirred at r.t. for 1 h, evaporated and triturated with ACN (50 mL). The solids were removed by filtration and the filtrate evaporated to give a dark solid (3.4 g) which was partitioned between DCM and 0.5M aq. NaOH solution. The organic phase was separated and washed with brine, dried (Na₂SO₄) and evaporated. Purification on silica (20 g cartridge, eluting DCM+7M ammonia MeOH 0 to 6%; purified twice) gave dark solids (1.0 g) which were used for the next step without further purification. LCMS: rt=2.5-2.9 min, m/z=365/367 [M+H]⁺.

Step 4: 2-(4-methyltetrahydro-2H-pyran-4-yl)-6-(pyrimidin-5-yl)-2,3-dihydro-5'H-spiro[indene-1,4'-oxazol]-2'-amine

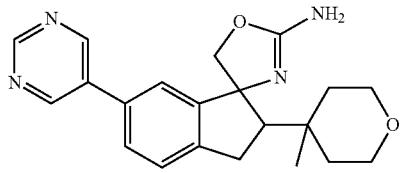 [SMILES: CC1(C2Cc3ccc(-c4cncnc4)cc3C23COC(N)=N3)CCOCC1]

The title compound (90 mg, white solid) was prepared according to General Procedure 1 using 6-bromo-2-(4-methyltetrahydro-2H-pyran-4-yl)-2,3-dihydro-5'H-spiro[indene-1,4'-oxazol]-2'-amine (220 mg, 0.60 mmol) and pyrimidin-5-ylboronic acid (86 mg, 0.69 mmol). ¹H NMR (400 MHz, CD₃OD, 35° C.) δ ppm 1.30 (3H, s), 1.50 (2H, brs), 1.80 (1H, br. t), 2.00 (1H, br. t), 2.60 (1H, t), 3.15-3.25 (2H, m), 3.74 (2H, q), 3.81 (2H, br. s), 5.25 (2H, ABq), 7.52 (1H, d), 7.75 (1H, dd), 7.90 (1H, d), 9.10 (2H, s), 9.14 (1H, s). 3H not observed. LCMS: rt=2.45 min, m/z=365 M+H]⁺.

Compound 97: 2-((2R,6S)-2,6-dimethyltetrahydro-2H-pyran-4-yl)-6-(pyrimidin-5-yl)-2,3-dihydro-5'H-spiro[indene-1,4'-oxazol]-2'-amine

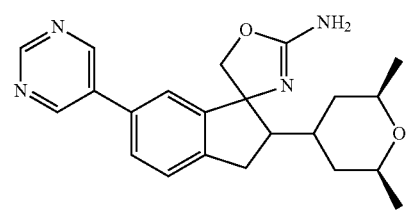 [SMILES: C[C@@H]1CC(C2Cc3ccc(-c4cncnc4)cc3C23COC(N)=N3)C[C@H](C)O1]

Step 1: 2,6-dimethyltetrahydro-4H-pyran-4-one (rac)

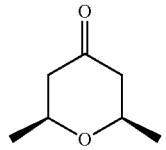

At 50° C., a solution of 2,6-dimethyl-4H-pyran-4-one (6.21 g, 50.0 mmol) in THF (93 mL) was treated with palladium on charcoal (0.53 g, 0.50 mmol). The mixture was put under H₂ (1 atm), stirred for 22 h at 50° C., cooled to r.t., filtered (Celite) and evaporated to leave an oil (9 g). Flash chromatography (40 g Si cartridge, 10% TBME in petrol ether) afforded a yellow oil (5.1 g). ¹H NMR (400 MHz, CDCl₃) δ ppm 1.30 (6H, d), 2.16 (2H, dd), 2.31 (2H, dd), 3.68-3.76 (2H, m). ¹³C NMR (100 MHz, CDCl₃) δ ppm 22.2 (CH₃), 49.2 (CH₂), 73.2 (OCH), 218.0 (C=O).

Step 2: 6-bromo-2-(2,6-dimethyltetrahydro-4H-pyran-4-ylidene)-2,3-dihydro-1H-inden-1-one

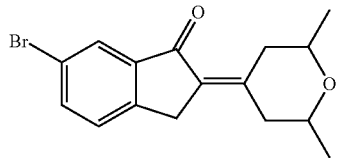 [SMILES: CC1CC(=C2Cc3ccc(Br)cc3C2=O)CC(C)O1]

At 0° C. under N₂, a solution of lithium bis(trimethylsilyl)amide (0.84 g, 5.00 mmol) in THF (5 mL) was treated with a solution of 6-bromo-2,3-dihydro-1H-inden-1-one (1.06 g, 5.00 mmol) in THF (10 mL), warmed to r.t. and treated with a solution of 2,6-dimethyltetrahydro-4H-pyran-4-one (0.64 g, 5.00 mmol) in THF (1 mL). The resulting mixture was stirred at 50° C. for 6 h, allowed to cool to r.t. and treated with diluted ammonium chloride solution. The layers were separated and aqueous layer extracted with EtOAc (2×25 mL). The combined organiclayers were washed with brine, dried (Na₂SO₄) and evaporated to leave a black oil (1.7 g). Flash chromatography (20 g Si cartridge, neat DCM) afforded the title compound as a brown solid (0.63 g). $^1$H NMR (400 MHz, CDCl₃) δ ppm 1.27 (6H, d), 1.78 (1H, td), 2.04 (1H, td), 2.35 (1H, dt), 3.43-3.57 (2H, m), 3.55 (2H, q), 4.37 (1H, dt), 7.29 (1H, d), 7.60 (1H, dd) and 7.85 (1H, d). $^{13}$C NMR (100 MHz, CDCl₃) δ ppm 22.22, 22.41, 31.36, 36.16, 40.73, 74.24, 76.81, 121.65, 127.02, 127.70, 128.13, 138.83, 142.17, 146.39, 152.27, 192.92. LCMS: rt=3.47 min, m/z=321/323 [M+H]⁺.

Step 3: 2-(2,6-dimethyltetrahydro-4H-pyran-4-ylidene)-6-(pyrimidin-5-yl)-2,3-dihydro-1H-inden-1-one

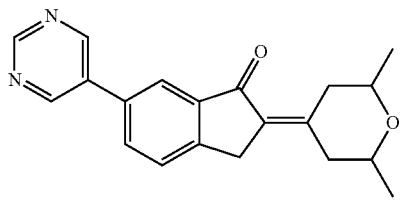 [SMILES: CC1CC(=C2Cc3ccc(-c4cncnc4)cc3C2=O)CC(C)O1]

The title compound (481 mg, yellow solid) was prepared according to General Procedure 1 using 6-bromo-2-(2,6-dimethyltetrahydro-4H-pyran-4-ylidene)-2,3-dihydro-1H-inden-1-one (626 mg, 1.95 mmol) and pyrimidin-5-ylboronic acid (241 mg, 1.95 mmol). $^1$H NMR (400 MHz, CDCl₃) δ ppm 1.33 (6H, d), 1.87 (1H, td), 2.12 (1H, td), 2.95 (1H, dt), 3.51-3.65 (2H, m), 3.75 (2H, q), 4.48 (1H, dt), 7.63 (1H, d), 7.78 (1H, dd), 8.00 (1H, d), 8.99 (2H, s), 9.23 (1H, s). LCMS: rt=3.14 min, m/z=321 [M+H]⁺.

Step 4: 2-((2R,6S)-2,6-dimethyltetrahydro-2H-pyran-4-yl)-6-(pyrimidin-5-yl)-2,3-dihydro-1H-inden-1-one

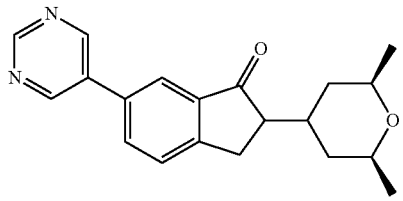 [SMILES: C[C@@H]1CC(C2Cc3ccc(-c4cncnc4)cc3C2=O)C[C@H](C)O1]

A stirred solution of 2-(2,6-dimethyltetrahydro-4H-pyran-4-ylidene)-6-(pyrimidin-5-yl)-2,3-dihydro-1H-inden-1-one (480 mg, 1.50 mmol) in THF (20 mL) was treated with palladium on charcoal (94 mg, 0.040 mmol) and stirred under H₂ (1 atm) at r.t. for 89 h. Rhodium on charcoal (50 mg) was added and the mixture was continued to stir under H₂ at r.t. for 18 h. The mixture was filtered (Celite), the filtrate treated with fresh Pd/C (90 mg) and stirred under H₂ (3 atm) at r.t. for 36 h, filtered (Celite) and concentrated in vacuo to leave a black oil (600 mg). Flash chromatography (12 g Si cartridge, 50% EtOAc in petrol ether) afforded a yellow syrup (260 mg) which was used for the next step without further purification (mixture of 2 diastereoisomers and some starting material). LCMS; rt=3.02 min, m/z=323 [M+H]⁺ (DP) and rt=3.07 min, m/z=323 [M+H]⁺.

Step 5: 5-(2-((2R,6S)-2,6-dimethyltetrahydro-2H-pyran-4-yl)-3-methylene-2,3-dihydro-1H-inden-5-yl)pyrimidine

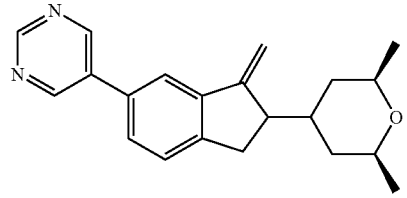 [SMILES: C=C1c2cc(-c3cncnc3)ccc2CC1C1C[C@@H](C)O[C@@H](C)C1]

At r.t. under N₂, a stirred solution of 2-((2R,6S)-2,6-dimethyltetrahydro-2H-pyran-4-yl)-6-(pyrimidin-5-yl)-2,3-dihydro-1H-inden-1-one (260 mg, 0.81 mmol) in THF (5 mL) was treated with a 1M solution of Tebbe's reagent (1.77 mL, 0.89 mmol) in toluene. The mixture was stirred at r.t. for 2 h, heated at 40° C. for 1 h and carefully quenched with 0.1M aq. NaOH solution (0.2 mL), stirred for 15 min and treated with MgSO₄. The mixture was filtered through Celite and washed with THF (10 mL). The filtrate was concentrated in vacuo to leave a brown gum (200 mg). Flash chromatography (4 g Si cartridge, 10-20% EtOAc in DCM) afforded yellow solids (23 mg). $^1$H NMR (400 MHz, CDCl₃) δ ppm 0.96-1.32 (7H, m), 1.38-1.46 (1H, m), 1.51-1.63 (1H, m), 1.80-1.92 (1H, m), 2.74-2.84 (1H, m), 2.90-3.16 (2H, m), 3.20-3.46 (2H, m), 3.70-3.84 (1H, m), 4.95 (d) and 5.03 (d) (1H), 5.60 (d) and 5.62 (d) (1H), 7.30-7.40 (2H, m), 7.57-7.59 (1H, m), 8.94 (2H, s) and 9.16 (1H, s). LCMS: rt=3.60 min, m/z=321 [M+H]⁺.

Step 6: 2-((2R,6S)-2,6-dimethyltetrahydro-2H-pyran-4-yl)-6-(pyrimidin-5-yl)-2,3-dihydro-5'H-spiro[indene-1,4'-oxazol]-2'-amine

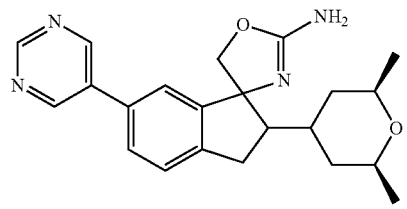 [SMILES: C[C@@H]1CC(C2Cc3ccc(-c4cncnc4)cc3C23COC(N)=N3)C[C@H](C)O1]

At r.t. under N₂, a stirred solution of 5-(2-((2R,6S)-2,6-dimethyltetrahydro-2H-pyran-4-yl)-3-methylene-2,3-dihydro-1H-inden-5-yl)pyrimidine (22 mg, 0.070 mmol) in THF (1 mL) and ACN (1 mL) was treated with isocyanatosilver (31 mg, 0.21 mmol) followed by iodine (27 mg, 0.11 mmol). The mixture was stirred r.t. for 1 h, filtered through Celite and concentrated in vacuo to leave a grey gum which was dissolved in THF (2 mL) and treated with sat. aq. ammonium hydroxide (1 mL). The mixture was stirred at r.t. for 1 h and evaporated to leave a residue (30 mg). Purification by HPLC (ACN/H₂O+0.1% TFA) gave the desired compound as a pale yellow gum (8 mg). $^1$H NMR (400

MHz, CD$_3$OD, 4 pairs of diastereomers) δ ppm 0.96-1.12 (1H, m), 1.13-1.23 (7H, m), 1.24-1.40 (1H, m), 1.48-1.59 (1H, m), 1.69-2.05 (1H, m), 2.14-2.53 (1H, m), 2.70-2.97 (1H, m), 3.14-3.28 (1H, m), 3.50-3.66 (1H, m), 3.80-4.04 (1H, m), 4.55-5.38 (2H, oxa-head CH2), 7.45-7.54 (1H, m), 7.71-7.79 (1H, m), 7.81-7.96 (1H, m), 9.12 (2H, s) and 9.15 (1H, s). LCMS: rt=2.52 min, m/z=379 [M+H]$^+$, purity=100%.

Compound 98: 2-morpholino-6-(pyrimidin-5-yl)-2,3-dihydro-5'H-spiro[indene-1,4'-oxazol]-2'-amine

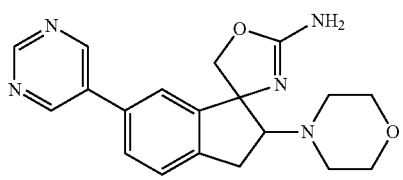 [SMILES: NC1=NC2(CO1)c1cc(-c3cncnc3)ccc1CC2N1CCOCC1]

Step 1: 2,6-dibromo-2,3-dihydro-1H-inden-1-one

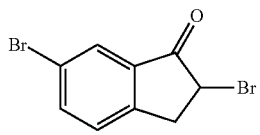 [SMILES: O=C1c2cc(Br)ccc2CC1Br]

A stirred suspension of 6-bromoindan-1-one (20 g, 94.7 mmol) in acetic acid (250 mL) was treated dropwise with a solution of hydrobromic acid (48 wt. % in H$_2$O, 1.0 mL, 18 mmol) and bromine (4.86 mL, 94.7 mmol) in acetic acid (50 mL) at ambient temperature. After 4 h, the solution was added in small portions to a stirring ice-water (800 mL). The mixture was diluted with EtOAc (1 L) and filtered. The organic phase was separated, washed with H$_2$O (2×500 mL), dried (Na$_2$SO$_4$) and evaporated to give a brown semi-solid. This material was suspended in hexane/Et$_2$O (1:1, 150 mL) and heated at 60° C. for 20 min. The hot suspension was filtered and the filtrate was cooled and concentrated in vacuo to give an orange solid. The material was stirred in Et$_2$O (45 mL) for 30 min to give a fine precipitate. The solids were collected by filtration and washed with Et$_2$O to afford the desired product as an off-white solid (9.5 g). $^1$H NMR (400 MHz, CDCl$_3$) δ ppm 3.35 (1H, dd), 3.77 (1H, dd), 4.65 (1H, dd), 7.34 (1H, dd), 7.75 (1H, dd), 7.94 (1H, s). LCMS: rt=3.25 min, m/z=291 [M+H]$^+$.

Step 2:
6-bromo-2-morpholino-2,3-dihydro-1H-inden-1-one

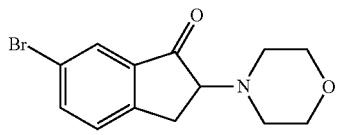 [SMILES: O=C1c2cc(Br)ccc2CC1N1CCOCC1]

A mixture of 2,6-dibromo-2,3-dihydro-1H-inden-1-one (7.50 g, 25.8 mmol) and K$_2$CO$_3$ (5.72 g, 41.4 mmol) in acetone (200 mL) was treated with morpholine (2.72 mL, 31.0 mmol) and stirred at r.t. After 18 h, the mixture was partitioned between H$_2$O (500 mL) and EtOAc (500 mL). The layers were separated and the aqueous phase was extracted with EtOAc (250 mL). The combined organic phases were dried (Na$_2$SO$_4$) and evaporated to give a dark purple oil (4.8 g). Purification of this material by column chromatography (silica gel, eluting 10-95% EtOAc in petroleum ether) gave the desired material as a dark green semi-solid (2.4 g). $^1$H NMR (400 MHz, CDCl$_3$) δ ppm 2.49-2.56 (2H, m), 2.71-2.78 (2H, m), 3.00-3.20 (2H, m), 3.65-3.74 (5H, m), 7.29 (1H, d), 7.65 (1H, dd), 7.81 (1H, d). LCMS: rt=2.44 min, m/z=296/298 [M+H]$^+$.

Step 3: 4-(6-bromo-1-methylene-2,3-dihydro-1H-inden-2-yl)morpholine

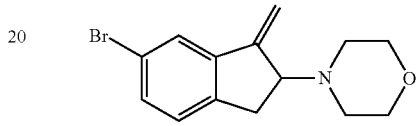

To a stirred solution of 6-bromo-2-morpholino-2,3-dihydro-1H-inden-1-one (2.1 g, 7.09 mmol) in THF (50 mL) at 0° C. was added dropwise a solution of Tebbe's reagent (0.5M toluene, 17.0 mL, 8.51 mmol) over 10 min. The mixture was maintained at this temperature for 1 h and allowed to warm up to r.t. overnight. The mixture was carefully treated with NaOH (0.1M aq. solution, 4.0 mL, 0.40 mmol), stirred for 20 min, treated with sodium sulphate and filtered through Celite. The filtrate evaporated to leave a brown gum (2.56 g) which was purified by column chromatography (silica gel, eluting with EtOAc), resulting in the desired product as a pale yellow oil (800 mg). $^1$H NMR (400 MHz, CDCl$_3$) δ ppm 2.48-2.59 (4H, m), 2.89-3.05 (2H, m), 3.58-3.73 (4H, m), 4.03-4.09 (1H, m), 5.32 (1H, d), 5.78 (1H, d), 7.16 (1H, d), 7.33 (1H, dd), 7.65 (1H, d). LCMS: rt=2.54 min, m/z=294/296 [M+H]$^+$.

Step 4: 6-bromo-2-morpholino-2,3-dihydro-5'H-spiro[indene-1,4'-oxazol]-2'-amine

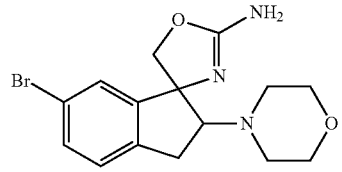 [SMILES: NC1=NC2(CO1)c1cc(Br)ccc1CC2N1CCOCC1]

To a stirred solution of 4-(6-bromo-1-methylene-2,3-dihydro-1H-inden-2-yl)morpholine (800 mg, 2.72 mmol) in THF (40 mL) and ACN (40 mL) at r.t. was added isocyanatosilver (1.22 g, 8.16 mmol), followed by a portionwise addition of molecular iodine (1.04 g, 4.08 mmol). The mixture was stirred at r.t. for 4 h, filtered through Celite and concentrated in vacuo to leave a yellow semi-solid. This material was dissolved in THF (6 mL) and treated with a sat. aqueous ammonium hydroxide solution (1 mL). The mixture was stirred at r.t. for 48 h, concentrated in vacuo and purified by RP-HPLC (Xterra, eluting ACN/H$_2$O+0.1% TFA) to afford a white solid (210 mg, mixture of 4 diastereoisomers as the bis-TFA salt). $^1$H NMR (400 MHz, CD$_3$OD) δ ppm 2.70-2.78 (2H, m), 2.79-2.88 (2H, m), 3.06-3.22 (2H, m), 3.62 (1H, t), 3.74 (4H, t), 5.00 (2H, d), 7.29 (1H, d), 7.56 (1H, dd), 7.75 (1H, d). LCMS: rt=2.34 min, m/z=352/354 [M+H]⁺.

Step 5: 2-morpholino-6-(pyrimidin-5-yl)-2,3-dihydro-5'H-spiro[indene-1,4'-oxazol]-2'-amine

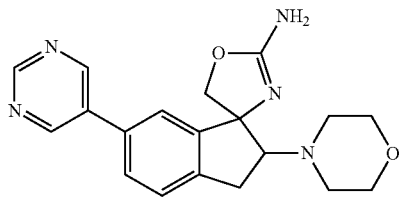 [SMILES: NC1=NC2(CO1)c1cc(-c3cncnc3)ccc1CC2N1CCOCC1]

The title compound (34 mg, white solids) was prepared according to General Procedure 1 using 6-bromo-2-morpholino-2,3-dihydro-5'H-spiro[indene-1,4'-oxazol]-2'-amine (60 mg, 0.10 mmol) and pyrimidin-5-ylboronic acid (50 mg, 0.40 mmol). ¹H NMR (400 MHz, CD₃OD, 35° C.) δ ppm 2.80 (2H, dt), 2.88 (2H, dt), 3.25 (2H, qd), 3.68 (1H, t), 3.77 (4H, t), 5.11 (2H, q), 7.56 (1H, d), 7.78 (1H, dd), 7.93 (1H, d), 9.09 (2H, s), 9.15 (1H, s), 4H not observed (inc.2TFA). LCMS: rt=2.12 min, m/z=352 [M+H]⁺, purity=97.8%.

Compound 99: 2-morpholino-6-(5-(prop-1-yn-1-yl)pyridin-3-yl)-2,3-dihydro-5'H-spiro[indene-1,4'-oxazol]-2'-amine

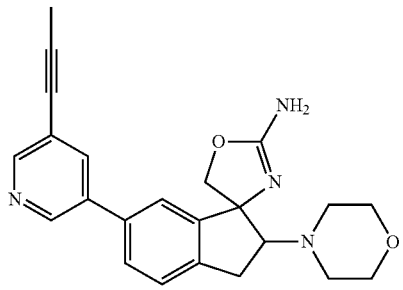 [SMILES: CC#Cc1cncc(-c2ccc3c(c2)C2(COC(N)=N2)C(N2CCOCC2)C3)c1]

The title compound (26 mg, white solids) was prepared according to General Procedure 1 using 6-bromo-2-morpholino-2,3-dihydro-5'H-spiro[indene-1,4'-oxazol]-2'-amine.2 TFA (65 mg, 0.11 mmol) and (5-prop-1-ynyl-3-pyridyl)boronic acid (45 mg, 0.28 mmol). ¹H NMR (400 MHz, CD₃OD, 35° C.) δ ppm 2.09 (3H, s), 2.70 (2H, dt), 2.78 (2H, dt), 3.25 (2H, qd), 3.52 (1H, t), 3.72 (4H, t), 5.03 (1H, d), 5.12 (1H, d), 7.51 (1H, d), 7.70 (1H, dd), 7.85 (1H, d), 8.11 (1H, t), 8.52 (1H, s), 8.73 (1H, s), 5H not observed (incl. 3 TFA). LCMS: rt=2.94 min, m/z=389 [M+H]⁺, purity=100%.

Compound 100: 3-(2'-amino-2-morpholino-2,3-dihydro-5'H-spiro[indene-1,4'-oxazol]-6-yl)-5-methoxybenzonitrile

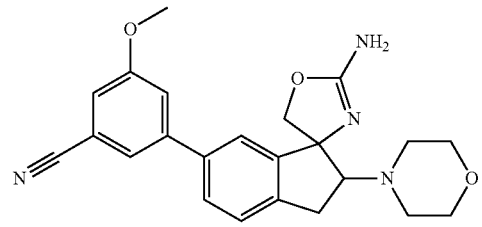 [SMILES: COc1cc(C#N)cc(-c2ccc3c(c2)C2(COC(N)=N2)C(N2CCOCC2)C3)c1]

The title compound (30 mg, white solids) was prepared according to General Procedure 1 using 6-bromo-2-morpholino-2,3-dihydro-5'H-spiro[indene-1,4'-oxazol]-2'-amine.2 TFA (65 mg, 0.11 mmol) and 3-methoxy-5-(4,4,5,5-tetramethyl-1,3,2-dioxaborolan-2-yl)benzonitrile (75 mg, 0.29 mmol). ¹H NMR (400 MHz, CD₃OD, 35° C.) δ ppm 2.70 (2H, dt), 2.78 (2H, dt), 3.19 (2H, qd), 3.52 (1H, t), 3.72 (4H, t), 3.90 (3H, s), 5.03 (1H, q), 5.12 (1H, d), 7.30 (1H, s), 7.45-7.56 (2H, m), 7.58 (1H, s), 7.70 (1H, dd), 7.83 (1H, s), 4H not observed (incl. 2 TFA). LCMS: rt=3.20 min, m/z=405 [M+H]⁺, purity=99.5%.

Compound 101: 3-(2'-amino-2-methyl-2-(tetrahydro-2H-pyran-4-yl)-2,3-dihydro-5'H-spiro[indene-1,4'-oxazol]-6-yl)-5-methoxybenzonitrile Step 1: 6-bromo-2-(2H-pyran-4(3H,5H,6H)-ylidene)-2,3-dihydro-1H-inden-1-one

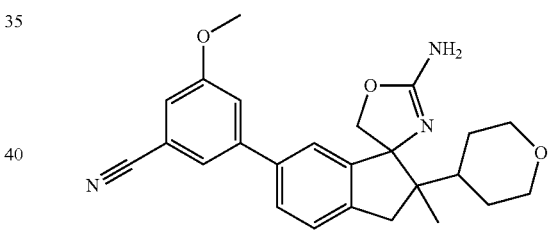

Under N₂ at −78° C., a solution of lithium bis(trimethylsilyl)amide (1M in THF, 126 mL, 26 mmol) was treated with 6-bromoindan-1-one (5.00 g, 23.7 mmol) in THF (30 mL) and stirred for 1.5 h. The mixture was treated with tetrahydro-4H-pyran-4-one (2.6 mL, 28 mmol) and stirred for 1 h at −78° C. and 12 h at r.t. Solvent was evaporated under reduced pressure. The residue was dissolved in EtOAc, washed with an aq. sat. NH₄Cl solution and extracted with EtOAc. The organic phase was separated and the aqueous phase was extracted with EtOAc. The combined organic extracts were washed with brine, dried over Na₂SO₄ and evaporated. The residue was dissolved in DCM (30 mL), treated with trifluoroacetic acid (1 mL, 13 mmol) and stirred at 40° C. for 12 h. Solvent was evaporated under reduced pressure. Purification of the residue by chromatography (0-25% EtOAc in hexane) afforded the title compound (2.3 g). $^1$H NMR (400 MHz, CDCl$_3$) δ ppm 2.48 (2H, t), 3.36 (2H, t), 3.62 (2H, s), 3.81 (2H, t), 3.87 (2H, t), 7.36 (1H, d), 7.67 (1H, d), 7.93 (1H, d).

Step 2: 3-methoxy-5-(3-oxo-2-(2H-pyran-4(3H,5H,6H)-ylidene)-2,3-dihydro-1H-inden-5-yl)benzonitrile

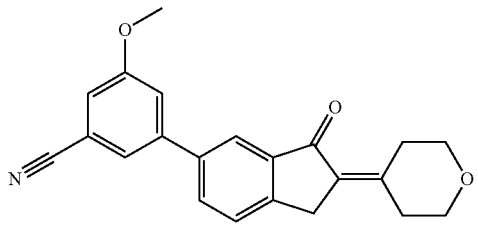 [SMILES: COc1cc(C#N)cc(-c2ccc3c(c2)C(=O)C(=C2CCOCC2)C3)c1]

Under N$_2$ at r.t., a degassed (15 min of N$_2$ bubbling) mixture of 6-bromo-2-(2H-pyran-4(3H,5H,6H)-ylidene)-2,3-dihydro-1H-inden-1-one (200 mg, 0.68 mmol), 3-methoxy-5-chlorophenylboronic acid pinacol ester (260 mg, 1.00 mmol), potassium phosphate (430 mg, 2.03 mmol) in 1,4-dioxane (5 mL) and H$_2$O (0.5 mL) was treated with tetrakis(triphenylphosphine)palladium(0) (120 mg, 0.10 mmol) and stirred at 100° C. for 24 h. The mixture was cooled to r.t., filtered through Celite and evaporated. Purification of the residue by chromatography (0-30% EtOAc in hexane) afforded the title compound (227 mg). $^1$H NMR (400 MHz, CDCl$_3$) δ ppm 2.51 (2H, t), 3.40 (2H, t), 3.73 (2H, s), 3.82 (2H, t), 3.87-3.90 (5H, m), 7.15 (1H, m), 7.36 (1H, m), 7.48 (1H, s), 7.58 (1H, d), 7.76 (1H, m), 7.98 (1H, s). MS: m/z=343.8 [M–H]$^-$.

Step 3: 3-methoxy-5-(3-oxo-2-(tetrahydro-2H-pyran-4-yl)-2,3-dihydro-1H-inden-5-yl)benzonitrile

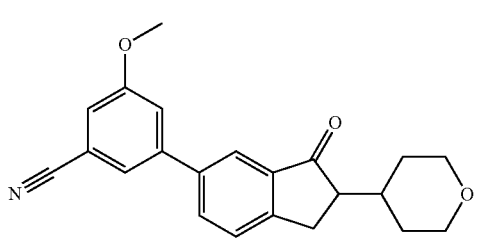 [SMILES: COc1cc(C#N)cc(-c2ccc3c(c2)C(=O)C(C2CCOCC2)C3)c1]

A stirred solution of 3-methoxy-5-(3-oxo-2-(2H-pyran-4(3H,5H,6H)-ylidene)-2,3-dihydro-1H-inden-5-yl)benzonitrile (220 mg, 0.64 mmol) in THF (20 mL) was treated with 10% Pd/C (200 mg) and stirred under H$_2$ (1 atm) at 35° C. for 5 h. The mixture was filtered through Celite and the filtrate evaporated. The residue (220 mg) was used into next step without further purification. $^1$H NMR (400 MHz, CDCl$_3$) δ ppm 2.75-2.77 (1H, m), 3.02-3.07 (1H, m), 3.37-3.48 (2H, m), 3.85-3.95 (5H, m), 4.00-4.04 (1H, m), 4.32-4.37 (2H, m), 7.15 (1H, s), 7.33 (1H, s), 7.46 (1H, s), 7.58-7.60 (1H, m), 7.77-7.80 (1H, m), 7.90 (1H, s), 8.09 (1H, s). MS: m/z=348.05 [M+H]$^+$.

Step 4: 3-methoxy-5-(2-methyl-3-oxo-2-(tetrahydro-2H-pyran-4-yl)-2,3-dihydro-1H-inden-5-yl)benzonitrile

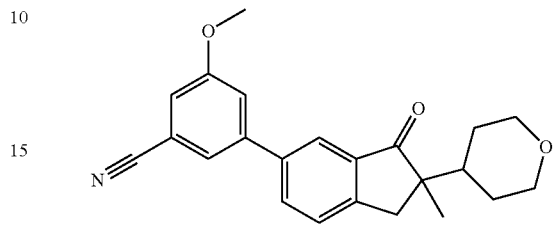

At 0° C. under N$_2$, a mixture of sodium hydride (95%, 33 mg, 1.31 mmol) in THF (5 mL) was treated with 3-methoxy-5-(3-oxo-2-(tetrahydro-2H-pyran-4-yl)-2,3-dihydro-1H-inden-5-yl)benzonitrile (180 mg, 0.52 mmol) in THF (5 mL) and stirred for 30 min. The mixture was treated dropwise with methyl iodide (0.10 mL, 1.6 mmol) and stirred for 12 h at r.t. Solvent was evaporated under reduced pressure. The residue was dissolved in EtOAc, washed by aq. sat. NH$_4$Cl and extracted with EtOAc. The organic phase was separated and the aqueous phase was further extracted with EtOAc. The combined organic extracts were washed with brine, dried over Na$_2$SO$_4$ and evaporated. Purification by chromatography (0-10% EtOAc in hexane) afforded the title compound (40 mg). $^1$H NMR (400 MHz, CDCl$_3$) δ ppm 1.24-1.31 (5H, m), 1.42-1.46 (1H, m), 1.72-1.75 (1H, m), 2.02-2.14 (1H, m), 2.77-2.82 (1H, m), 3.25-3.45 (3H, m), 3.85-3.90 (4H, m), 4.03-4.07 (1H, m), 7.15 (1H, s), 7.33 (1H, s), 7.46 (1H, m), 7.57 (1H, m), 7.81 (1H, m), 7.90 (1H, s). MS: m/z=362.2 [M–H]$^-$.

Step 5: 3-methoxy-5-(2-methyl-3-methylene-2-(tetrahydro-2H-pyran-4-yl)-2,3-dihydro-1H-inden-5-yl)benzonitrile

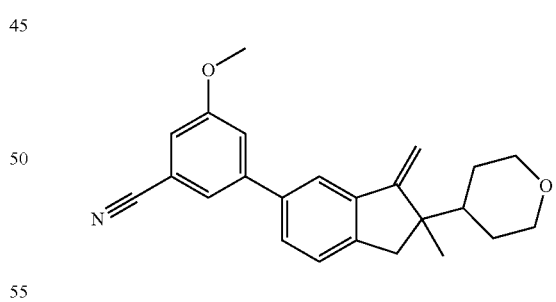

At r.t. under N$_2$, n-butyllithium (2.5M in hexanes, 0.2 mL, 0.5 mmol) was added to a suspension of methyl(triphenyl)phosphonium iodide (130 mg, 0.32 mmol) in THF (5 mL). The mixture was stirred for 15 min, treated with a solution of 3-methoxy-5-(2-methyl-3-oxo-2-(tetrahydro-2H-pyran-4-yl)-2,3-dihydro-1H-inden-5-yl)benzonitrile (55 mg, 0.15 mmol) in THF (5 mL) and stirred at r.t. for 48 h. The mixture was filtered and the filtrate evaporated. Purification of the residue by chromatography (silica, 10 g cartridge, eluting DCM/0-2% MeOH) followed by HPLC (Xbridge, eluting ACN, 20-95%/H$_2$O+0.2% NH$_3$) gave the desired compound (6 mg). $^1$H NMR (400 MHz, CDCl$_3$) δ ppm 1.15-1.3 (4H, m), 1.35-1.45 (2H, m), 1.6-1.7 (2H, m), 2.63 (1H, d), 3.08 (1H, d), 3.30 (1H, td), 3.35 (1H, td), 3.88 (3H, s), 3.95 (1H, dd), 4.05 (1H, dd), 4.95 (1H, s), 5.65 (1H, s), 7.10 (1H, d), 7.30 (2H, m), 7.40 (1H, dd), 7.47 (1H, d), 7.59 (1H, d). LCMS: rt=3.71 min, m/z=360 [M+H]$^+$.

Step 6: 3-(2'-amino-2-methyl-2-(tetrahydro-2H-pyran-4-yl)-2,3-dihydro-5'H-spiro[indene-1,4'-oxazol]-6-yl)-5-methoxybenzonitrile

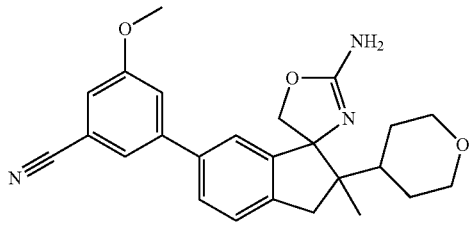 [SMILES: COc1cc(C#N)cc(-c2ccc3c(c2)C2(COC(N)=N2)C(C)(C2CCOCC2)C3)c1]

At r.t. under N$_2$, a solution of 3-methoxy-5-(2-methyl-3-methylene-2-(tetrahydro-2H-pyran-4-yl)-2,3-dihydro-1H-inden-5-yl)benzonitrile (6 mg, 0.02 mmol) in THF (5 mL) and ACN (5 mL) was treated with isocyanatosilver (9.0 mg, 0.06 mmol) followed by iodine (8 mg, 0.03 mmol) and stirred at r.t. for 1 h. The suspension was filtered through Celite, washed with THF (3 mL) and the filtrate was evaporated. The residue was dissolved in THF (5 mL), treated with ammonia (880, 1 mL), stirred at r.t. for 1 h and evaporated. Purification by HPLC (Xbridge, eluting ACN (20-95%)/H$_2$O+0.2% NH$_3$) gave the desired product as a white solid (6 mg). $^1$H NMR (400 MHz, CD$_3$OD, 35° C., 5:1 diastereomeric ratio) δ ppm 0.91 & 1.00 (3H, pair s), 1.4-1.7 (4H, m), 2.03 & 2.13 (1H, pair br. t), 2.69 (1H, d), 2.79 & 3.03 (1H, pair d), 4.6 (2H, br. q), 3.89 (3H, s), 3.9-4.1 (3H, m), 4.68 & 4.90 (1H, pair d), 7.22 (1H, s), 7.28 & 7.29 (1H, pair d), 7.40 (2H, br. d), 7.48 (1H, d), 7.51 (1H, s), 2H not observed. LCMS: rt=3.34 min, m/z=418 [M+H]$^+$, purity=98.2%.

Compound 102: 2-methyl-6-(pyrimidin-5-yl)-2-(tetrahydro-2H-pyran-4-yl)-2,3-dihydro-5'H-spiro[indene-1,4'-oxazol]-2'-amine (4 diastereoisomers)

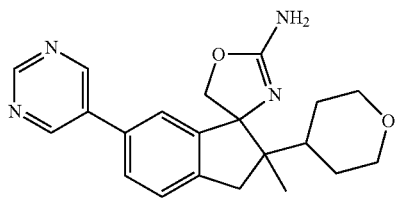 [SMILES: CC1(C2CCOCC2)Cc2ccc(-c3cncnc3)cc2C12COC(N)=N2]

At r.t. under N$_2$, a solution of 5-(2-methyl-3-methylene-2-(tetrahydro-2H-pyran-4-yl)-2,3-dihydro-1H-inden-5-yl)pyrimidine (441 mg, 1.44 mmol) in THF (10 mL) was treated with isocyanatosilver (647 mg, 4.32 mmol) followed by iodine (548 mg, 2.16 mmol), stirred at r.t. for 4 h and filtered through Celite. The filtrate was treated with aq. ammonia (4 mL) and the resulting mixture stirred at r.t. for 12 h. The solvents were removed at reduced pressure and the residue dissolved in EtOAc and preabsorbed onto silica. Purification by flash chromatography (Si 20 g, DCM and 5% of 0.1M NH$_3$ in MeOH) afforded an orange solid (102 mg) which was further purified by chiral HPLC. The crude material was dissolved to 7 mg/mL in MeOH and purified by HPLC using a Lux C1 column (250 mm×20 mm, 5 um). The eluent was HEPT/IPA (DEA was added as a modifier). The flow rate was 21 mL/min. This procedure resulted in both minor isomers and a mixture of both major isomers. The mixture of major isomers was dissolved in MeOH (15 mL) and purified by HPLC (Lux C1 column, 250 mm×20 mm, 5 um). The eluent was HEPT/EtOH (DEA was added as a modifier). The flow rate was 21 mL/min. Each isomer was dissolved in MeOH (1 mL) and purified by HPLC (Lux C1 column, 250 mm×20 mm, 5 um). The eluent was HEPT/IPA (DEA was added as a modifier).

Isomer 1: (6.0 mg, purity=98.2%, ee=100%)
$^1$H NMR (400 MHz, CD$_3$OD) δ ppm 0.91 (3H, s), 1.47-1.55 (2H, m), 1.57-1.73 (2H, m), 2.19-2.27 (1H, m), 2.72 (1H, d), 3.07 (1H, d), 3.40 (1H, td), 3.48 (1H, td), 3.92-4.04 (2H, m), 4.68 (2H, AB q), 7.39 (1H, d), 7.55-7.59 (2H, m), 9.05 (2H, s), 9.11 (1H, s).

Isomer 2: (4.8 mg, purity=97.2%, ee=96%)
$^1$H NMR (400 MHz, CD$_3$OD) δ ppm 0.91 (3H, s), 1.47-1.55 (2H, m), 1.57-1.73 (2H, m), 2.19-2.27 (1H, m), 2.72 (1H, d), 3.07 (1H, d), 3.40 (1H, td), 3.48 (1H, td), 3.92-4.04 (2H, m), 4.68 (2H, AB q), 7.39 (1H, d), 7.55-7.59 (2H, m), 9.05 (2H, s), 9.11 (1H, s).

Isomer 3: (9.1 mg, purity=99.4%, ee=99.7%)
$^1$H NMR (400 MHz, CD$_3$OD) δ ppm 1.00 (3H, s), 1.39-1.47 (1H, m), 1.49-1.69 (3H, m), 2.04-2.12 (1H, m), 2.77 (2H, AB q), 3.41-3.54 (2H, m), 3.90-4.02 (3H, m), 4.90 (1H, d), 7.34 (1H, d), 7.47 (1H, d), 7.56 (1H, dd), 9.05 (2H, s), 9.11 (1H, s).

Isomer 4 (10.2 mg, purity=98.1%, ee=99.1%)
$^1$H NMR (400 MHz, CD$_3$OD) δ ppm 1.00 (3H, s), 1.39-1.47 (1H, m), 1.49-1.69 (3H, m), 2.04-2.12 (1H, m), 2.77 (2H, AB q), 3.41-3.54 (2H, m), 3.90-4.02 (3H, m), 4.90 (1H, d), 7.34 (1H, d), 7.47 (1H, d), 7.56 (1H, dd), 9.05 (2H, s), 9.11 (1H, s).

Compound 103: {(1S,1'R,3S,4S)-6'-(2-fluoro-5-chloropyridin-3-yl)-4-(methoxy-d$_3$)-3-methyl-3'H,5''H-dispiro[cyclohexane-1,2'-indene-1',4''-oxazol]-5'',5''-d$_2$-2''-amine}

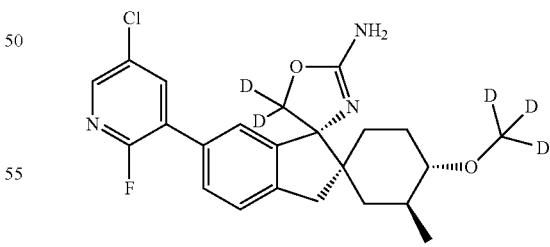

The title compound (14 mg, white solids) was prepared according to General Procedure 1 using (1S,1'R,3S,4S)-6'-bromo-4-(methoxy-d$_3$)-3-methyl-3'H,5''H-dispiro[cyclohexane-1,2'-indene-1',4''-oxazol]-5'',5''-d$_2$-2''-amine (39 mg, 0.10 mmol) and (5-chloro-2-fluoro-3-pyridyl)boronic acid (43 mg, 0.12 mmol). $^1$H NMR (400 MHz, CD$_3$OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 7.34 (1H, d), 7.4-7.5 (2H, m), 8.03 (1H, dd), 8.14 (1H, d), 2H not observed. LCMS: rt=3.50 min, m/z=435/437 [M+H]+, purity=100%.

Compound 104: {(1S,1'R,3S,4S)-6'-(4-fluoropyridin-3-yl)-4-(methoxy-d₃)-3-methyl-3'H,5"H-dispiro[cyclohexane-1,2'-indene-1',4"-oxazol]-5",5"-d₂-2"-amine}

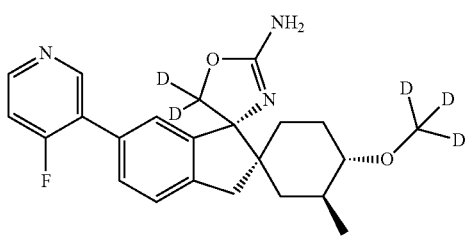 [SMILES: [2H]C([2H])([2H])O[C@H]1CC[C@@]2(Cc3ccc(-c4cnccc4F)cc3[C@]23N=C(N)OC3([2H])[2H])C[C@@H]1C]

A mixture of (1S,1'R,3S,4S)-6'-bromo-4-(methoxy-d₃)-3-methyl-3'H,5"H-dispiro[cyclohexane-1,2'-indene-1',4"-oxazol]-5",5"-d₂-2"-amine (50 mg, 0.13 mmol), bis(pinacolato)diboron (66 mg, 0.26 mmol), potassium acetate (26 mg, 0.26 mmol), Pd(DPPF)Cl₂ (4 mg, 0.01 mmol) in 1,4-dioxane (4 mL) under N₂ was heated at 100° C. for 3 h, treated with additional Pd(DPPF)Cl₂ (4 mg, 0.01 mmol), and cooled to room temperature. The crude mixture was treated with 3-bromo-4-fluoropyridine (46 mg, 0.26 mmol) and Pd118 (8.5 mg, 0.01 mmol) in 1,4-dioxane (4 mL) under N₂. A solution of potassium carbonate (54 mg, 0.39 mmol) in water (1 mL) was added and the mixture was heated at 100° C. for 2 h and cooled to room temperature. The mixture was treated with Deloxan (Pd scavenger resin), stirred for 15 min and concentrated in vacuo. The residue was suspended in DCM, filtered and concentrated in vacuo to leave a crude dark gum (~105 mg) which was purified by HPLC (Gilson, 0.2% NH₄OH/CH₃CN) to afford the title compound as a flocculent solid (33 mg). ¹H NMR (400 MHz, CD₃OD) δ ppm 0.97 (3H, d), 1.03 (1H, t), 1.22-1.34 (2H, m), 1.47-1.67 (4H, m), 2.07-2.14 (1H, m), 2.67-2.77 (1H, m), 2.94 (2H, AB q), 7.29-7.36 (2H, m), 7.38-7.44 (2H, m), 8.51 (1H, dd), 8.64 (1H, d). LCMS: rt=3.18 min, m/z=401 [M+H]+, purity=98%.

Compound 105: {(1S,1'R,3S,4S)-6'-(5-cyanopyridin-3-yl)-4-(methoxy-d₃)-3-methyl-3'H,5"H-dispiro[cyclohexane-1,2'-indene-1',4"-oxazol]-5",5"-d₂-2"-amine}

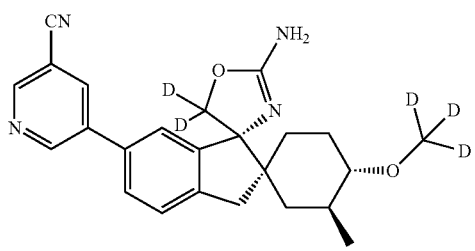 [SMILES: [2H]C([2H])([2H])O[C@H]1CC[C@@]2(Cc3ccc(-c4cncc(C#N)c4)cc3[C@]23N=C(N)OC3([2H])[2H])C[C@@H]1C]

The title compound (35 mg, flocculent solids) was prepared according to General Procedure 1 using (1S,1'R,3S,4S)-6'-bromo-4-(methoxy-d₃)-3-methyl-3'H,5"H-dispiro[cyclohexane-1,2'-indene-1',4"-oxazol]-5",5"-d₂-2"-amine (39 mg, 0.10 mmol) and (5-cyano-3-pyridyl)boronic acid (30 mg, 0.20 mmol). ¹H NMR (400 MHz, CD₃OD) δ ppm 0.96 (3H, d), 1.04 (1H, t), 1.22-1.34 (1H, m), 1.47-1.65 (4H, m), 2.06-2.14 (1H, m), 2.67-2.75 (1H, m), 2.94 (2H, AB q), 7.34 (1H, d), 7.53-7.57 (2H, m), 8.45 (1H, d), 8.85 (1H, d), 9.05 (1H, d), 2H not observed. LCMS: rt=3.22 min, m/z=408 [M+H]+, purity=98.5%.

Compound 106: {(1R,1'R,3R,4R)-4-(methoxy-d₃)-3-methyl-6'-(2-fluoro-5-chloropyridin-3-yl)-3'H,5"H-dispiro[cyclohexane-1,2'-indene-1',4"-oxazol]-5",5"-d₂-2"-amine}

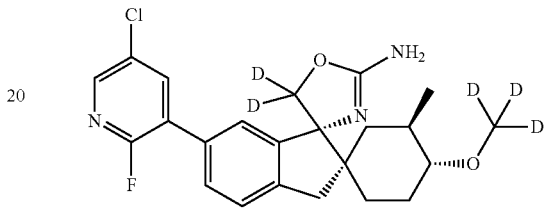

The title compound (19 mg, white solids) was prepared according to General Procedure 1 using (1R,1'R,3R,4R)-6'-bromo-4-(methoxy-d₃)-3-methyl-3'H,5"H-dispiro[cyclohexane-1,2'-indene-1',4"-oxazol]-5",5"-d₂-2"-amine (42 mg, 0.11 mmol) and (5-chloro-2-fluoro-3-pyridyl)boronic acid (40 mg, 0.11 mmol). ¹H NMR (400 MHz, CD₃OD, 35° C.) δ ppm 0.96 (3H, d), 1.2-1.4 (3H, m), 1.5-1.7 (3H, m), 2.05-2.15 (1H, m), 2.71 (1H, td), 2.95 (2H, ABq), 7.34 (1H, d), 7.4-7.5 (2H, m), 8.04 (1H, dd), 8.13 (1H, d), 2H not observed. LCMS: rt=3.54 min, m/z=435/437 [M+H]+, purity=100%.

Compound 107: {(1R,1'R,3R,4R)-4-(methoxy-d₃)-3-methyl-6'-(4-fluoropyridin-3-yl)-3'H,5"H-dispiro[cyclohexane-1,2'-indene-1',4"-oxazol]-5",5"-d₂-2"-amine}

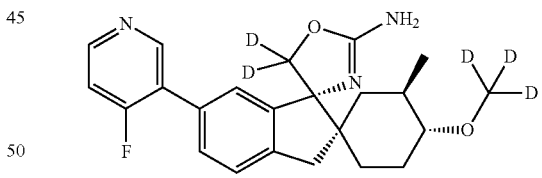

A mixture of (1R,1'R,3R,4R)-6'-bromo-4-(methoxy-d₃)-3-methyl-3'H,5"H-dispiro[cyclohexane-1,2'-indene-1',4"-oxazol]-5",5"-d₂-2"-amine (50 mg, 0.13 mmol), bis(pinacolato)diboron (66 mg, 0.26 mmol), potassium acetate (26 mg, 0.26 mmol), Pd(DPPF)Cl₂ (4 mg, 0.01 mmol) in 1,4-dioxane (4 mL) under N₂ was heated at 100° C. for 3 h, treated with additional Pd(DPPF)Cl₂ (4 mg, 0.01 mmol), stirred at 100° C. for another 6 h and cooled to room temperature. Under N₂, the mixture was treated with 3-bromo-4-fluoropyridine (46 mg, 0.26 mmol) and Pd118 (8.5 mg, 0.01 mmol) in 1,4-dioxane (4 mL) and an aqueous solution of potassium carbonate (54 mg, 0.39 mmol in 1 mL). the mixture was heated at 100° C. for 2 h and cooled to room temperature, treated with Deloxan (Pd scavenger resin), stirred for 15 min and concentrated in vacuo. The residue was suspended in DCM, filtered and concentrated in vacuo to leave a crude dark gum (~130 mg) which was purified by HPLC (Gilson, 0.2% NH$_4$OH/CH$_3$CN) and freeze dried to afford a floculent solid (24 mg). $^1$H NMR (400 MHz, CD$_3$OD) δ ppm 0.97 (3H, d), 1.23-1.36 (3H, m), 1.50-1.65 (3H, m), 2.04-2.15 (1H, m), 2.66-2.77 (1H, m), 2.95 (2H, AB q), 7.29-7.38 (2H, m), 7.40-7.45 (2H, m), 8.51 (1H, dd) and 8.64 (1H, d), 2H not observed. LCMS: rt 3.05 min, m/z=401 [M+H]$^+$, purity=98.5%.

Compound 108: {(1R,1'R,3R,4R)-4-(methoxy-d$_3$)-3-methyl-6'-(5-cyanopyridin-3-yl)-3'H,5"H-dispiro[cyclohexane-1,2'-indene-1',4"-oxazol]-5",5"-d$_2$-2"-amine}

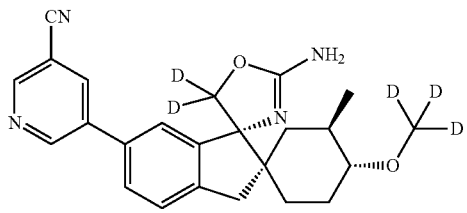 [SMILES: [2H]C([2H])([2H])O[C@@H]1CC[C@]2(Cc3ccc(-c4cncc(C#N)c4)cc3[C@]23N=C(N)OC3([2H])[2H])C[C@H]1C]

The title compound (30 mg, floculent solids) was prepared according to General Procedure 1 using (1R,1'R,3R,4R)-6'-bromo-4-(methoxy-d$_3$)-3-methyl-3'H,5"H-dispiro[cyclohexane-1,2'-indene-1',4"-oxazol]-5",5"-d$_2$-2"-amine (38 mg, 0.10 mmol) and (5-cyano-3-pyridyl)boronic acid (29 mg, 0.20 mmol). $^1$H NMR (400 MHz, CD$_3$OD) δ ppm 0.97 (3H, d), 1.24-1.38 (3H, m), 1.48-1.64 (3H, m), 2.05-2.15 (1H, m), 2.69-2.76 (1H, m), 2.95 (2H, AB q), 7.39 (1H, d), 7.50-7.58 (3H, m), 8.45 (1H, d), 8.85 (1H, d) and 9.05 (1H, d). LCMS: rt=3.21 min, m/z=408 [M+H]$^+$, purity=98.8%.

Compound 109: {(1R,1'R,3R,4R)-6'-(2,5-difluoropyridin-3-yl)-4-methoxy-3-methyl-3'H,5"H-dispiro[cyclohexane-1,2'-indene-1',4"-oxazol]-5",5"-d$_2$-2"-amine}

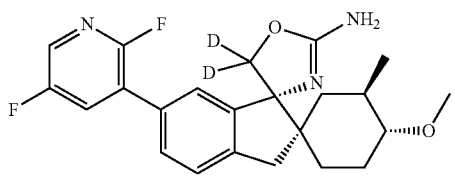 [SMILES: [2H]C1([2H])OC(N)=N[C@]12c1cc(-c3cc(F)cnc3F)ccc1C[C@]21CC[C@@H](OC)[C@H](C)C1]

The title compound (27 mg, floculent solid) was prepared according to General Procedure 1 using (1R,1'R,3R,4R)-6'-bromo-4-methoxy-3-methyl-3'H,5"H-dispiro[cyclohexane-1,2'-indene-1',4"-oxazol]-5",5"-d$_2$-2"-amine (35 mg, 0.09 mmol) and (2,5-difluoro-3-pyridyl)boronic acid (29 mg, 0.18 mmol). $^1$H NMR (400 MHz, CD$_3$OD) δ ppm 0.97 (3H, d), 1.23-1.38 (3H, m), 1.50-1.65 (3H, m), 2.07-2.16 (1H, m), 2.68-2.77 (1H, td), 2.94 (2H, ABq), 3.37 (3H, s), 7.34 (1H, d), 7.43-7.48 (2H, m), 7.89 (1H, td), 8.04 (1H, d), 2H not observed. LCMS: rt=3.42 min, m/z=416 [M+H]$^+$, purity=98.3%.

Compound 110: {(1S,3S,4S)-4-methoxy-3-methyl-6'-(3,5-difluorophenyl)-3'H,5"H-dispiro[cyclohexane-1,2'-indene-1',4"-oxazol]-5",5"-d$_2$-2"-amine}

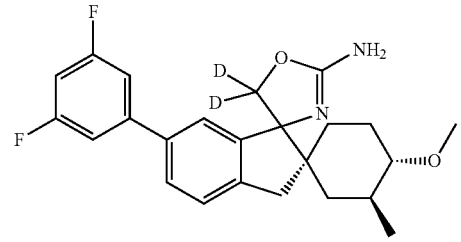

The title compound (24 mg, floculent solid) was prepared according to General Procedure 1 using (1S,3S,4S)-6'-bromo-4-methoxy-3-methyl-3'H,5"H-dispiro[cyclohexane-1,2'-indene-1',4"-oxazol]-5",5"-d$_2$-2"-amine (38 mg, 0.10 mmol) and 3,5-difluorophenylboronic acid (32 mg, 0.20 mmol). $^1$H NMR (400 MHz, CD$_3$OD) δ ppm 0.96 (3H, d), 1.22-1.36 (2H, m), 1.48-1.66 (4H, m), 2.05-2.15 (1H, m), 2.68-2.75 (1H, m), 2.91 (2H, ABq), 3.37 (3H, s), 6.88 (1H, tt), 7.15-7.24 (2H, m), 7.30 (1H, d) and 7.43-7.49 (2H, m), 2H not observed. LCMS: rt=3.73 min, m/z=415 [M+H]$^+$, purity=99%.

Compound 111: {(1S,3S,4S)-4-methoxy-3-methyl-6'-(4-hydroxypyridin-4-yl)-3'H,5"H-dispiro[cyclohexane-1,2'-indene-1',4"-oxazol]-5",5"-d$_2$-2"-amine}

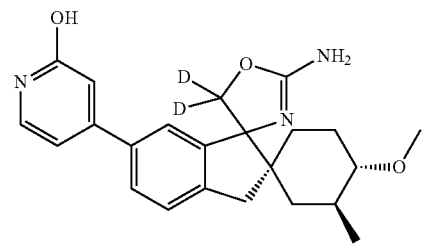

The title compound (6 mg, floculent solid) was prepared according to General Procedure 1 using (1S,3S,4S)-6'-bromo-4-methoxy-3-methyl-3'H,5"H-dispiro[cyclohexane-1,2'-indene-1',4"-oxazol]-5",5"-d$_2$-2"-amine (38 mg, 0.10 mmol) and (2-hydroxy-4-pyridyl)boronic acid (28 mg, 0.20 mmol). $^1$H NMR (400 MHz, CD$_3$OD) δ ppm 0.97 (3H, d), 1.21-1.36 (2H, m), 1.46-1.67 (4H, m), 2.06-2.16 (1H, m), 2.67-2.77 (1H, m), 2.94 (2H, ABq), 3.37 (3H, s), 6.71-6.77 (2H, m), 7.34 (1H, d) and 7.47-7.59 (3H, m), 3H not observed. LCMS: rt=2.95 min, m/z=396 [M+H]$^+$, purity=93.7%.

Compound 112: {(1S,1'R,3S,4S)-4-methoxy-3-methyl-6'-(pyridin-4-yl)-3'H,5"H-dispiro[cyclohexane-1,2'-indene-1',4"-oxazol]-5",5"-d$_2$-2"-amine}

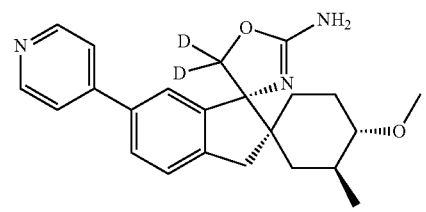 [SMILES: [2H]C1([2H])OC(N)=N[C@]12c1cc(-c3ccncc3)ccc1C[C@@]21CC[C@H](OC)[C@@H](C)C1]

The title compound (18 mg, white solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (30 mg, 0.08 mmol) pyridine-4-boronic acid (30 mg, 0.12 mmol). ¹H NMR (400 MHz, CD₃OD, 35° C.) δ ppm 0.96 (3H, d), 1.03 (1H, t), 1.30 (1H, qd), 1.45-1.70 (4H, m), 2.08 (1H, dq), 2.71 (1H, td), 2.95 (2H, ABq), 3.37 (3H, s), 7.34 (1H, d), 7.5-7.6 (2H, m), 7.68 (2H, d), 8.55 (2H, d), 2H not observed. LCMS: rt=1.49 min, m/z 380 [M+H]⁺, purity=99.0%.

Compound 113: {(1S,1'R,3S,4S)-4-methoxy-3-methyl-6'-(5-cyanopyridin-3-yl)-3'H,5"H-dispiro[cyclohexane-1,2'-indene-1',4"-oxazol]-5",5"-d₂-2"-amine}

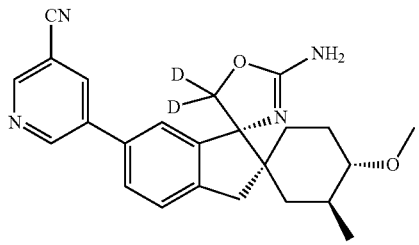 [SMILES: [2H]C1([2H])OC(N)=N[C@]12c1cc(-c3cncc(C#N)c3)ccc1C[C@@]21CC[C@H](OC)[C@@H](C)C1]

The title compound (2 mg, solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (30 mg, 0.08 mmol) and (5-cyano-3-pyridyl)boronic acid (30 mg, 0.10 mmol)). ¹H NMR (400 MHz, CD₃OD, 35° C.) δ ppm 0.96 (3H, d), 1.03 (1H, t), 1.30 (1H, qd), 1.45-1.70 (4H, m), 2.08 (1H, dq), 2.71 (1H, td), 2.95 (2H, ABq), 3.37 (3H, s), 7.34 (1H, d), 7.54-7.58 (2H, m), 8.42 (1H, d), 8.84 (1H, d), 9.04 (1H, d), 2H not observed. LCMS: rt=1.78 min, m/z 380 [M+H]⁺, purity=94.5%.

Compound 114: {(1S,1'R,3S,4S)-4-methoxy-3-methyl-6'-(pyridin-2-yl)-3'H,5"H-dispiro[cyclohexane-1,2'-indene-1',4"-oxazol]-5",5"-d₂-2"-amine}

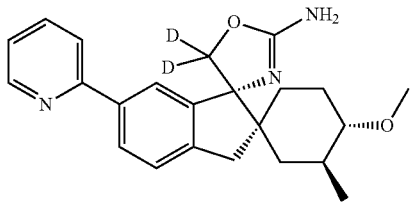 [SMILES: [2H]C1([2H])OC(N)=N[C@]12c1cc(-c3ccccn3)ccc1C[C@@]21CC[C@H](OC)[C@@H](C)C1]

A mixture of bis(pinacolato)diboron (40 mg, 0.16 mmol), (1S,1'R,3S,4S)-6'-bromo-4-methoxy-3-methyl-3'H,5"H-dispiro[cyclohexane-1,2'-indene-1',4"-oxazol]-5",5"-d₂-2"-amine (35 mg, 0.09 mmol), potassium acetate (20 mg, 0.20 mmol), Pd(DPPF)Cl₂ (5 mg, 0.01 mmol) in 1,4-dioxane (4 mL) under N₂ was heated at 100° C. for 3 h, treated with additional bis(pinacolato)diboron (50 mg) and Pd(dppf)Cl₂ (10 mg) and stirred at 100° C. for 3 h. The mixture was cooled to room temperature, treated with 2-bromopyridine (40 mg, 0.25 mmol), potassium carbonate (40 mg, 0.29 mmol), Pd118 (10 mg, 0.02 mmol), water (0.5 mL) and stirred at 100° C. for 3 h. Several purifications by HPLC gave the title compound (5 mg). ¹H NMR (400 MHz, CD₃OD, 35° C.) δ ppm 0.98 (3H, d), 1.11 (1H, t), 1.30-1.45 (2H, m), 1.50-1.70 (3H, m), 2.22 (1H, br.d), 2.80 (1H, br.t), 3.09 (2H, br.s), 3.39 (3H, s), 7.45-7.55 (2H, m), 7.90-8.20 (4H, m), 8.68 (1H, br.s), 4H not observed. LCMS: rt=2.88 min, m/z 380 [M+H]⁺, purity=95.5%.

Compound 115: {(1S,1'R,3S,4S)-4-methoxy-3-methyl-6'-(pyridazin-4-yl)-3'H,5"H-dispiro[cyclohexane-1,2'-indene-1',4"-oxazol]-5",5"-d₂-2"-amine}

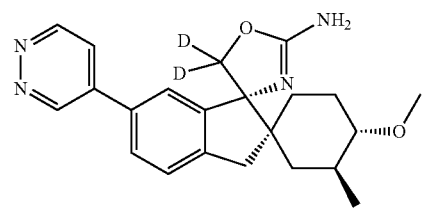 [SMILES: [2H]C1([2H])OC(N)=N[C@]12c1cc(-c3ccnnc3)ccc1C[C@@]21CC[C@H](OC)[C@@H](C)C1]

The title compound (4 mg, grey solid) was prepared according to General Procedure 1 using (1S,1'R,3S,4S)-6'-bromo-4-methoxy-3-methyl-3'H,5"H-dispiro[cyclohexane-1,2'-indene-1',4"-oxazol]-5",5"-d₂-2"-amine (30 mg, 0.08 mmol) and 4-(4,4,5,5-tetramethyl-1,3,2-dioxaborolan-2-yl)pyridazine (50 mg, 0.12 mmol). ¹H NMR (400 MHz, CD₃OD, 35° C.) δ ppm 0.96 (3H, d), 1.03 (1H, t), 1.30 (1H, qd), 1.45-1.7 (4H, m), 2.08 (1H, dq), 2.71 (1H, td), 2.95 (2H, ABq), 3.38 (3H, s), 7.41 (1H, d), 7.6-7.7 (2H, m), 7.97 (1H, dd), 9.14 (1H, d), 9.51 (1H, d), 2H not observed. LCMS: rt=1.65 min, m/z 382 [M+H]⁺, purity=96.3%.

Compound 116: {(1r,1'R,4R)-4-methoxy-6'-(4-methylpyrimidin-5-yl)-3'H,5"H-dispiro[cyclohexane-1,2'-indene-1',4"-oxazol]-5",5"-d₂-2"-amine}

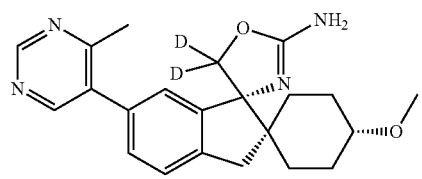 [SMILES: [2H]C1([2H])OC(N)=N[C@]12c1cc(-c3cncnc3C)ccc1C[C@]21CC[C@@H](OC)CC1]

The title compound (44 mg, off-white solids) was prepared according to General Procedure 1 using (1r,1'R,4R)-6'-bromo-4-methoxy-3-methyl-3'H,5"H-dispiro[cyclohexane-1,2'-indene-1',4"-oxazol]-5",5"-d₂-2"-amine (64 mg, 0.17 mmol) and 4-methyl-5-(4,4,5,5-tetramethyl-1,3,2-dioxaborolan-2-yl)pyrimidine (200 mg, 0.45 mmol). ¹H NMR (400 MHz, CD₃OD) δ ppm 1.30-1.45 (3H, m), 1.50-1.70 (3H, m), 2.00 (1H, br.d), 2.50 (3H, s), 2.95 (2H, ABq), 3.15 (1H, tt), 3.38 (3H, s), 7.24 (2H, br.s), 7.38 (1H, d), 8.53 (1H, s), 8.97 (1H, s), 2H not observed. LCMS: rt=3.55 min, m/z=381 [M+H]⁺, purity=97.5%.

Compound 117: {(1r,1'R,4R)-4-methoxy-6'-(pyrimidin-3-yl)-3'H,5"H-dispiro[cyclohexane-1,2'-indene-1',4"-oxazol]-5",5"-d₂-2"-amine}

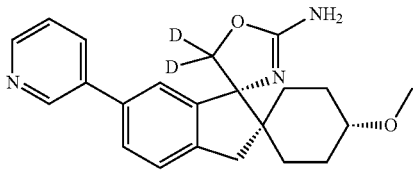 [SMILES: [2H]C1([2H])OC(N)=N[C@]12c1cc(-c3cccnc3)ccc1C[C@]21CC[C@@H](OC)CC1]

The title compound (27 mg, white solids) was prepared according to General Procedure 1 using (1r,1'R,4R)-6'-bromo-4-methoxy-3-methyl-3'H,5"H-dispiro[cyclohexane-1,2'-indene-1',4"-oxazol]-5",5"-d₂-2"-amine (37 mg, 0.10 mmol) and 3-pyridylboronic acid (25 mg, 0.20 mmol). $^1$H NMR (400 MHz, CD$_3$OD) δ ppm 1.26-1.43 (3H, m), 1.50-1.64 (3H, m), 1.96-2.08 (2H, m), 2.92 (2H, AB q), 3.11-3.21 (1H, m), 3.36 (3H, s), 3.88 (3H, s), 7.35 (1H, d), 7.45-7.52 (3H, m), 8.07 (1H, d), 8.49 (1H, d), 8.70 (1H, d). LCMS: rt=2.59 min, m/z=366 [M+H]⁺, purity=99.3%.

Compound 118: {(1r,1'R,4R)-4-methoxy-6'-(pyrimidin-5-yl)-3'H,5"H-dispiro[cyclohexane-1,2'-indene-1',4"-oxazol]-5",5"-d₂-2"-amine}

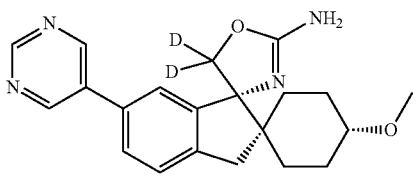 [SMILES: [2H]C1([2H])OC(N)=N[C@]12c1cc(-c3cncnc3)ccc1C[C@]21CC[C@@H](OC)CC1]

The title compound (23 mg, off-white solids) was prepared according to General Procedure 1 using (1r,1'R,4R)-6'-bromo-4-methoxy-3-methyl-3'H,5"H-dispiro[cyclohexane-1,2'-indene-1',4"-oxazol]-5",5"-d₂-2"-amine (40 mg, 0.11 mmol) and pyrimidin-5-ylboronic acid (60 mg, 0.24 mmol). $^1$H NMR (400 MHz, CD$_3$OD, 35° C.) δ ppm 1.20-1.45 (3H, m), 1.50-1.70 (3H, m), 2.00 (1H, br.d), 2.95 (2H, ABq), 3.15 (1H, tt), 3.38 (3H, s), 7.38 (1H, d), 7.55 (2H, d), 9.03 (1H, s), 9.09 (1H, s), 2H not observed. LCMS: rt=1.62 min, m/z=367 [M+H]⁺, purity=96%.

Compound 119: {(1R,1'R,3R,4R)-6'-cyano-4-methoxy-3-methyl-3'H,5"H-dispiro[cyclohexane-1,2'-indene-1',4"-oxazol]-5",5"-d₂-2"-amine}

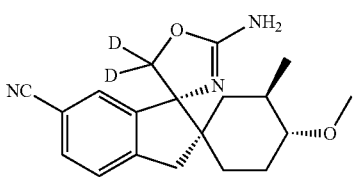 [SMILES: [2H]C1([2H])OC(N)=N[C@]12c1cc(C#N)ccc1C[C@]21CC[C@@H](OC)[C@H](C)C1]

A mixture of (1R,1'R,3R,4R)-6'-bromo-4-methoxy-3-methyl-3'H,5"H-dispiro[cyclohexane-1,2'-indene-1',4"-oxazol]-5",5"-d₂-2"-amine (38 mg, 0.10 mmol), Pd₂(dba)₃ (8.2 mg, 0.010 mmol) and zinc cyanide (16 mg, 0.14 mmol) in DMF (2 mL) under N₂ was heated at 170° C. for 4 h, cooled to room temperature, treated with Deloxan (Pd scavenger resin), stirred for 30 min and concentrated in vacuo. The residue was suspended in DCM (10 mL), filtered and concentrated in vacuo to leave a black residue (59 mg) which was purified by HPLC (0.2% NH₄OH/CH₃CN) to give title compound as a flocculent white solid (10 mg). $^1$H NMR (400 MHz, CD$_3$OD) δ ppm 0.96 (3H, d), 1.19-1.35 (3H, m), 1.40-1.60 (3H, m), 2.06-2.14 (1H, m), 2.66-2.72 (1H, m), 2.97 (2H, AB q), 3.36 (3H, s), 7.39 (1H, d), 7.56 (1H, s) and 7.57 (1H, d), 2H not observed. LCMS: rt=3.03 min, m/z=328 [M+H]⁺, purity=100%.

Compound 120: {(1S,1'R,3S,4S)-6'-cyano-4-methoxy-3-methyl-3'H,5"H-dispiro[cyclohexane-1,2'-indene-1',4"-oxazol]-5",5"-d₂-2"-amine}

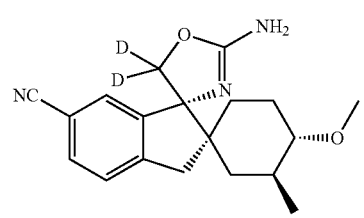 [SMILES: [2H]C1([2H])OC(N)=N[C@]12c1cc(C#N)ccc1C[C@@]21CC[C@H](OC)[C@@H](C)C1]

A mixture of (1S,1'R,3S,4S)-6'-bromo-4-methoxy-3-methyl-3'H,5"H-dispiro[cyclohexane-1,2'-indene-1',4"-oxazol]-5",5"-d₂-2"-amine (38 mg, 0.10 mmol), Pd₂(dba)₃ (8.2 mg, 0.010 mmol) and zinc cyanide (16 mg, 0.14 mmol) in DMF (2 mL) under N₂ was stirred at 170° C. for 4 h, cooled to room temperature, treated with Deloxan (Pd scavenger resin), stirred for 30 min and concentrated in vacuo. The residue was suspended in DCM (10 mL), filtered and concentrated in vacuo to leave a brown wax (64 mg) which was purified by HPLC (0.2% NH₄OH/CH₃CN) to give the title compound as flocculent off-white solid (13 mg). $^1$H NMR (400 MHz, CD$_3$OD) δ ppm 0.94 (3H, d), 1.00 (1H, t), 1.19-1.31 (1H, m), 1.38-1.45 (1H, m), 1.50-1.63 (3H, m), 2.06-2.14 (1H, m), 2.67-2.75 (1H, m), 2.96 (2H, AB q), 3.36 (3H, s), 7.38 (1H, d), 7.56 (1H, s) and 7.57 (1H, dd), 2H not observed. LCMS: rt=3.05 min, m/z=328 [M+H]⁺, purity=100%.

Example 2: Biological Activity

Assays

The level of activity of the compounds was tested using the following methods:

TR-FRET Assay

The β-secretase enzyme used in the TR-FRET was prepared as follows:

Human BACE1: the cDNA for the soluble part of the human β-Secretase1 (AA1-AA460) was cloned using the BACE1 (1-460)-(AVT)-Fc-pGEN-IRES-neo mammalian expression vector. The gene was fused to the Fc domain of IgG1 (affinity tag) and stably cloned into HEK 293 cells. Purified sBACE-Fc was stored in −80° C. in Tris buffer, pH 9.2 and had a purity of ~40%, Human BACE2: the cDNA for the soluble part of the human β-Secretase2 (AA1-AA473) was cloned using BACE2(1-473)-(AVT)-Fc-pDEST12.2 mammalian expression vector. The gene was fused to the Fc domain of IgG1 (affinity tag) and stably cloned into HEK 293 cells. Purified sBACE-Fc was stored in −80° C. in 50 mM Glycine, 10 mM Tris-HCl, pH 7-8, and had a purity of ~70%.

The enzyme (truncated form) was diluted to 6 μg/mL (stock hBace1: 1.3 mg/mL, hBace2: 1.6 mg/ml) and the TruPoint BACE1 Substrate to 200 nM (stock 120 uM) in reaction buffer (NaAcetate, chaps, triton x-100, EDTA pH4.5). A multidrop Combi was used for the liquid handling. Enzyme (7 μL) was added to the compound plate (containing 0.8 μL of compound in dimethylsulphoxide). The plate was incubated for 10 minutes. Substrate (8 μL) was then added, and the reaction proceeded for 17 minutes at r.t. The reaction was stopped with the addition of Stop solution (5.5 μL, NaOAC, pH 9). Fluorescence was measured on a Pherastar plate reader using HTRF module. The assay was preformed in a 384 well polystyrene, black, round bottom, small volume plate (Greiner 784076). The final concentration of the enzyme was 2.7 μg/mL; the final concentration of substrate was 100 nM (Km hBACE1: 250 nM, hBACE2: 350 nM). The dimethylsulphoxide control, instead of test compound, defined the 100% activity level and 0% activity was defined by a control inhibitor compound (2-amino-6-(3'-methoxybiphenyl-3-yl)-3,6-dimethyl-5,6-dihydropyrimidin-4(3H)-one, at a final concentration of 50 μM). 5 reference inhibitors with different affinities were used at all screen occasions in dose response.

Diluted TR-FRET Assay

Compounds with a high affinity were further tested in a diluted TR-FRET assay, conditions as described above for the TR-FRET assay, but with 50 times less enzyme and a 6.5 h reaction time at r.t. in the dark.

sAPPβ Release Assay

SH-SY5Y cells were cultured in DMEM/F-12 with Glutamax, 10% FCS and 1% non-essential amino acids and cryopreserved and stored at −140° C. at a concentration of $7.5-9.5\times1.0^6$ cells per vial.

Cells were thawed and seeded at a concentration of around 10000 cells/well in DMEM/F-12 with Glutamax, 10% FCS and 1% non-essential amino acids to a 384-well tissue culture treated plate, 30 μL cell susp/well. The cell plates were then incubated for 7-24 h at 37° C., 5% $CO_2$.

The cell medium was removed, followed by addition of 50 μL compound diluted in DMEM/F-12 with Glutamax, 10% FCS, 1% non-essential amino acids to a final conc of 0.5% DMSO. The compounds were incubated with the cells for 16-17 h (overnight) at 37° C., 5% $CO_2$.

Meso Scale Discovery (MSD) plates were used for the detection of sAPP release. MSD sAPPβ plates were blocked in 1% BSA in Tris wash buffer for 1 h on shake at r.t. and washed 1 time in Tris wash buffer. 20 μL of medium was transferred to the pre-blocked and washed MSD sAPP microplates, and the cell plates were further used in an ATP assay to measure cytotoxicity. The MSD plates were incubated with shaking at r.t. for 2 h and the media discarded. 10 μL detection antibody was added (1 nM) per well followed by incubation with shaking at r.t. for 2 h and then discarded. 35 μL Read Buffer was added per well and the plates were read in a Meso Scale Discovery SECTOR6000 Imager.

ATP Assay

As indicated in the sAPPβ release assay, after transferring 20 μL A medium from the cell plates for sAPPβ detection, the plates were used to analyse cytotoxicity using the ViaLight™ Plus cell proliferation/cytotoxicity kit from Cambrex Bioscience that measures total cellular ATP. The assay was performed according to the manufacture's protocol. Briefly, 10 μL cell lysis reagent was added per well. The plates were incubated at r.t. for 10 min. Two min after addition of 25 μL reconstituted ViaLight™ Plus ATP reagent, the luminescence was measured in an Envision reader. Tox threshold is a signal below 70% of the control.

Results

TABLE 1

$IC_{50}$ values of compounds 1-43, 45-53, and 56-120 in cells measured with aTR-FRET assay, diluted TR-FRET assay, or SAPPβ release assay.

| Compound | Cell (sAPPβ release, nM) | BACE1 (dil. TR-FRET, nM) | BACE2 (TR-FRET, nM) |
| --- | --- | --- | --- |
| 1 | 5.3 | 239 | 144 |
| 2 | 0.27 | 6.2 | 17 |
| 3 | 0.20 | 1.1 | 16 |
| 4 | 0.39 | 6.8 | 37.8 |
| 5 | 1.6 | 32.5 | 888 |
| 6 | 2.2 | 54 | 99 |
| 7 | 0.45 | 11.7 | 22.7 |
| 8 | 0.76 | 54.7 | 716 |
| 9 | 0.50 | 31 | 118 |
| 10 | 0.89 | 129 | 2033 |
| 11 | 0.90 | 266 | 518.9 |
| 12 | 5.9 | 135 | 128 |
| 13 | 1.7 | 161 | 217 |
| 14 | 1.1 | 21.3 | 931 |
| 15 | 1.1 | 16 | 23 |
| 16 | 3.8 | 127.7 | 105.5 |
| 17 | 2.1 | 46.7 | 30.2 |
| 18 | 3.3 | 43.7 | 29.3 |
| 19 | 2.0 | 243.9 | 43.6 |
| 20 | 2.9 | 143 | 186 |
| 21 | 1.6 | 67 | 256 |
| 22 | 1.5 | 67 | 1348 |
| 23 | 1.5 | 7.3 | 21.4 |
| 24 | 3.2 | 18 | 18 |
| 25 | 1.8 | 27 | 135 |
| 26 | 2.6 | 19.6 | 78.4 |
| 27 | 2.8 | 12 | 24.7 |
| 28 | 1.6 | 67 | 255 |
| 29 | 2.6 | 55.7 | 79.2 |
| 30 | 11.3 | 169 | 344 |
| 31 | 2.4 | 24.3 | 90.8 |
| 32 | 2.8 | 7.3 | 26.2 |
| 33 | 2.2 | 81 | 1519 |
| 34 | 0.5 | 11.7 | 22.7 |
| 35 | 4.8 | 15.3 | 28.2 |
| 36 | 4.0 | 150 | 27 |
| 37 | 3.7 | 12.8 | 17.4 |
| 38 | 4.3 | 166 | 315 |
| 39 | 4.3 | 4.7 | 50.7 |
| 40 | 4.4 | 32.9 | 118 |
| 41 | 5.1 | 1554 | 907 |
| 42 | 7.3 | 307 | 221 |
| 43 | 7.5 | 13.6 | 193.6 |
| 45 | 7.8 | 289 | 589 |
| 46 | 8.8 | 218.7 | 300 |
| 47 | 9.1 | 151.6 | 2220 |
| 48 | 10.5 | 2106 | 1054 |
| 49 | 15.8 | 166 | 69 |
| 50 | 16 | 579 | >5000 |
| 51 | 20.6 | 188 | 306 |
| 52 | 4.3 | 4.7 | 50.7 |
| 53 | 24.8 | 664.5 | 652 |
| 56 | 57 | 1633 | 3235 |
| 57 | 94.8 | 341 | >5000 |
| 58 | 102 | 301 | 139 |
| 59 | 128 | 2249 | 4992 |
| 60 | 206 | >5000 | >5000 |
| 61 | 207 | 1964 | 3435 |
| 62 | 250 | >5000 | >5000 |
| 63 | 266 | 1461 | >5000 |
| 64 | 307 | >5000 | >5000 |
| 65 | >5000 | >5000 | >5000 |
| 66 | <0.16 | 41 | 133.7 |
| 67 | 1.7 | 55 | 736 |
| 68 | 1.9 | 63 | 2777 |
| 69 | 17 | 423 | >5000 |
| 70 | 26.6 | 1131 | >5000 |

TABLE 1-continued

IC$_{50}$ values of compounds 1-43, 45-53, and 56-120 in cells measured with aTR-FRET assay, diluted TR-FRET assay, or SAPPβ release assay.

| Compound | Cell (sAPPβ release, nM) | BACE1 (dil. TR-FRET, nM) | BACE2 (TR-FRET, nM) |
|---|---|---|---|
| 71 | 1.3 | 30 | 1087 |
| 72 | 3.6 | 203 | >5000 |
| 73 | 6.1 | 223.9 | 2775 |
| 74 | 0.39 | 27 | 1051 |
| 75 | 0.9 | 46.9 | 598 |
| 76 | 0.5 | 26.9 | 230.6 |
| 77 | 7.5 | 497 | 505 |
| 78 | 1.5 | 105 | 895 |
| 79 | 2.1 | 53.5 | 207 |
| 80 | <0.16 | 45 | 600 |
| 81 | 17 | 423 | >5000 |
| 82 | 23 | 138 | 1790 |
| 83 | nd | nd | nd |
| 84 | 4.8 | 88.7 | 102.6 |
| 85 | 3.5 | 31.8 | 62.5 |
| 86 | 5.9 | 144 | 4749 |
| 87 | 4.7 | 262 | 3483 |
| 88 | 450 | 1954 | 340 |
| 89 | 889 | >5000 | >5000 |
| 90 | 715 | >5000 | >5000 |
| 91 | 330.9 | 4664 | 701.4 |
| 92 | 222.8 | 4162 | 436.8 |
| 93 | 560.7 | >5000 | 1215 |
| 94 | 330.9 | 4664 | 701.4 |
| 95 | 889.1 | >5000 | >5000 |
| 96 | 204.7 | >5000 | 1789 |
| 97 | 1418 | >5000 | >5000 |
| 98 | 1839 | >5000 | >1581 |
| 99 | 489 | 3187 | 519 |
| 100 | 2165 | >5000 | 1368 |
| 101 | 75.6 | 194 | 274 |
| 102 | 32.9 | 2191 | >5000 |
| 103 | 0.6 | 22 | 55 |
| 104 | 0.7 | 77 | 1012 |
| 105 | 0.4 | 13 | 71 |
| 106 | 2.8 | 49 | 80 |
| 107 | 1.8 | 294 | 2113 |
| 108 | 1.5 | 56 | 58 |
| 109 | 1.8 | 123 | 458 |
| 110 | 10 | 67 | 96 |
| 111 | 89 | 2163 | >5000 |
| 112 | 14 | 2031 | 4819 |
| 113 | 0.2 | 17 | 64 |
| 114 | 8 | 770 | 1840 |
| 115 | 13 | 346 | 2225 |
| 116 | 26 | 1131 | >5000 |
| 117 | 7 | 341 | 1791 |
| 118 | 6 | 287 | 2749 |
| 119 | 13 | 294 | 1090 |
| 120 | 7 | 191 | 1629 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject application have been discussed, the above specification is illustrative and not restrictive. Many variations of the subject of the application will become apparent to those skilled in the art upon review of this specification and the claims below. The full scope of the application should be determined by reference to the claims, along with their full scope of equivalents, and the specification, along with such variations.

What is claimed is:

1. A compound of formula (I),

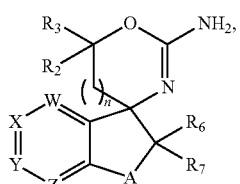

or a pharmaceutically acceptable salt of the compound of formula (I), wherein:
A represents O, CH$_2$, S, or SO$_2$;
X, Y, Z, and W each independently represent N or CR$_1$;
n is 0 or 1;
R$_1$, independently for each occurrence, is selected from hydrogen, halogen, CN, and optionally substituted alkyl, alkenyl, alkynyl, alkoxy, aryl, heteroaryl, or oxime;
R$_2$ and R$_3$ are independently selected from protium, deuterium, tritium, and optionally substituted alkyl, provided that when n is 1, R$_2$ and R$_3$ are independently selected from protium, deuterium, and tritium; and
R$_6$ and R$_7$ are independently selected from hydrogen, halogen, and optionally substituted alkyl, alkoxyalkyl, cycloalkyl, or heterocycloalkyl, provided that R$_6$ and R$_7$ are not simultaneously hydrogen; or
R$_6$ and R$_7$ together with the carbon to which they are attached, form an optionally substituted carbocyclic or heterocyclic ring.

2. The compound of claim 1, wherein R$_2$ and R$_3$ both represent deuterium or tritium, or a pharmaceutically acceptable salt thereof.

3. The compound of claim 1, wherein A represents CH$_2$, or a pharmaceutically acceptable salt thereof.

4. The compound of claim 1, wherein X represents CR$_1$, and Y, Z, and W each represent CH, or a pharmaceutically acceptable salt thereof.

5. The compound of claim 1, wherein n is 0, or a pharmaceutically acceptable salt thereof.

6. The compound of claim 1, wherein n is 1, or a pharmaceutically acceptable salt thereof.

7. The compound of claim 1, wherein R$_1$, independently for each occurrence, represents aryl or heteroaryl, wherein the aryl or heteroaryl is optionally substituted with one or more R$_{11}$, wherein R$_{11}$ represents optionally substituted alkyl, cycloalkyl, heterocycloalkyl, alkynyl, alkoxy, CN, or halogen, or a pharmaceutically acceptable salt thereof.

8. The compound of claim 7, wherein R$_1$ represents

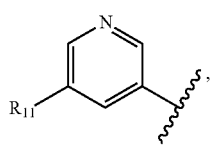

or a pharmaceutically acceptable salt thereof.

9. The compound of claim 1, wherein $R_1$, independently for each occurrence, is selected from optionally substituted alkyl, alkenyl, alkynyl, alkoxy, and oxime, wherein the oxime is optionally substituted with optionally substituted alkyl or cycloalkyl, or a pharmaceutically acceptable salt thereof.

10. The compound of claim 1, wherein $R_2$ and $R_3$ both represent deuterium, or a pharmaceutically acceptable salt thereof.

11. The compound of claim 1, wherein $R_6$ and $R_7$, together with the carbon to which they are attached, form an optionally substituted cyclohexyl ring, or a pharmaceutically acceptable salt thereof.

12. The compound of claim 11, wherein $R_6$ and $R_7$, together with the carbon to which they are attached, form a cyclohexyl ring, wherein the cyclohexyl ring is optionally substituted with one or more $R_{12}$, wherein $R_{12}$ is selected from OH and optionally substituted alkyl or alkoxy, or when two occurrences of $R_{12}$ bound to the same carbon, taken together with the carbon to which they are attached, form a carbocyclic ring, or a pharmaceutically acceptable salt thereof.

13. The compound of claim 12, wherein $R_6$ and $R_7$ form a ring with the structure

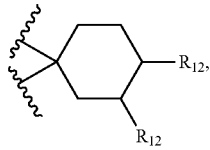

or a pharmaceutically acceptable salt thereof.

14. The compound of claim 13, wherein $R_6$ and $R_7$ form a ring with the structure

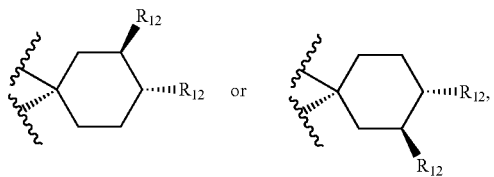

or a pharmaceutically acceptable salt thereof.

15. The compound of claim 12, wherein $R_6$ and $R_7$ form a ring with the structure

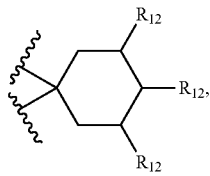

or a pharmaceutically acceptable salt thereof.

16. The compound of claim 15, wherein $R_6$ and $R_7$ form a ring with the structure

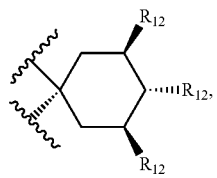

or a pharmaceutically acceptable salt thereof.

17. The compound of claim 12, wherein $R_6$ and $R_7$ form a ring with the structure

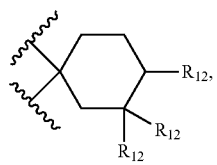

or a pharmaceutically acceptable salt thereof.

18. The compound of claim 17, wherein $R_6$ and $R_7$ form a ring with the structure

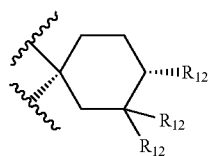 or 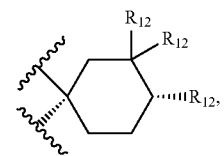

or a pharmaceutically acceptable salt thereof.

19. The compound of claim 1, wherein A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 0; $R_2$ and $R_3$ both represent protium; and $R_6$ and $R_7$ together with the carbon to which they are attached to form an optionally substituted cyclohexyl ring, or a pharmaceutically acceptable salt thereof.

20. The compound of claim 1, wherein A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 0; $R_2$ and $R_3$ both represent deuterium; and $R_6$ and $R_7$ together with the carbon to which they are attached to form an optionally substituted cyclohexyl ring, or a pharmaceutically acceptable salt thereof.

21. The compound of claim 1, wherein A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 1; $R_2$ and $R_3$ both represent protium; and $R_6$ and $R_7$ together with the carbon to which they are attached to form an optionally substituted cyclohexyl ring, or a pharmaceutically acceptable salt thereof.

22. The compound of claim 1, wherein A represents $CH_2$; X represents $CR_1$, wherein $R_1$, independently for each occurrence, is selected from halogen, CN, and optionally substituted alkyl, alkenyl, alkynyl, alkoxy, aryl, heteroaryl, or oxime; Y, Z, and W each represent CH; n is 1; $R_2$ and $R_3$ both represent deuterium; and $R_6$ and $R_7$ together with the carbon to which they are attached to form an optionally substituted cyclohexyl ring, or a pharmaceutically acceptable salt thereof.

23. The compound of claim 1, wherein the compound is selected from any one of compounds 1-43, 45-53, and 56-120, or a pharmaceutically acceptable salt thereof:

Compound 1: {(1R,1'R,3R,4R)-6'-(5-cyclopropylpyridin-3-yl)-4-methoxy-3-methyl-3'H,5"H-dispiro[cyclohexane-1,2'-indene-1',4"-oxazol]-5",5"-d₂-2"-amine formate salt}

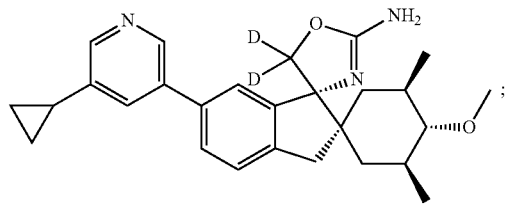 [SMILES: [2H]C1([2H])OC(N)=N[C@]12c1cc(-c3cncc(C4CC4)c3)ccc1C[C@@]21C[C@@H](C)[C@H](OC)[C@@H](C)C1]

Compound 2: {(1R,1'R,3R,4R)-4-methoxy-3-methyl-6'-(5-(prop-1-yn-1-yl)pyridin-3-yl)-3'H,5"H-dispiro[cyclohexane-1,2'-indene-1',4"-oxazol]-5",5"-d₂-2"-amine}

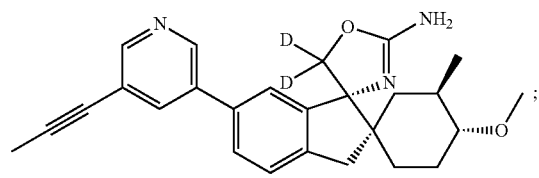 [SMILES: [2H]C1([2H])OC(N)=N[C@]12c1cc(-c3cncc(C#CC)c3)ccc1C[C@]21CC[C@@H](OC)[C@H](C)C1]

Compound 3: {(1S,1'R,3S,4S)-4-methoxy-3-methyl-6'-(5-(prop-1-yn-1-yl)pyridin-3-yl)-3'H,5"H-dispiro[cyclohexane-1,2'-indene-1',4"-oxazol]-5",5"-d₂-2"-amine}

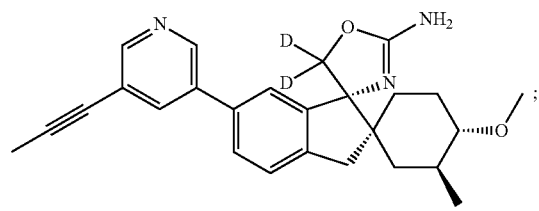 [SMILES: [2H]C1([2H])OC(N)=N[C@]12c1cc(-c3cncc(C#CC)c3)ccc1C[C@@]21CC[C@H](OC)[C@@H](C)C1]

Compound 4: {(1S,1'R,3 S,4S)-6'-(5-chloropyridin-3-yl)-4-methoxy-3-methyl-3'H,5"H-dispiro[cyclohexane-1,2'-indene-1',4"-oxazol]-5",5"-d₂-2"-amine}

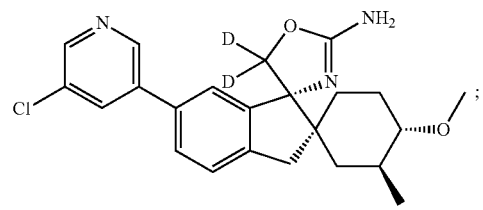

Compound 5: {(1S,1'R,3 S,4S)-6'-(2-fluoropyridin-3-yl)-4-methoxy-3-methyl-3'H, 5"H-dispiro[cyclohexane-1,2'-indene-1',4"-oxazol]-5",5"-d₂-2"-amine}

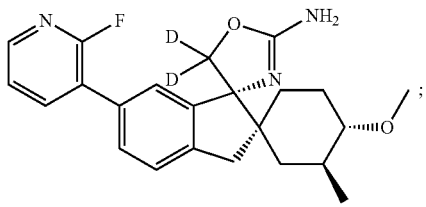 [SMILES: [2H]C1([2H])OC(N)=N[C@]12c1cc(-c3cccnc3F)ccc1C[C@@]21CC[C@H](OC)[C@@H](C)C1]

Compound 6: {(1S,1'R,3 S,4S)-6'-(5-cyclopropylpyridin-3-yl)-4-methoxy-3-methyl-3'H,5"H-dispiro[cyclohexane-1,2'-indene-1',4"-oxazol]-5",5"-d₂-2"-amine}

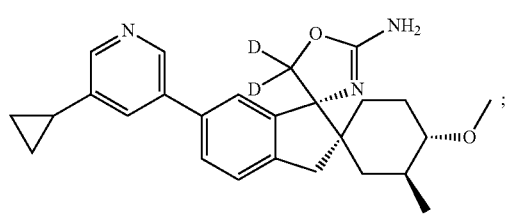 [SMILES: [2H]C1([2H])OC(N)=N[C@]12c1cc(-c3cncc(C4CC4)c3)ccc1C[C@@]21CC[C@H](OC)[C@@H](C)C1]

Compound 7: {(1R,1'R,3R,4R)-6'-(5-chloropyridin-3-yl)-4-methoxy-3-methyl-3'H,5"H-dispiro[cyclohexane-1,2'-indene-1',4"-oxazol]-5",5"-d₂-2"-amine}

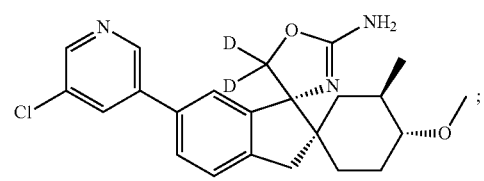 [SMILES: [2H]C1([2H])OC(N)=N[C@]12c1cc(-c3cncc(Cl)c3)ccc1C[C@]21CC[C@@H](OC)[C@H](C)C1]

Compound 8: {(1S,1'R,3 S,4S)-4-methoxy-3-methyl-6'-(pyridin-3-yl)-3'H, 5"H-dispiro[cyclohexane-1,2'-indene-1',4"-oxazol]-5",5"-d₂-2"-amine}

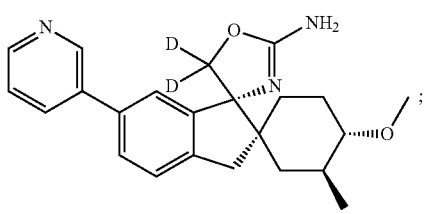 [SMILES: [2H]C1([2H])OC(N)=N[C@]12c1cc(-c3cccnc3)ccc1C[C@@]21CC[C@H](OC)[C@@H](C)C1]

Compound 9: {(1S,1'R,3 S,4S)-6'-(5-fluoropyridin-3-yl)-4-methoxy-3-methyl-3'H, 5"H-dispiro[cyclohexane-1,2'-indene-1',4"-oxazol]-5",5"-d₂-2"-amine}

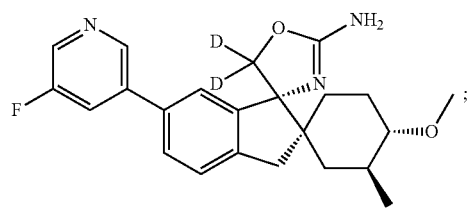 [SMILES: [2H]C1([2H])OC(N)=N[C@]12c1cc(-c3cncc(F)c3)ccc1C[C@@]21CC[C@H](OC)[C@@H](C)C1]

Compound 10: {(1R,1'R,3R,4R)-4-methoxy-3-methyl-6'-(pyrimidin-5-yl)-3'H,5"H-dispiro[cyclohexane-1,2'-indene-1',4"-oxazol]-5",5"-d₂-2"-amine TFA salt}

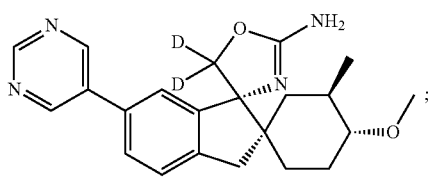 [SMILES: [2H]C1([2H])OC(N)=N[C@]12c1cc(-c3cncnc3)ccc1C[C@]21CC[C@@H](OC)[C@H](C)C1]

Compound 11: four isomers {(1S,3 S,4S)-2"-amino-3-methyl-6'-(3-methylbut-1-yn-1-yl)-3'H,5"H-dispiro[cyclohexane-1,2'-indene-1',4"-oxazol]-5",5"-d₂-4-ol} and {(1R,3R,4R)-2"-amino-3-methyl-6'-(3-methylbut-1-yn-1-yl)-3'H,5"H-dispiro[cyclohexane-1,2'-indene-1',4"-oxazol]-5",5"-d₂-4-ol TFA salt}

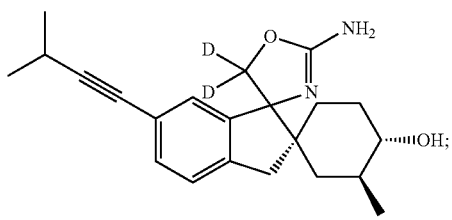

Compound 12: {(1r,4r)-4-methoxy-6'-(3-methylbut-1-yn-1-yl)-3'H,5"H-dispiro[cyclohexane-1,2'-indene-1',4"-oxazol]-2"-amine}

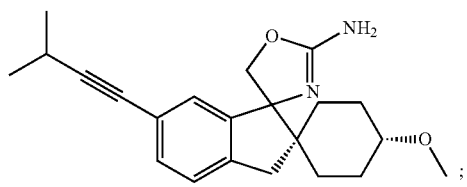

Compound 13: {(1R,1'R,3R,4R)-4-methoxy-3-methyl-6'-(pyridin-3-yl)-3'H,5"H-dispiro[cyclohexane-1,2'-indene-1',4"-oxazol]-5",5"-d₂-2"-amine}

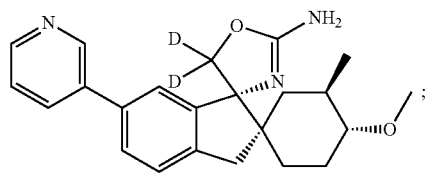 [SMILES: [2H]C1([2H])OC(N)=N[C@]12c1cc(-c3cccnc3)ccc1C[C@]21CC[C@@H](OC)[C@H](C)C1]

Compound 14: {(1S,1'R,3 S,4S)-4-methoxy-3-methyl-6'-(pyrimidin-5-yl)-3'H,5"H-dispiro[cyclohexane-1,2'-indene-1',4"-oxazol]-5",5"-d₂-2"-amine TFA salt}

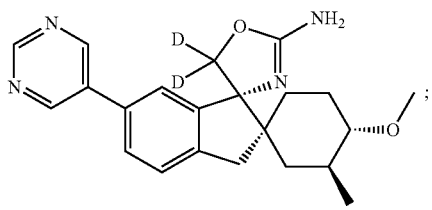 [SMILES: [2H]C1([2H])OC(N)=N[C@]12c1cc(-c3cncnc3)ccc1C[C@@]21CC[C@H](OC)[C@@H](C)C1]

Compound 15: {(1r,4r)-4-methoxy-6'-(5-(prop-1-yn-1-yl)pyridin-3-yl)-3'H,5"H-dispiro[cyclohexane-1,2'-indene-1',4"-oxazol]-2"-amine formate salt}

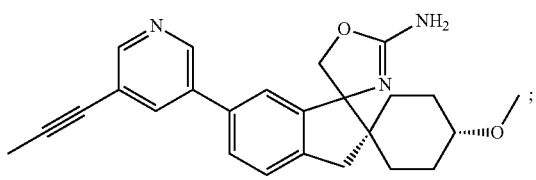

Compound 16: {(1r,4r)-6'-(5-chloropyridin-3-yl)-4-methoxy-3'H,5"H-dispiro[cyclohexane-1,2'-indene-1',4"-oxazol]-5",5"-d₂-2"-amine}

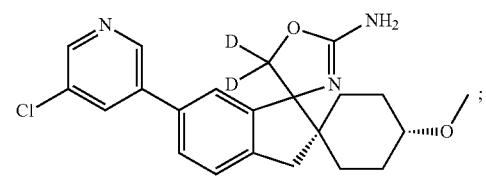

Compound 17: {3-((1R,1'R,3R,4R)-2"-amino-4-methoxy-3-methyl-3'H,5"H-dispiro[cyclohexane-1,2'-indene-1',4"-oxazol]-6'-yl-5",5"-d₂)-5-fluorobenzonitrile formate salt}

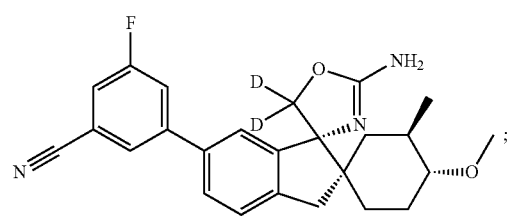 [SMILES: [2H]C1([2H])OC(N)=N[C@]12c1cc(-c3cc(F)cc(C#N)c3)ccc1C[C@]21CC[C@@H](OC)[C@H](C)C1]

Compound 18: {3-((1r,4r)-2"-amino-4-methoxy-3'H,5"H-dispiro[cyclohexane-1,2'-indene-1',4"-oxazol]-6'-yl-5",5"-d₂)-5-chlorobenzonitrile formate salt}

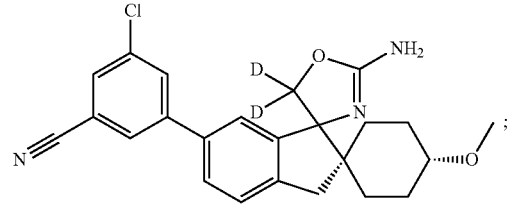

Compound 19: {3-((1S,1'R,3 S,4S)-2"-amino-4-methoxy-3-methyl-3'H,5"H-dispiro[cyclohexane-1,2'-indene-1',4"-oxazol]-6'-yl-5",5"-d₂)-5-fluorobenzonitrile}

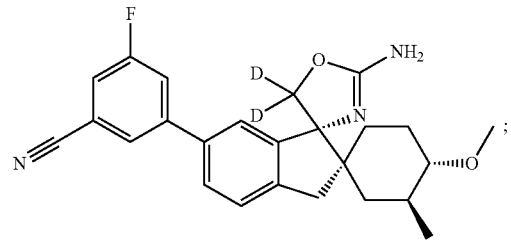 [SMILES: [2H]C1([2H])OC(N)=N[C@]12c1cc(-c3cc(F)cc(C#N)c3)ccc1C[C@@]21CC[C@H](OC)[C@@H](C)C1]

Compound 20: {(1R,1'R,3R,4R)-4-methoxy-3-methyl-6'-(5-methylpyridin-3-yl)-3'H,5"H-dispiro[cyclohexane-1,2'-indene-1',4"-oxazol]-5",5"-d₂-2"-amine formate salt}

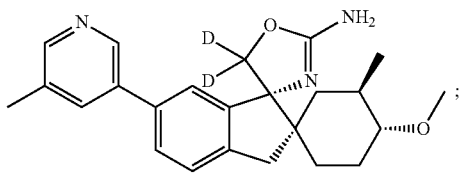

Compound 21: {(1S,3S,4S)-4-methoxy-3-methyl-6'-(5-methylpyridin-3-yl)-3'H,5"H-dispiro[cyclohexane-1,2'-indene-1',4"-oxazol]-5",5"-d₂-2"-amine}

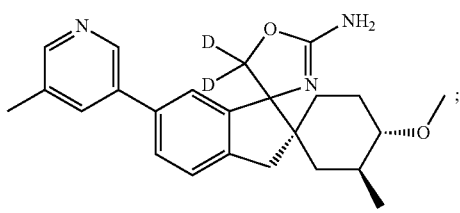

Compound 22: {(1r,3R,4r,5S)-4-methoxy-3,5-dimethyl-6'-(pyrimidin-5-yl)-3'H,5"H-dispiro[cyclohexane-1,2'-indene-1',4"-oxazol]-5",5"-d₂-2"-amine}

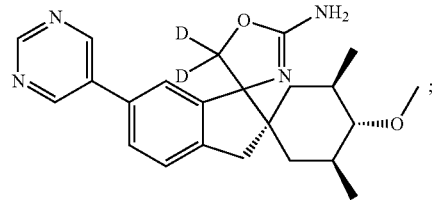

Compound 23: {3-((1S,1'R,3S,4S)-2"-amino-4-methoxy-3-methyl-3'H,5"H-dispiro[cyclohexane-1,2'-indene-1',4"-oxazol]-6'-yl-5",5"-d₂)-5-methoxybenzonitrile TFA salt}

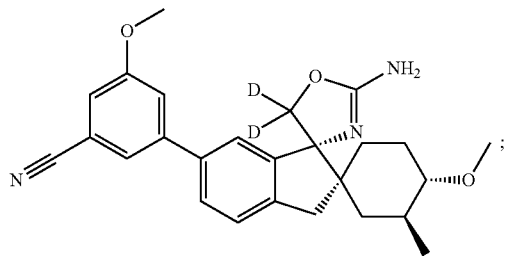 [SMILES: [2H]C1([2H])OC(N)=N[C@]12c1cc(-c3cc(C#N)cc(OC)c3)ccc1C[C@@]21CC[C@H](OC)[C@@H](C)C1]

Compound 24: {3-((1R,1'R,3R,4R)-2"-amino-4-methoxy-3-methyl-3'H,5"H-dispiro[cyclohexane-1,2'-indene-1',4"-oxazol]-6'-yl-5",5"-d₂)-5-methoxybenzonitrile TFA salt}

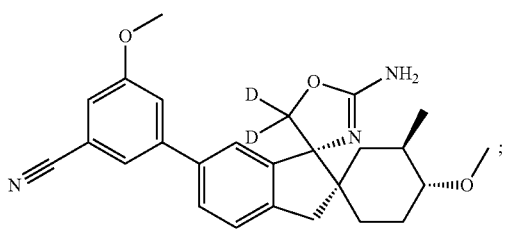 [SMILES: [2H]C1([2H])OC(N)=N[C@]12c1cc(-c3cc(C#N)cc(OC)c3)ccc1C[C@]21CC[C@@H](OC)[C@H](C)C1]

Compound 25: {(1R,1'R,3R,4R)-6'-(5-fluoropyridin-3-yl)-4-methoxy-3-methyl-3'H,5"H-dispiro[cyclohexane-1,2'-indene-1',4"-oxazol]-5",5"-d₂-2"-amine}

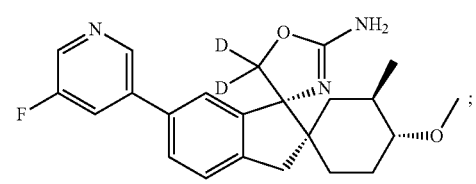 [SMILES: [2H]C1([2H])OC(N)=N[C@]12c1cc(-c3cncc(F)c3)ccc1C[C@]21CC[C@@H](OC)[C@H](C)C1]

Compound 26: {(1S,1'R,3 S,4S)-4-methoxy-3-methyl-6'-(5-(trifluoromethyl)pyridin-3-yl)-3'H,5"H-dispiro[cyclohexane-1,2'-indene-1',4"-oxazol]-5",5"-d₂-2"-amine bis TFA salt}

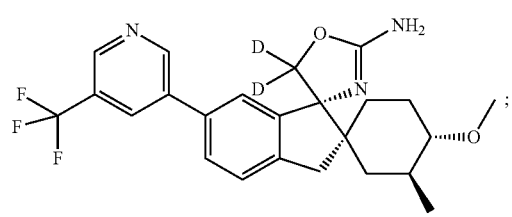 [SMILES: [2H]C1([2H])OC(N)=N[C@]12c1cc(-c3cncc(C(F)(F)F)c3)ccc1C[C@@]21CC[C@H](OC)[C@@H](C)C1]

Compound 27: {(1S,1'R,3S,4S)-6'-(3-chlorophenyl)-4-methoxy-3-methyl-3'H,5"H-dispiro[cyclohexane-1,2'-indene-1',4"-oxazol]-5",5"-d₂-2"-amine}

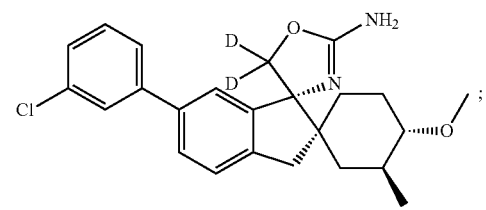 [SMILES: [2H]C1([2H])OC(N)=N[C@]12c1cc(-c3cccc(Cl)c3)ccc1C[C@@]21CC[C@H](OC)[C@@H](C)C1]

Compound 28: {(1S,1'R,3S,4S)-4-methoxy-3-methyl-6'-(5-methylpyridin-3-yl)-3'H,5"H-dispiro[cyclohexane-1,2'-indene-1',4"-oxazol]-5",5"-d₂-2"-amine}

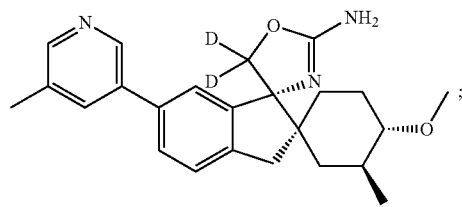

Compound 29: {(1R,1'R,3R,4R)-4-methoxy-3-methyl-6'-(5-(trifluoromethyl)pyridin-3-yl)-3'H,5"H-dispiro[cyclohexane-1,2'-indene-1',4"-oxazol]-5",5"-d₂-2"-amine formate salt}

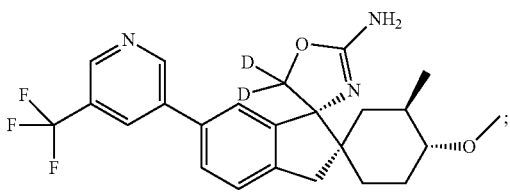 [SMILES: [2H]C1([2H])OC(N)=N[C@]12c1cc(-c3cncc(C(F)(F)F)c3)ccc1C[C@]21CC[C@@H](OC)[C@H](C)C1]

Compound 30: {(1r,3R,4r,5S)-4-methoxy-3,5-dimethyl-6'-(5-(trifluoromethyl)pyridin-3-yl)-3'H,5"H-dispiro[cyclohexane-1,2'-indene-1',4"-oxazol]-2"-amine}

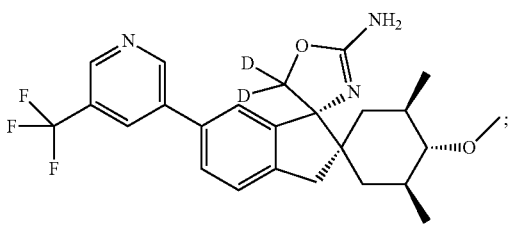 [SMILES: [2H]C1([2H])OC(N)=N[C@]12c1cc(-c3cncc(C(F)(F)F)c3)ccc1C[C@@]21C[C@@H](C)[C@H](OC)[C@@H](C)C1]

Compound 31: {5-((1r,3R,4r,5S)-2"-amino-4-methoxy-3,5-dimethyl-3'H,5"H-dispiro[cyclohexane-1,2'-indene-1',4"-oxazol]-6'-yl)nicotinonitrile}

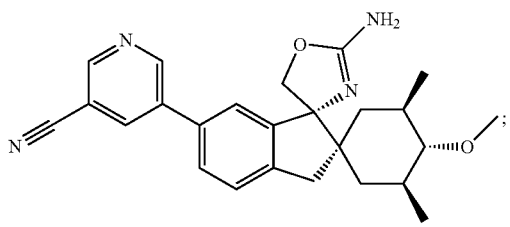 [SMILES: CO[C@H]1[C@H](C)C[C@@]2(Cc3ccc(-c4cncc(C#N)c4)cc3[C@@]23COC(N)=N3)C[C@@H]1C]

Compound 32: {3-((1r,3R,4r,5 S)-2"-amino-4-methoxy-3,5-dimethyl-3'H,5"H-dispiro[cyclohexane-1,2'-indene-1',4"-oxazol]-6'-yl-5",5"-d₂)-5-methoxybenzonitrile}

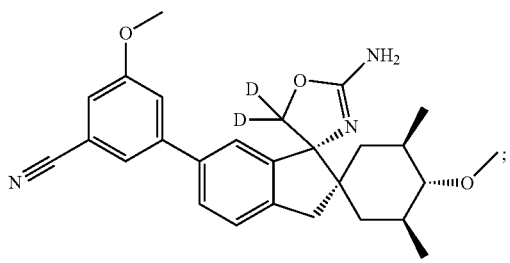 [SMILES: [2H]C1([2H])OC(N)=N[C@]12c1cc(-c3cc(C#N)cc(OC)c3)ccc1C[C@@]21C[C@@H](C)[C@H](OC)[C@@H](C)C1]

Compound 33: {(1R,1'R,3R,4R)-4-methoxy-3-methyl-6'-(pyrimidin-5-yl)-3'H,5"H-dispiro[cyclohexane-1,2'-indene-1',4"-oxazol]-2"-amine}

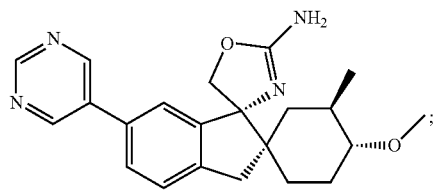 [SMILES: CO[C@@H]1CC[C@]2(Cc3ccc(-c4cncnc4)cc3[C@@]23COC(N)=N3)C[C@H]1C]

Compound 34: {(1R,1'R,3R,4R)-6'-(5-chloropyridin-3-yl)-4-methoxy-3-methyl-3'H,5"H-dispiro[cyclohexane-1,2'-indene-1',4"-oxazol]-5",5"-d₂-2"-amine}

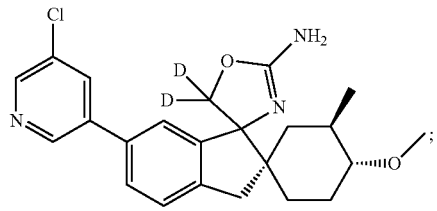

Compound 35: {3-((1r,1'R,4R)-2"-amino-4-methoxy-3'H,5"H-dispiro[cyclohexane-1,2'-indene-1',4"-oxazol]-6'-yl-5",5"-d₂)-5-chlorobenzonitrile formate salt}

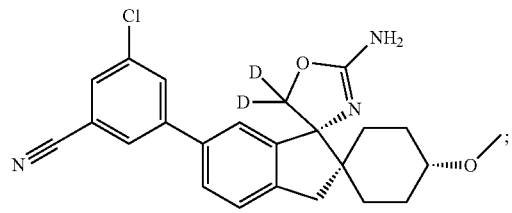 [SMILES: [2H]C1([2H])OC(N)=N[C@]12c1cc(-c3cc(Cl)cc(C#N)c3)ccc1C[C@]21CC[C@@H](OC)CC1]

Compound 36: {3-((1r,4r)-2"-amino-4-methoxy-3'H,5"H-dispiro[cyclohexane-1,2'-indene-1',4"-oxazol]-6'-yl-5",5"-d₂)-5-methoxybenzonitrile formate salt}

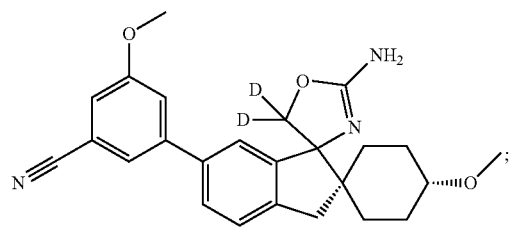

Compound 37: {(1R,1'R,3R,4R)-6'-(3-chlorophenyl)-4-methoxy-3-methyl-3'H,5"H-dispiro[cyclohexane-1,2'-indene-1',4"-oxazol]-5",5"-d₂-2"-amine}

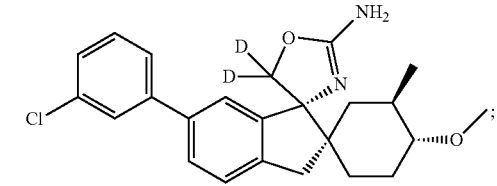 [SMILES: [2H]C1([2H])OC(N)=N[C@]12c1cc(-c3cccc(Cl)c3)ccc1C[C@]21CC[C@@H](OC)[C@H](C)C1]

Compound 38: {5-((1r,1'R,4R)-2"-amino-4-methoxy-3'H,5"H-dispiro[cyclohexane-1,2'-indene-1',4"-oxazol]-6'-yl)nicotinonitrile formate salt}

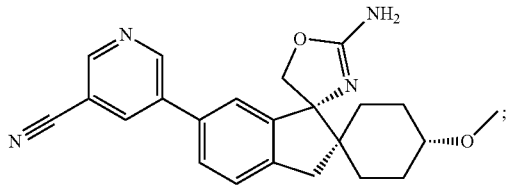 [SMILES: CO[C@H]1CC[C@]2(CC1)Cc1ccc(-c3cncc(C#N)c3)cc1[C@@]21COC(N)=N1]

Compound 39: {3-((1r,3R,4r,5S)-2"-amino-4-methoxy-3,5-dimethyl-3'H,5"H-dispiro[cyclohexane-1,2'-indene-1',4"-oxazol]-6'-yl-5",5"-d₂)-5-chlorobenzonitrile}

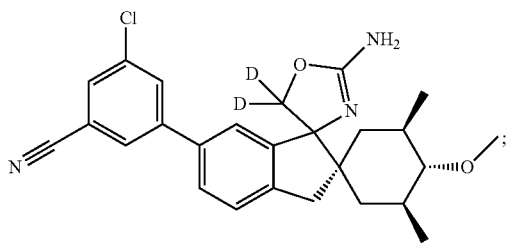

Compound 40: {(1r,3R,4r,5S)-4-methoxy-3,5-dimethyl-6'-(3-methylbutyl-1,1,2,2-d₄)-3'H,5"H-dispiro[cyclohexane-1,2'-indene-1',4"-oxazol]-5",5"-d₂-2"-amine}

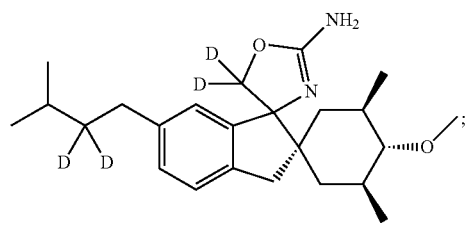

Compound 41: {(1r,4r)-4-methoxy-6'-(5-methylpyridin-3-yl)-3'H,5"H-dispiro[cyclohexane-1,2'-indene-1',4"-oxazol]-2"-amine formate salt}

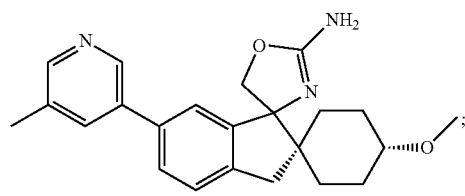

Compound 42: {(1r,4r)-4-methoxy-6'-(5-(trifluoromethyl)pyridin-3-yl)-3'H,5"H-dispiro[cyclohexane-1,2'-indene-1',4"-oxazol]-2"-amine formate salt}

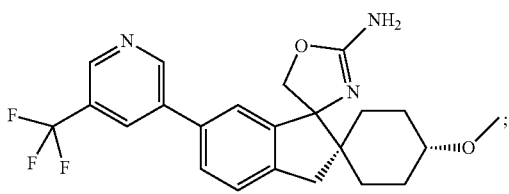

Compound 43: {(1r,3R,4r,5S)-6'-isopentyl-4-methoxy-3,5-dimethyl-3'H,5"H-dispiro[cyclohexane-1,2'-indene-1',4"-oxazol]-5",5"-d₂-2"-amine}

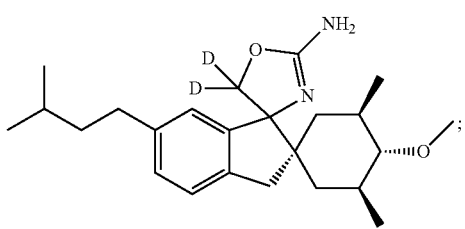

Compound 45: {(1r,4r)-4-methoxy-6'-(3,3,3-trifluoropropoxy)-3'H,5"H-dispiro[cyclohexane-1,2'-indene-1',4"-oxazol]-5",5"-d₂-2"-amine}

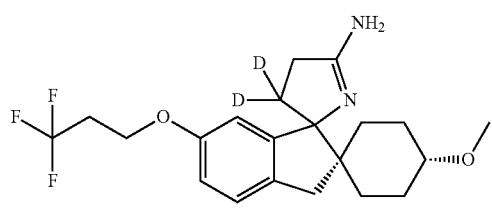

Compound 46: {5-((1r,4r)-2"-amino-4-methoxy-3'H,5"H-dispiro[cyclohexane-1,2'-indene-1',4"-oxazol]-6'-yl)nicotinonitrile formate salt}

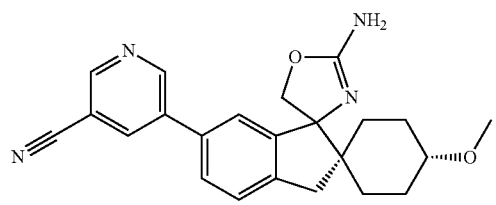

Compound 47: {(1r,1'R,4R)-4-methoxy-6'-(pyrimidin-5-yl)-3'H,5"H-dispiro[cyclohexane-1,2'-indene-1',4"-oxazol]-2"-amine formate salt}

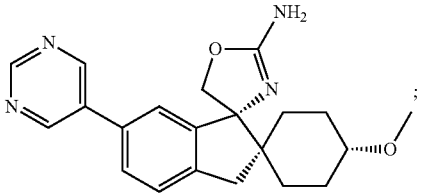 [SMILES: CO[C@H]1CC[C@]2(CC1)Cc1ccc(-c3cncnc3)cc1[C@@]21COC(N)=N1]

Compound 48: {(1r,4r)-4-methoxy-6'-(5-methylpyridin-3-yl)-3'H,5"H-dispiro[cyclohexane-1,2'-indene-1',4"-oxazol]-5",5"-d₂-2"-amine formate salt}

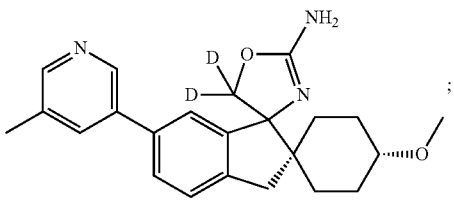

Compound 49: Mixture of 4 diastereomers {3-((1S,3S,4S)-2"-amino-4-hydroxy-3-methyl-3'H,5"H-dispiro[cyclohexane-1,2'-indene-1',4"-oxazol]-6'-yl-5",5"-d₂)-5-methoxybenzonitrile TFA salt}

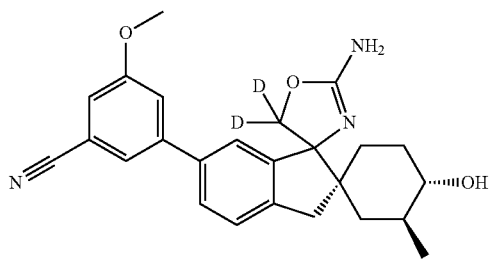

Compound 50: {(1r,4r)-4-methoxy-6'-(pyrimidin-5-yl)-3'H,5"H-dispiro[cyclohexane-1,2'-indene-1',4"-oxazol]-2"-amine formate salt}

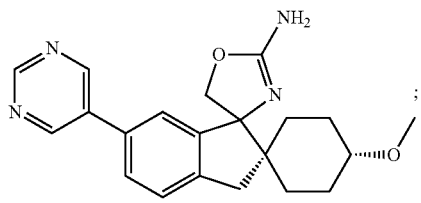

Compound 51: {(1r,4r)-6'-isopentyl-4-methoxy-3'H,5"H-dispiro[cyclohexane-1,2'-indene-1',4"-oxazol]-2"-amine}

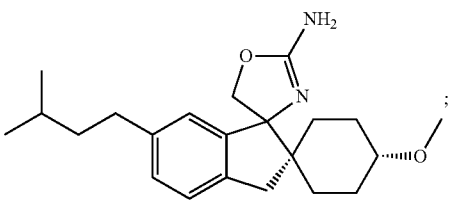

Compound 52: {3-((1r,3R,4r,5S)-2"-amino-4-methoxy-3,5-dimethyl-3'H,5"H-dispiro[cyclohexane-1,2'-indene-1',4"-oxazol]-6'-yl-5",5"-d₂)-5-chlorobenzonitrile}

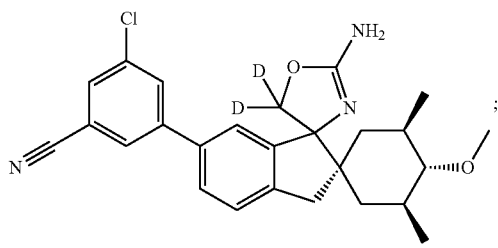

Compound 53: {(E)-2"-amino-4-methoxy-3'H,5"H-dispiro[cyclohexane-1,2'-indene-1',4"-oxazole]-5",5"-d₂-6'-carbaldehyde O-propyl oxime}

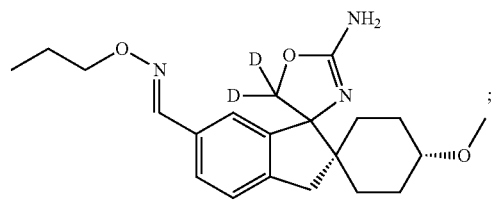

Compound 56: {(E)-2"-amino-4-methoxy-3'H,5"H-dispiro[cyclohexane-1,2'-indene-1',4"-oxazole]-5",5"-d₂-6'-carbaldehyde O-ethyl oxime}

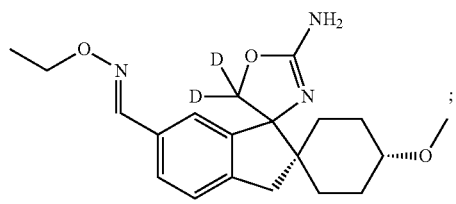

Compound 57: {(1R,3R,4R)-2"-amino-3-methyl-6'-(pyrimidin-5-yl)-3'H,5"H-dispiro[cyclohexane-1,2'-indene-1',4"-oxazol]-5",5"-d₂-4-ol TFA salt}

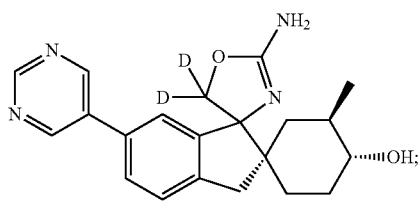

Compound 58: {3-((1R,3R,4R)-2"-amino-4-hydroxy-3-methyl-3'H,5"H-dispiro[cyclohexane-1,2'-indene-1',4"-oxazol]-6'-yl-5",5"-d₂)-5-methoxybenzonitrile TFA salt}

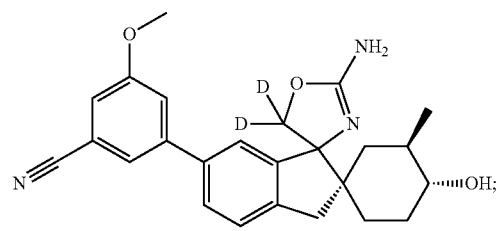

Compound 59: (1r,4r)-4-methoxy-6'-(pyridazin-3-yl)-3'H,5"H-dispiro[cyclohexane-1,2'-indene-1',4"-oxazol]-2"-amine

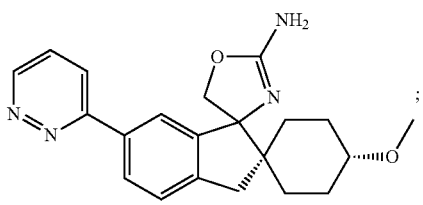

Compound 60: {(E)-1-((1r,4r)-2"-amino-4-methoxy-3'H,5"H-dispiro[cyclohexane-1,2'-indene-1',4"-oxazol]-6'-yl-5",5"-d₂)ethan-1-one O-(3,3,3-trifluoropropyl) oxime}

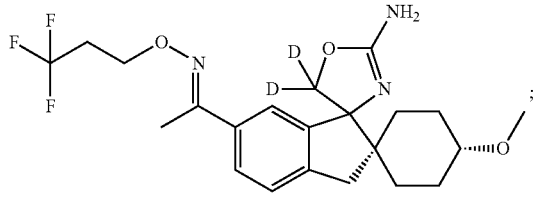

Compound 61: {(E)-2"-amino-4-methoxy-3'H,5"H-dispiro[cyclohexane-1,2'-indene-1',4"-oxazole]-5",5"-d₂-6'-carbaldehyde O-cyclobutyl oxime}

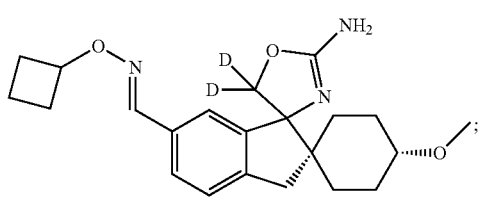

Compound 62: {(1r,4r)-4-methoxy-6'-(pyridazin-4-yl)-3'H,5"H-dispiro[cyclohexane-1,2'-indene-1',4"-oxazol]-2"-amine formate salt}

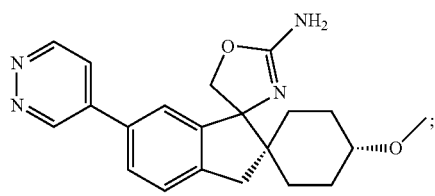

Compound 63: {(1S,3S,4S)-2"-amino-3-methyl-6'-(pyrimidin-5-yl)-3'H,5"H-dispiro[cyclohexane-1,2'-indene-1',4"-oxazol]-5",5"-d₂-4-ol TFA salt}

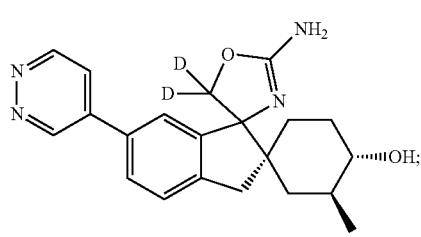

Compound 64: {(1r,4r)-4-methoxy-3'H,5"H-dispiro[cyclohexane-1,2'-indene-1',4"-oxazol]-2"-amine formate salt}

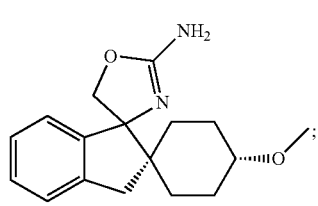

Compound 65: {(E)-1-((1r,4r)-2"-amino-4-methoxy-3'H,5"H-dispiro[cyclohexane-1,2'-indene-1',4"-oxazol]-6'-yl-5",5"-d₂)ethan-1-one O-ethyl oxime}

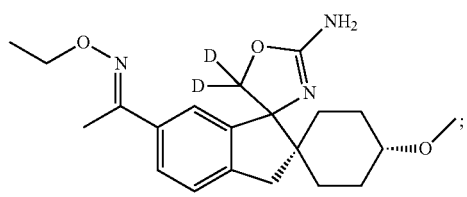

Compound 66: {(1S,1'R,3S,4S)-6'-(5-fluoropyridin-3-yl)-4-(methoxy-d₃)-3-methyl-3'H,5"H-dispiro[cyclohexane-1,2'-indene-1',4"-oxazol]-5",5"-d₂-2"-amine}

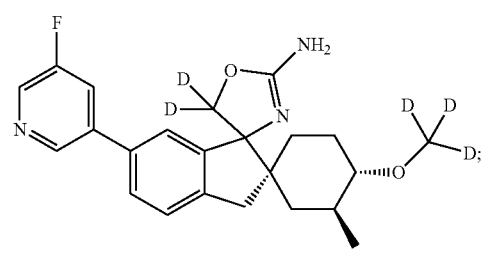

Compound 67: {(1R,1'R,3R,4R)-6'-(2-fluoropyridin-3-yl)-4-methoxy-3-methyl-3'H,5"H-dispiro[cyclohexane-1,2'-indene-1',4"-oxazol]-5",5"-d₂-2"-amine}

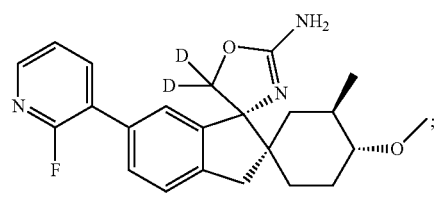 [SMILES: [2H]C1([2H])OC(N)=N[C@]12c1cc(-c3cccnc3F)ccc1C[C@]21CC[C@@H](OC)[C@H](C)C1]

Compound 68: {(1S,1'R,3 S,4S)-3-ethyl-4-methoxy-6'-(pyrimidin-5-yl)-3'H,5"H-dispiro[cyclohexane-1,2'-indene-1',4"-oxazol]-5",5"-d₂-2"-amine}

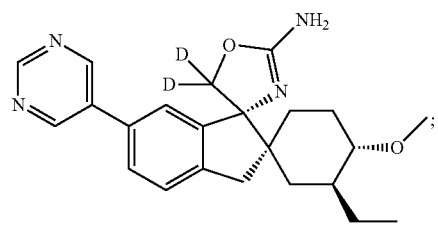 [SMILES: [2H]C1([2H])OC(N)=N[C@]12c1cc(-c3cncnc3)ccc1C[C@@]21CC[C@H](OC)[C@@H](CC)C1]

Compound 69: {(1R,1'R,3R,4R)-4-methoxy-3-methyl-6'-(pyrazin-2-yl)-3'H,5"H-dispiro[cyclohexane-1,2'-indene-1',4"-oxazol]-5",5"-d₂-2"-amine}

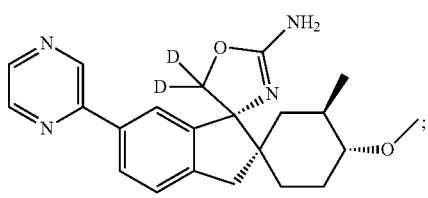 [SMILES: [2H]C1([2H])OC(N)=N[C@]12c1cc(-c3cnccn3)ccc1C[C@]21CC[C@@H](OC)[C@H](C)C1]

Compound 70: (1S,1'R,3 S,4S)-4-methoxy-3-methyl-6'-(4-methylpyrimidin-5-yl)-3'H,5"H-dispiro[cyclohexane-1,2'-indene-1',4"-oxazol]-5",5"-d₂-2"-amine}

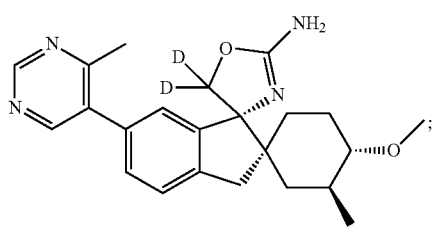 [SMILES: [2H]C1([2H])OC(N)=N[C@]12c1cc(-c3cncnc3C)ccc1C[C@@]21CC[C@H](OC)[C@@H](C)C1]

Compound 71: {(1S,1'R,3 S,4S)-4-(methoxy-d₃)-3-methyl-6'-(pyrimidin-5-yl)-3'H,5"H-dispiro[cyclohexane-1,2'-indene-1',4"-oxazol]-5",5"-d₂-2"-amine}

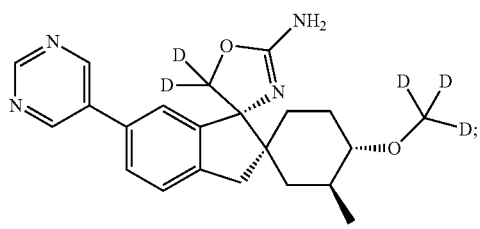

Compound 72: {(1S,1'R,3 S,4S)-4-(methoxy-d₃)-3-methyl-6'-(pyrazin-2-yl)-3'H,5"H-dispiro[cyclohexane-1,2'-indene-1',4"-oxazol]-5",5"-d₂-2"-amine}

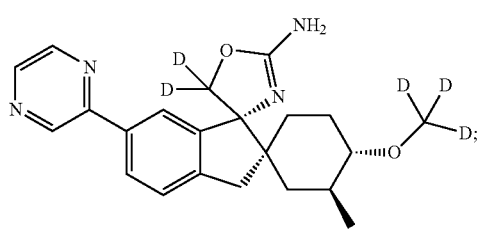

Compound 73: {(1R,1'R,3R,4R)-4-(methoxy-d₃)-3-methyl-6'-(pyrimidin-5-yl)-3'H,5"H-dispiro[cyclohexane-1,2'-indene-1',4"-oxazol]-5",5"-d₂-2"-amine}

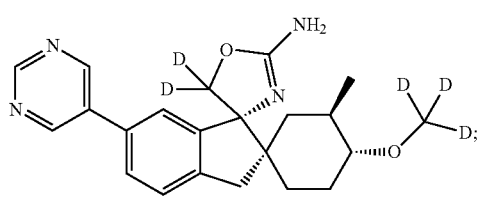

Compound 74: {(1S,1'R,3 S,4S)-6'-(2-fluoropyridin-3-yl)-4-(methoxy-d₃)-3-methyl-3'H,5"H-dispiro[cyclohexane-1,2'-indene-1',4"-oxazol]-5",5"-d₂-2"-amine}

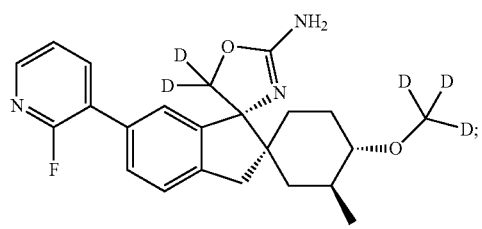

Compound 75: {(1R,1'R,3R,4R)-3-ethyl-4-methoxy-6'-(pyrimidin-5-yl)-3'H,5"H-dispiro[cyclohexane-1,2'-indene-1',4"-oxazol]-5",5"-d₂-2"-amine}

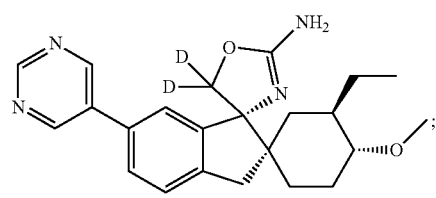 [SMILES: [2H]C1([2H])OC(N)=N[C@]12c1cc(-c3cncnc3)ccc1C[C@]21CC[C@@H](OC)[C@H](CC)C1]

Compound 76: (1S,1'R,3 S,4S)-6'-(2,5-difluoropyridin-3-yl)-4-methoxy-3-methyl-3'H,5"H-dispiro[cyclohexane-1,2'-indene-1',4"-oxazol]-5",5"-d2-2"-amine

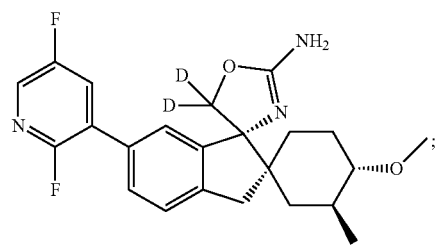 [SMILES: [2H]C1([2H])OC(N)=N[C@]12c1cc(-c3cc(F)cnc3F)ccc1C[C@@]21CC[C@H](OC)[C@@H](C)C1]

Compound 77: (1r,1'R,4R)-4-methoxy-6'-(5-methylpyridin-3-yl)-3'H,5"H-dispiro[cyclohexane-1,2'-indene-1',4"-oxazol]-2"-amine formate salt

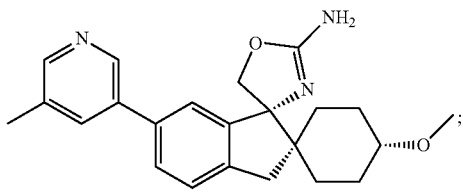

Compound 78: (1R,1'R,3R,4R)-6'-(2-fluoropyridin-3-yl)-4-(methoxy-d₃)-3-methyl-3'H,5"H-dispiro[cyclohexane-1,2'-indene-1',4"-oxazol]-5",5"-d₂-2"-amine

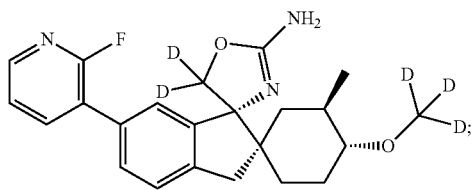

Compound 79: (1R,1'R,3R,4R)-6'-(5-fluoropyridin-3-yl)-4-(methoxy-d₃)-3-methyl-3'H,5"H-dispiro[cyclohexane-1,2'-indene-1',4"-oxazol]-5",5"-d₂-2"-amine

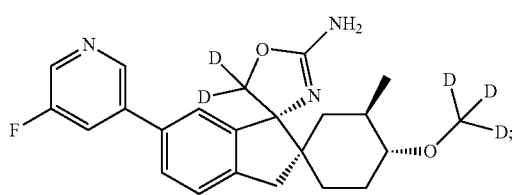

Compound 80: (1R,1'R,3R,4R)-4-(methoxy-d₃)-3-methyl-6'-(pyridin-3-yl)-3'H,5"H-dispiro[cyclohexane-1,2'-indene-1',4"-oxazol]-5",5"-d₂-2"-amine

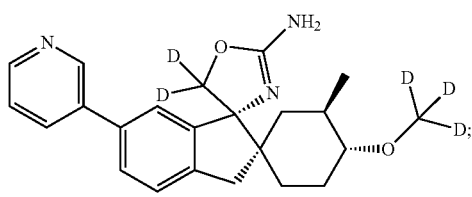

Compound 81: (1R,1'R,3R,4R)-4-(methoxy-d₃)-3-methyl-6'-(pyrazin-2-yl)-3'H,5"H-dispiro[cyclohexane-1,2'-indene-1',4"-oxazol]-5",5"-d₂-2"-amine

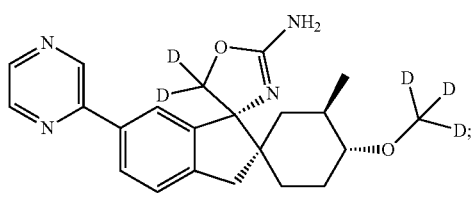

Compound 82: (1r,4r)-4-methoxy-6'-(pyrimidin-5-yl)-5",6"-dihydro-3'H-dispiro[cyclohexane-1,2'-indene-1',4"-[1,3]oxazin]-6",6"-d₂-2"-amine TFA salt

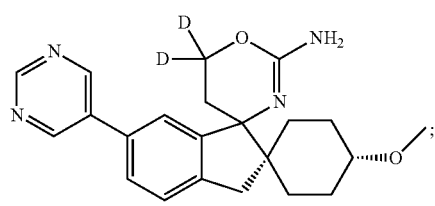

Compound 83: 3-((1r,4r)-2"-amino-4-methoxy-5",6"-dihydro-3'H-dispiro[cyclohexane-1,2'-indene-1',4"-[1,3]oxazin]-6'-yl-6",6"-d₂)-5-chlorobenzonitrile TFA salt

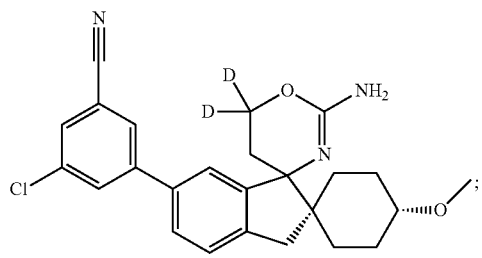

Compound 84: 5-((1r,4r)-2"-amino-4-methoxy-5",6"-dihydro-3'H-dispiro[cyclohexane-1,2'-indene-1',4"-[1,3]oxazin]-6'-yl-6",6"-d₂)nicotinonitrile bis TFA salt

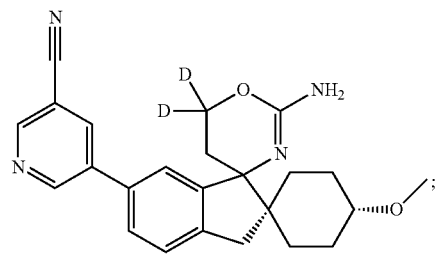

Compound 85: 3-((1r,4r)-2"-amino-4-methoxy-5",6"-dihydro-3'H-dispiro[cyclohexane-1,2'-indene-1',4"-[1,3]oxazin]-6'-yl-6",6"-d₂)-5-methoxybenzonitrile TFA salt

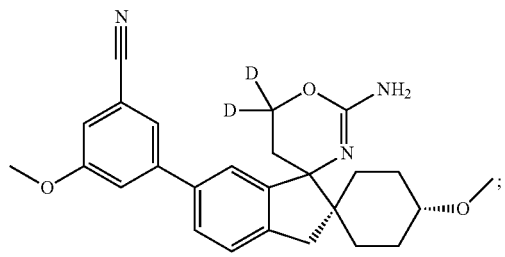

Compound 86: mixture of (1R,4'S)-4'-methoxy-6"-(pyrimidin-5-yl)-3"H,5"'H-trispiro[cyclopropane-1,3'-cyclohexane-1',2"-indene-1",4"'-oxazol]-5"',5"'-d2-2"'-amine and (1'S,4'R)-4'-methoxy-6"-(pyrimidin-5-yl)-3"H,5"'H-trispiro[cyclopropane-1,3'-cyclohexane-1',2"-indene-1",4"'-oxazol]-5"',5"'-d₂-2"'-amine

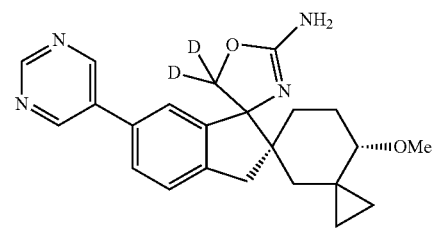

-continued

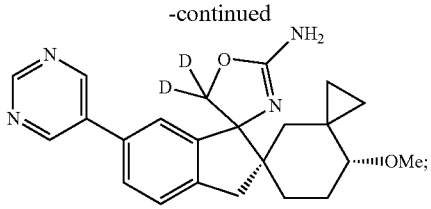

Compound 87: mixture of (1'R,4'S)-4'-methoxy-6"-(pyridin-3-yl)-3"H,5"'H-trispiro[cyclopropane-1,3'-cyclohexane-1',2"-indene-1",4'''-oxazol]-5''',5'''-d$_2$-2'''-amine and (1'S,4'R)-4'-methoxy-6"-(pyridin-3-yl)-3"H,5"'H-trispiro[cyclopropane-1,3'-cyclohexane-1',2"-indene-1",4'''-oxazol]-5''',5'''-d$_2$-2'''-amine

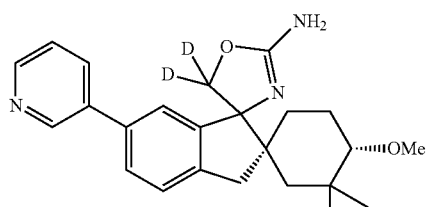

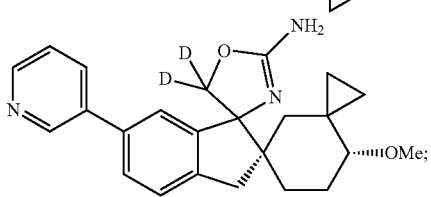

Compound 88: 3-(2'-amino-2-(3-methoxypropyl)-2-methyl-2,3-dihydro-5'H-spiro[indene-1,4'-oxazol]-6-yl)-5-methoxybenzonitrile

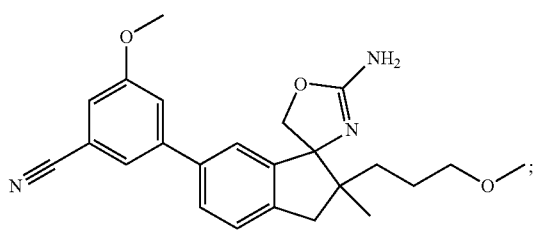 [SMILES: COCCCC1(C)Cc2ccc(-c3cc(C#N)cc(OC)c3)cc2C12COC(N)=N2]

Compound 89: 3-(2'-amino-2-methyl-2-(tetrahydro-2H-pyran-4-yl)-2,3-dihydro-5'H-spiro[indene-1,4'-oxazol]-6-yl-5',5'-d$_2$)-5-methoxybenzonitrile

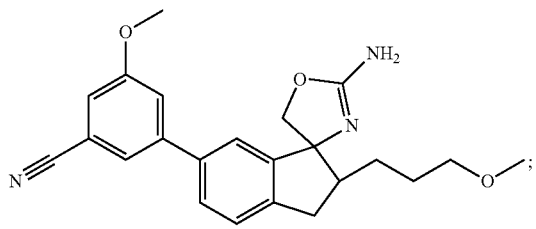 [SMILES: COCCCC1Cc2ccc(-c3cc(C#N)cc(OC)c3)cc2C12COC(N)=N2]

Compound 90: 3-(2'-amino-2-(3-methoxypropyl)-2,3-dihydro-5'H-spiro[indene-1,4'-oxazol]-6-yl)-5-methoxybenzonitrile

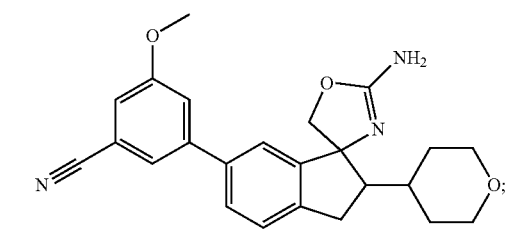 [SMILES: COc1cc(C#N)cc(-c2ccc3c(c2)C2(COC(N)=N2)C(C2CCOCC2)C3)c1]

Compound 91: 3-(2'-Amino-2-(tetrahydro-2H-pyran-4-yl)-2,3-dihydro-5'H-spiro[indene-1,4'-oxazol]-6-yl)-5-methoxybenzonitrile

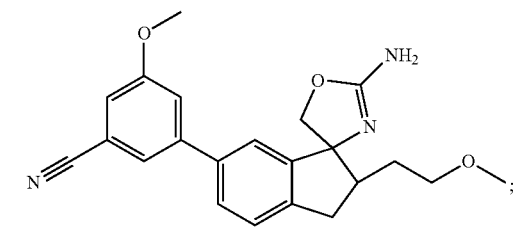 [SMILES: COCCC1Cc2ccc(-c3cc(C#N)cc(OC)c3)cc2C12COC(N)=N2]

Compound 92: 3-(2'-amino-2-(2-methoxyethyl)-2,3-dihydro-5'H-spiro[indene-1,4'-oxazol]-6-yl)-5-methoxybenzonitrile

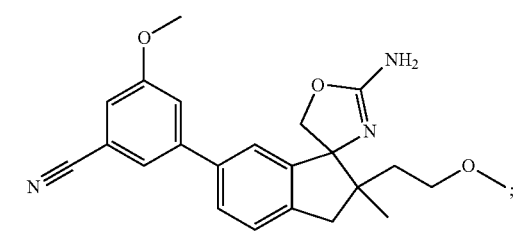 [SMILES: COCCC1(C)Cc2ccc(-c3cc(C#N)cc(OC)c3)cc2C12COC(N)=N2]

Compound 93: 3-(2'-amino-2-(2-methoxyethyl)-2-methyl-2,3-dihydro-5'H-spiro[indene-1,4'-oxazol]-6-yl)-5-methoxybenzonitrile

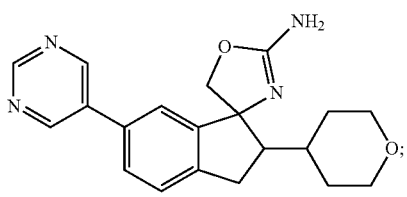 [SMILES: NC1=NC2(CO1)c1cc(-c3cncnc3)ccc1CC2C1CCOCC1]

Compound 94: 6-(pyrimidin-5-yl)-2-(tetrahydro-2H-pyran-4-yl)-2,3-dihydro-5'H-spiro[indene-1,4'-oxazol]-2'-amine Compound 95: 2-methyl-6-(pyrimidin-5-yl)-2-(tetrahydro-2H-pyran-4-yl)-2,3-dihydro-5'H-spiro[indene-1,4'-oxazol]-2'-amine

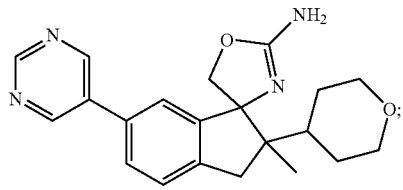 [SMILES: CC1(C2CCOCC2)Cc2ccc(-c3cncnc3)cc2C12COC(N)=N2]

Compound 96: 2-(4-methyltetrahydro-2H-pyran-4-yl)-6-(pyrimidin-5-yl)-2,3-dihydro-5'H-spiro[indene-1,4'-oxazol]-2'-amine

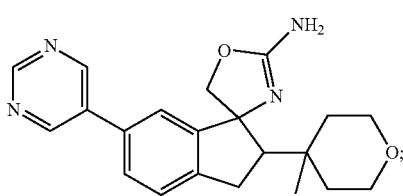 [SMILES: CC1(C2Cc3ccc(-c4cncnc4)cc3C23COC(N)=N3)CCOCC1]

Compound 97: 2-((2R,6S)-2,6-dimethyltetrahydro-2H-pyran-4-yl)-6-(pyrimidin-5-yl)-2,3-dihydro-5'H-spiro[indene-1,4'-oxazol]-2'-amine

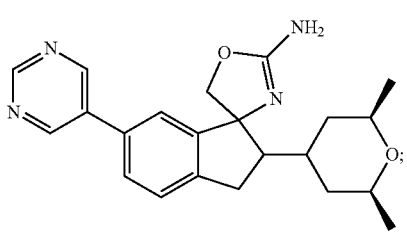 [SMILES: C[C@@H]1CC(C2Cc3ccc(-c4cncnc4)cc3C23COC(N)=N3)C[C@H](C)O1]

Compound 98: 2-morpholino-6-(pyrimidin-5-yl)-2,3-dihydro-5'H-spiro[indene-1,4'-oxazol]-2'-amine

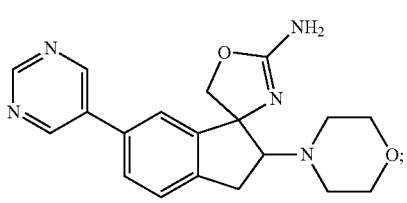 [SMILES: NC1=NC2(CO1)c1cc(-c3cncnc3)ccc1CC2N1CCOCC1]

Compound 99: 2-morpholino-6-(5-(prop-1-yn-1-yl)pyridin-3-yl)-2,3-dihydro-5'H-spiro[indene-1,4'-oxazol]-2'-amine

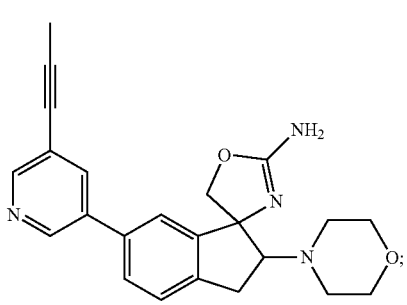 [SMILES: CC#Cc1cncc(-c2ccc3c(c2)C2(COC(N)=N2)C(N2CCOCC2)C3)c1]

Compound 100: 3-(2'-amino-2-morpholino-2,3-dihydro-5'H-spiro[indene-1,4'-oxazol]-6-yl)-5-methoxybenzonitrile

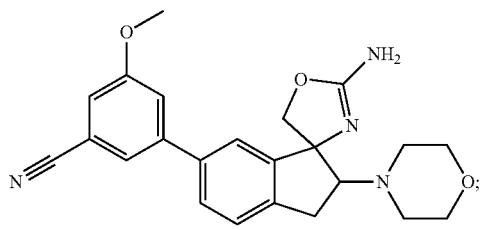 [SMILES: COc1cc(C#N)cc(-c2ccc3c(c2)C2(COC(N)=N2)C(N2CCOCC2)C3)c1]

Compound 101: 3-(2'-amino-2-methyl-2-(tetrahydro-2H-pyran-4-yl)-2,3-dihydro-5'H-spiro[indene-1,4'-oxazol]-6-yl)-5-methoxybenzonitrile

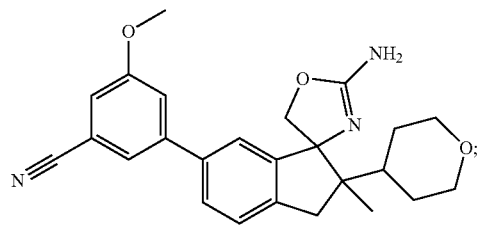 [SMILES: COc1cc(C#N)cc(-c2ccc3c(c2)C2(COC(N)=N2)C(C)(C2CCOCC2)C3)c1]

Compound 102: 2-methyl-6-(pyrimidin-5-yl)-2-(tetrahydro-2H-pyran-4-yl)-2,3-dihydro-5'H-spiro[indene-1,4'-oxazol]-2'-amine (4 diastereoisomers)

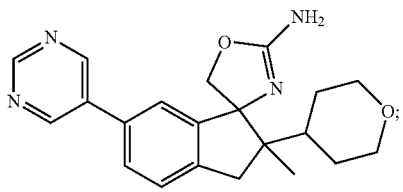 [SMILES: CC1(C2CCOCC2)Cc2ccc(-c3cncnc3)cc2C12COC(N)=N2]

Compound 103: {(1S,1'R,3 S,4S)-6'-(2-fluoro-5-chloropyridin-3-yl)-4-(methoxy-d₃)-3-methyl-3'H,5"H-dispiro[cyclohexane-1,2'-indene-1',4"-oxazol]-5",5"-d₂-2"-amine}

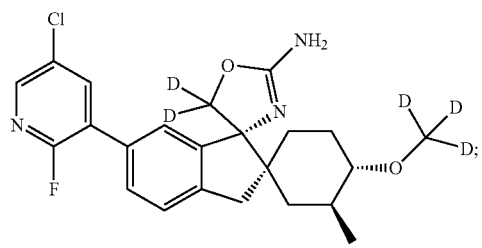

Compound 104: {(1S,1'R,3 S,4S)-6'-(4-fluoropyridin-3-yl)-4-(methoxy-d₃)-3-methyl-3'H,5"H-dispiro[cyclohexane-1,2'-indene-1',4"-oxazol]-5",5"-d₂-2"-amine}

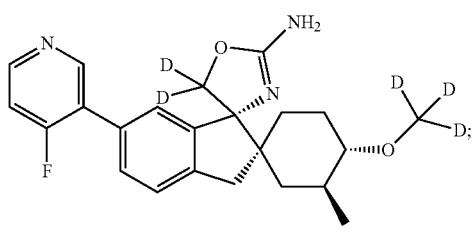

Compound 105: {(1S,1'R,3 S,4S)-6'-(5-cyanopyridin-3-yl)-4-(methoxy-d₃)-3-methyl-3'H,5"H-dispiro[cyclohexane-1,2'-indene-1',4"-oxazol]-5",5"-d₂-2"-amine}

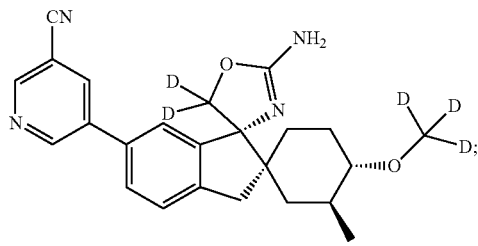

Compound 106: {(1R,1'R,3R,4R)-4-(methoxy-d₃)-3-methyl-6'-(2-fluoro-5-chloropyridin-3-yl)-3'H,5"H-dispiro[cyclohexane-1,2'-indene-1',4"-oxazol]-5",5"-d₂-2"-amine}

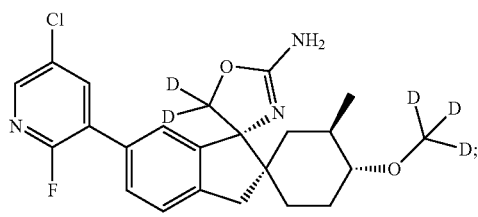

Compound 107: {(1R,1'R,3R,4R)-4-(methoxy-d₃)-3-methyl-6'-(4-fluoropyridin-3-yl)-3'H,5"H-dispiro[cyclohexane-1,2'-indene-1',4"-oxazol]-5",5"-d₂-2"-amine}

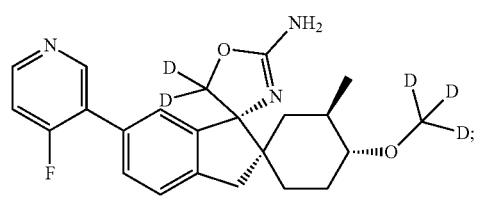

Compound 108: {(1R,1'R,3R,4R)-4-(methoxy-d₃)-3-methyl-6'-(5-cyanopyridin-3-yl)-3'H,5"H-dispiro[cyclohexane-1,2'-indene-1',4"-oxazol]-5",5"-d₂-2"-amine}

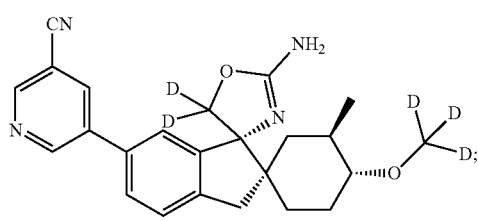

Compound 109: {(1R,1'R,3R,4R)-6'-(2,5-difluoropyridin-3-yl)-4-methoxy-3-methyl-3'H,5"H-dispiro[cyclohexane-1,2'-indene-1',4"-oxazol]-5",5"-d₂-2"-amine}

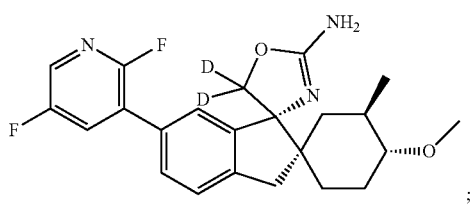 [SMILES: [2H]C1([2H])OC(N)=N[C@]12c1cc(-c3cc(F)cnc3F)ccc1C[C@]21CC[C@@H](OC)[C@H](C)C1]

Compound 110: {(1S,3 S,4S)-4-methoxy-3-methyl-6'-(3,5-difluorophenyl)-3'H,5"H-dispiro[cyclohexane-1,2'-indene-1',4"-oxazol]-5",5"-d₂-2"-amine}

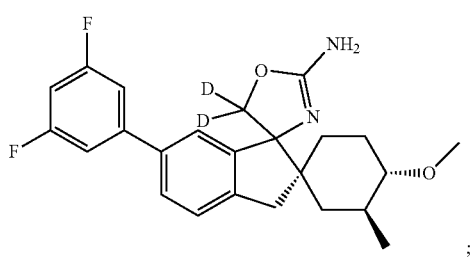

Compound 111: {(1S,3 S,4S)-4-methoxy-3-methyl-6'-(4-hydroxypyridin-4-yl)-3'H,5"H-dispiro[cyclohexane-1,2'-indene-1',4"-oxazol]-5",5"-d₂-2"-amine}

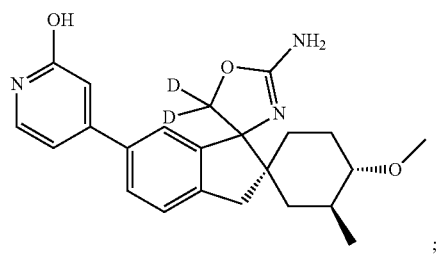

Compound 112: {(1S,1'R,3 S,4S)-4-methoxy-3-methyl-6'-(pyridin-4-yl)-3'H,5"H-dispiro[cyclohexane-1,2'-indene-1',4"-oxazol]-5",5"-d₂-2"-amine}

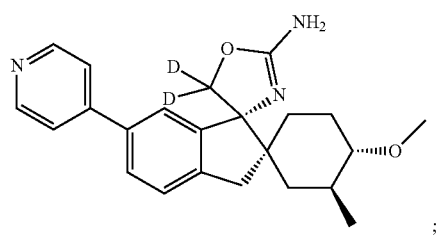

Compound 113: {(1S,1'R,3 S,4S)-4-methoxy-3-methyl-6'-(5-cyanopyridin-3-yl)-3'H,5"H-dispiro[cyclohexane-1,2'-indene-1',4"-oxazol]-5",5"-d₂-2"-amine}

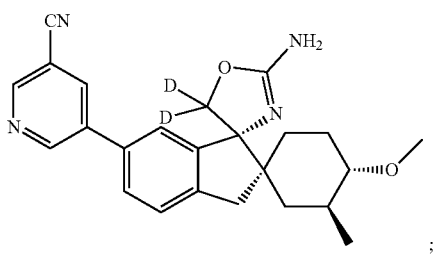

Compound 114: {(1S,1'R,3 S,4S)-4-methoxy-3-methyl-6'-(pyridin-2-yl)-3'H,5"H-dispiro[cyclohexane-1,2'-indene-1',4"-oxazol]-5",5"-d₂-2"-amine}

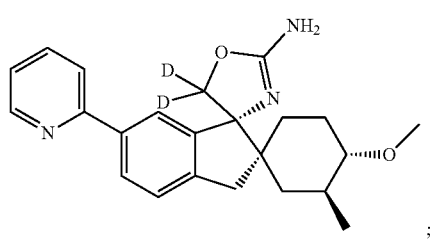 [SMILES: [2H]C1([2H])OC(N)=N[C@]12c1cc(-c3ccccn3)ccc1C[C@@]21CC[C@H](OC)[C@@H](C)C1]

Compound 115: {(1S,1'R,3 S,4S)-4-methoxy-3-methyl-6'-(pyridazin-4-yl)-3'H,5"H-dispiro[cyclohexane-1,2'-indene-1',4"-oxazol]-5",5"-d₂-2"-amine}

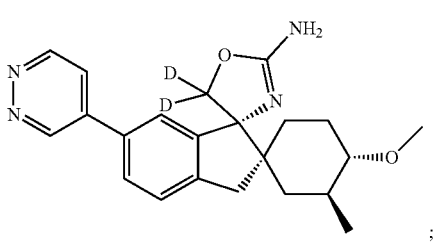 [SMILES: [2H]C1([2H])OC(N)=N[C@]12c1cc(-c3ccnnc3)ccc1C[C@@]21CC[C@H](OC)[C@@H](C)C1]

Compound 116: {(1r,1'R,4R)-4-methoxy-6'-(4-methylpyrimidin-5-yl)-3'H,5"H-dispiro[cyclohexane-1,2'-indene-1',4"-oxazol]-5",5"-d₂-2"-amine}

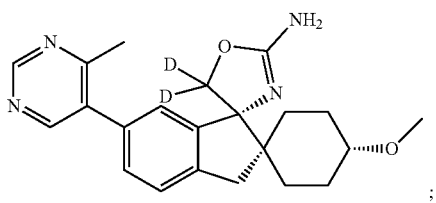

Compound 117: {(1r,1'R,4R)-4-methoxy-6'-(pyrimidin-3-yl)-3'H,5"H-dispiro[cyclohexane-1,2'-indene-1',4"-oxazol]-5",5"-d₂-2"-amine}

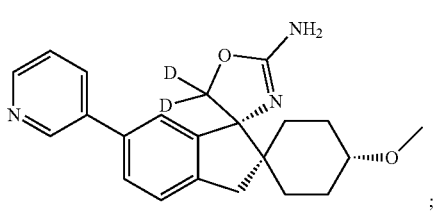 [SMILES: [2H]C1([2H])OC(N)=N[C@]12c1cc(-c3cccnc3)ccc1C[C@]21CC[C@@H](OC)CC1]

Compound 118: {(1r,1'R,4R)-4-methoxy-6'-(pyrimidin-5-yl)-3'H,5"H-dispiro[cyclohexane-1,2'-indene-1',4"-oxazol]-5",5"-d₂-2"-amine}

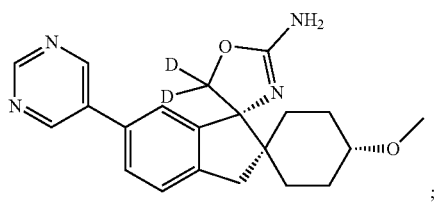

Compound 119: {(1R,1'R,3R,4R)-6'-cyano-4-methoxy-3-methyl-3'H,5"H-dispiro[cyclohexane-1,2'-indene-1',4"-oxazol]-5",5"-d₂-2"-amine}

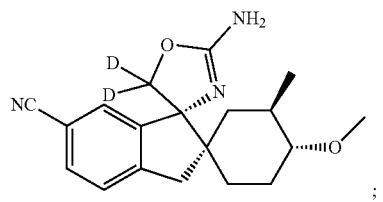 [SMILES: [2H]C1([2H])OC(N)=N[C@]12c1cc(C#N)ccc1C[C@]21CC[C@@H](OC)[C@H](C)C1]

and

Compound 120: {(1S,1'R,3S,4S)-6'-cyano-4-methoxy-3-methyl-3'H,5"H-dispiro[cyclohexane-1,2'-indene-1',4"-oxazol]-5",5"-d₂-2"-amine}

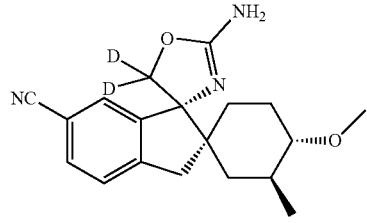

24. A pharmaceutical composition comprising as active ingredient a therapeutically effective amount of a compound according to claim 1, or a pharmaceutically acceptable salt or prodrug thereof, in association with at least one pharmaceutically acceptable excipient, carrier or diluent.

25. A method of treating an Aβ-related pathology in a patient in need thereof, comprising administering to said patient a therapeutically effective amount of a compound of formula (I),

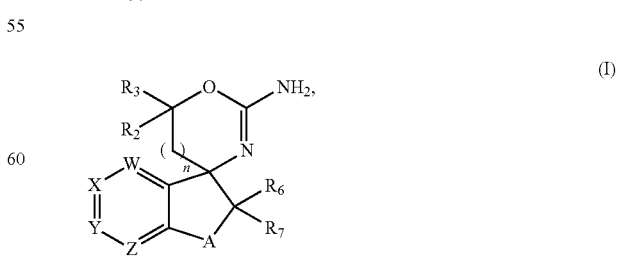

or a pharmaceutically acceptable salt of the compound of formula (I), wherein:

A represents O, CH$_2$, S, or SO$_2$,

X, Y, Z, and W each independently represent N or CR$_1$;

n is 0 or 1;

R$_1$, independently for each occurrence, is selected from hydrogen, halogen, CN, and optionally substituted alkyl, alkenyl, alkynyl, alkoxy, aryl, heteroaryl, or oxime;

R$_2$ and R$_3$ are independently selected from protium, deuterium, tritium, and optionally substituted alkyl, provided that when n is 1, R$_2$ and R$_3$ are independently selected from protium, deuterium, or tritium; and R$_6$ and R$_7$ are independently selected from hydrogen, halogen, and optionally substituted alkyl, alkoxyalkyl, cycloalkyl, or heterocycloalkyl, provided that R$_6$ and R$_7$ are not simultaneously hydrogen; or R$_6$ and R$_7$ together with the carbon to which they are attached, form an optionally substituted carbocyclic or heterocyclic ring;

wherein said Aβ-related pathology is Down's syndrome, a β-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, dementia of mixed vascular origin, dementia of degenerative origin, pre-senile dementia, senile dementia, dementia associated with Parkinson's disease, progressive supranuclear palsy or cortical basal degeneration.

\* \* \* \* \*

UNITED STATES PATENT AND TRADEMARK OFFICE
CERTIFICATE OF CORRECTION

PATENT NO. : 10,053,453 B2
APPLICATION NO. : 15/516848
DATED : August 21, 2018
INVENTOR(S) : Roland Bürli et al.

It is certified that error appears in the above-identified patent and that said Letters Patent is hereby corrected as shown below:

In the Claims

In Claim 23, Column 161, Lines 13-20, in Compound 1, the formula should read:

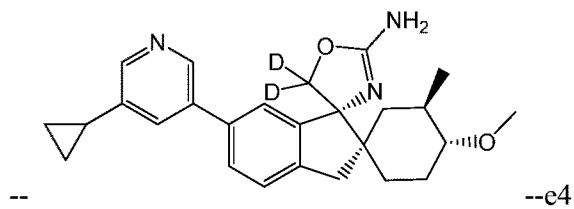

-- --e4

In Claim 23, Column 167, Lines 21-30, in Compound 30, the formula should read:

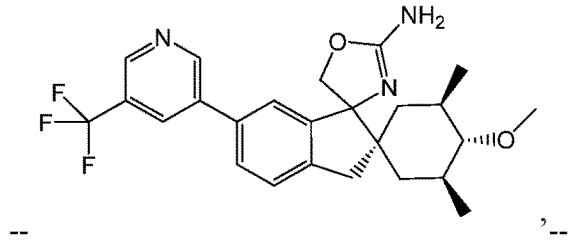

-- '--

In Claim 23, Column 167, Lines 37-45, in Compound 31, the formula should read:

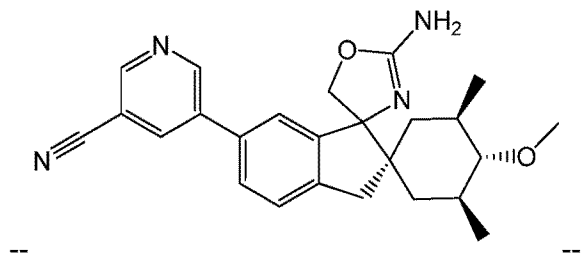

-- --

Signed and Sealed this
Eighteenth Day of December, 2018

Andrei Iancu
*Director of the United States Patent and Trademark Office*

CERTIFICATE OF CORRECTION (continued)

U.S. Pat. No. 10,053,453 B2

In Claim 23, Column 167, Lines 53-63, in Compound 32, the formula should read:

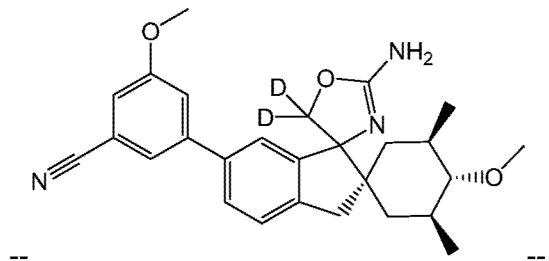

-- --

In Claim 23, Column 169, Lines 31-39, in Compound 40, the formula should read:

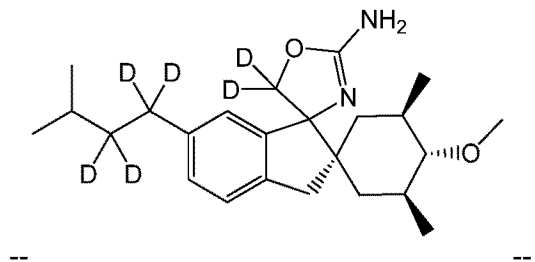

-- --

In Claim 23, Column 174, Lines 20-30, in Compound 66, the formula should read:

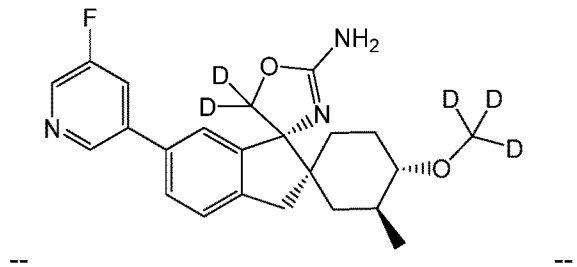

-- --